US009345787B2

(12) United States Patent
Hemminki et al.

(10) Patent No.: US 9,345,787 B2
(45) Date of Patent: May 24, 2016

(54) ADENOVIRAL VECTORS AND METHODS AND USES RELATED THERETO

(75) Inventors: Akseli Hemminki, Helsinki (FI); Anna Kanerva, Helsinki (FI); Vincenzo Cerullo, Helsinki (FI); Sari Pesonen, Helsinki (FI)

(73) Assignee: Targovax Oy, Helsinki (FI)

( * ) Notice: Subject to any disclaimer, the term of this patent is extended or adjusted under 35 U.S.C. 154(b) by 0 days.

(21) Appl. No.: 12/643,140

(22) Filed: Dec. 21, 2009

(65) Prior Publication Data

US 2010/0166799 A1 Jul. 1, 2010

Related U.S. Application Data

(63) Continuation-in-part of application No. 12/585,971, filed on Sep. 29, 2009, now abandoned.

(30) Foreign Application Priority Data

Dec. 22, 2008 (FI) .................................... 20080671
Apr. 27, 2009 (FI) .................................... 20095466

(51) Int. Cl.

| | |
|---|---|
| ***C12N 15/00*** | (2006.01) |
| ***A61K 48/00*** | (2006.01) |
| ***A61K 31/7088*** | (2006.01) |
| ***A61K 38/19*** | (2006.01) |
| ***A61K 45/06*** | (2006.01) |
| ***A61K 31/277*** | (2006.01) |
| ***A61K 31/4188*** | (2006.01) |
| ***A61K 31/661*** | (2006.01) |
| ***A61N 5/10*** | (2006.01) |
| ***C12N 15/86*** | (2006.01) |

(52) U.S. Cl.

CPC ............ *A61K 48/005* (2013.01); *A61K 31/277* (2013.01); *A61K 31/4188* (2013.01); *A61K 31/661* (2013.01); *A61K 31/7088* (2013.01); *A61K 38/193* (2013.01); *A61K 45/06* (2013.01); *A61N 5/10* (2013.01); *C12N 15/86* (2013.01); *A61N 2005/1098* (2013.01); *C12N 2710/10021* (2013.01); *C12N 2710/10043* (2013.01)

(58) Field of Classification Search

None

See application file for complete search history.

(56) References Cited

U.S. PATENT DOCUMENTS

2005/0079158 A1 4/2005 Zhou et al.
2006/0147420 A1 7/2006 Fueyo et al.

FOREIGN PATENT DOCUMENTS

WO 2005/030261 A1 4/2005
WO WO 2006122971 A2 * 11/2006
WO 2007/068772 A1 6/2007
WO 2007/103825 A2 9/2007

OTHER PUBLICATIONS

Kanerva, A. et al., "Noninvasive dual modality in vivo monitoring of the persistnece and potency of a tumor targeted conditionally replicating adenovirus", 2005, Gene. Ther., vol. 12: pp. 87-94.*

Soiffer, R. et al., "Vaccination with irradiated autologous melanoma cells engineered to secrete human granulocyte-macrophage colony-stimulating factor generates potent antitumor immunity in patients with metastatic melanoma", 1998, PNAS, vol. 95: pp. 13141-13146.*

Lei, et al., "An oncolytic adenovirus expressing granulocyte macrophage colony-stimulating factor shows improved specificity and efficacy for treating human solid tumors", Cancer Gene Therapy, vol. 16, pp. 33-43, (2009).

Raki, et al., "Utility of TK/GCV in the context of highly effective oncolysis mediated by a serotype 3 receptor targeted oncolytic adenovirus", Gene Therapy, vol. 14, pp. 1380-1388, (2007).

Zhou, et al., "Novel Oncolytic Adenovirus Selectively Targets Tumor-Associated Polo-Like Kinase 1 and Tumor Cell Viability", Clin Cancer Res, vol. 11, No. 23, pp. 8431-8440, (2005).

Choi, et al., "Concurrent delivery of GM-CSF and B7-1 using an oncolytic adenovirus elicits potent antitumor effect", Gene Therapy, vol. 13, pp. 1010-1020, (2006).

Bauerschmitz, et al., "Tissue-Specific Promoters Active in CD44+CD24−/low Breast Cancer Cells", Cancer Res, vol. 68, No. 14, pp. 5533-5539, (2008).

Bristol, et al., "In Vitro and in Vivo Activities of an Oncolytic Adenoviral Vector Designed to Express GM-CSF", Molecular Therapy, vol. 7, No. 6, pp. 755-764, (2003).

Luo, et al., "Treatment of Cancer with a Novel Dual-Targeted Conditionally Replicative Adenovirus Armed with mda-7/IL-24 Gene", Clin Cancer Res, vol. 14, No. 8, pp. 2450-2457, (2008).

(Continued)

*Primary Examiner* — Michael Burkhart

(74) *Attorney, Agent, or Firm* — Cooley LLP; Ivor R. Elrifi; Matthew Pavao

(57) ABSTRACT

The present invention relates to the fields of life sciences and medicine. Specifically, the invention relates to cancer therapies. More specifically, the present invention relates to oncolytic adenoviral vectors and cells and pharmaceutical compositions comprising said vectors. The present invention also relates to a use of said vectors in the manufacture of a medicament for treating cancer in a subject and a method of treating cancer in a subject. Furthermore, the present invention relates to methods of producing GM-CSF in a cell and increasing tumor specific immune response in a subject, as well as uses of the oncolytic adenoviral vector of the invention for producing GM-CSF in a cell and increasing tumor specific immune response in a subject.

1 Claim, 38 Drawing Sheets

(56) References Cited

OTHER PUBLICATIONS

Filipazzi et al., "Identification of a New Subset of Myeloid Suppressor Cells in Peripheral Blood of Melanoma Patients with Modulation by a Granulocyte-Macrophage Colony-Stimulation Factor-Based Antitumor Vaccine", *Journal of Clinical Oncology*, vol. 25, No. 18, pp. 2546-2553 (2007).

Kusmartsev et al. "Reversal of Myeloid Cell-Mediated Immunosuppression in Patients with Metastatic Renal Cell Carcinoma", *Clinical Cancer Research* 2008: 14(24), pp. 8270-8278 (2008).

Mann et al., "Up- and Down-Regulation of Granulocyte/Macrophage-Colony Stimulating Factor Activity in Murine Skin Increase Susceptibility to Skin Carcinogenesis by Independent Mechanisms", *Cancer Research*, pp. 2311-2319, (2001).

Marigo et al., "Tumor-Induced Tolerance and Immune Suppression by Myeloid Derived Suppressor Cells", *Immunological Reviews* vol. 222: pp. 162-179 (2008).

Parmiani et al. "Opposite Immune Functions of GM-CSF Administered as Vaccine Adjuvant in Cancer Patients", *Annals of Oncology* 18: pp. 226-232 (2007).

Robertson et al., "Granulocyte-macrophage colony stimulating factor gene expression and function during tumor promotion", *Carcinogenesis*, vol. 15, No. 5: pp. 1017-1029 (1994).

Slingluff et al "Effect of Granulocyte/Macrophage Colony-Stimulating Factor on Circulating CD8+ and CD4+ T-Cell Responses to a Multipeptide Melanoma Vaccine: Outcome of a Multicenter Randomized Trial", *Clinical Cancer Research* 2009: 15: pp. 7036-7044 (2009).

Somani, et al., "A randomized, placebo-controlled trial of subcutaneous administration of GM-CSF as a vaccine adjuvant: effect on cellular and humoral immune responses", Vaccine 21: pp. 221-230 (2002).

Von Mehren, et al., "The Influence of Granulocyte Macrophage Colony-Stimulating Factor and Prior Chemotherapy on the Immunological Response to a Vaccine (ALVAC-CEA B7.1) in Patients with Metastatic Carcinoma", Clinical Cancer Research, vol. 7, pp. 1181-1191 (2001).

* cited by examiner

Does GMCSF impair virus replication?

MBA-MD 436

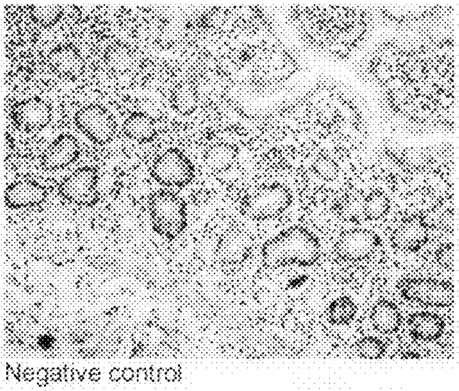

Negative control

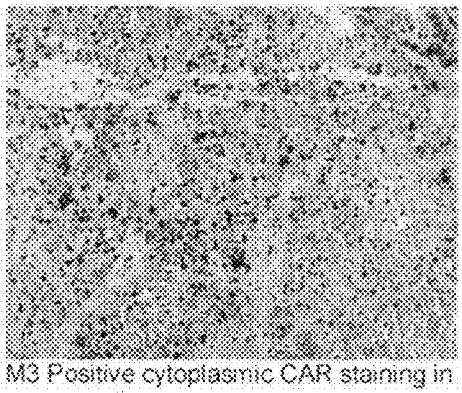

M3 Positive cytoplasmic CAR staining in cancer cells

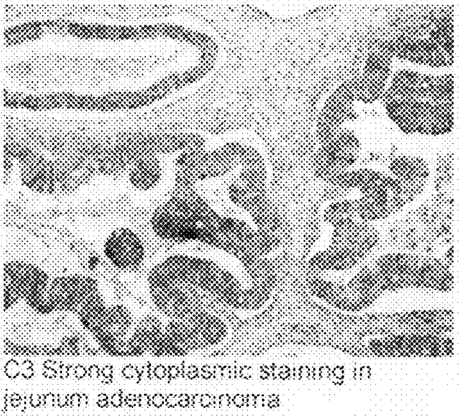

C3 Strong cytoplasmic staining in jejunum adenocarcinoma

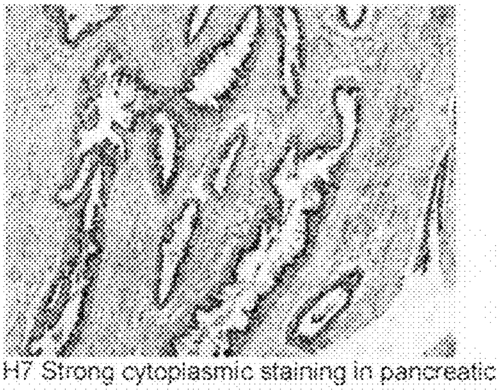

H7 Strong cytoplasmic staining in pancreatic carcinoma

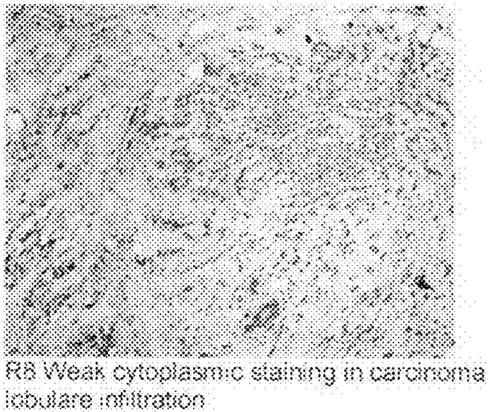

R8 Weak cytoplasmic staining in carcinoma lobulare infiltration

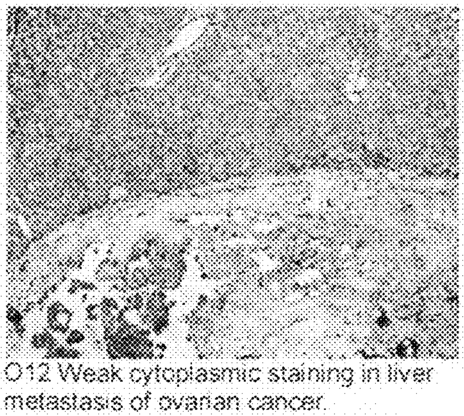

O12 Weak cytoplasmic staining in liver metastasis of ovarian cancer. Positively stained normal hepatocytes

Figure 7c

1. PCR out hGM-CSF, create SunI/MunI sites => 445 bp (pORF-GM-CSF as a template)

2. SunI/MunI digestion of PCR product and pTHSN

3. Sticky-end ligation => pTHSN-GMCSF

*Pme*I linearized pShuttle-D24 + pAdEasy5/3 => pAd5/3-D24

Ad5-D24-GM-CSF

Homol recomb: *SrfI* linearized pAd5/3-D24 + *FspI* linearized pTHSN-GMCSF => pAd5/3-D24-GMCSF Homol recomb: *SrfI* linearized pAd5/3-D24 + *FspI* linearized pTHSN-GMCSF => pAd5/3-D24-GMCSF

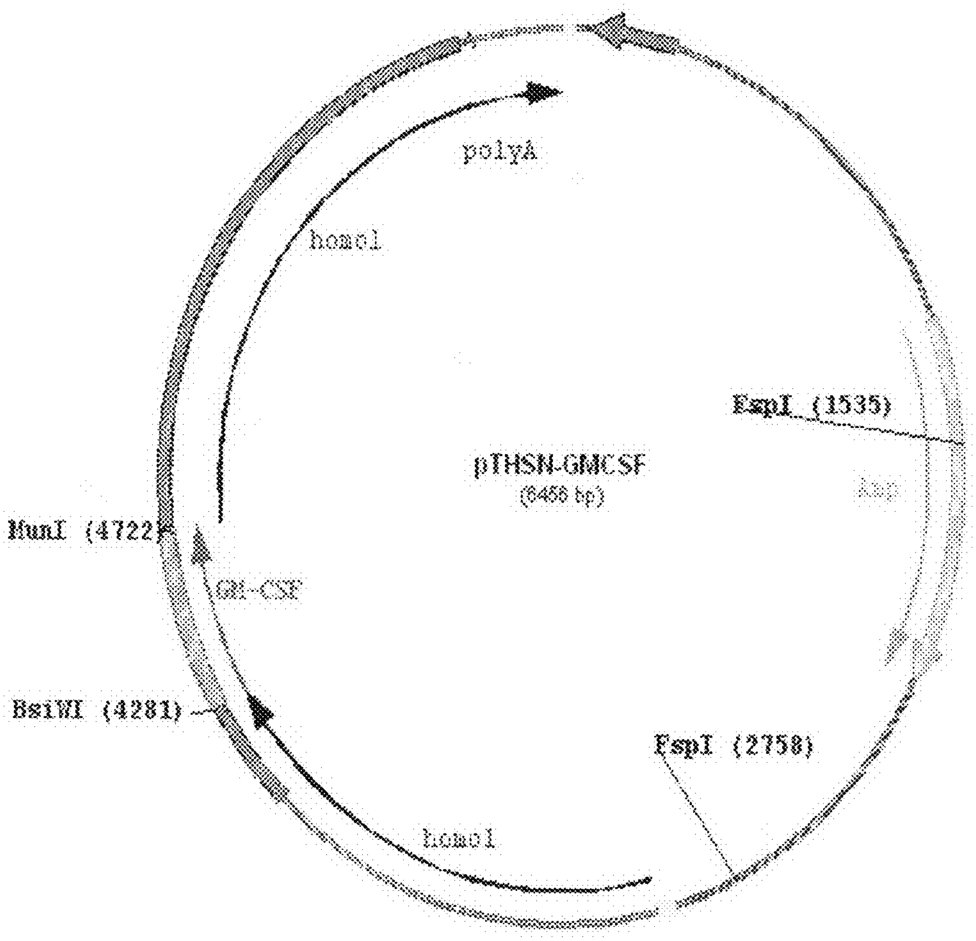
Figure 13h
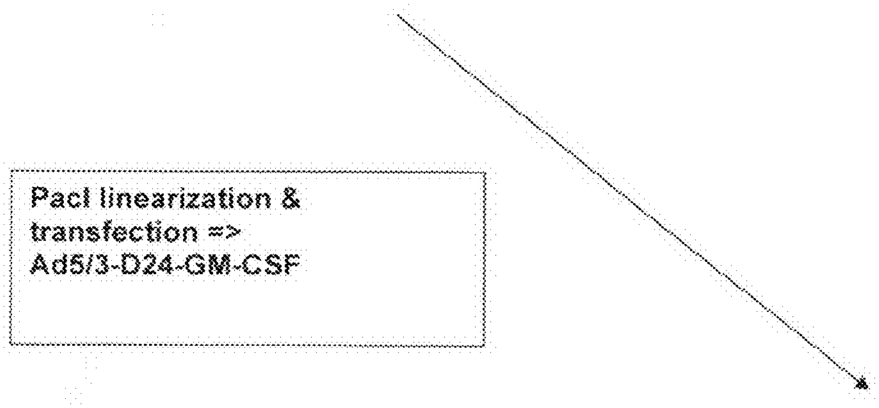

Figure 14

Bolded: D24 deleted E1A (563-1694)
<u>Underlined</u>: GMCSF (28380-28814)
*Italics*: Ad3 knob (31701-32272)

TAACATCATCAATTATACCTTCCATTTTGGATTGAAGCCAATATGATAATGAGGGGGTGGAGTTTGTGACGTGGCGCGGGGCGTGGGA
ACGGGGCGGGTGACGTAGTAGTGTGGCGGAAGTGTGATGTTGCAAGTGTGGCGGAACACATGTAAGCGACGGATGTGGCAAAAGTG
ACGTTTTTGGTGTGCGCCGGTGTACACAGGAAGTGACAATTTTCGCGCGGTTTTAGGCGGATGTTGTAGTAAATTTGGGCGTAACCGA
GTAAGATTTGGCCATTTTCGCGGGAAAACTGAATAAGAGGAAGTGAAATCTGAATAATTTTGTGTTACTCATAGCGCGTAATATTTGT
CTAGGGCCGCGGGGACTTTGACCGTTTACGTGGAGACTCGCCCAGGTGTTTTTCTCAGGTGTTTTCCGCGTTCCGGGTCAAAGTTGGC
GTTTTATTATTATAGTCAGCTGACGTGTAGTGTATTTATACCCGGTGAGTTCCTCAAGAGGCCACTCTTGAGTGCCAGCGAGTAGAGTT
TTCTCCTCCGAGCCGCTCCGACACCGGGACTGAAAATGAGACATATTATCTGCCACGGAGGTGTTATTACCGAAGAAATGGCCGC
CAGTCTTTTGGACCAGCTGATCGAAGAGGTACTGGCTGATAATCTTCCACCTCCTAGCCATTTTGAACCACCTACCCTTCACG
AACTGTATGATTTAGACGTGACGGCCCCCGAAGATCCCAACGAGGAGGCGGTTTCGCAGATTTTTCCCGACTCTGTAATGTTG
GCGGTGCAGGAAGGGATTGACTTACTCACTTTTCCGCCGGCGCCCGGTTCTCCGGAGCCGCCTCACCTTTCCCGGCAGCCCG
AGCAGCCGGAGCAGAGAGCCTTGGGTCCGGTTTCTATGCCAAACCTTGTACCGGAGGTGATCGATCCACCCAGTGACGACGA
GGATGAAGAGGGTGAGGAGTTTGTGTTAGATTATGTGGAGCACCCCGGGCACGGTTGCAGGTCTTGTCATTATCACCGGAGG
AATACGGGGGACCCAGATATTATGTGTTCGCTTTGCTATATGAGGACCTGTGGCATGTTTGTCTACAGTAAGTGAAAATTATG
GGCAGTGGGTGATAGAGTGGTGGGTTTGGTGTGGTAATTTTTTTTTTAATTTTTACAGTTTTGTGGTTTAAAGAATTTTGTATT
GTGATTTTTTTAAAAGGTCCTGTGTCTGAACCTGAGCCTGAGCCCGAGCCAGAACCGGAGCCTGCAAGACCTACCCGCCGTC
CTAAAATGGCGCCTGCTATCCTGAGACGCCCGACATCACCTGTGTCTAGAGAATGCAATAGTAGTACGGATAGCTGTGACTCC
GGTCCTTCTAACACACCTCCTGAGATACACCCGGTGGTCCCGCTGTGCCCCATTAAACCAGTTGCCGTGAGAGTTGGTGGGC
GTCGCCAGGCTGTGGAATGTATCGAGGACTTGCTTAACGAGCCTGGGCAACCTTTGGACTTGAGCTGTAAACGCCCCAGGCC
ATAAGGTGTAAACCTGTGATTGCGTGTGTGGTTAACGCCTTTGTTTGCTGAATGAGTTGATGTAAGTTTAATAAAGGGTGAGA
TAATGTTTAACTTGCATGGCGTGTTAAATGGGGCGGGGCTTAAAGGGTATATAATGCGCCGTGGGCTAATCTTGGTTACATCT
GACCTCATGGAGGCTTGGGAGTGTTTGGAAGATTTTTCTGCTGTGCGTAACTTGCTGGAACAGAGCTCTAACAGTACCTCTTGGTTTT
GGAGGTTTCTGTGGGGCTCATCCCAGGCAAAGTTAGTCTGCAGAATTAAGGAGGATTACAAGTGGGAATTTGAAGAGCTTTTGAAAT
CCTGTGGTGAGCTGTTTGATTCTTTGAATCTGGGTCACCAGGCGCTTTTCCAAGAGAAGGTCATCAAGACTTTGGATTTTTCCACACCG
GGGCGCGCTGCGGCTGCTGTTGCTTTTTTGAGTTTTATAAAGGATAAATGGAGCGAAGAAACCCATCTGAGCGGGGGGTACCTGCTG
GATTTTCTGGCCATGCATCTGTGGAGAGCGGTTGTGAGACACAAGAATCGCCTGCTACTGTTGTCTTCCGTCCGCCCGGCGATAATAC
CGACGGAGGAGCAGCAGCAGCAGCAGGAGGAAGCCAGGCGGCGGCGGCAGGAGCAGAGCCCATGGAACCCGAGAGCCGGCCTGGA
CCCTCGGGAATGAATGTTGTACAGGTGGCTGAACTGTATCCAGAACTGAGACGCATTTTGACAATTACAGAGGATGGGCAGGGGCTA
AAGGGGGTAAAGAGGGAGCGGGGGGCTTGTGAGGCTACAGAGGAGGCTAGGAATCTAGCTTTTAGCTTAATGACCAGACACCGTCC
TGAGTGTATTACTTTTCAACAGATCAAGGATAATTGCGCTAATGAGCTTGATCTGCTGGCGCAGAAGTATTCCATAGAGCAGCTGACC
ACTTACTGGCTGCAGCCAGGGGATGATTTTGAGGAGGCTATTAGGGTATATGCAAAGGTGGCACTTAGGCCAGATTGCAAGTACAAG
ATCAGCAAACTTGTAAATATCAGGAATTGTTGCTACATTTCTGGGAACGGGGCCGAGGTGGAGATAGATACGGAGGATAGGGTGGCC
TTTAGATGTAGCATGATAAATATGTGGCCGGGGGTGCTTGGCATGGACGGGGTGGTTATTATGAATGTAAGGTTTACTGGCCCCAATT
TTAGCGGTACGGTTTTCCTGGCCAATACCAACCTTATCCTACACGGTGTAAGCTTCTATGGGTTTAACAATACCTGTGTGGAAGCCTG
GACCGATGTAAGGGTTCGGGGCTGTGCCTTTTACTGCTGCTGGAAGGGGGTGGTGTGTCGCCCCAAAAGCAGGGCTTCAATTAAGAA
ATGCCTCTTTGAAAGGTGTACCTTGGGTATCCTGTCTGAGGGTAACTCCAGGGTGCGCCACAATGTGGCCTCCGACTGTGGTTGCTTC
ATGCTAGTGAAAAGCGTGGCTGTGATTAAGCATAACATGGTATGTGGCAACTGCGAGGACAGGGCCTCTCAGATGCTGACCTGCTCG
GACGGCAACTGTCACCTGCTGAAGACCATTCACGTAGCCAGCCACTCTCGCAAGGCCTGGCCAGTGTTTGAGCATAACATACTGACCC
GCTGTTCCTTGCATTTGGGTAACAGGAGGGGGGTGTTCCTACCTTACCAATGCAATTTGAGTCACACTAAGATATTGCTTGAGCCCGA
GAGCATGTCCAAGGTGAACCTGAACGGGGTGTTTGACATGACCATGAAGATCTGGAAGGTGCTGAGGTACGATGAGACCCGCACCAG
GTGCAGACCCTGCGAGTGTGGCGGTAAACATATTAGGAACCAGCCTGTGATGCTGGATGTGACCGAGGAGCTGAGGCCCGATCACTT
GGTGCTGGCCTGCACCCGCGCTGAGTTTGGCTCTAGCGATGAAGATACAGATTGAGGTACTGAAATGTGTGGGCGTGGCTTAAGGGT
GGGAAAGAATATATAAGGTGGGGGTCTTATGTAGTTTTGTATCTGTTTTGCAGCAGCCGCCGCCGCCATGAGCACCAACTCGTTTGAT
GGAAGCATTGTGAGCTCATATTTGACAACGCGCATGCCCCCATGGGCCGGGGTGCGTCAGAATGTGATGGGCTCCAGCATTGATGGT
CGCCCCGTCCTGCCCGCAAACTCTACTACCTTGACCTACGAGACCGTGTCTGGAACGCCGTTGGAGACTGCAGCCTCCGCCGCCGCTT
CAGCCGCTGCAGCCACCGCCCGCGGGATTGTGACTGACTTTGCTTTCCTGAGCCCGCTTGCAAGCAGTGCAGCTTCCCGTTCATCCGC
CCGCGATGACAAGTTGACGGCTCTTTTGGCACAATTGGATTCTTTGACCCGGGAACTTAATGTCGTTTCTCAGCAGCTGTTGGATCTGC
GCCAGCAGGTTTCTGCCCTGAAGGCTTCCTCCCCTCCCAATGCGGTTTAAAACATAAATAAAAAACCAGACTCTGTTTGGATTTGGAT
CAAGCAAGTGTCTTGCTGTCTTTATTTAGGGGTTTTGCGCGCGCGGTAGGCCCGGGACCAGCGGTCTCGGTCGTTGAGGGTCCTGTGT
ATTTTTTCCAGGACGTGGTAAAGGTGACTCTGGATGTTCAGATACATGGGCATAAGCCCGTCTCTGGGGTGGAGGTAGCACCACTGCA
GAGCTTCATGCTGCGGGGTGGTGTTGTAGATGATCCAGTCGTAGCAGGAGCGCTGGGCGTGGTGCCTAAAAATGTCTTTCAGTAGCA
AGCTGATTGCCAGGGGCAGGCCCTTGGTGTAAGTGTTTACAAAGCGGTTAAGCTGGGATGGGTGCATACGTGGGGATATGAGATGCA
TCTTGGACTGTATTTTTAGGTTGGCTATGTTCCCAGCCATATCCCTCCGGGGATTCATGTTGTGCAGAACCACCAGCACAGTGTATCCG
GTGCACTTGGGAAATTTGTCATGTAGCTTAGAAGGAAATGCGTGGAAGAACTTGGAGACGCCCTTGTGACCTCCAAGATTTTCCATGC
ATTCGTCCATAATGATGGCAATGGGCCCACGGGCGGCGGCCTGGGCGAAGATATTTCTGGGATCACTAACGTCATAGTTGTGTTCCAG
GATGAGATCGTCATAGGCCATTTTTACAAAGCGCGGGCGGAGGGTGCCAGACTGCGGTATAATGGTTCCATCCGGCCCAGGGGCGTA
GTTACCCTCACAGATTTGCATTTCCCACGCTTTGAGTTCAGATGGGGGGATCATGTCTACCTGCGGGGCGATGAAGAAAACGGTTTCC
GGGGTAGGGGAGATCAGCTGGGAAGAAAGCAGGTTCCTGAGCAGCTGCGACTTACCGCAGCCGGTGGGCCCGTAAATCACACCTATT
ACCGGGTGCAACTGGTAGTTAAGAGAGCTGCAGCTGCCGTCATCCCTGAGCAGGGGGGCCACTTCGTTAAGCATGTCCCTGACTCGC
ATGTTTTCCCTGACCAAATCCGCCAGAAGGCGCTCGCCGCCCAGCGATAGCAGTTCTTGCAAGGAAGCAAAGTTTTTCAACGGTTTGA
GACCGTCCGCCGTAGGCATGCTTTTGAGCGTTTGACCAAGCAGTTCCAGGCGGTCCCACAGCTCGGTCACCTGCTCTACGGCATCTCG
ATCCAGCATATCTCCTCGTTTCGCGGGTTGGGGCGGCTTTCGCTGTACGGCAGTAGTCGGTGCTCGTCCAGACGGGCCAGGGTCATGT
CTTTCCACGGGCGCAGGGTCCTCGTCAGCGTAGTCTGGGTCACGGTGAAGGGGTGCGCTCCGGGCTGCGCGCTGGCCAGGGTGCGCT
TGAGGCTGGTCCTGCTGGTGCTGAAGCGCTGCCGGTCTTCGCCCTGCGCGTCGGCCAGGTAGCATTTGACCATGGTGTCATAGTCCAG
CCCCTCCGCGGCGTGGCCCTTGGCGCGCAGCTTGCCCTTGGAGGAGGCGCCGCACGAGGGGCAGTGCAGACTTTTGAGGGCGTAGAG
CTTGGGCGCGAGAAATACCGATTCCGGGGAGTAGGCATCCGCGCCGCAGGCCCCGCAGACGGTCTCGCATTCCACGAGCCAGGTGAG
CTCTGGCCGTTCGGGGTCAAAAACCAGGTTTCCCCCATGCTTTTTGATGCGTTTCTTACCTCTGGTTTCCATGAGCCGGTGTCCACGCT
CGGTGACGAAAAGGCTGTCCGTGTCCCCGTATACAGACTNNNGTTTTGAGAGGCCTGTCCTCGAGCGGTGTTCCGCGGTCCTCCTCGT
ATAGAAACTCGGACCACTCTGAGACAAAGGCTCGCGTCCAGGCCAGCACGAAGGAGGCTAAGTGGGAGGGGTAGCGGTCGTTGTCC
ACTAGGGGGTCCACTCGCTCCAGGGTGTGAAGACACATGTCGCCCTCTTCGGCATCAAGGAAGGTGATTGGTTTGTAGGTGTAGGCC

Figure 14 (continued)

ACGTGACCGGGTGTTCCTGAAGGGGGGCTATAAAAGGGGGTGGGGGCGCGTTCGTCCTCACTCTCTTCCGCATCGCTGTCTGCGAGG
GCCAGCTGTTGGGGTGAGTACTCCCTCTGAAAAGCGGGCATGACTTCTGCGCTAAGATTGTCAGTTTCCAAAAACGAGGAGGATTTG
ATATTCACCTGGCCCGCGGTGATGCCTTTGAGGGTGGCCGCATCCATCTGGTCAGAAAAGACAATCTTTTTGTTGTCAAGCTTGGTGG
CAAACGACCCGTAGAGGGCGTTGGACAGCAACTTGGCGATGGAGCGCAGGGTTTGGTTTTTGTCGCGATCGGCGCGCTCCTTGGCCG
CGATGTTTAGCTGCACGTATTCGCGCGCAACGCACCGCCATTCGGGAAAGACGGTGGTGCGCTCGTCGGGCACCAGGTGCACGCGCC
AACCGCGGTTGTGCAGGGTGACAAGGTCAACGCTGGTGGCTACCTCTCCGCGTAGGCGCTCGTTGGTCCAGCAGAGGCGGCCGCCCT
TGCGCGAGCAGAATGGCGGTAGGGGGTCTAGCTGCGTCTCGTCCGGGGGGTCTGCGTCCACGGTAAAGACCCCGGGCAGCAGGCGCG
CGTCGAAGTAGTCTATCTTGCATCCTTGCAAGTCTAGCGCCTGCTGCCATGCGCGGGCGGCAAGCGCGCGCTCGTATGGGTTGAGTGG
GGGACCCCATGGCATGGGGTGGGTGAGCGCGGAGGCGTACATGCCGCAAATGTCGTAAACGTAGAGGGGCTCTCTGAGTATTCCAAG
ATATGTAGGGTAGCATCTTCCACCGCGGATGCTGGCGCGCACGTAATCGTATAGTTCGTGCGAGGGAGCGAGGAGGTCGGGACCGAG
GTTGCTACGGGCGGGCTGCTCTGCTCGGAAGACTATCTGCCTGAAGATGGCATGTGAGTTGGATGATATGGTTGGACGCTGGAAGAC
GTTGAAGCTGGCGTCTGTGAGACCTACCGCGTCACGCACGAAGGAGGCGTAGGAGTCGCGCAGCTTGTTGACCAGCTCGGCGGTGAC
CTGCACGTCTAGGGCGCAGTAGTCCAGGGTTTCCTTGATGATGTCATACTTATCCTGTCCCTTTTTTTTCCACAGCTCGCGGTTGAGGA
CAAACTCTTCGCGGTCTTTCCAGTACTCTTGGATCGGAAACCCGTCGGCCTCCGAACGGTAAGAGCCTAGCATGTAGAACTGGTTGAC
GGCCTGGTAGGCGCAGCATCCCTTTTCTACGGGTAGCGCGTATGCCTGCGCGGCCTTCCGGAGCGAGGTGTGGGTGAGCGCAAAGGT
GTCCCTGACCATGACTTTGAGGTACTGGTATTTGAAGTCAGTGTCGTCGCATCCGCCCTGCTCCCAGAGCAAAAAGTCCGTGCGCTTT
TTGGAACGCGGATTTGGCAGGGCGAAGGTGACATCGTTGAAGAGTATCTTTCCCGCGCGAGGCATAAAGTTGCGTGTGATGCGGAAG
GGTCCCGGCACCTCGGAACGGTTGTTAATTACCTGGGCGGCGAGCACGATCTCGTCAAAGCCGTTGATGTTGTGGCCCACAATGTAAA
GTTCCAAGAAGCGCGGGATGCCCTTGATGGAAGGCAATTTTTTAAGTTCCTCGTAGGTGAGCTCTTCAGGGGAGCTGAGCCCGTGCTC
TGAAAGGGCCCAGTCTGCAAGATGAGGGTTGGAAGCGACGAATGAGCTCCACAGGTCACGGGCCATTAGCATTTGCAGGTGGTCGCG
AAAGGTCCTAAACTGGCGACCTATGGCCATTTTTTCTGGGGTGATGCAGTAGAAGGTAAGCGGGTCTTGTTCCCAGCGGTCCCATCCA
AGGTTCGCGGCTAGGTCTCGCGCGGCAGTCACTAGAGGCTCATCTCCGCCGAACTTCATGACCAGCATGAAGGGCACGAGCTGCTTC
CCAAAGGCCCCCATCCAAGTATAGGTCTCTACATCGTAGGTGACAAAGAGACGCTCGGTGCGAGGATGCGAGCCGATCGGGAAGAA
CTGGATCTCCCGCCACCAATTGGAGGAGTGGCTATTGATGTGGTGAAAGTAGAAGTCCCTGCGACGGGCCGAACACTCGTGCTGGCT
TTTGTAAAAACGTGCGCAGTACTGGCAGCGGTGCACGGGCTGTACATCCTGCACGAGGTTGACCTGACGACCGCGCACAAGGAAGCA
GAGTGGGAATTTGAGCCCCTCGCCTGGCGGGTTTGGCTGGTGGTCTTCTACTTCGGCTGCTTGTCCTTGACCGTCTGGCTGCTCGAGGG
GAGTTACGGTGGATCGGACCACCACGCCGCGCGAGCCCAAAGTCCAGATGTCCGCGCGCGGCGGTCGGAGCTTGATGACAACATCGC
GCAGATGGGAGCTGTCCATGGTCTGGAGCTCCCGCGGCGTCAGGTCAGGCGGGAGCTCCTGCAGGTTTACCTCGCATAGACGGGTCA
GGGCGCGGGCTAGATCCAGGTGATACCTAATTTCCAGGGGCTGGTTGGTGGCGGCGTCGATGGCTTGCAAGAGGCCGCATCCCCGCG
GCGCGACTACGGTACCGCGCGGCGGGCGGTGGGCCGCGGGGGTGTCCTTGGATGATGCATCTAAAAGCGGTGACGCGGGCGAGCCC
CCGGAGGTAGGGGGGGCTCCGGACCCGCCGGGAGAGGGGGCAGGGGCACGTCGGCGCCGCGCGCGGGCAGGAGCTGGTGCTGCGCG
CGTAGGTTGCTGGCGAACGCGACGACGCGGCGGTTGATCTCCTGAATCTGGCGCCTCTGCGTGAAGACGACGGGCCCGGTGAGCTTG
AGCCTGAAAGAGAGTTCGACAGAATCAATTTCGGTGTCGTTGACGGCGGCCTGGCGCAAAATCTCCTGCACGTCTCCTGAGTTGTCTT
GATAGGCGATCTCGGCCATGAACTGCTCGATCTCTTCCTCCTGGAGATCTCCGCGTCCGGCTCGCTCCACGGTGGCGGCGAGGTCGTT
GGAAATGCGGGCCATGAGCTGCGAGAAGGCGTTGAGGCCTCCCTCGTTCCAGACGCGGCTGTAGACCACGCCCCCTTCGGCATCGCG
GGCGCGCATGACCACCTGCGCGAGATTGAGCTCCACGTGCCGGGCGAAGACGGCGTAGTTTCGCAGGCGCTGAAAGAGGTAGTTGAG
GGTGGTGGCGGTGTGTTCTGCCACGAAGAAGTACATAACCCAGCGTCGCAACGTGGATTCGTTGATATCCCCCAAGGCCTCAAGGCG
CTCCATGGCCTCGTAGAAGTCCACGGCGAAGTTGAAAAACTGGGAGTTGCGCGCCGACACGGTTAACTCCTCCTCCAGAAGACGGAT
GAGCTCGGCGACAGTGTCGCGCACCTCGCGCTCAAAGGCTACAGGGGCCTCTTCTTCTTCTTCAATCTCCTCTTCCATAAGGGCCTCCC
CTTCTTCTTCTTCTGGCGGCGGTGGGGGAGGGGGGACACGGCGGCGACGACGGCGCACCGGGAGGCGGTCGACAAAGCGCTCGATCA
TCTCCCCGCGGCGACGGCGCATGGTCTCGGTGACGGCGCGGCCGTTCTCGCGGGGGCGCAGTTGGAAGACGCCGCCCGTCATGTCCC
GGTTATGGGTTGGCGGGGGGCTGCCATGCGGCAGGGATACGGCGCTAACGATGCATCTCAACAATTGTTGTGTAGGTACTCCGCCGC
CGAGGGACCTGAGCGAGTCCGCATCGACCGGATCGGAAAACCTCTCGAGAAAGGCGTCTAACCAGTCACAGTCGCAAGGTAGGCTG
AGCACCGTGGCGGGCGGCAGCGGGCGGCGGTCGGGGTTGTTTCTGGCGGAGGTGCTGCTGATGATGTAATTAAAGTAGGCGGTCTTG
AGACGGCGGATGGTCGACAGAAGCACCATGTCCTTGGGTCCGGCCTGCTGAATGCGCAGGCGGTCGGCCATGCCCCAGGCTTCGTTT
TGACATCGGCGCAGGTCTTTGTAGTAGTCTTGCATGAGCCTTTCTACCGGCACTTCTTCTTCTCCTTCCTCTTGTCCTGCATCTCTTGCA
TCTATCGCTGCGGCGGCGGCGGAGTTTGGCCGTAGGTGGCGCCCTCTTCCTCCCATGCGTGTGACCCCGAAGCCCCTCATCGGCTGAA
GCAGGGCTAGGTCGGCGACAACGCGCTCGGCTAATATGGCCTGCTGCACCTGCGTGAGGGTAGACTGGAAGTCATCCATGTCCACAA
AGCGGTGGTATGCGCCCGTGTTGATGGTGTAAGTGCAGTTGGCCATAACGGACCAGTTAACGGTCTGGTGACCCGGCTGCGAGAGCT
CGGTGTACCTGAGACGCGAGTAAGCCCTCGAGTCAAATACGTAGTCGTTGCAAGTCCGCACCAGGTACTGGTATCCCACCAAAAAGT
GCGGCGGCGGCTGGCGGTAGAGGGGCCAGCGTAGGGTGGCCGGGGCTCCGGGGGCGAGATCTTCCAACATAAGGCGATGATATCCG
TAGATGTACCTGGACATCCAGGTGATGCCGGCGGCGGTGGTGGAGGCGCGCGGAAAGTCGCGGACGCGGTTCCAGATGTTGCGCAGC
GGCAAAAAGTGCTCCATGGTCGGGACGCTCTGGCCGGTCAGGCGCGCGCAATCGTTGACGCTCTACCGTGCAAAAGGAGAGCCTGTA
AGCGGGCACTCTTCCGTGGTCTGGTGGATAAATTCGCAAGGGTATCATGGCGGACGACCGGGGTTCGAGCCCCGTATCCGGCCGTCC
GCCGTGATCCATGCGGTTACCGCCCGCGTGTCGAACCCAGGTGTGCGACGTCAGACAACGGGGGAGTGCTCCTTTTGGCTTCCTTCCA
GGCGCGGCGGCTGCTGCGCTAGCTTTTTTGGCCACTGGCCGCGCGCAGCGTAAGCGGTTAGGCTGGAAAGCGAAAGCATTAAGTGGC
TCGCTCCCTGTAGCCGGAGGGTTATTTTCCAAGGGTTGAGTCGCGGGACCCCCGGTTCGAGTCTCGGACCGGCCGGACTGCGGCGAAC
GGGGGTTTGCCTCCCCGTCATGCAAGACCCCGCTTGCAAATTCCTCCGGAAACAGGGACGAGCCCCTTTTTTGCTTTTCCCAGATGCA
TCCGGTGCTGCGGCAGATGCGCCCCCCTCCTCAGCAGCGGCAAGAGCAAGAGCAGCGGCAGACATGCAGGGCACCCTCCCCTCCTCC
TACCGCGTCAGGAGGGGCGACATCCGCGGTTGACGCGGCAGCAGATGGTGATTACGAACCCCCGCGGCGCCGGGCCCGGCACTACCT
GGACTTGGAGGAGGGCGAGGGCCTGGCGCGGCTAGGAGCGCCCTCTCCTGAGCGGTACCCAAGGGTGCAGCTGAAGCGTGATACGC
GTGAGGCGTACGTGCCGCGGCAGAACCTGTTTCGCGACCGCGAGGGAGAGGAGCCCGAGGAGATGCGGGATCGAAAGTTCCACGCA
GGGCGCGAGCTGCGGCATGGCCTGAATCGCGAGCGGTTGCTGCGCGAGGAGGACTTTGAGCCCGACGCGCGAACCGGGATTAGTCCC
GCGCGCGCACACGTGGCGGCCGCCGACCTGGTAACCGCATACGAGCAGACGGTGAACCAGGAGATTAACTTTCAAAAAAGCTTTAAC
AACCACGTGCGTACGCTTGTGGCGCGCGAGGAGGTGGCTATAGGACTGATGCATCTGTGGGACTTTGTAAGCGCGCTGGAGCAAAAC
CCAAATAGCAAGCCGCTCATGGCGCAGCTGTTCCTTATAGTGCAGCACAGCAGGGACAACGAGGCATTCAGGGATGCGCTGCTAAAC
ATAGTAGAGCCCGAGGGCCGCTGGCTGCTCGATTTGATAAACATCCTGCAGAGCATAGTGGTGCAGGAGCGCAGCTTGAGCCTGGCT
GACAAGGTGGCCGCCATCAACTATTCCATGCTTAGCCTGGGCAAGTTTTACGCCCGCAAGATATACCATACCCCTTACGTTCCCATAG
ACAAGGAGGTAAAGATCGAGGGGTTCTACATGCGCATGGCGCTGAAGGTGCTTACCTTGAGCGACGACCTGGGCGTTTATCGCAACG
AGCGCATCCACAAGGCCGTGAGCGTGAGCCGGCGGCGCGAGCTCAGCGACCGCGAGCTGATGCACAGCCTGCAAAGGGCCCTGGCT
GGCACGGGCAGCGGCGATAGAGAGGCCGAGTCCTACTTTGACGCGGGCGCTGACCTGCGCTGGGCCCCAAGCCGACGCGCCCTGGA
GGCAGCTGGGGCCGGACCTGGGCTGGCGGTGGCACCCGCGCGCGCTGGCAACGTCGGCGGCGTGGAGGAATATGACGAGGACGATG
AGTACGAGCCAGAGGACGGCGAGTACTAAGCGGTGATGTTTCTGATCAGATGATGCAAGACGCAACGGACCCGGCGGTGCGGGCGG
CGCTGCAGAGCCAGCCGTCCGGCCTTAACTCCACGGACGACTGGCGCCAGGTCATGGACCGCATCATGTCGCTGACTGCGCGCAATC
CTGACGCGTTCCGGCAGCAGCCGCAGGCCAACCGGCTCTCCGCAATTCTGGAAGCGGTGGTCCCGGCGCGCGCAAACCCCACGCACG
AGAAGGTGCTGGCGATCGTAAACGCGCTGGCCGAAAACAGGGCCATCCGGCCCGACGAGGCCGGCCTGGTCTACGACGCGCTGCTTC
AGCGCGTGGCTCGTTACAACAGCGGCAACGTGCAGACCAACCTGGACCGGCTGGTGGGGGATGTGCGCGAGGCCGTGGCGCAGCGT
GAGCGCGCGCAGCAGCAGGGCAACCTGGGCTCCATGGTTGCACTAAACGCCTTCCTGAGTACACAGCCCGCCAACGTGCCGCGGGGA

Figure 14 (continued)

CAGGAGGACTACACCAACTTTGTGAGCGCACTGCGGCTAATGGTGACTGAGACACCGCAAAGTGAGGTGTACCAGTCTGGGCCAGAC
TATTTTTTCCAGACCAGTAGACAAGGCCTGCAGACCGTAAACCTGAGCCAGGCTTTCAAAAACTTGCAGGGGCTGTGGGGGGTGCGG
GCTCCCACAGGCGACCGCGCGACCGTGTCTAGCTTGCTGACGCCCAACTCGCGCCTGTTGCTGCTGCTAATAGCGCCCTTCACGGACA
GTGGCAGCGTGTCCCGGGACACATACCTAGGTCACTTGCTGACACTGTACCGCGAGGCCATAGGTCAGGCGCATGTGGACGAGCATA
CTTTCCAGGAGATTACAAGTGTCAGCCGCGCGCTGGGGCAGGAGGACACGGGCAGCCTGGAGGCAACCCTAAACTACCTGCTGACCA
ACCGGCGGCAGAAGATCCCCTCGTTGCACAGTTTAAACAGCGAGGAGGAGCGCATTTTGCGCTACGTGCAGCAGAGCGTGAGCCTTA
ACCTGATGCGCGACGGGGTAACGCCCAGCGTGGCGCTGGACATGACCGCGCGCAACATGGAACCGGGCATGTATGCCTCAAACCGGC
CGTTTATCAACCGCCTAATGGACTACTTGCATCGCGCGGCCGCCGTGAACCCCGAGTATTTCACCAATGCCATCTTGAACCCGCACTG
GCTACCGCCCCCTGGTTTCTACACCGGGGGATTCGAGGTGCCCGAGGGTAACGATGGATTCCTCTGGGACGACATAGACGACAGCGT
GTTTTCCCCGCAACCGCAGACCCTGCTAGAGTTGCAACAGCGCGAGCAGGCAGAGGCGGCGCTGCGAAAGGAAAGCTTCCGCAGGCC
AAGCAGCTTGTCCGATCTAGGCGCTGCGGCCCCGCGGTCAGATGCTAGTAGCCCATTTCCAAGCTTGATAGGGTCTCTTACCAGCACT
CGCACCACCCGCCCGCGCCTGCTGGGCGAGGAGGAGTACCTAAACAACTCGCTGCTGCAGCCGCAGCGCGAAAAAAACCTGCCTCCG
GCATTTCCCAACAACGGGATAGAGAGCCTAGTGGACAAGATGAGTAGATGGAAGACGTACGCGCAGGAGCACAGGGACGTGCCAGG
CCCGCGCCCGCCCACCCGTCGTCAAAGGCACGACCGTCAGCGGGGTCTGGTGTGGGAGGACGATGACTCGGCAGACGACAGCAGCGT
CCTGGATTTGGGAGGGAGTGGCAACCCGTTTGCGCACCTTCGCCCCAGGCTGGGGAGAATGTTTTAAAAAAAAAAAAAGCATGATGCA
AAATAAAAAACTCACCAAGGCCATGGCACCGAGCGTTGGTTTTCTTGTATTCCCCTTAGTATGCGGCGCGCGGCGATGTATGAGGAA
GGTCCTCCTCCCTCCTACGAGAGTGTGGTGAGCGCGGCGCCAGTGGCGGCGGCGCTGGGTTCTCCCTTCGATGCTCCCCTGGACCCGC
CGTTTGTGCCTCCGCGGTACCTGCGGCCTACCGGGGGGAGAAACAGCATCCGTTACTCTGAGTTGGCACCCCTATTCGACACCACCCG
TGTGTACCTGGTGGACAACAAGTCAACGGATGTGGCATCCCTGAACTACCAGAACGACCACAGCAACTTTCTGACCACGGTCATTCA
AAACAATGACTACAGCCCGGGGGAGGCAAGCACACAGACCATCAATCTTGACGACCGGTCGCACTGGGGCGGCGACCTGAAAACCA
TCCTGCATACCAACATGCCAAATGTGAACGAGTTCATGTTTACCAATAAGTTTAAGGCGCGGGTGATGGTGTCGCGCTTGCCTACTAA
GGACAATCAGGTGGAGCTGAAATACGAGTGGGTGGAGTTCACGCTGCCCGAGGGCAACTACTCCGAGACCATGACCATAGACCTTAT
GAACAACGCGATCGTGGAGCACTACTTGAAAGTGGGCAGACAGAACGGGGTTCTGGAAAGCGACATCGGGGTAAAGTTTGACACCC
GCAACTTCAGACTGGGGTTTGACCCCGTCACTGGTCTTGTCATGCCTGGGGTATATACAAACGAAGCCTTCCATCCAGACATCATTTT
GCTGCCAGGATGCGGGGTGGACTTCACCCACAGCCGCCTGAGCAACTTGTTGGGCATCCGCAAGCGGCAACCCTTCCAGGAGGGCTT
TAGGATCACCTACGATGATCTGGAGGGTGGTAACATTCCCGCACTGTTGGATGTGGACGCCTACCAGGCGAGCTTGAAAGATGACAC
CGAACAGGGCGGGGGTGGCGCAGGCGGCAGCAACAGCAGTGGCAGCGGCGCGGAAGAGAACTCCAACGCGGCAGCCGCGGCAATG
CAGCCGGTGGAGGACATGAACGATCATGCCATTCGCGGCGACACCTTTGCCACACGGGCTGAGGAGAAGCGCGCTGAGGCCGAAGC
AGCGGCCGAAGCTGCCGCCCCCGCTGCGCAACCCGAGGTCGAGAAGCCTCAGAAGAAACCGGTGATCAAACCCCTGACAGAGGACA
GCAAGAAACGCAGTTACAACCTAATAAGCAATGACAGCACCTTCACCCAGTACCGCAGCTGGTACCTTGCATACAACTACGGCGACC
CTCAGACCGGAATCCGCTCATGGACCCTGCTTTGCACTCCTGACGTAACCTGCGGCTCGGAGCAGGTCTACTGGTCGTTGCCAGACAT
GATGCAAGACCCCGTGACCTTCCGCTCCACGCGCCAGATCAGCAACTTTCCGGTGGTGGGCGCCGAGCTGTTGCCCGTGCACTCCAAG
AGCTTCTACAACGACCAGGCCGTCTACTCCCAACTCATCCGCCAGTTTACCTCTCTGACCCACGTGTTCAATCGCTTTCCCGAGAACCA
GATTTTGGCGCGCCCGCCAGCCCCCACCATCACCACCGTCAGTGAAAACGTTCCTGCTCTCACAGATCACGGGACGCTACCGCTGCGC
AACAGCATCGGAGGAGTCCAGCGAGTGACCATTACTGACGCCAGACGCCGCACCTGCCCCTACGTTTACAAGGCCCTGGGCATAGTC
TCGCCGCGCGTCCTATCGAGCCGCACTTTTTGAGCAAGCATGTCCATCCTTATATCGCCCAGCAATAACACAGGCTGGGGCCTGCGCT
TCCCAAGCAAGATGTTTGGCGGGGCCAAGAAGCGCTCCGACCAACACCCAGTGCGCGTGCGCGGGCACTACCGCGCGCCCTGGGGCG
CGCACAAACGCGGCCGCACTGGGCGCACCACCGTCGATGACGCCATCGACGCGGTGGTGGAGGAGGCGCGCAACTACACGCCCACG
CCGCCACCAGTGTCCACAGTGGACGCGGCCATTCAGACCGTGGTGCGCGGAGCCCGGCGCTATGCTAAAATGAAGAGACGGCGGAG
GCGCGTAGCACGTCGCCACCGCCGCCGACCCGGCACTGCCGCCCAACGCGCGGCGGCGGCCCTGCTTAACCGCGCACGTCGCACCGG
CCGACGGGCGGCCATGCGGGCCGCTCGAAGGCTGGCCGCGGGTATTGTCACTGTGCCCCCCAGGTCCAGGCGACGAGCGGCCGCCGC
AGCAGCCGCGGCCATTAGTGCTATGACTCAGGGTCGCAGGGGCAACGTGTATTGGGTGCGCGACTCGGTTAGCGGCCTGCGCGTGCC
CGTGCGCACCCGCCCCCCGCGCAACTAGATTGCAAGAAAAAACTACTTAGACTCGTACTGTTGTATGTATCCAGCGGCGGCGGCGCG
CAACGAAGCTATGTCCAAGCGCAAAATCAAAGAAGAGATGCTCCAGGTCATCGCGCCGGAGATCTATGGCCCCCCGAAGAAGGAAG
AGCAGGATTACAAGCCCCGAAAGCTAAAGCGGGTCAAAAAGAAAAAGAAAGATGATGATGATGAACTTGACGACGAGGTGGAACTG
CTGCACGCTACCGCGCCCAGGCGACGGGTACAGTGGAAAGGTCGACGCGTAAAACGTGTTTTGCGACCCGGCACCACCGTAGTCTTT
ACGCCCGGTGAGCGCTCCACCCGCACCTACAAGCGCGTGTATGATGAGGTGTACGGCGACGAGGACCTGCTTGAGCAGGCCAACGAG
CGCCTCGGGGAGTTTGCCTACGGAAAGCGGCATAAGGACATGCTGGCGTTGCCGCTGGACGAGGGCAACCCAACACCTAGCCTAAAG
CCCGTAACACTGCAGCAGGTGCTGCCCGCGCTTGCACCGTCCGAAGAAAAGCGCGGCCTAAAGCGCGAGTCTGGTGACTTGGCACCC
ACCGTGCAGCTGATGGTACCCAAGCGCCAGCGACTGGAAGATGTCTTGGAAAAAATGACCGTGGAACCTGGGCTGGAGCCCGAGGTC
CGCGTGCGGCCAATCAAGCAGGTGGCGCCGGGACTGGGCGTGCAGACCGTGGACGTTCAGATACCCACTACCAGTAGCACCAGTATT
GCCACCGCCACAGAGGGCATGGAGACACAAACGTCCCCGGTTGCCTCAGCGGTGGCGGATGCCGCGGTGCAGGCGGTCGCTGCGGCC
GCGTCCAAGACCTCTACGGAGGTGCAAACGGACCCGTGGATGTTTCGCGTTTCAGCCCCCCGGCGCCCGCGCGGTTCGAGGAAGTAC
GGCGCCGCCAGCGCGCTACTGCCCGAATATGCCCTACATCCTTCCATTGCGCCTACCCCCGGCTATCGTGGCTACACCTACCGCCCCA
GAAGACGAGCAACTACCCGACGCCGAACCACCACTGGAACCCGCCGCCGCCGTCGCCGTCGCCAGCCCGTGCTGGCCCCGATTTCCG
TGCGCAGGGTGGCTCGCGAAGGAGGCAGGACCCTGGTGCTGCCAACAGCGCGCTACCACCCCAGCATCGTTTAAAAGCCGGTCTTTG
TGGTTCTTGCAGATATGGCCCTCACCTGCCGCCTCCGTTTCCCGGTGCCGGGATTCCGAGGAAGAATGCACCGTAGGAGGGGCATGGC
CGGCCACGGCCTGACGGGCGGCATGCGTCGTGCGCACCACCGGCGGCGGCGCGCGTCGCACCGTCGCATGCGCGGCGGTATCCTGCC
CCTCCTTATTCCACTGATCGCCGCGGCGATTGGCGCCGTGCCCGGAATTGCATCCGTGGCCTTGCAGGCGCAGAGACACTGATTAAAA
ACAAGTTGCATGTGGAAAAATCAAAATAAAAAGTCTGGACTCTCACGCTCGCTTGGTCCTGTAACTATTTTGTAGAATGGAAGACATC
AACTTTGCGTCTCTGGCCCCGCGACACGGCTCGCGCCCGTTCATGGGAAACTGGCAAGATATCGGCACCAGCAATATGAGCGGTGGC
GCCTTCAGCTGGGGCTCGCTGTGGAGCGGCATTAAAAATTTCGGTTCCACCGTTAAGAACTATGGCAGCAAGGCCTGGAACAGCAGC
ACAGGCCAGATGCTGAGGGATAAGTTGAAAGAGCAAAATTTCCAACAAAAGGTGGTAGATGGCCTGGCCTCTGGCATTAGCGGGGT
GGTGGACCTGGCCAACCAGGCAGTGCAAAATAAGATTAACAGTAAGCTTGATCCCCGCCCTCCCGTAGAGGAGCCTCCACCGGCCGT
GGAGACAGTGTCTCCAGAGGGGCGTGGCGAAAAGCGTCCGCGCCCCGACAGGGAAGAAACTCTGGTGACGCAAATAGACGAGCCTC
CCTCGTACGAGGAGGCACTAAAGCAAGGCCTGCCCACCACCCGTCCCATCGCGCCCATGGCTACCGGAGTGCTGGGCCAGCACACAC
CCGTAACGCTGGACCTGCCTCCCCCCGCCGACACCCAGCAGAAACCTGTGCTGCCAGGCCCGACCGCCGTTGTTGTAACCCGTCCTAG
CCGCGCGTCCCTGCGCCGCGCCGCCAGCGGTCCGCGATCGTTGCGGCCCGTAGCCAGTGGCAACTGGCAAAGCACACTGAACAGCAT
CGTGGGTCTGGGGGTGCAATCCCTGAAGCGCCGACGATGCTTCTGAATAGCTAACGTGTCGTATGTGTGTCATGTATGCGTCCATGTC
GCCGCCAGAGGAGCTGCTGAGCCGCCGCGCGCCCGCTTTCCAAGATGGCTACCCCTTCGATGATGCCGCAGTGGTCTTACATGCACAT
CTCGGGCCAGGACGCCTCGGAGTACCTGAGCCCCGGGCTGGTGCAGTTTGCCCGCGCCACCGAGACGTACTTCAGCCTGAATAACAA
GTTTAGAAACCCCACGGTGGCGCCTACGCACGACGTGACCACAGACCGGTCCCAGCGTTTGACGCTGCGGTTCATCCCTGTGGACCGT
GAGGATACTGCGTACTCGTACAAGGCGCGGTTCACCCTAGCTGTGGGTGATAACCGTGTGCTGGACATGGCTTCCACGTACTTTGACA
TCCGCGGCGTGCTGGACAGGGGCCCTACTTTTAAGCCCTACTCTGGCACTGCCTACAACGCCCTGGCTCCCAAGGGTGCCCCAAATCC
TTGCGAATGGGATGAAGCTGCTACTGCTCTTGAAATAAACCTAGAAGAAGAGGACGATGACAACGAAGACGAAGTAGACGAGCAAG
CTGAGCAGCAAAAAACTCACGTATTTGGGCAGGCGCCTTATTCTGGTATAAATATTACAAAGGAGGGTATTCAAATAGGTGTCGAAG
GTCAAACACCTAAATATGCCGATAAAACATTTCAACCTGAACCTCAAATAGGAGAATCTCAGTGGTACGAAACTGAAATTAATCATG
CAGCTGGGAGAGTCCTTAAAAAGACTACCCCAATGAAACCATGTTACGGTTCATATGCAAAACCCACAAATGAAAATGGAGGGCAA

Figure 14 (continued)

GGCATTCTTGTAAAGCAACAAAATGGAAAGCTAGAAAGTCAAGTGGAAATGCAATTTTTCTCAACTACTGAGGCGACCGCAGGCAAT
GGTGATAACTTGACTCCTAAAGTGGTATTGTACAGTGAAGATGTAGATATAGAAACCCCAGACACTCATATTTCTTACATGCCCACTA
TTAAGGAAGGTAACTCACGAGAACTAATGGGCCAACAATCTATGCCCAACAGGCCTAATTACATTGCTTTTAGGGACAATTTTATTGG
TCTAATGTATTACAACAGCACGGGTAATATGGGTGTTCTGGCGGGCCAAGCATCGCAGTTGAATGCTGTTGTAGATTTGCAAGACAGA
AACACAGAGCTTTCATACCAGCTTTTGCTTGATTCCATTGGTGATAGAACCAGGTACTTTTCTATGTGGAATCAGGCTGTTGACAGCTA
TGATCCAGATGTTAGAATTATTGAAAATCATGGAACTGAAGATGAACTTCCAAATTACTGCTTTCCACTGGGAGGTGTGATTAATACA
GAGACTCTTACCAAGGTAAAACCTAAAACAGGTCAGGAAAATGGATGGGAAAAAGATGCTACAGAATTTTCAGATAAAAATGAAAT
AAGAGTTGGAAATAATTTTGCCATGGAAATCAATCTAAATGCCAACCTGTGGAGAAATTTCCTGTACTCCAACATAGCGCTGTATTTG
CCCGACAAGCTAAAGTACAGTCCTTCCAACGTAAAAATTTCTGATAACCCAAACACCTACGACTACATGAACAAGCGAGTGGTGGCT
CCCGGGTTAGTGGACTGCTACATTAACCTTGGAGCACGCTGGTCCCTTGACTATATGGACAACGTCAACCCATTTAACCACCACCGCA
ATGCTGGCCTGCGCTACCGCTCAATGTTGCTGGGCAATGGTCGCTATGTGCCCTTCCACATCCAGGTGCCTCAGAAGTTCTTTGCCATT
AAAAACCTCCTTCTCCTGCCGGGCTCATACACCTACGAGTGGAACTTCAGGAAGGATGTTAACATGGTTCTGCAGAGCTCCCTAGGAA
ATGACCTAAGGGTTGACGGAGCCAGCATTAAGTTTGATAGCATTTGCCTTTACGCCACCTTCTTCCCCATGGCCCACAACACCGCCTC
CACGCTTGAGGCCATGCTTAGAAACGACACCAACGACCAGTCCTTTAACGACTATCTCTCCGCCGCCAACATGCTCTACCCTATACCC
GCCAACGCTACCAACGTGCCCATATCCATCCCCTCCCGCAACTGGGCGGCTTTCCGCGGCTGGGCCTTCACGCGCCTTAAGACTAAGG
AAACCCCATCACTGGGCTCGGGCTACGACCCTTATTACACCTACTCTGGCTCTATACCCTACCTAGATGGAACCTTTTACCTCAACCAC
ACCTTTAAGAAGGTGGCCATTACCTTTGACTCTTCTGTCAGCTGGCCTGGCAATGACCGCCTGCTTACCCCCAACGAGTTTGAAATTA
AGCGCTCAGTTGACGGGGAGGGTTACAACGTTGCCCAGTGTAACATGACCAAAGACTGGTTCCTGGTACAAATGCTAGCTAACTACA
ACATTGGCTACCAGGGCTTCTATATCCCAGAGAGCTACAAGGACCGCATGTACTCCTTCTTTAGAAACTTCCAGCCCATGAGCCGTCA
GGTGGTGGATGATACTAAATACAAGGACTACCAACAGGTGGGCATCCTACACCAACACAACAACTCTGGATTTGTTGGCTACCTTGC
CCCCACCATGCGCGAAGGACAGGCCTACCCTGCTAACTTCCCCTATCCGCTTATAGGCAAGACCGCAGTTGACAGCATTACCCAGAA
AAAGTTTCTTTGCGATCGCACCCTTTGGCGCATCCCATTCTCCAGTAACTTTATGTCCATGGGCGCACTCACAGACCTGGGCCAAAAC
CTTCTCTACGCCAACTCCGCCCACGCGCTAGACATGACTTTTGAGGTGGATCCCATGGACGAGCCCACCCTTCTTTATGTTTTGTTTGA
AGTCTTTGACGTGGTCCGTGTGCACCGGCCGCACCGCGGCGTCATCGAAACCGTGTACCTGCGCACGCCCTTCTCGGCCGGCAACGCC
ACAACATAAAGAAGCAAGCAACATCAACAACAGCTGCCGCCATGGGCTCCAGTGAGCAGGAACTGAAAGCCATTGTCAAAGATCTT
GGTTGTGGGCCATATTTTTTGGGCACCTATGACAAGCGCTTTCCAGGCTTTGTTTCTCCACACAAGCTCGCCTGCGCCATAGTCAATAC
GGCCGGTCGCGAGACTGGGGGCGTACACTGGATGGCCTTTGCCTGGAACCCGCACTCAAAAACATGCTACCTCTTTGAGCCCTTTGGC
TTTTCTGACCAGCGACTCAAGCAGGTTTACCAGTTTGAGTACGAGTCACTCCTGCGCCGTAGCGCCATTGCTTCTTCCCCCGACCGCTG
TATAACGCTGGAAAAGTCCACCCAAAGCGTACAGGGGCCCAACTCGGCCGCCTGTGGACTATTCTGCTGCATGTTTCTCCACGCCTTT
GCCAACTGGCCCCAAACTCCCATGGATCACAACCCCACCATGAACCTTATTACCGGGGTACCCAACTCCATGCTCAACAGTCCCCAGG
TACAGCCCACCCTGCGTCGCAACCAGGAACAGCTCTACAGCTTCCTGGAGCGCCACTCGCCCTACTTCCGCAGCCACAGTGCGCAGAT
TAGGAGCGCCACTTCTTTTTGTCACTTGAAAAACATGTAAAAATAATGTACTAGAGACACTTTCAATAAAGGCAAATGCTTTTATTTG
TACACTCTCGGGTGATTATTTACCCCCACCCTTGCCGTCTGCGCCGTTTAAAAATCAAAGGGGTTCTGCCGCGCATCGCTATGCGCCAC
TGGCAGGGACACGTTGCGATACTGGTGTTTAGTGCTCCACTTAAACTCAGGCACAACCATCCGCGGCAGCTCGGTGAAGTTTTCACTC
CACAGGCTGCGCACCATCACCAACGCGTTTAGCAGGTCGGGCGCCGATATCTTGAAGTCGCAGTTGGGGCCTCCGCCCTGCGCGCGC
GAGTTGCGATACACAGGGTTGCAGCACTGGAACACTATCAGCGCCGGGTGGTGCACGCTGGCCAGCACGCTCTTGTCGGAGATCAGA
TCCGCGTCCAGGTCCTCCGCGTTGCTCAGGGCGAACGGAGTCAACTTTGGTAGCTGCCTTCCCAAAAAGGGCGCGTGCCCAGGCTTTG
AGTTGCACTCGCACCGTAGTGGCATCAAAAGGTGACCGTGCCCGGTCTGGGCGTTAGGATACAGCGCCTGCATAAAAGCCTTGATCT
GCTTAAAAGCCACCTGAGCCTTTGCGCCTTCAGAGAAGAACATGCCGCAAGACTTGCCGGAAAACTGATTGGCCGGACAGGCCGCGT
CGTGCACGCAGCACCTTGCGTCGGTGTTGGAGATCTGCACCACATTTCGGCCCCACCGGTTCTTCACGATCTTGGCCTTGCTAGACTGC
TCCTTCAGCGCGCGCTGCCCGTTTTCGCTCGTCACATCCATTTCAATCACGTGCTCCTTATTTATCATAATGCTTCCGTGTAGACACTTA
AGCTCGCCTTCGATCTCAGCGCAGCGGTGCAGCCACAACGCGCAGCCCGTGGGCTCGTGATGCTTGTAGGTCACCTCTGCAAACGACT
GCAGGTACGCCTGCAGGAATCGCCCCATCATCGTCACAAAGGTCTTGTTGCTGGTGAAGGTCAGCTGCAACCCGCGGTGCTCCTCGTT
CAGCCAGGTCTTGCATACGGCCGCCAGAGCTTCCACTTGGTCAGGCAGTAGTTTGAAGTTCGCCTTTAGATCGTTATCCACGTGGTAC
TTGTCCATCAGCGCGCGCGCAGCCTCCATGCCCTTCTCCCACGCAGACACGATCGGCACACTCAGCGGGTTCATCACCGTAATTTCAC
TTTCCGCTTCGCTGGGCTCTTCCTCTTCCTCTTGCGTCCGCATACCACGCGCCACTGGGTCGTCTTCATTCAGCCGCCGCACTGTGCGCT
TACCTCCTTTGCCATGCTTGATTAGCACCGGTGGGTTGCTGAAACCCACCATTTGTAGCGCCACATCTTCTCTTTCTTCCTCGCTGTCCA
CGATTACCTCTGGTGATGGCGGGCGCTCGGGCTTGGGAGAAGGGCGCTTCTTTTTCTTCTTGGGCGCAATGGCCAAATCCGCCGCCGA
GGTCGATGGCCGCGGGCTGGGTGTGCGCGGCACCAGCGCGTCTTGTGATGAGTCTTCCTCGTCCTCGGACTCGATACGCCGCCTCATC
CGCTTTTTTGGGGGCGCCCGGGGAGGCGGCGGCGACGGGGACGGGGACGACACGTCCTCCATGGTTGGGGGACGTCGCGCCGCACCG
CGTCCGCGCTCGGGGGTGGTTTCGCGCTGCTCCTCTTCCCGACTGGCCATTTCCTTCTCCTATAGGCAGAAAAAGATCATGGAGTCAG
TCGAGAAGAAGGACAGCCTAACCGCCCCCTCTGAGTTCGCCACCACCGCCTCCACCGATGCCGCCAACGCGCCTACCACCTTCCCCGT
CGAGGCACCCCCGCTTGAGGAGGAGGAAGTGATTATCGAGCAGGACCCAGGTTTTGTAAGCGAAGACGACGAGGACCGCTCAGTAC
CAACAGAGGATAAAAAGCAAGACCAGGACAACGCAGAGGCAAACGAGGAACAAGTCGGGCGGGGGGACGAAAGGCATGGCGACTA
CCTAGATGTGGGAGACGACGTGCTGTTGAAGCATCTGCAGCGCCAGTGCGCCATTATCTGCGACGCGTTGCAAGAGCGCAGCGATGT
GCCCCTCGCCATAGCGGATGTCAGCCTTGCCTACGAACGCCACCTATTCTCACCGCGCGTACCCCCCAAACGCCAAGAAAACGGCAC
ATGCGAGCCCAACCCGCGCCTCAACTTCTACCCCGTATTTGCCGTGCCAGAGGTGCTTGCCACCTATCACATCTTTTTCCAAAACTGCA
AGATACCCCTATCCTGCCGTGCCAACCGCAGCCGAGCGGACAAGCAGCTGGCCTTGCGGCAGGGCGCTGTCATACCTGATATCGCCT
CGCTCAACGAAGTGCCAAAAATCTTTGAGGGTCTTGGACGCGACGAGAAGCGCGCGGCAAACGCTCTGCAACAGGAAAACAGCGAA
AATGAAAGTCACTCTGGAGTGTTGGTGGAACTCGAGGGTGACAACGCGCGCCTAGCCGTACTAAAACGCAGCATCGAGGTCACCCAC
TTTGCCTACCCGGCACTTAACCTACCCCCCAAGGTCATGAGCACAGTCATGAGTGAGCTGATCGTGCGCCGTGCGCAGCCCCTGGAGA
GGGATGCAAATTTGCAAGAACAAACAGAGGAGGGCCTACCCGCAGTTGGCGACGAGCAGCTAGCGCGCTGGCTTCAAACGCGCGAG
CCTGCCGACTTGGAGGAGCGACGCAAACTAATGATGGCCGCAGTGCTCGTTACCGTGGAGCTTGAGTGCATGCAGCGGTTCTTTGCTG
ACCCGGAGATGCAGCGCAAGCTAGAGGAAACATTGCACTACACCTTTCGACAGGGCTACGTACGCCAGGCCTGCAAGATCTCCAACG
TGGAGCTCTGCAACCTGGTCTCCTACCTTGGAATTTTGCACGAAAACCGCCTTGGGCAAAACGTGCTTCATTCCACGCTCAAGGGCGA
GGCGCGCCGCGACTACGTCCGCGACTGCGTTTACTTATTTCTATGCTACACCTGGCAGACGGCCATGGGCGTTTGGCAGCAGTGCTTG
GAGGAGTGCAACCTCAAGGAGCTGCAGAAACTGCTAAAGCAAAACTTGAAGGACCTATGGACGGCCTTCAACGAGCGCTCCGTGGC
CGCGCACCTGGCGGACATCATTTTCCCCGAACGCCTGCTTAAAACCCTGCAACAGGGTCTGCCAGACTTCACCAGTCAAAGCATGTTG
CAGAACTTTAGGAACTTTATCCTAGAGCGCTCAGGAATCTTGCCCGCCACCTGCTGTGCACTTCCTAGCGACTTTGTGCCCATTAAGTA
CCGCGAATGCCCTCCGCCGCTTTGGGGCCACTGCTACCTTCTGCAGCTAGCCAACTACCTTGCCTACCACTCTGACATAATGGAAGAC
GTGAGCGGTGACGGTCTACTGGAGTGTCACTGTCGCTGCAACCTATGCACCCCGCACCGCTCCCTGGTTTGCAATTCGCAGCTGCTTA
ACGAAAGTCAAATTATCGGTACCTTTGAGCTGCAGGGTCCCTCGCCTGACGAAAAGTCCGCGGCTCCGGGGTTGAAACTCACTCCGG
GGCTGTGGACGTCGGCTTACCTTCGCAAATTTGTACCTGAGGACTACCACGCCCACGAGATTAGGTTCTACGAAGACCAATCCCGCCC
GCCAAATGCGGAGCTTACCGCCTGCGTCATTACCCAGGGCCACATTCTTGGCCAATTGCAAGCCATCAACAAAGCCCGCCAAGAGTTT
CTGCTACGAAAGGGACGGGGGGTTTACTTGGACCCCCAGTCCGGCGAGGAGCTCAACCCAATCCCCCCGCCGCCGCAGCCCTATCAG
CAGCAGCCGCGGGCCCTTGCTTCCCAGGATGGCACCCAAAAAGAAGCTGCAGCTGCCGCCGCCACCCACGGACGAGGAGGAATACT
GGGACAGTCAGGCAGAGGAGGTTTTGGACGAGGAGGAGGAGGACATGATGGAAGACTGGGAGAGCCTAGACGAGGAAGCTTCCGA
GGTCGAAGAGGTGTCAGACGAAACACCGTCACCCTCGGTCGCATTCCCCTCGCCGGCGCCCCAGAAATCGGCAACCGGTTCCAGCAT

Figure 14 (continued)

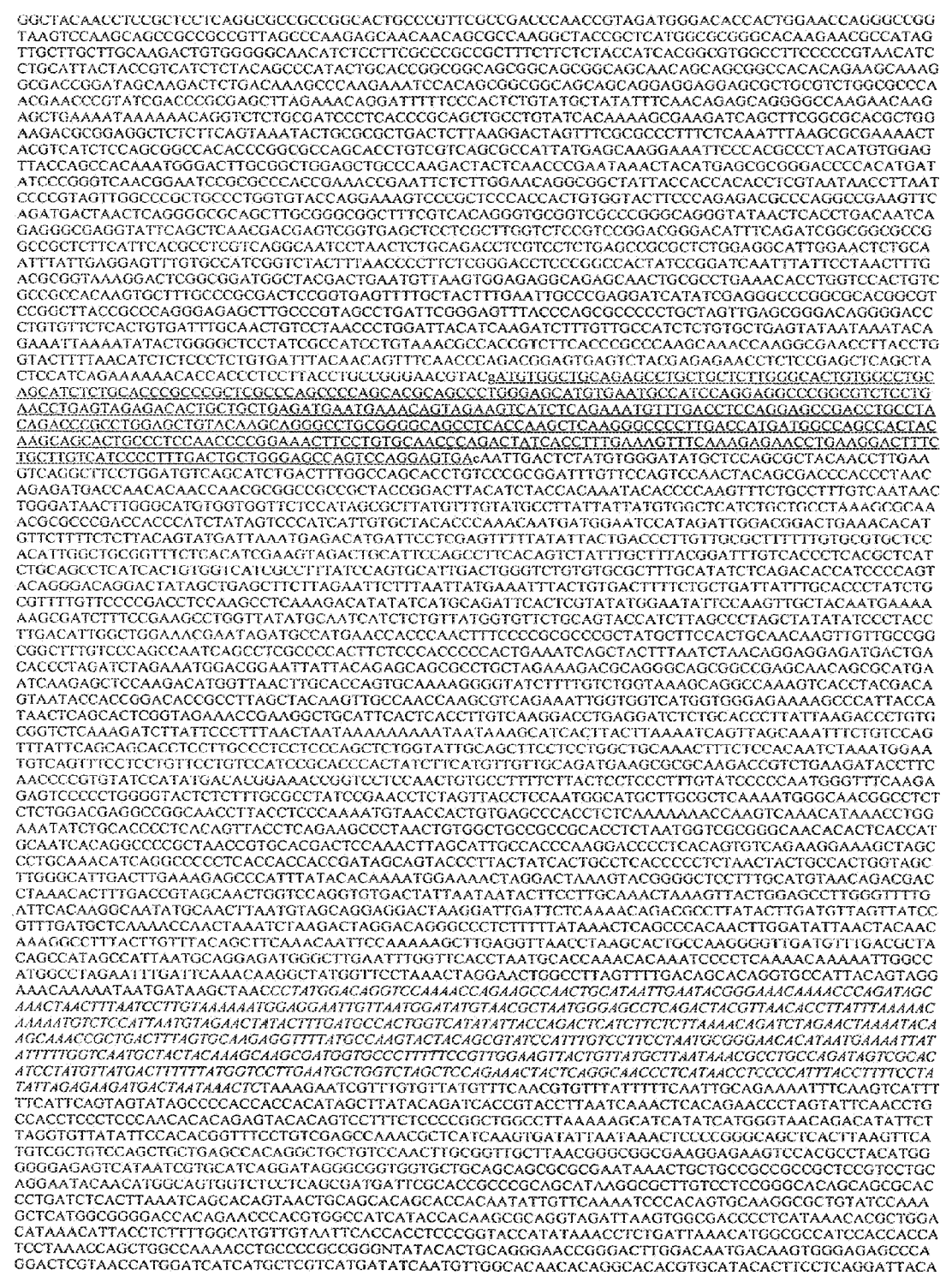

GGCTACAACCTCCGCTCCTCAGGCGCCGCCGGCACTGCCCGTTCGCCGACCCAACCGTAGATGGGACACCACTGGAACCAGGGCCGG
TAAGTCCAAGCAGCCGCCGCCGTTAGCCCAAGAGCAACAACAGCGCCAAGGCTACCGCTCATGGCGCGGGCACAAGAACGCCATAG
TTGCTTGCTTGCAAGACTGTGGGGGCAACATCTCCTTCGCCCGCCGCTTTCTTCTCTACCATCACGGCGTGGCCTTCCCCCGTAACATC
CTGCATTACTACCGTCATCTCTACAGCCCATACTGCACCGGCGGCAGCGGCAGCGGCAGCAACAGCAGCGGCCACACAGAAGCAAAG
GCGACCGGATAGCAAGACTCTGACAAAGCCCAAGAAATCCACAGCGGCGGCAGCAGCAGGAGGAGGAGCGCTGCGTCTGGCGCCCA
ACGAACCCGTATCGACCCGCGAGCTTAGAAACAGGATTTTTCCCACTCTGTATGCTATATTTCAACAGAGCAGGGGCCAAGAACAAG
AGCTGAAAATAAAAAACAGGTCTCTGCGATCCCTCACCCGCAGCTGCCTGTATCACAAAAGCGAAGATCAGCTTCGGCGCACGCTGG
AAGACGCGGAGGCTCTCTTCAGTAAATACTGCGCGCTGACTCTTAAGGACTAGTTTCGCGCCCTTTCTCAAATTTAAGCGCGAAAACT
ACGTCATCTCCAGCGGCCACACCCGGCGCCAGCACCTGTCGTCAGCGCCATTATGAGCAAGGAAATTCCCACGCCCTACATGTGGAG
TTACCAGCCACAAATGGGACTTGCGGCTGGAGCTGCCCAAGACTACTCAACCCGAATAAACTACATGAGCGCGGGACCCCACATGAT
ATCCCGGGTCAACGGAATCCGCGCCCACCGAAACCGAATTCTCTTGGAACAGGCGGCTATTACCACCACACCTCGTAATAACCTTAAT
CCCCGTAGTTGGCCCGCTGCCCTGGTGTACCAGGAAAGTCCCGCTCCCACCACTGTGGTACTTCCCAGAGACGCCCAGGCCGAAGTTC
AGATGACTAACTCAGGGGCGCAGCTTGCGGGCGGCTTTCGTCACAGGGTGCGGTCGCCCGGGCAGGGTATAACTCACCTGACAATCA
GAGGGCGAGGTATTCAGCTCAACGACGAGTCGGTGAGCTCCTCGCTTGGTCTCCGTCCGGACGGGACATTTCAGATCGGCGGCGCCG
GCCGCTCTTCATTCACGCCTCGTCAGGCAATCCTAACTCTGCAGACCTCGTCCTCTGAGCCGCGCTCTGGAGGCATTGGAACTCTGCA
ATTTATTGAGGAGTTTGTGCCATCGGTCTACTTTAACCCCTTCTCGGGACCTCCCGGCCACTATCCGGATCAATTTATTCCTAACTTTG
ACGCGGTAAAGGACTCGGCGGATGGCTACGACTGAATGTTAAGTGGAGAGGCAGAGCAACTGCGCCTGAAACACCTGGTCCACTGTC
GCCGCCACAAGTGCTTTGCCCGCGACTCCGGTGAGTTTTGCTACTTTGAATTGCCCGAGGATCATATCGAGGGCCCGGCGCACGGCGT
CCGGCTTACCGCCCAGGGAGAGCTTGCCCGTAGCCTGATTCGGGAGTTTACCCAGCGCCCCCTGCTAGTTGAGCGGGACAGGGGACC
CTGTGTTCTCACTGTGATTTGCAACTGTCCTAACCCTGGATTACATCAAGATCTTTGTTGCCATCTCTGTGCTGAGTATAATAAATACA
GAAATTAAAATATACTGGGGCTCCTATCGCCATCCTGTAAACGCCACCGTCTTCACCCGCCCAAGCAAACCAAGGCGAACCTTACCTG
GTACTTTTAACATCTCTCCCTCTGTGATTTACAACAGTTTCAACCCAGACGGAGTGAGTCTACGAGAGAACCTCTCCGAGCTCAGCTA
CTCCATCAGAAAAAACACCACCCTCCTTACCTGCCGGGAACGTACgATGTGGCTGCAGAGCCTGCTGCTCTTGGGCACTGTGGCCCTGC
AGCATCTCTGCACCCGCCCGCTCGCCCAGCCCCAGCACGCAGCCCTGGGAGCATGTGAATGCCATCCAGGAGGCCCGGCGTCTCCTG
AACCTGAGTAGAGACACTGCTGCTGAGATGAATGAAACAGTAGAAGTCATCTCAGAAATGTTTGACCTCCAGGAGCCGACCTGCCTA
CAGACCCGCCTGGAGCTGTACAAGCAGGGCCTGCGGGGCAGCCTCACCAAGCTCAAGGGCCCCTTGACCATGATGGCCAGCCACTAC
AAGCAGCACTGCCCTCCAACCCCGGAAACTTCCTGTGCAACCCAGACTATCACCTTTGAAAGTTTCAAAGAGAACCTGAAGGACTTTC
TGCTTGTCATCCCCTTTGACTGCTGGGAGCCAGTCCAGGAGTGAcAATTGACTCTATGTGGGATATGCTCCAGCGCTACAACCTTGAA
GTCAGGCTTCCTGGATGTCAGCATCTGACTTTGGCCAGCACCTGTCCCGCGGATTTGTTCCAGTCCAACTACAGCGACCCACCCTAAC
AGAGATGACCAACACAACCAACGCGGCCGCCGCTACCGGACTTACATCTACCACAAATACACCCCAAGTTTCTGCCTTTGTCAATAAC
TGGGATAACTTGGGCATGTGGTGGTTCTCCATAGCGCTTATGTTTGTATGCCTTATTATTATGTGGCTCATCTGCTGCCTAAAGCGCAA
ACGCGCCCGACCACCCATCTATAGTCCCATCATTGTGCTACACCCAAACAATGATGGAATCCATAGATTGGACGGACTGAAACACAT
GTTCTTTTCTCTTACAGTATGATTAAATGAGACATGATTCCTCGAGTTTTTATATTACTGACCCTTGTTGCGCTTTTTTGTGCGTGCTCC
ACATTGGCTGCGGTTTCTCACATCGAAGTAGACTGCATTCCAGCCTTCACAGTCTATTTGCTTTACGGATTTGTCACCCTCACGCTCAT
CTGCAGCCTCATCACTGTGGTCATCGCCTTTATCCAGTGCATTGACTGGGTCTGTGTGCGCTTTGCATATCTCAGACACCATCCCCAGT
ACAGGGACAGGACTATAGCTGAGCTTCTTAGAATTCTTTAATTATGAAATTTACTGTGACTTTTCTGCTGATTATTTGCACCCTATCTG
CGTTTTGTTCCCCGACCTCCAAGCCTCAAAGACATATATCATGCAGATTCACTCGTATATGGAATATTCCAAGTTGCTACAATGAAAA
AAGCGATCTTTCCGAAGCCTGGTTATATGCAATCATCTCTGTTATGGTGTTCTGCAGTACCATCTTAGCCCTAGCTATATATCCCTACC
TTGACATTGGCTGGAAACGAATAGATGCCATGAACCACCCAACTTTCCCCGCGCCCGCTATGCTTCCACTGCAACAAGTTGTTGCCGG
CGGCTTTGTCCCAGCCAATCAGCCTCGCCCCACTTCTCCCACCCCCACTGAAATCAGCTACTTTAATCTAACAGGAGGAGATGACTGA
CACCCTAGATCTAGAAATGGACGGAATTATTACAGAGCAGCGCCTGCTAGAAAGACGCAGGGCAGCGGCCGAGCAACAGCGCATGA
ATCAAGAGCTCCAAGACATGGTTAACTTGCACCAGTGCAAAAGGGGTATCTTTTGTCTGGTAAAGCAGGCCAAAGTCACCTACGACA
GTAATACCACCGGACACCGCCTTAGCTACAAGTTGCCAACCAAGCGTCAGAAATTGGTGGTCATGGTGGGAGAAAAGCCCATTACCA
TAACTCAGCACTCGGTAGAAACCGAAGGCTGCATTCACTCACCTTGTCAAGGACCTGAGGATCTCTGCACCCTTATTAAGACCCTGTG
CGGTCTCAAAGATCTTATTCCCTTTAACTAATAAAAAAAAATAATAAAGCATCACTTACTTAAAATCAGTTAGCAAATTTCTGTCCAG
TTTATTCAGCAGCACCTCCTTGCCCTCCTCCCAGCTCTGGTATTGCAGCTTCCTCCTGGCTGCAAACTTTCTCCACAATCTAAATGGAA
TGTCAGTTTCCTCCTGTTCCTGTCCATCCGCACCCACTATCTTCATGTTGTTGCAGATGAAGCGCGCAAGACCGTCTGAAGATACCTTC
AACCCCGTGTATCCATATGACACGGAAACCGGTCCTCCAACTGTGCCTTTTCTTACTCCTCCCTTTGTATCCCCCAATGGGTTTCAAGA
GAGTCCCCCTGGGGTACTCTCTTTGCGCCTATCCGAACCTCTAGTTACCTCCAATGGCATGCTTGCGCTCAAAATGGGCAACGGCCTCT
CTCTGGACGAGGCCGGCAACCTTACCTCCCAAAATGTAACCACTGTGAGCCCACCTCTCAAAAAAACCAAGTCAAACATAAACCTGG
AAATATCTGCACCCCTCACAGTTACCTCAGAAGCCCTAACTGTGGCTGCCGCCGCACCTCTAATGGTCGCGGGCAACACACTCACCAT
GCAATCACAGGCCCCGCTAACCGTGCACGACTCCAAACTTAGCATTGCCACCCAAGGACCCCTCACAGTGTCAGAAGGAAAGCTAGC
CCTGCAAACATCAGGCCCCCTCACCACCACCGATAGCAGTACCCTTACTATCACTGCCTCACCCCCTCTAACTACTGCCACTGGTAGC
TTGGGCATTGACTTGAAAGAGCCCATTTATACACAAAATGGAAAACTAGGACTAAAGTACGGGGCTCCTTTGCATGTAACAGACGAC
CTAAACACTTTGACCGTAGCAACTGGTCCAGGTGTGACTATTAATAATACTTCCTTGCAAACTAAAGTTACTGGAGCCTTGGGTTTTG
ATTCACAAGGCAATATGCAACTTAATGTAGCAGGAGGACTAAGGATTGATTCTCAAAACAGACGCCTTATACTTGATGTTAGTTATCC
GTTTGATGCTCAAAACCAACTAAATCTAAGACTAGGACAGGGCCCTCTTTTTATAAACTCAGCCCACAACTTGGATATTAACTACAAC
AAAGGCCTTTACTTGTTTACAGCTTCAAACAATTCCAAAAAGCTTGAGGTTAACCTAAGCACTGCCAAGGGGTTGATGTTTGACGCTA
CAGCCATAGCCATTAATGCAGGAGATGGGCTTGAATTTGGTTCACCTAATGCACCAAACACAAATCCCCTCAAAACAAAAATTGGCC
ATGGCCTAGAATTTGATTCAAACAAGGCTATGGTTCCTAAACTAGGAACTGGCCTTAGTTTTGACAGCACAGGTGCCATTACAGTAGG
AAACAAAAATAATGATAAGCTAAC*CCTATGGACAGGTCCAAAACCAGAAGCCAACTGCATAATTGAATACGGGAAACAAAACCCAGATAGC*
*AAACTAACTTTAATCCTTGTAAAAAATGGAGGAATTGTTAATGGATATGTAACGCTAATGGGAGCCTCAGACTACGTTAACACCTTATTTAAAAAC*
*AAAAATGTCTCCATTAATGTAGAACTATACTTTGATGCCACTGGTCATATATTACCAGACTCATCTTCTCTTAAAACAGATCTAGAACTAAAATACA*
*AGCAAACCGCTGACTTTAGTGCAAGAGGTTTTATGCCAAGTACTACAGCGTATCCATTTGTCCTTCCTAATGCGGGAACACATAATGAAAATTAT*
*ATTTTTGGTCAATGCTACTACAAAGCAAGCGATGGTGCCCTTTTTCCGTTGGAAGTTACTGTTATGCTTAATAAACGCCTGCCAGATAGTCGCAC*
*ATCCTATGTTATGACTTTTTTATGGTCCTTGAATGCTGGTCTAGCTCCAGAAACTACTCAGGCAACCCTCATAACCTCCCCATTTACCTTTTCCTA*
*TATTAGAGAAGATGACTAATAAACTC*TAAAGAATCGTTTGTGTTATGTTTCAACGTGTTTATTTTTCAATTGCAGAAAATTTCAAGTCATTT
TTCATTCAGTAGTATAGCCCCACCACCACATAGCTTATACAGATCACCGTACCTTAATCAAACTCACAGAACCCTAGTATTCAACCTG
CCACCTCCCTCCCAACACACAGAGTACACAGTCCTTTCTCCCCGGCTGGCCTTAAAAAGCATCATATCATGGGTAACAGACATATTCT
TAGGTGTTATATTCCACACGGTTTCCTGTCGAGCCAAACGCTCATCAGTGATATTAATAAACTCCCCGGGCAGCTCACTTAAGTTCA
TGTCGCTGTCCAGCTGCTGAGCCACAGGCTGCTGTCCAACTTGCGGTTGCTTAACGGGCGGCGAAGGAGAAGTCCACGCCTACATGG
GGGGAGAGTCATAATCGTGCATCAGGATAGGGCGGTGGTGCTGCAGCAGCGCGCGAATAAACTGCTGCCGCCGCCGCTCCGTCCTGC
AGGAATACAACATGGCAGTGGTCTCCTCAGCGATGATTCGCACCGCCCGCAGCATAAGGCGCTTGTCCTCCGGGCACAGCAGCGCAC
CCTGATCTCACTTAAATCAGCACAGTAACTGCAGCACAGCACCACAATATTGTTCAAAATCCCACAGTGCAAGGCGCTGTATCCAAA
GCTCATGGCGGGGACCACAGAACCCACGTGGCCATCATACCACAAGCGCAGGTAGATTAAGTGGCGACCCCTCATAAACACGCTGGA
CATAAACATTACCTCTTTTGGCATGTTGTAATTCACCACCTCCCGGTACCATATAAACCTCTGATTAAACATGGCGCCATCCACCACCA
TCCTAAACCAGCTGGCCAAAACCTGCCCCGCCGGGNTATACACTGCAGGGAACCGGGACTTGGACAATGACAAGTGGGAGAGCCCA
GGACTCGTAACCATGGATCATCATGCTCGTCATGATATCAATGTTGGCACAACACAGGCACACGTGCATACACTTCCTCAGGATTACA

Figure 14 (continued)

AGCTCCTCCCGCGTTAGAACCATATCCCAGGGAACAACCCATTCCTGAATCAGCGTAAATCCCACACTGCAGGGAAGACCTCGCACG
TAACTCACGTTGTGCATTGTCAAAGTGTTACATTCGGGCAGCAGCGGATGATCCTCCAGTATGGTAGCGCGGGTTTCTGTCTCAAAAG
GAGGTAGACGATCCCTACTGTACGGAGTGCGCCGAGACAACCGAGATCGTGTTGGTCGTAGTGTCATGCCAAATGGAACGCCGGACG
TAGTCATATTTCCTGAAGCAAAACCAGGTGCGGGCGTGACAAACAGATCTGCGTCTCCGGTCTCGCCGCTTAGATCGCTCTGTGTAGT
AGTTGTAGTATATCCACTCTCTCAAAGCATCCAGGCGCCCCCTGGCTTCGGGTTCTATGTAAACTCCTTCATGCGCCGCTGCCCTGATA
ACATCCACCACCGCAGAATAAGCCACACCCAGCCAACCTACACATTCGTTCTGCGAGTCACACACGGGAGGAGCGGGAAGAGCTGG
AAGAACCATGTTTTTTTTTTTATTCCAAAAGATTATCCAAAACCTCAAAATGAAGATCTATTAAGTGAACGCGCTCCCCTCCGGTGGC
GTGGTCAAACTCTACAGCCAAAGAACAGATAATGGCATTTGTAAGATGTTGCACAATGGCTTCCAAAAGGCAAACGGCCCTCACGTC
CAAGTGGACGTAAAGGCTAAACCCTTCAGGGTGAATCTCCTCTATAAACATTCCAGCACCTTCAACCATGCCCAAATAATTCTCATCT
CGCCACCTTCTCAATATATCTCTAAGCAAATCCCGAATATTTAAGTCCGGGCCATTGTAAAAAATTTGGCTCCAGAGCGCCCTCCACC
TTCAGCCTCAAGCAGCGAATCATGATTGCAAAAATTCAGGTTCCTCACAGACCTGTATAAGATTCAAAAGCGGAACATTAACAAAAA
TACCGCGATCCCGTAGGTCCCTTCGCAGGGCCAGCTGAACATAATCGTGCAGGTCTGCACGGACCAGCGCGGCCACTTCCCCGCCAG
GAACCATGACAAAAGAACCCACACTGATTATGACACGCATACTCGGAGCTATGCTAACCAGCGTAGCCCCGATGTAAGCTTGTTGCA
TGGGCGGCGATATAAAATGCAAGGTGCTGCTCAAAAAATCAGGCAAAGCCTCGCGCAAAAAAGAAAGCACATCGTAGTCATGCTCA
TGCAGATAAAGGCAGGTAAGCTCCGGAACCACCACAGAAAAAGACACCATTTTTCTCTCAAACATGTCTGCGGGTTTCTGCATAAAC
ACAAAATAAAATAACAAAAAAACATTTAAACATTAGAAGCCTGTCTTACAACAGGAAAAACAACCCTTATAAGCATAAGACGGACT
ACGGCCATGCCGGCGTGACCGTAAAAAAACTGGTCACCGTGATTAAAAAGCACCACCGACAGCTCCTCGGTCAGTCCGGAGTCATAA
TGTAAGACTCGGTAAACACATCAGGTTGATTCACATCGGTCAGTGTTAAAAAGCGACCGAAATAGCCNGGGGGAATACAATACCCGC
AGGCGTAGAGACAACATTACAGCCCCCATAGGAGGTATAACAAAATTAATAGGAGAGAAAAACACATAAACACCTGAAAAACCCTC
CTGCCTAGGCAAAATAGCACCCTCCCGCTCCAGAACAACATACAGCGCTTCCACAGCGGCAGCCATAACAGTCAGCCTTACCAGTAA
AAAAGAAAACCTATTAAAAAAACACCACTCGACACGGCACCAGCTCAATCAGTCACAGTGTAAAAAAGGGCCAAGTGCAGAGCGAG
TATATATAGGACTAAAAAATGACGGTAACGGTTAAAGTCCACAAAAAACACCCAGAAAACCGCACGCGAACCTACGCCCAGAAACG
AAAGCCAAAAAACCCACAACTTCCTCAAATCGTCACTTCCGTTTTCCCACGTTACGTCACTTCCCATTTTAAGAAAACTACAATTCCCA
ACACATACAAGTTACTCCGCCCTAAAACCTACGTCACCCGCCCCGTTCCCACGCCCCGCGCCACGTCACAAACTCCACCCCCTCATTA
TCATATTGGCTTCAATCCAAAATAAGGTATATTATTGATGATGTTAAT

SEQUENCE LISTING

<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: oligonucleotide

<400> SEQUENCE: 1
tccggtttct atgccaaacc t 21

<210> SEQ ID NO 2
<211> LENGTH: 22
<212> TYPE: DNA
<213> ORGANISM: Artificial sequence
<220> FEATURE:
<223> OTHER INFORMATION: oligonucleotide

<400> SEQUENCE: 2
tcctccggtg ataatgacaa ga 22

<210> SEQ ID NO 3
<211> LENGTH: 19
<212> TYPE: DNA
<213> ORGANISM: Artificial sequence
<220> FEATURE:
<223> OTHER INFORMATION: oligonucleotide

<400> SEQUENCE: 3
tgatcgatcc acccagtga 19

<210> SEQ ID NO 4
<211> LENGTH: 16
<212> TYPE: DNA
<213> ORGANISM: Artificial sequence
<220> FEATURE:
<223> OTHER INFORMATION: oligonucleotide

<400> SEQUENCE: 4
tacctgccac gaggct 16

<210> SEQ ID NO 5
<211> LENGTH: 21
<212> TYPE: DNA
<213> ORGANISM: Artificial sequence
<220> FEATURE:
<223> OTHER INFORMATION: oligonucleotide

<400> SEQUENCE: 5

```
aaacaccacc ctccttacct g                                             21


<210> SEQ ID NO 6
<211> LENGTH: 21
<212> TYPE: DNA
<213> ORGANISM: Artificial sequence
<220> FEATURE:
<223> OTHER INFORMATION: oligonucleotide

<400> SEQUENCE: 6

tcattcatct cagcagcagt g                                             21


<210> SEQ ID NO 7
<211> LENGTH: 35440
<212> TYPE: DNA
<213> ORGANISM: Artificial Sequence
<220> FEATURE:
<223> OTHER INFORMATION: Ad5/3-D24-GMCSF
<220> FEATURE:
<221> NAME/KEY: misc_feature
<222> LOCATION: (5754)..(5756)
<223> OTHER INFORMATION: n is a, c, g, or t
<220> FEATURE:
<221> NAME/KEY: misc_feature
<222> LOCATION: (33162)..(33162)
<223> OTHER INFORMATION: n is a, c, g, or t
<220> FEATURE:
<221> NAME/KEY: misc_feature
<222> LOCATION: (34851)..(34851)
<223> OTHER INFORMATION: n is a, c, g, or t

<400> SEQUENCE: 7

taacatcatc aattatacct tccattttgg attgaagcca atatgataat gaggggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatatttgt ctagggccgc    360

ggggactttg accgtttacg tggagactcg cccaggtgtt tttctcaggt gttttccgcg    420

ttccgggtca aagttggcgt tttattatta tagtcagctg acgtgtagtg tatttatacc    480

cggtgagttc ctcaagaggc cactcttgag tgccagcgag tagagttttc tcctccgagc    540

cgctccgaca ccgggactga aaatgagaca tattatctgc cacggaggtg ttattaccga    600

agaaatggcc gccagtcttt tggaccagct gatcgaagag gtactggctg ataatcttcc    660

acctcctagc cattttgaac cacctaccct tcacgaactg tatgatttag acgtgacggc    720

ccccgaagat cccaacgagg aggcggtttc gcagattttt cccgactctg taatgttggc    780

ggtgcaggaa gggattgact tactcacttt tccgccggcg cccggttctc cggagccgcc    840

tcacctttcc cggcagcccg agcagccgga gcagagagcc ttgggtccgg tttctatgcc    900

aaaccttgta ccggaggtga tcgatccacc cagtgacgac gaggatgaag agggtgagga    960

gtttgtgtta gattatgtgg agcaccccgg gcacggttgc aggtcttgtc attatcaccg   1020

gaggaatacg gggacccag atattatgtg ttcgctttgc tatatgagga cctgtggcat   1080

gtttgtctac agtaagtgaa aattatgggc agtgggtgat agagtggtgg gtttggtgtg   1140

gtaatttttt ttttaatttt tacagttttg tggtttaaag aattttgtat tgtgattttt   1200

ttaaaaggtc ctgtgtctga acctgagcct gagcccgagc cagaaccgga gcctgcaaga   1260
```

-continued

```
cctacccgcc gtcctaaaat ggcgcctgct atcctgagac gcccgacatc acctgtgtct   1320
agagaatgca atagtagtac ggatagctgt gactccggtc cttctaacac acctcctgag   1380
atacacccgg tggtcccgct gtgccccatt aaaccagttg ccgtgagagt tggtgggcgt   1440
cgccaggctg tggaatgtat cgaggacttg cttaacgagc ctgggcaacc tttggacttg   1500
agctgtaaac gccccaggcc ataaggtgta aacctgtgat tgcgtgtgtg gttaacgcct   1560
ttgtttgctg aatgagttga tgtaagttta ataaagggtg agataatgtt taacttgcat   1620
ggcgtgttaa atggggcggg gcttaaaggg tatataatgc gccgtgggct aatcttggtt   1680
acatctgacc tcatggaggc ttgggagtgt ttggaagatt tttctgctgt gcgtaacttg   1740
ctggaacaga gctctaacag tacctcttgg ttttggaggt ttctgtgggg ctcatcccag   1800
gcaaagttag tctgcagaat taaggaggat tacaagtggg aatttgaaga gcttttgaaa   1860
tcctgtggtg agctgtttga ttctttgaat ctgggtcacc aggcgctttt ccaagagaag   1920
gtcatcaaga ctttggattt ttccacaccg gggcgcgctg cggctgctgt tgcttttttg   1980
agttttataa aggataaatg gagcgaagaa acccatctga gcggggggta cctgctggat   2040
tttctggcca tgcatctgtg gagagcggtt gtgagacaca agaatcgcct gctactgttg   2100
tcttccgtcc gcccggcgat aataccgacg gaggagcagc agcagcagca ggaggaagcc   2160
aggcggcggc ggcaggagca gagcccatgg aacccgagag ccggcctgga ccctcgggaa   2220
tgaatgttgt acaggtggct gaactgtatc cagaactgag acgcattttg acaattacag   2280
aggatgggca ggggctaaag ggggtaaaga gggagcgggg ggcttgtgag gctacagagg   2340
aggctaggaa tctagctttt agcttaatga ccagacaccg tcctgagtgt attacttttc   2400
aacagatcaa ggataattgc gctaatgagc ttgatctgct ggcgcagaag tattccatag   2460
agcagctgac cacttactgg ctgcagccag gggatgattt tgaggaggct attagggtat   2520
atgcaaaggt ggcacttagg ccagattgca agtacaagat cagcaaactt gtaaatatca   2580
ggaattgttg ctacatttct gggaacgggg ccgaggtgga gatagatacg gaggataggg   2640
tggcctttag atgtagcatg ataaatatgt ggccgggggt gcttggcatg gacggggtgg   2700
ttattatgaa tgtaaggttt actggcccca attttagcgg tacggttttc ctggccaata   2760
ccaaccttat cctacacggt gtaagcttct atgggtttaa caatacctgt gtggaagcct   2820
ggaccgatgt aagggttcgg ggctgtgcct tttactgctg ctggaagggg gtggtgtgtc   2880
gccccaaaag cagggcttca attaagaaat gcctctttga aaggtgtacc ttgggtatcc   2940
tgtctgaggg taactccagg gtgcgccaca atgtggcctc cgactgtggt tgcttcatgc   3000
tagtgaaaag cgtggctgtg attaagcata acatggtatg tggcaactgc gaggacaggg   3060
cctctcagat gctgacctgc tcggacggca actgtcacct gctgaagacc attcacgtag   3120
ccagccactc tcgcaaggcc tggccagtgt ttgagcataa catactgacc cgctgttcct   3180
tgcatttggg taacaggagg ggggtgttcc taccttacca atgcaatttg agtcacacta   3240
agatattgct tgagcccgag agcatgtcca aggtgaacct gaacggggtg tttgacatga   3300
ccatgaagat ctggaaggtg ctgaggtacg atgagacccg caccaggtgc agaccctgcg   3360
agtgtggcgg taaacatatt aggaaccagc ctgtgatgct ggatgtgacc gaggagctga   3420
ggcccgatca cttggtgctg gcctgcaccc gcgctgagtt tggctctagc gatgaagata   3480
cagattgagg tactgaaatg tgtgggcgtg gcttaagggt gggaaagaat atataaggtg   3540
ggggtcttat gtagttttgt atctgttttg cagcagccgc cgccgccatg agcaccaact   3600
cgtttgatgg aagcattgtg agctcatatt tgacaacgcg catgccccca tgggccgggg   3660
```

-continued

```
tgcgtcagaa tgtgatgggc tccagcattg atggtcgccc cgtcctgccc gcaaactcta   3720
ctaccttgac ctacgagacc gtgtctggaa cgccgttgga gactgcagcc tccgccgccg   3780
cttcagccgc tgcagccacc gcccgcggga ttgtgactga ctttgctttc ctgagcccgc   3840
ttgcaagcag tgcagcttcc cgttcatccg cccgcgatga caagttgacg gctcttttgg   3900
cacaattgga ttctttgacc cgggaactta atgtcgtttc tcagcagctg ttggatctgc   3960
gccagcaggt ttctgccctg aaggcttcct cccctcccaa tgcggtttaa aacataaata   4020
aaaaaccaga ctctgtttgg atttggatca agcaagtgtc ttgctgtctt tatttagggg   4080
ttttgcgcgc gcggtaggcc cgggaccagc ggtctcggtc gttgagggtc ctgtgtattt   4140
tttccaggac gtggtaaagg tgactctgga tgttcagata catgggcata agcccgtctc   4200
tggggtggag gtagcaccac tgcagagctt catgctgcgg ggtggtgttg tagatgatcc   4260
agtcgtagca ggagcgctgg gcgtggtgcc taaaaatgtc tttcagtagc aagctgattg   4320
ccaggggcag gcccttggtg taagtgttta caaagcggtt aagctgggat gggtgcatac   4380
gtggggatat gagatgcatc ttggactgta tttttaggtt ggctatgttc ccagccatat   4440
ccctccgggg attcatgttg tgcagaacca ccagcacagt gtatccggtg cacttgggaa   4500
atttgtcatg tagcttagaa ggaaatgcgt ggaagaactt ggagacgccc ttgtgacctc   4560
caagattttc catgcattcg tccataatga tggcaatggg cccacgggcg gcggcctggg   4620
cgaagatatt tctgggatca ctaacgtcat agttgtgttc caggatgaga tcgtcatagg   4680
ccatttttac aaagcgcggg cggagggtgc cagactgcgg tataatggtt ccatccggcc   4740
caggggcgta gttaccctca cagatttgca tttcccacgc tttgagttca gatgggggga   4800
tcatgtctac ctgcggggcg atgaagaaaa cggtttccgg ggtaggggag atcagctggg   4860
aagaaagcag gttcctgagc agctgcgact taccgcagcc ggtgggcccg taaatcacac   4920
ctattaccgg gtgcaactgg tagttaagag agctgcagct gccgtcatcc ctgagcaggg   4980
gggccacttc gttaagcatg tccctgactc gcatgttttc cctgaccaaa tccgccagaa   5040
ggcgctcgcc gcccagcgat agcagttctt gcaaggaagc aaagtttttc aacggtttga   5100
gaccgtccgc cgtaggcatg cttttgagcg tttgaccaag cagttccagg cggtcccaca   5160
gctcggtcac ctgctctacg gcatctcgat ccagcatatc tcctcgtttc gcgggttggg   5220
gcggctttcg ctgtacggca gtagtcggtg ctcgtccaga cgggccaggg tcatgtcttt   5280
ccacgggcgc agggtcctcg tcagcgtagt ctgggtcacg gtgaaggggt gcgctccggg   5340
ctgcgcgctg gccagggtgc gcttgaggct ggtcctgctg gtgctgaagc gctgccggtc   5400
ttcgccctgc gcgtcggcca ggtagcattt gaccatggtg tcatagtcca gcccctccgc   5460
ggcgtggccc ttggcgcgca gcttgccctt ggaggaggcg ccgcacgagg ggcagtgcag   5520
acttttgagg gcgtagagct tgggcgcgag aaataccgat tccggggagt aggcatccgc   5580
gccgcaggcc ccgcagacgg tctcgcattc cacgagccag gtgagctctg gccgttcggg   5640
gtcaaaaacc aggtttcccc catgcttttt gatgcgtttc ttacctctgg tttccatgag   5700
ccggtgtcca cgctcggtga cgaaaaggct gtccgtgtcc ccgtatacag actnnngttt   5760
tgagaggcct gtcctcgagc ggtgttccgc ggtcctcctc gtatagaaac tcggaccact   5820
ctgagacaaa ggctcgcgtc caggccagca cgaaggaggc taagtgggag gggtagcggt   5880
cgttgtccac tagggggtcc actcgctcca gggtgtgaag acacatgtcg ccctcttcgg   5940
catcaaggaa ggtgattggt ttgtaggtgt aggccacgtg accgggtgtt cctgaagggg   6000
```

-continued

```
ggctataaaa gggggtgggg gcgcgttcgt cctcactctc ttccgcatcg ctgtctgcga   6060
gggccagctg ttggggtgag tactccctct gaaaagcggg catgacttct gcgctaagat   6120
tgtcagtttc caaaaacgag gaggatttga tattcacctg gcccgcggtg atgcctttga   6180
gggtggccgc atccatctgg tcagaaaaga caatcttttt gttgtcaagc ttggtggcaa   6240
acgacccgta gagggcgttg gacagcaact tggcgatgga gcgcagggtt tggtttttgt   6300
cgcgatcggc gcgctccttg gccgcgatgt ttagctgcac gtattcgcgc gcaacgcacc   6360
gccattcggg aaagacggtg gtgcgctcgt cgggcaccag gtgcacgcgc caaccgcggt   6420
tgtgcagggt gacaaggtca acgctggtgg ctacctctcc gcgtaggcgc tcgttggtcc   6480
agcagaggcg gccgcccttg cgcgagcaga atggcggtag gggtctagc tgcgtctcgt    6540
ccgggggtc tgcgtccacg gtaaagaccc cgggcagcag gcgcgcgtcg aagtagtcta    6600
tcttgcatcc ttgcaagtct agcgcctgct gccatgcgcg ggcggcaagc gcgcgctcgt   6660
atgggttgag tgggggaccc catggcatgg ggtgggtgag cgcggaggcg tacatgccgc   6720
aaatgtcgta aacgtagagg ggctctctga gtattccaag atatgtaggg tagcatcttc   6780
caccgcggat gctggcgcgc acgtaatcgt atagttcgtg cgagggagcg aggaggtcgg   6840
gaccgaggtt gctacgggcg ggctgctctg ctcggaagac tatctgcctg aagatggcat   6900
gtgagttgga tgatatggtt ggacgctgga agacgttgaa gctggcgtct gtgagaccta   6960
ccgcgtcacg cacgaaggag gcgtaggagt cgcgcagctt gttgaccagc tcggcggtga   7020
cctgcacgtc tagggcgcag tagtccaggg tttccttgat gatgtcatac ttatcctgtc   7080
cctttttttt ccacagctcg cggttgagga caaactcttc gcggtctttc cagtactctt   7140
ggatcggaaa cccgtcggcc tccgaacggt aagagcctag catgtagaac tggttgacgg   7200
cctggtaggc gcagcatccc ttttctacgg gtagcgcgta tgcctgcgcg gccttccgga   7260
gcgaggtgtg ggtgagcgca aaggtgtccc tgaccatgac tttgaggtac tggtatttga   7320
agtcagtgtc gtcgcatccg ccctgctccc agagcaaaaa gtccgtgcgc tttttggaac   7380
gcggatttgg cagggcgaag gtgacatcgt tgaagagtat ctttcccgcg cgaggcataa   7440
agttgcgtgt gatgcggaag ggtcccggca cctcggaacg gttgttaatt acctgggcgg   7500
cgagcacgat ctcgtcaaag ccgttgatgt tgtggcccac aatgtaaagt tccaagaagc   7560
gcgggatgcc cttgatggaa ggcaattttt taagttcctc gtaggtgagc tcttcagggg   7620
agctgagccc gtgctctgaa agggcccagt ctgcaagatg agggttggaa gcgacgaatg   7680
agctccacag gtcacgggcc attagcattt gcaggtggtc gcgaaaggtc ctaaactggc   7740
gacctatggc cattttttct ggggtgatgc agtagaaggt aagcgggtct tgttcccagc   7800
ggtcccatcc aaggttcgcg gctaggtctc gcgcggcagt cactagaggc tcatctccgc   7860
cgaacttcat gaccagcatg aagggcacga gctgcttccc aaaggccccc atccaagtat   7920
aggtctctac atcgtaggtg acaaagagac gctcggtgcg aggatgcgag ccgatcggga   7980
agaactggat ctcccgccac caattggagg agtggctatt gatgtggtga aagtagaagt   8040
ccctgcgacg ggccgaacac tcgtgctggc ttttgtaaaa acgtgcgcag tactggcagc   8100
ggtgcacggg ctgtacatcc tgcacgaggt tgacctgacg accgcgcaca aggaagcaga   8160
gtgggaattt gagcccctcg cctggcgggt ttggctggtg gtcttctact tcggctgctt   8220
gtccttgacc gtctggctgc tcgaggggag ttacggtgga tcggaccacc acgccgcgcg   8280
agcccaaagt ccagatgtcc gcgcgcggcg gtcggagctt gatgacaaca tcgcgcagat   8340
gggagctgtc catggtctgg agctcccgcg gcgtcaggtc aggcgggagc tcctgcaggt   8400
```

ttacctcgca tagacgggtc agggcgcggg ctagatccag gtgataccta atttccaggg 8460
gctggttggt ggcggcgtcg atggcttgca agaggccgca tccccgcggc gcgactacgg 8520
taccgcgcgg cgggcggtgg gccgcggggg tgtccttgga tgatgcatct aaaagcggtg 8580
acgcgggcga gcccccggag gtaggggggg ctccggaccc gccgggagag gggcagggg 8640 cacgtcggcg ccgcgcgcgg gcaggagctg gtgctgcgcg cgtaggttgc tggcgaacgc 8700
gacgacgcgg cggttgatct cctgaatctg gcgcctctgc gtgaagacga cgggcccggt 8760
gagcttgagc ctgaaagaga gttcgacaga atcaatttcg gtgtcgttga cggcggcctg 8820
gcgcaaaatc tcctgcacgt ctcctgagtt gtcttgatag gcgatctcgg ccatgaactg 8880
ctcgatctct tcctcctgga gatctccgcg tccggctcgc tccacggtgg cggcgaggtc 8940
gttggaaatg cgggccatga gctgcgagaa ggcgttgagg cctccctcgt tccagacgcg 9000
gctgtagacc acgccccctt cggcatcgcg ggcgcgcatg accacctgcg cgagattgag 9060
ctccacgtgc cgggcgaaga cggcgtagtt tcgcaggcgc tgaaagaggt agttgagggt 9120
ggtggcggtg tgttctgcca cgaagaagta cataacccag cgtcgcaacg tggattcgtt 9180
gatatccccc aaggcctcaa ggcgctccat ggcctcgtag aagtccacgg cgaagttgaa 9240
aaactgggag ttgcgcgccg acacggttaa ctcctcctcc agaagacgga tgagctcggc 9300
gacagtgtcg cgcacctcgc gctcaaaggc tacaggggcc tcttcttctt cttcaatctc 9360
ctcttccata agggcctccc cttcttcttc ttctggcggc ggtgggggag gggggacacg 9420
gcggcgacga cggcgcaccg ggaggcggtc gacaaagcgc tcgatcatct ccccgcggcg 9480
acggcgcatg gtctcggtga cggcgcggcc gttctcgcgg gggcgcagtt ggaagacgcc 9540
gcccgtcatg tcccggttat gggttggcgg ggggctgcca tgcggcaggg atacggcgct 9600
aacgatgcat ctcaacaatt gttgtgtagg tactccgccg ccgagggacc tgagcgagtc 9660
cgcatcgacc ggatcggaaa acctctcgag aaaggcgtct aaccagtcac agtcgcaagg 9720
taggctgagc accgtggcgg gcggcagcgg gcggcggtcg gggttgtttc tggcggaggt 9780
gctgctgatg atgtaattaa agtaggcggt cttgagacgg cggatggtcg acagaagcac 9840
catgtccttg ggtccggcct gctgaatgcg caggcggtcg gccatgcccc aggcttcgtt 9900
ttgacatcgg cgcaggtctt tgtagtagtc ttgcatgagc ctttctaccg gcacttcttc 9960
ttctccttcc tcttgtcctg catctcttgc atctatcgct gcggcggcgg cggagtttgg 10020
ccgtaggtgg cgccctcttc ctcccatgcg tgtgaccccg aagcccctca tcggctgaag 10080
cagggctagg tcggcgacaa cgcgctcggc taatatggcc tgctgcacct gcgtgagggt 10140
agactggaag tcatccatgt ccacaaagcg gtggtatgcg cccgtgttga tggtgtaagt 10200
gcagttggcc ataacggacc agttaacggt ctggtgaccc ggctgcgaga gctcggtgta 10260
cctgagacgc gagtaagccc tcgagtcaaa tacgtagtcg ttgcaagtcc gcaccaggta 10320
ctggtatccc accaaaaagt gcggcggcgg ctggcggtag aggggccagc gtagggtggc 10380
cggggctccg gggcgagat cttccaacat aaggcgatga tatccgtaga tgtacctgga 10440
catccaggtg atgccggcgg cggtggtgga ggcgcgcgga aagtcgcgga cgcggttcca 10500
gatgttgcgc agcggcaaaa agtgctccat ggtcgggacg ctctggccgg tcaggcgcgc 10560
gcaatcgttg acgctctacc gtgcaaaagg agagcctgta agcgggcact cttccgtggt 10620
ctggtggata aattcgcaag ggtatcatgg cggacgaccg gggttcgagc cccgtatccg 10680
gccgtccgcc gtgatccatg cggttaccgc ccgcgtgtcg aacccaggtg tgcgacgtca 10740
gacaacgggg gagtgctcct tttggcttcc ttccaggcgc ggcggctgct gcgctagctt 10800
ttttggccac tggccgcgcg cagcgtaagc ggttaggctg gaaagcgaaa gcattaagtg 10860
gctcgctccc tgtagccgga gggttatttt ccaagggttg agtcgcggga cccccggttc 10920
gagtctcgga ccggccggac tgcggcgaac gggggtttgc ctccccgtca tgcaagaccc 10980
cgcttgcaaa ttcctccgga aacagggacg agcccctttt ttgcttttcc cagatgcatc 11040
cggtgctgcg gcagatgcgc ccccctcctc agcagcggca agagcaagag cagcggcaga 11100
catgcagggc accctcccct cctcctaccg cgtcaggagg ggcgacatcc gcggttgacg 11160
cggcagcaga tggtgattac gaacccccgc ggcgccgggc ccggcactac ctggacttgg 11220
aggagggcga gggcctggcg cggctaggag cgccctctcc tgagcggtac ccaagggtgc 11280
agctgaagcg tgatacgcgt gaggcgtacg tgccgcggca gaacctgttt cgcgaccgcg 11340
agggagagga gcccgaggag atgcgggatc gaaagttcca cgcagggcgc gagctgcggc 11400
atggcctgaa tcgcgagcgg ttgctgcgcg aggaggactt tgagcccgac gcgcgaaccg 11460
ggattagtcc cgcgcgcgca cacgtggcgg ccgccgacct ggtaaccgca tacgagcaga 11520
cggtgaacca ggagattaac tttcaaaaaa gctttaacaa ccacgtgcgt acgcttgtgg 11580
cgcgcgagga ggtggctata ggactgatgc atctgtggga ctttgtaagc gcgctggagc 11640
aaaacccaaa tagcaagccg ctcatggcgc agctgttcct tatagtgcag cacagcaggg 11700
acaacgaggc attcagggat gcgctgctaa acatagtaga gcccgagggc cgctggctgc 11760
tcgatttgat aaacatcctg cagagcatag tggtgcagga gcgcagcttg agcctggctg 11820
acaaggtggc cgccatcaac tattccatgc ttagcctggg caagttttac gcccgcaaga 11880
tataccatac cccttacgtt cccatagaca aggaggtaaa gatcgagggg ttctacatgc 11940
gcatggcgct gaaggtgctt accttgagcg acgacctggg cgtttatcgc aacgagcgca 12000
tccacaaggc cgtgagcgtg agccggcggc gcgagctcag cgaccgcgag ctgatgcaca 12060
gcctgcaaag ggccctggct ggcacgggca gcggcgatag agaggccgag tcctactttg 12120
acgcgggcgc tgacctgcgc tgggccccaa gccgacgcgc cctggaggca gctggggccg 12180
gacctgggct ggcggtggca cccgcgcgcg ctggcaacgt cggcggcgtg gaggaatatg 12240
acgaggacga tgagtacgag ccagaggacg gcgagtacta agcggtgatg tttctgatca 12300
gatgatgcaa gacgcaacgg acccggcggt gcgggcggcg ctgcagagcc agccgtccgg 12360
ccttaactcc acggacgact ggcgccaggt catggaccgc atcatgtcgc tgactgcgcg 12420
caatcctgac gcgttccggc agcagccgca ggccaaccgg ctctccgcaa ttctggaagc 12480
ggtggtcccg gcgcgcgcaa accccacgca cgagaaggtg ctggcgatcg taaacgcgct 12540
ggccgaaaac agggccatcc ggcccgacga ggccggcctg gtctacgacg cgctgcttca 12600
gcgcgtggct cgttacaaca gcggcaacgt gcagaccaac ctggaccggc tggtggggga 12660
tgtgcgcgag gccgtggcgc agcgtgagcg cgcgcagcag cagggcaacc tgggctccat 12720
ggttgcacta aacgccttcc tgagtacaca gcccgccaac gtgccgcggg gacaggagga 12780
ctacaccaac tttgtgagcg cactgcggct aatggtgact gagacaccgc aaagtgaggt 12840
gtaccagtct gggccagact atttttttcca gaccagtaga caaggcctgc agaccgtaaa 12900
cctgagccag gctttcaaaa acttgcaggg gctgtggggg gtgcgggctc ccacaggcga 12960
ccgcgcgacc gtgtctagct tgctgacgcc caactcgcgc ctgttgctgc tgctaatagc 13020
gcccttcacg gacagtggca gcgtgtcccg ggacacatac ctaggtcact tgctgacact 13080
gtaccgcgag gccataggtc aggcgcatgt ggacgagcat actttccagg agattacaag 13140

-continued

```
tgtcagccgc gcgctggggc aggaggacac gggcagcctg gaggcaaccc taaactacct  13200
gctgaccaac cggcggcaga agatcccctc gttgcacagt ttaaacagcg aggaggagcg  13260
cattttgcgc tacgtgcagc agagcgtgag ccttaacctg atgcgcgacg ggtaacgcc  13320
cagcgtggcg ctggacatga ccgcgcgcaa catggaaccg ggcatgtatg cctcaaaccg  13380
gccgtttatc aaccgcctaa tggactactt gcatcgcgcg gccgccgtga accccgagta  13440
tttcaccaat gccatcttga acccgcactg gctaccgccc cctggtttct acaccggggg  13500
attcgaggtg cccgagggta acgatggatt cctctgggac gacatagacg acagcgtgtt  13560
ttccccgcaa ccgcagaccc tgctagagtt gcaacagcgc gagcaggcag aggcggcgct  13620
gcgaaaggaa agcttccgca ggccaagcag cttgtccgat ctaggcgctg cggccccgcg  13680
gtcagatgct agtagcccat ttccaagctt gatagggtct cttaccagca ctcgcaccac  13740
ccgcccgcgc ctgctgggcg aggaggagta cctaaacaac tcgctgctgc agccgcagcg  13800
cgaaaaaaac ctgcctccgg catttcccaa caacgggata gagagcctag tggacaagat  13860
gagtagatgg aagacgtacg cgcaggagca cagggacgtg ccaggcccgc gcccgcccac  13920
ccgtcgtcaa aggcacgacc gtcagcgggg tctggtgtgg gaggacgatg actcggcaga  13980
cgacagcagc gtcctggatt tgggagggag tggcaacccg tttgcgcacc ttcgccccag  14040
gctggggaga atgttttaaa aaaaaaaaag catgatgcaa aataaaaaac tcaccaaggc  14100
catggcaccg agcgttggtt ttcttgtatt ccccttagta tgcggcgcgc ggcgatgtat  14160
gaggaaggtc ctcctccctc ctacgagagt gtggtgagcg cggcgccagt ggcggcggcg  14220
ctgggttctc ccttcgatgc tcccctggac ccgccgtttg tgcctccgcg gtacctgcgg  14280
cctaccgggg ggagaaacag catccgttac tctgagttgg cacccctatt cgacaccacc  14340
cgtgtgtacc tggtggacaa caagtcaacg gatgtggcat ccctgaacta ccagaacgac  14400
cacagcaact ttctgaccac ggtcattcaa aacaatgact acagcccggg ggaggcaagc  14460
acacagacca tcaatcttga cgaccggtcg cactggggcg gcgacctgaa aaccatcctg  14520
cataccaaca tgccaaatgt gaacgagttc atgtttacca ataagtttaa ggcgcgggtg  14580
atggtgtcgc gcttgcctac taaggacaat caggtggagc tgaaatacga gtgggtggag  14640
ttcacgctgc ccgagggcaa ctactccgag accatgacca tagaccttat gaacaacgcg  14700
atcgtggagc actacttgaa agtgggcaga cagaacgggg ttctggaaag cgacatcggg  14760
gtaaagtttg acacccgcaa cttcagactg gggtttgacc ccgtcactgg tcttgtcatg  14820
cctggggtat atacaaacga agccttccat ccagacatca ttttgctgcc aggatgcggg  14880
gtggacttca cccacagccg cctgagcaac ttgttgggca tccgcaagcg gcaacccttc  14940
caggagggct ttaggatcac ctacgatgat ctggagggtg gtaacattcc cgcactgttg  15000
gatgtggacg cctaccaggc gagcttgaaa gatgacaccg aacagggcgg gggtggcgca  15060
ggcggcagca acagcagtgg cagcggcgcg gaagagaact ccaacgcggc agccgcggca  15120
atgcagccgg tggaggacat gaacgatcat gccattcgcg gcgacacctt tgccacacgg  15180
gctgaggaga agcgcgctga ggccgaagca gcggccgaag ctgccgcccc cgctgcgcaa  15240
cccgaggtcg agaagcctca gaagaaaccg gtgatcaaac ccctgacaga ggacagcaag  15300
aaacgcagtt acaacctaat aagcaatgac agcaccttca cccagtaccg cagctggtac  15360
cttgcataca actacggcga ccctcagacc ggaatccgct catggaccct gctttgcact  15420
cctgacgtaa cctgcggctc ggagcaggtc tactggtcgt tgccagacat gatgcaagac  15480
```

-continued cccgtgacct tccgctccac gcgccagatc agcaactttc cggtggtggg cgccgagctg 15540
ttgcccgtgc actccaagag cttctacaac gaccaggccg tctactccca actcatccgc 15600
cagtttacct ctctgaccca cgtgttcaat cgctttcccg agaaccagat tttggcgcgc 15660
ccgccagccc ccaccatcac caccgtcagt gaaaacgttc ctgctctcac agatcacggg 15720
acgctaccgc tgcgcaacag catcggagga gtccagcgag tgaccattac tgacgccaga 15780
cgccgcacct gcccctacgt ttacaaggcc ctgggcatag tctcgccgcg cgtcctatcg 15840
agccgcactt tttgagcaag catgtccatc cttatatcgc ccagcaataa cacaggctgg 15900
ggcctgcgct tcccaagcaa gatgtttggc ggggccaaga agcgctccga ccaacaccca 15960
gtgcgcgtgc gcgggcacta ccgcgcgccc tggggcgcgc acaaacgcgg ccgcactggg 16020
cgcaccaccg tcgatgacgc catcgacgcg gtggtggagg aggcgcgcaa ctacacgccc 16080
acgccgccac cagtgtccac agtggacgcg gccattcaga ccgtggtgcg cggagcccgg 16140
cgctatgcta aaatgaagag acggcggagg cgcgtagcac gtcgccaccg ccgccgaccc 16200
ggcactgccg cccaacgcgc ggcggcggcc ctgcttaacc gcgcacgtcg caccggccga 16260
cgggcggcca tgcgggccgc tcgaaggctg gccgcgggta ttgtcactgt gccccccagg 16320
tccaggcgac gagcggccgc cgcagcagcc gcggccatta gtgctatgac tcagggtcgc 16380
aggggcaacg tgtattgggt gcgcgactcg gttagcggcc tgcgcgtgcc cgtgcgcacc 16440
cgcccccgc gcaactagat tgcaagaaaa aactacttag actcgtactg ttgtatgtat 16500
ccagcggcgg cggcgcgcaa cgaagctatg tccaagcgca aaatcaaaga agagatgctc 16560
caggtcatcg cgccggagat ctatggcccc ccgaagaagg aagagcagga ttacaagccc 16620
cgaaagctaa agcgggtcaa aaagaaaaag aaagatgatg atgatgaact tgacgacgag 16680
gtggaactgc tgcacgctac cgcgcccagg cgacgggtac agtggaaagg tcgacgcgta 16740
aaacgtgttt tgcgacccgg caccaccgta gtctttacgc ccggtgagcg ctccacccgc 16800
acctacaagc gcgtgtatga tgaggtgtac ggcgacgagg acctgcttga gcaggccaac 16860
gagcgcctcg gggagtttgc ctacggaaag cggcataagg acatgctggc gttgccgctg 16920
gacgagggca acccaacacc tagcctaaag cccgtaacac tgcagcaggt gctgcccgcg 16980
cttgcaccgt ccgaagaaaa gcgcggccta aagcgcgagt ctggtgactt ggcacccacc 17040
gtgcagctga tggtacccaa gcgccagcga ctggaagatg tcttggaaaa aatgaccgtg 17100
gaacctgggc tggagcccga ggtccgcgtg cggccaatca agcaggtggc gccgggactg 17160
ggcgtgcaga ccgtggacgt tcagataccc actaccagta gcaccagtat tgccaccgcc 17220
acagagggca tggagacaca aacgtccccg gttgcctcag cggtggcgga tgccgcggtg 17280
caggcggtcg ctgcggccgc gtccaagacc tctacggagg tgcaaacgga cccgtggatg 17340
tttcgcgttt cagccccccg gcgcccgcgc ggttcgagga agtacggcgc cgccagcgcg 17400
ctactgcccg aatatgccct acatccttcc attgcgccta cccccggcta tcgtggctac 17460
acctaccgcc ccagaagacg agcaactacc cgacgccgaa ccaccactgg aacccgccgc 17520
cgccgtcgcc gtcgccagcc cgtgctggcc ccgatttccg tgcgcagggt ggctcgcgaa 17580
ggaggcagga ccctggtgct gccaacagcg cgctaccacc ccagcatcgt ttaaaagccg 17640
gtctttgtgg ttcttgcaga tatggccctc acctgccgcc tccgtttccc ggtgccggga 17700
ttccgaggaa gaatgcaccg taggaggggc atggccggcc acggcctgac gggcggcatg 17760
cgtcgtgcgc accaccggcg gcggcgcgcg tcgcaccgtc gcatgcgcgg cggtatcctg 17820
cccctcctta ttccactgat cgccgcggcg attggcgccg tgcccggaat tgcatccgtg 17880
gccttgcagg cgcagagaca ctgattaaaa acaagttgca tgtggaaaaa tcaaaataaa 17940
aagtctggac tctcacgctc gcttggtcct gtaactattt tgtagaatgg aagacatcaa 18000
ctttgcgtct ctggccccgc gacacggctc gcgcccgttc atgggaaact ggcaagatat 18060
cggcaccagc aatatgagcg gtggcgcctt cagctggggc tcgctgtgga gcggcattaa 18120
aaatttcggt tccaccgtta agaactatgg cagcaaggcc tggaacagca gcacaggcca 18180
gatgctgagg gataagttga aagagcaaaa tttccaacaa aaggtggtag atggcctggc 18240
ctctggcatt agcggggtgg tggacctggc caaccaggca gtgcaaaata agattaacag 18300
taagcttgat ccccgccctc ccgtagagga gcctccaccg gccgtggaga cagtgtctcc 18360
agaggggcgt ggcgaaaagc gtccgcgccc cgacagggaa gaaactctgg tgacgcaaat 18420
agacgagcct ccctcgtacg aggaggcact aaagcaaggc ctgcccacca cccgtcccat 18480
cgcgcccatg gctaccggag tgctgggcca gcacacaccc gtaacgctgg acctgcctcc 18540
ccccgccgac acccagcaga aacctgtgct gccaggcccg accgccgttg ttgtaacccg 18600
tcctagccgc gcgtccctgc gccgcgccgc cagcggtccg cgatcgttgc ggcccgtagc 18660
cagtggcaac tggcaaagca cactgaacag catcgtgggt ctgggggtgc aatccctgaa 18720
gcgccgacga tgcttctgaa tagctaacgt gtcgtatgtg tgtcatgtat gcgtccatgt 18780
cgccgccaga ggagctgctg agccgccgcg cgcccgcttt ccaagatggc taccccttcg 18840
atgatgccgc agtggtctta catgcacatc tcgggccagg acgcctcgga gtacctgagc 18900
cccgggctgg tgcagtttgc ccgcgccacc gagacgtact tcagcctgaa taacaagttt 18960
agaaacccca cggtggcgcc tacgcacgac gtgaccacag accggtccca gcgtttgacg 19020
ctgcggttca tccctgtgga ccgtgaggat actgcgtact cgtacaaggc gcggttcacc 19080
ctagctgtgg gtgataaccg tgtgctggac atggcttcca cgtactttga catccgcggc 19140
gtgctggaca ggggccctac ttttaagccc tactctggca ctgcctacaa cgccctggct 19200
cccaagggtg ccccaaatcc ttgcgaatgg gatgaagctg ctactgctct tgaaataaac 19260
ctagaagaag aggacgatga caacgaagac gaagtagacg agcaagctga gcagcaaaaa 19320
actcacgtat ttgggcaggc gccttattct ggtataaata ttacaaagga gggtattcaa 19380
ataggtgtcg aaggtcaaac acctaaatat gccgataaaa catttcaacc tgaacctcaa 19440
ataggagaat ctcagtggta cgaaactgaa attaatcatg cagctgggag agtccttaaa 19500
aagactaccc caatgaaacc atgttacggt tcatatgcaa aacccacaaa tgaaaatgga 19560
gggcaaggca ttcttgtaaa gcaacaaaat ggaaagctag aaagtcaagt ggaaatgcaa 19620
tttttctcaa ctactgaggc gaccgcaggc aatggtgata acttgactcc taaagtggta 19680
ttgtacagtg aagatgtaga tatagaaacc ccagacactc atatttctta catgcccact 19740
attaaggaag gtaactcacg agaactaatg ggccaacaat ctatgcccaa caggcctaat 19800
tacattgctt ttagggacaa ttttattggt ctaatgtatt acaacagcac gggtaatatg 19860
ggtgttctgg cgggccaagc atcgcagttg aatgctgttg tagatttgca agacagaaac 19920
acagagcttt cataccagct tttgcttgat tccattggtg atagaaccag gtacttttct 19980
atgtggaatc aggctgttga cagctatgat ccagatgtta gaattattga aaatcatgga 20040
actgaagatg aacttccaaa ttactgcttt ccactgggag gtgtgattaa tacagagact 20100
cttaccaagg taaaacctaa aacaggtcag gaaaatggat gggaaaaaga tgctacagaa 20160
ttttcagata aaaatgaaat aagagttgga aataattttg ccatggaaat caatctaaat 20220

-continued gccaacctgt ggagaaattt cctgtactcc aacatagcgc tgtatttgcc cgacaagcta 20280
aagtacagtc cttccaacgt aaaaatttct gataacccaa acacctacga ctacatgaac 20340
aagcgagtgg tggctcccgg gttagtggac tgctacatta accttggagc acgctggtcc 20400
cttgactata tggacaacgt caacccattt aaccaccacc gcaatgctgg cctgcgctac 20460
cgctcaatgt tgctgggcaa tggtcgctat gtgcccttcc acatccaggt gcctcagaag 20520
ttctttgcca ttaaaaacct ccttctcctg ccgggctcat acacctacga gtggaacttc 20580
aggaaggatg ttaacatggt tctgcagagc tccctaggaa atgacctaag ggttgacgga 20640
gccagcatta agtttgatag catttgcctt tacgccacct tcttccccat ggcccacaac 20700
accgcctcca cgcttgaggc catgcttaga aacgacacca acgaccagtc ctttaacgac 20760
tatctctccg ccgccaacat gctctaccct atacccgcca acgctaccaa cgtgcccata 20820
tccatcccct cccgcaactg ggcggctttc cgcggctggg ccttcacgcg ccttaagact 20880
aaggaaaccc catcactggg ctcgggctac gacccttatt acacctactc tggctctata 20940
ccctacctag atggaacctt ttacctcaac cacaccttta agaaggtggc cattaccttt 21000
gactcttctg tcagctggcc tggcaatgac cgcctgctta cccccaacga gtttgaaatt 21060
aagcgctcag ttgacgggga gggttacaac gttgcccagt gtaacatgac caaagactgg 21120
ttcctggtac aaatgctagc taactacaac attggctacc agggcttcta tatcccagag 21180
agctacaagg accgcatgta ctccttcttt agaaacttcc agcccatgag ccgtcaggtg 21240
gtggatgata ctaaatacaa ggactaccaa caggtgggca tcctacacca acacaacaac 21300
tctggatttg ttggctacct tgcccccacc atgcgcgaag gacaggccta ccctgctaac 21360
ttcccctatc cgcttatagg caagaccgca gttgacagca ttacccagaa aaagtttctt 21420
tgcgatcgca ccctttggcg catcccattc tccagtaact ttatgtccat gggcgcactc 21480
acagacctgg gccaaaacct tctctacgcc aactccgccc acgcgctaga catgactttt 21540
gaggtggatc ccatggacga gcccaccctt ctttatgttt tgtttgaagt ctttgacgtg 21600
gtccgtgtgc accggccgca ccgcggcgtc atcgaaaccg tgtacctgcg cacgcccttc 21660
tcggccggca acgccacaac ataaagaagc aagcaacatc aacaacagct gccgccatgg 21720
gctccagtga gcaggaactg aaagccattg tcaaagatct tggttgtggg ccatattttt 21780
tgggcaccta tgacaagcgc tttccaggct ttgtttctcc acacaagctc gcctgcgcca 21840
tagtcaatac ggccggtcgc gagactgggg gcgtacactg gatggccttt gcctggaacc 21900
cgcactcaaa aacatgctac ctctttgagc cctttggctt ttctgaccag cgactcaagc 21960
aggtttacca gtttgagtac gagtcactcc tgcgccgtag cgccattgct tcttcccccg 22020
accgctgtat aacgctggaa aagtccaccc aaagcgtaca ggggcccaac tcggccgcct 22080
gtggactatt ctgctgcatg tttctccacg cctttgccaa ctggccccaa actcccatgg 22140
atcacaaccc caccatgaac cttattaccg gggtacccaa ctccatgctc aacagtcccc 22200
aggtacagcc caccctgcgt cgcaaccagg aacagctcta cagcttcctg gagcgccact 22260
cgccctactt ccgcagccac agtgcgcaga ttaggagcgc cacttctttt tgtcacttga 22320
aaaacatgta aaaataatgt actagagaca ctttcaataa aggcaaatgc ttttatttgt 22380
acactctcgg gtgattattt acccccaccc ttgccgtctg cgccgtttaa aaatcaaagg 22440
ggttctgccg cgcatcgcta tgcgccactg gcagggacac gttgcgatac tggtgtttag 22500
tgctccactt aaactcaggc acaaccatcc gcggcagctc ggtgaagttt tcactccaca 22560
ggctgcgcac catcaccaac gcgtttagca ggtcgggcgc cgatatcttg aagtcgcagt 22620

```
tggggcctcc gccctgcgcg cgcgagttgc gatacacagg gttgcagcac tggaacacta  22680
tcagcgccgg gtggtgcacg ctggccagca cgctcttgtc ggagatcaga tccgcgtcca  22740
ggtcctccgc gttgctcagg gcgaacggag tcaactttgg tagctgcctt cccaaaaagg  22800
gcgcgtgccc aggctttgag ttgcactcgc accgtagtgg catcaaaagg tgaccgtgcc  22860
cggtctgggc gttaggatac agcgcctgca taaaagcctt gatctgctta aaagccacct  22920
gagcctttgc gccttcagag aagaacatgc cgcaagactt gccggaaaac tgattggccg  22980
gacaggccgc gtcgtgcacg cagcaccttg cgtcggtgtt ggagatctgc accacatttc  23040
ggccccaccg gttcttcacg atcttggcct tgctagactg ctccttcagc gcgcgctgcc  23100
cgttttcgct cgtcacatcc atttcaatca cgtgctcctt atttatcata atgcttccgt  23160
gtagacactt aagctcgcct tcgatctcag cgcagcggtg cagccacaac gcgcagcccg  23220
tgggctcgtg atgcttgtag gtcacctctg caaacgactg caggtacgcc tgcaggaatc  23280
gccccatcat cgtcacaaag gtcttgttgc tggtgaaggt cagctgcaac ccgcggtgct  23340
cctcgttcag ccaggtcttg catacggccg ccagagcttc cacttggtca ggcagtagtt  23400
tgaagttcgc ctttagatcg ttatccacgt ggtacttgtc catcagcgcg cgcgcagcct  23460
ccatgccctt ctcccacgca gacacgatcg gcacactcag cgggttcatc accgtaattt  23520
cactttccgc ttcgctgggc tcttcctctt cctcttgcgt ccgcatacca cgcgccactg  23580
ggtcgtcttc attcagccgc cgcactgtgc gcttacctcc tttgccatgc ttgattagca  23640
ccggtgggtt gctgaaaccc accatttgta gcgccacatc ttctctttct tcctcgctgt  23700
ccacgattac ctctggtgat ggcgggcgct cgggcttggg agaagggcgc ttctttttct  23760
tcttgggcgc aatggccaaa tccgccgccg aggtcgatgg ccgcgggctg ggtgtgcgcg  23820
gcaccagcgc gtcttgtgat gagtcttcct cgtcctcgga ctcgatacgc cgcctcatcc  23880
gcttttttgg gggcgcccgg ggaggcggcg gcgacgggga cggggacgac acgtcctcca  23940
tggttggggg acgtcgcgcc gcaccgcgtc cgcgctcggg ggtggtttcg cgctgctcct  24000
cttcccgact ggccatttcc ttctcctata ggcagaaaaa gatcatggag tcagtcgaga  24060
agaaggacag cctaaccgcc ccctctgagt tcgccaccac cgcctccacc gatgccgcca  24120
acgcgcctac caccttcccc gtcgaggcac cccgcttga ggaggaggaa gtgattatcg  24180
agcaggaccc aggttttgta agcgaagacg acgaggaccg ctcagtacca acagaggata  24240
aaaagcaaga ccaggacaac gcagaggcaa acgaggaaca agtcgggcgg ggggacgaaa  24300
ggcatggcga ctacctagat gtgggagacg acgtgctgtt gaagcatctg cagcgccagt  24360
gcgccattat ctgcgacgcg ttgcaagagc gcagcgatgt gcccctcgcc atagcggatg  24420
tcagccttgc ctacgaacgc cacctattct caccgcgcgt acccccccaaa cgccaagaaa  24480
acggcacatg cgagcccaac ccgcgcctca acttctaccc cgtatttgcc gtgccagagg  24540
tgcttgccac ctatcacatc tttttccaaa actgcaagat acccctatcc tgccgtgcca  24600
accgcagccg agcggacaag cagctggcct tgcggcaggg cgctgtcata cctgatatcg  24660
cctcgctcaa cgaagtgcca aaaatctttg agggtcttgg acgcgacgag aagcgcgcgg  24720
caaacgctct gcaacaggaa aacagcgaaa atgaaagtca ctctggagtg ttggtggaac  24780
tcgagggtga caacgcgcgc ctagccgtac taaaacgcag catcgaggtc acccactttg  24840
cctacccggc acttaaccta ccccccaagg tcatgagcac agtcatgagt gagctgatcg  24900
tgcgccgtgc gcagcccctg gagagggatg caaatttgca agaacaaaca gaggagggcc  24960
```

-continued

```
tacccgcagt tggcgacgag cagctagcgc gctggcttca aacgcgcgag cctgccgact  25020
tggaggagcg acgcaaacta atgatggccg cagtgctcgt taccgtggag cttgagtgca  25080
tgcagcggtt ctttgctgac ccggagatgc agcgcaagct agaggaaaca ttgcactaca  25140
cctttcgaca gggctacgta cgccaggcct gcaagatctc caacgtggag ctctgcaacc  25200
tggtctccta ccttggaatt ttgcacgaaa accgccttgg gcaaaacgtg cttcattcca  25260
cgctcaaggg cgaggcgcgc cgcgactacg tccgcgactg cgtttactta tttctatgct  25320
acacctggca gacggccatg ggcgtttggc agcagtgctt ggaggagtgc aacctcaagg  25380
agctgcagaa actgctaaag caaaacttga aggacctatg gacggccttc aacgagcgct  25440
ccgtggccgc gcacctggcg gacatcattt tccccgaacg cctgcttaaa accctgcaac  25500
agggtctgcc agacttcacc agtcaaagca tgttgcagaa ctttaggaac tttatcctag  25560
agcgctcagg aatcttgccc gccacctgct gtgcacttcc tagcgacttt gtgcccatta  25620
agtaccgcga atgccctccg ccgctttggg gccactgcta ccttctgcag ctagccaact  25680
accttgccta ccactctgac ataatggaag acgtgagcgg tgacggtcta ctggagtgtc  25740
actgtcgctg caacctatgc accccgcacc gctccctggt ttgcaattcg cagctgctta  25800
acgaaagtca aattatcggt acctttgagc tgcagggtcc ctcgcctgac gaaaagtccg  25860
cggctccggg gttgaaactc actccggggc tgtggacgtc ggcttacctt cgcaaatttg  25920
tacctgagga ctaccacgcc cacgagatta ggttctacga agaccaatcc cgcccgccaa  25980
atgcggagct taccgcctgc gtcattaccc agggccacat tcttggccaa ttgcaagcca  26040
tcaacaaagc ccgccaagag tttctgctac gaaagggacg gggggtttac ttggaccccc  26100
agtccggcga ggagctcaac ccaatccccc cgccgccgca gccctatcag cagcagccgc  26160
gggcccttgc ttcccaggat ggcacccaaa aagaagctgc agctgccgcc gccacccacg  26220
gacgaggagg aatactggga cagtcaggca gaggaggttt tggacgagga ggaggaggac  26280
atgatggaag actgggagag cctagacgag gaagcttccg aggtcgaaga ggtgtcagac  26340
gaaacaccgt caccctcggt cgcattcccc tcgccggcgc cccagaaatc ggcaaccggt  26400
tccagcatgg ctacaacctc cgctcctcag gcgccgccgg cactgcccgt tcgccgaccc  26460
aaccgtagat gggacaccac tggaaccagg gccggtaagt ccaagcagcc gccgccgtta  26520
gcccaagagc aacaacagcg ccaaggctac cgctcatggc gcgggcacaa gaacgccata  26580
gttgcttgct tgcaagactg tgggggcaac atctccttcg cccgccgctt tcttctctac  26640
catcacggcg tggccttccc ccgtaacatc ctgcattact accgtcatct ctacagccca  26700
tactgcaccg gcggcagcgg cagcggcagc aacagcagcg gccacacaga agcaaaggcg  26760
accggatagc aagactctga caaagcccaa gaaatccaca gcggcggcag cagcaggagg  26820
aggagcgctg cgtctggcgc ccaacgaacc cgtatcgacc cgcgagctta gaaacaggat  26880
ttttcccact ctgtatgcta tatttcaaca gagcaggggc caagaacaag agctgaaaat  26940
aaaaaacagg tctctgcgat ccctcacccg cagctgcctg tatcacaaaa gcgaagatca  27000
gcttcggcgc acgctggaag acgcggaggc tctcttcagt aaatactgcg cgctgactct  27060
taaggactag tttcgcgccc tttctcaaat ttaagcgcga aaactacgtc atctccagcg  27120
gccacacccg gcgccagcac ctgtcgtcag cgccattatg agcaaggaaa ttcccacgcc  27180
ctacatgtgg agttaccagc cacaaatggg acttgcggct ggagctgccc aagactactc  27240
aacccgaata aactacatga gcgcgggacc ccacatgata tcccgggtca acggaatccg  27300
cgcccaccga aaccgaattc tcttggaaca ggcggctatt accaccacac ctcgtaataa  27360
```

-continued

```
ccttaatccc cgtagttggc ccgctgccct ggtgtaccag gaaagtcccg ctcccaccac  27420
tgtggtactt cccagagacg cccaggccga agttcagatg actaactcag gggcgcagct  27480
tgcgggcggc tttcgtcaca gggtgcggtc gcccgggcag ggtataactc acctgacaat  27540
cagagggcga ggtattcagc tcaacgacga gtcggtgagc tcctcgcttg gtctccgtcc  27600
ggacgggaca tttcagatcg gcggcgccgg ccgctcttca ttcacgcctc gtcaggcaat  27660
cctaactctg cagacctcgt cctctgagcc gcgctctgga ggcattggaa ctctgcaatt  27720
tattgaggag tttgtgccat cggtctactt taacccottc tcgggacctc ccggccacta  27780
tccggatcaa tttattccta actttgacgc ggtaaaggac tcggcggatg gctacgactg  27840
aatgttaagt ggagaggcag agcaactgcg cctgaaacac ctggtccact gtcgccgcca  27900
caagtgcttt gcccgcgact ccggtgagtt ttgctacttt gaattgcccg aggatcatat  27960
cgagggcccg gcgcacggcg tccggcttac cgcccaggga gagcttgccc gtagcctgat  28020
tcgggagttt acccagcgcc ccctgctagt tgagcgggac aggggaccct gtgttctcac  28080
tgtgatttgc aactgtccta accctggatt acatcaagat ctttgttgcc atctctgtgc  28140
tgagtataat aaatacagaa attaaaatat actggggctc ctatcgccat cctgtaaacg  28200
ccaccgtctt cacccgccca agcaaaccaa ggcgaacctt acctggtact tttaacatct  28260
ctccctctgt gatttacaac agtttcaacc cagacggagt gagtctacga gagaacctct  28320
ccgagctcag ctactccatc agaaaaaaca ccaccctcct tacctgccgg gaacgtacga  28380
tgtggctgca gagcctgctg ctcttgggca ctgtggcctg cagcatctct gcacccgccc  28440
gctcgcccag ccccagcacg cagccctggg agcatgtgaa tgccatccag gaggcccggc  28500
gtctcctgaa cctgagtaga gacactgctg ctgagatgaa tgaaacagta gaagtcatct  28560
cagaaatgtt tgacctccag gagccgacct gcctacagac ccgcctggag ctgtacaagc  28620
agggcctgcg gggcagcctc accaagctca agggcccctt gaccatgatg gccagccact  28680
acaagcagca ctgccctcca accccggaaa cttcctgtgc aacccagact atcacctttg  28740
aaagtttcaa agagaacctg aaggactttc tgcttgtcat cccctttgac tgctgggagc  28800
cagtccagga gtgacaattg actctatgtg ggatatgctc cagcgctaca accttgaagt  28860
caggcttcct ggatgtcagc atctgacttt ggccagcacc tgtcccgcgg atttgttcca  28920
gtccaactac agcgacccac cctaacagag atgaccaaca caaccaacgc ggccgccgct  28980
accggactta catctaccac aaatacaccc caagtttctg cctttgtcaa taactgggat  29040
aacttgggca tgtggtggtt ctccatagcg cttatgtttg tatgccttat tattatgtgg  29100
ctcatctgct gcctaaagcg caaacgcgcc cgaccaccca tctatagtcc catcattgtg  29160
ctacacccaa acaatgatgg aatccataga ttggacggac tgaaacacat gttcttttct  29220
cttacagtat gattaaatga gacatgattc ctcgagtttt tatattactg acccttgttg  29280
cgcttttttg tgcgtgctcc acattggctg cggtttctca catcgaagta gactgcattc  29340
cagccttcac agtctatttg ctttacggat ttgtcaccct cacgctcatc tgcagcctca  29400
tcactgtggt catcgccttt atccagtgca ttgactgggt ctgtgtgcgc tttgcatatc  29460
tcagacacca tccccagtac agggacagga ctatagctga gcttcttaga attctttaat  29520
tatgaaattt actgtgactt ttctgctgat tatttgcacc ctatctgcgt tttgttcccc  29580
gacctccaag cctcaaagac atatatcatg cagattcact cgtatatgga atattccaag  29640
ttgctacaat gaaaaaagcg atctttccga agcctggtta tatgcaatca tctctgttat  29700
```

-continued

```
ggtgttctgc agtaccatct tagccctagc tatatatccc taccttgaca ttggctggaa  29760
acgaatagat gccatgaacc acccaacttt ccccgcgccc gctatgcttc cactgcaaca  29820
agttgttgcc ggcggctttg tcccagccaa tcagcctcgc cccacttctc ccacccccac  29880
tgaaatcagc tactttaatc taacaggagg agatgactga caccctagat ctagaaatgg  29940
acggaattat tacagagcag cgcctgctag aaagacgcag ggcagcggcc gagcaacagc  30000
gcatgaatca agagctccaa gacatggtta acttgcacca gtgcaaaagg ggtatctttt  30060
gtctggtaaa gcaggccaaa gtcacctacg acagtaatac caccggacac cgccttagct  30120
acaagttgcc aaccaagcgt cagaaattgg tggtcatggt gggagaaaag cccattacca  30180
taactcagca ctcggtagaa accgaaggct gcattcactc accttgtcaa ggacctgagg  30240
atctctgcac ccttattaag accctgtgcg gtctcaaaga tcttattccc tttaactaat  30300
aaaaaaaaat aataaagcat cacttactta aaatcagtta gcaaatttct gtccagttta  30360
ttcagcagca cctccttgcc ctcctcccag ctctggtatt gcagcttcct cctggctgca  30420
aactttctcc acaatctaaa tggaatgtca gtttcctcct gttcctgtcc atccgcaccc  30480
actatcttca tgttgttgca gatgaagcgc gcaagaccgt ctgaagatac cttcaacccc  30540
gtgtatccat atgacacgga aaccggtcct ccaactgtgc cttttcttac tcctcccttt  30600
gtatccccca atgggtttca agagagtccc cctggggtac tctctttgcg cctatccgaa  30660
cctctagtta cctccaatgg catgcttgcg ctcaaaatgg gcaacggcct ctctctggac  30720
gaggccggca accttacctc ccaaaatgta accactgtga gcccacctct caaaaaaacc  30780
aagtcaaaca taaacctgga aatatctgca cccctcacag ttacctcaga agccctaact  30840
gtggctgccg ccgcacctct aatggtcgcg ggcaacacac tcaccatgca atcacaggcc  30900
ccgctaaccg tgcacgactc caaacttagc attgccaccc aaggacccct cacagtgtca  30960
gaaggaaagc tagccctgca aacatcaggc cccctcacca ccaccgatag cagtaccctt  31020
actatcactg cctcaccccc tctaactact gccactggta gcttgggcat tgacttgaaa  31080
gagcccattt atacacaaaa tggaaaacta ggactaaagt acggggctcc tttgcatgta  31140
acagacgacc taaacacttt gaccgtagca actggtccag gtgtgactat taataatact  31200
tccttgcaaa ctaaagttac tggagccttg ggttttgatt cacaaggcaa tatgcaactt  31260
aatgtagcag gaggactaag gattgattct caaaacagac gccttatact tgatgttagt  31320
tatccgtttg atgctcaaaa ccaactaaat ctaagactag gacagggccc tctttttata  31380
aactcagccc acaacttgga tattaactac aacaaaggcc tttacttgtt tacagcttca  31440
aacaattcca aaaagcttga ggttaaccta agcactgcca aggggttgat gtttgacgct  31500
acagccatag ccattaatgc aggagatggg cttgaatttg gttcacctaa tgcaccaaac  31560
acaaatcccc tcaaaacaaa aattggccat ggcctagaat ttgattcaaa caaggctatg  31620
gttcctaaac taggaactgg ccttagtttt gacagcacag gtgccattac agtaggaaac  31680
aaaaataatg ataagctaac cctatggaca ggtccaaaac cagaagccaa ctgcataatt  31740
gaatacggga aacaaaaccc agatagcaaa ctaactttaa tccttgtaaa aaatggagga  31800
attgttaatg gatatgtaac gctaatggga gcctcagact acgttaacac cttatttaaa  31860
aacaaaaatg tctccattaa tgtagaacta tactttgatg ccactggtca tatattacca  31920
gactcatctt ctcttaaaac agatctagaa ctaaaataca agcaaaccgc tgactttagt  31980
gcaagaggtt ttatgccaag tactacagcg tatccatttg tccttcctaa tgcgggaaca  32040
cataatgaaa attatatttt tggtcaatgc tactacaaag caagcgatgg tgccctttt   32100
```

-continued

```
ccgttggaag ttactgttat gcttaataaa cgcctgccag atagtcgcac atcctatgtt  32160
atgacttttt tatggtcctt gaatgctggt ctagctccag aaactactca ggcaaccctc  32220
ataacctccc catttacctt ttcctatatt agagaagatg actaataaac tctaaagaat  32280
cgtttgtgtt atgtttcaac gtgtttattt ttcaattgca gaaaatttca agtcattttt  32340
cattcagtag tatagcccca ccaccacata gcttatacag atcaccgtac cttaatcaaa  32400
ctcacagaac cctagtattc aacctgccac ctccctccca acacacagag tacacagtcc  32460
tttctccccg gctggcctta aaaagcatca tatcatgggt aacagacata ttcttaggtg  32520
ttatattcca cacggtttcc tgtcgagcca aacgctcatc aagtgatatt aataaactcc  32580
ccgggcagct cacttaagtt catgtcgctg tccagctgct gagccacagg ctgctgtcca  32640
acttgcggtt gcttaacggg cggcgaagga gaagtccacg cctacatggg ggagagtca   32700
taatcgtgca tcaggatagg gcggtggtgc tgcagcagcg cgcgaataaa ctgctgccgc  32760
cgccgctccg tcctgcagga atacaacatg gcagtggtct cctcagcgat gattcgcacc  32820
gcccgcagca taaggcgctt gtcctccggg cacagcagcg caccctgatc tcacttaaat  32880
cagcacagta actgcagcac agcaccacaa tattgttcaa aatcccacag tgcaaggcgc  32940
tgtatccaaa gctcatggcg gggaccacag aacccacgtg gccatcatac cacaagcgca  33000
ggtagattaa gtggcgaccc ctcataaaca cgctggacat aaacattacc tcttttggca  33060
tgttgtaatt caccacctcc cggtaccata taaacctctg attaaacatg gcgccatcca  33120
ccaccatcct aaaccagctg gccaaaacct gccccgccgg gntatacact gcagggaacc  33180
gggacttgga caatgacaag tgggagagcc caggactcgt aaccatggat catcatgctc  33240
gtcatgatat caatgttggc acaacacagg cacacgtgca tacacttcct caggattaca  33300
agctcctccc gcgttagaac catatcccag ggaacaaccc attcctgaat cagcgtaaat  33360
cccacactgc agggaagacc tcgcacgtaa ctcacgttgt gcattgtcaa agtgttacat  33420
tcgggcagca gcggatgatc ctccagtatg gtagcgcggg tttctgtctc aaaaggaggt  33480
agacgatccc tactgtacgg agtgcgccga gacaaccgag atcgtgttgg tcgtagtgtc  33540
atgccaaatg gaacgccgga cgtagtcata tttcctgaag caaaaccagg tgcgggcgtg  33600
acaaacagat ctgcgtctcc ggtctcgccg cttagatcgc tctgtgtagt agttgtagta  33660
tatccactct ctcaaagcat ccaggcgccc cctggcttcg ggttctatgt aaactccttc  33720
atgcgccgct gccctgataa catccaccac cgcagaataa gccacaccca gccaacctac  33780
acattcgttc tgcgagtcac acacgggagg agcgggaaga gctggaagaa ccatgttttt  33840
tttttattc caaaagatta tccaaaacct caaaatgaag atctattaag tgaacgcgct   33900
cccctccggt ggcgtggtca aactctacag ccaaagaaca gataatggca tttgtaagat  33960
gttgcacaat ggcttccaaa aggcaaacgg ccctcacgtc caagtggacg taaaggctaa  34020
acccttcagg gtgaatctcc tctataaaca ttccagcacc ttcaaccatg cccaaataat  34080
tctcatctcg ccaccttctc aatatatctc taagcaaatc ccgaatattt aagtccgggc  34140
cattgtaaaa aatttggctc cagagcgccc tccaccttca gcctcaagca gcgaatcatg  34200
attgcaaaaa ttcaggttcc tcacagacct gtataagatt caaaagcgga acattaacaa  34260
aaataccgcg atcccgtagg tcccttcgca gggccagctg aacataatcg tgcaggtctg  34320
cacggaccag cgcggccact tccccgccag gaaccatgac aaaagaaccc acactgatta  34380
tgacacgcat actcggagct atgctaacca gcgtagcccc gatgtaagct tgttgcatgg  34440
```

```
gcggcgatat aaaatgcaag gtgctgctca aaaaatcagg caaagcctcg cgcaaaaaag  34500

aaagcacatc gtagtcatgc tcatgcagat aaaggcaggt aagctccgga accaccacag  34560

aaaaagacac catttttctc tcaaacatgt ctgcgggttt ctgcataaac acaaaataaa  34620

ataacaaaaa aacatttaaa cattagaagc ctgtcttaca acaggaaaaa caacccttat  34680

aagcataaga cggactacgg ccatgccggc gtgaccgtaa aaaaactggt caccgtgatt  34740

aaaaagcacc accgacagct cctcggtcag tccggagtca taatgtaaga ctcggtaaac  34800

acatcaggtt gattcacatc ggtcagtgtt aaaaagcgac cgaaatagcc ngggggaata  34860

caatacccgc aggcgtagag acaacattac agcccccata ggaggtataa caaaattaat  34920

aggagagaaa aacacataaa cacctgaaaa accctcctgc ctaggcaaaa tagcaccctc  34980

ccgctccaga acaacataca gcgcttccac agcggcagcc ataacagtca gccttaccag  35040

taaaaaagaa aacctattaa aaaaacacca ctcgacacgg caccagctca atcagtcaca  35100

gtgtaaaaaa gggccaagtg cagagcgagt atatatagga ctaaaaaatg acggtaacgg  35160

ttaaagtcca caaaaaacac ccagaaaacc gcacgcgaac ctacgcccag aaacgaaagc  35220

caaaaaaccc acaacttcct caaatcgtca cttccgtttt cccacgttac gtcacttccc  35280

attttaagaa aactacaatt cccaacacat acaagttact ccgccctaaa acctacgtca  35340

cccgccccgt tcccacgccc cgcgccacgt cacaaactcc accccctcat tatcatattg  35400

gcttcaatcc aaaataaggt atattattga tgatgttaat                        35440
```

```
<210> SEQ ID NO 8
<211> LENGTH: 38303
<212> TYPE: DNA
<213> ORGANISM: Artificial Sequence
<220> FEATURE:
<223> OTHER INFORMATION: Ad5-D24-GMCSF
<220> FEATURE:
<221> NAME/KEY: misc_feature
<222> LOCATION: (36714)..(36719)
<223> OTHER INFORMATION: n is a, c, g, or t

<400> SEQUENCE: 8
```

```
taacatcatc aattatacct tccattttgg attgaagcca atatgataat gagggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatatttgt ctagggccgc    360

ggggactttg accgtttacg tggagactcg cccaggtgtt tttctcaggt gttttccgcg    420

ttccgggtca aagttggcgt tttattatta tagtcagctg acgtgtagtg tatttatacc    480

cggtgagttc ctcaagaggc cactcttgag tgccagcgag tagagttttc tcctccgagc    540

cgctccgaca ccgggactga aaatgagaca tattatctgc cacggaggtg ttattaccga    600

agaaatggcc gccagtcttt tggaccagct gatcgaagag gtactggctg ataatcttcc    660

acctcctagc cattttgaac cacctaccct tcacgaactg tatgatttag acgtgacggc    720

ccccgaagat cccaacgagg aggcggtttc gcagattttt cccgactctg taatgttggc    780

ggtgcaggaa gggattgact tactcacttt tccgccggcg cccggttctc cggagccgcc    840

tcacctttcc cggcagcccg agcagccgga gcagagagcc ttgggtccgg tttctatgcc    900

aaaccttgta ccggaggtga tcgatccacc cagtgacgac gaggatgaag agggtgagga    960
```

-continued

```
gtttgtgtta gattatgtgg agcaccccgg gcacggttgc aggtcttgtc attatcaccg   1020
gaggaatacg ggggacccag atattatgtg ttcgctttgc tatatgagga cctgtggcat   1080
gtttgtctac agtaagtgaa aattatgggc agtgggtgat agagtggtgg gtttggtgtg   1140
gtaatttttt ttttaatttt tacagttttg tggtttaaag aattttgtat tgtgattttt   1200
ttaaaaggtc ctgtgtctga acctgagcct gagcccgagc cagaaccgga gcctgcaaga   1260
cctacccgcc gtcctaaaat ggcgcctgct atcctgagac gcccgacatc acctgtgtct   1320
agagaatgca atagtagtac ggatagctgt gactccggtc cttctaacac acctcctgag   1380
atacacccgg tggtcccgct gtgccccatt aaaccagttg ccgtgagagt tggtgggcgt   1440
cgccaggctg tggaatgtat cgaggacttg cttaacgagc ctgggcaacc tttggacttg   1500
agctgtaaac gccccaggcc ataaggtgta aacctgtgat tgcgtgtgtg gttaacgcct   1560
ttgtttgctg aatgagttga tgtaagttta ataaagggtg agataatgtt taacttgcat   1620
ggcgtgttaa atggggcggg gcttaaaggg tatataatgc gccgtgggct aatcttggtt   1680
acatctgacc tcatggaggc ttgggagtgt ttggaagatt tttctgctgt gcgtaacttg   1740
ctggaacaga gctctaacag tacctcttgg ttttggaggt ttctgtgggg ctcatcccag   1800
gcaaagttag tctgcagaat taaggaggat tacaagtggg aatttgaaga gcttttgaaa   1860
tcctgtggtg agctgtttga ttctttgaat ctgggtcacc aggcgctttt ccaagagaag   1920
gtcatcaaga ctttggattt ttccacaccg gggcgcgctg cggctgctgt tgcttttttg   1980
agttttataa aggataaatg gagcgaagaa acccatctga gcggggggta cctgctggat   2040
tttctggcca tgcatctgtg gagagcggtt gtgagacaca agaatcgcct gctactgttg   2100
tcttccgtcc gcccggcgat aataccgacg gaggagcagc agcagcagca ggaggaagcc   2160
aggcggcggc ggcaggagca gagcccatgg aacccgagag ccggcctgga ccctcgggaa   2220
tgaatgttgt acaggtggct gaactgtatc cagaactgag acgcattttg acaattacag   2280
aggatgggca ggggctaaag ggggtaaaga gggagcgggg ggcttgtgag gctacagagg   2340
aggctaggaa tctagctttt agcttaatga ccagacaccg tcctgagtgt attacttttc   2400
aacagatcaa ggataattgc gctaatgagc ttgatctgct ggcgcagaag tattccatag   2460
agcagctgac cacttactgg ctgcagccag gggatgattt tgaggaggct attagggtat   2520
atgcaaaggt ggcacttagg ccagattgca agtacaagat cagcaaactt gtaaatatca   2580
ggaattgttg ctacatttct gggaacgggg ccgaggtgga gatagatacg gaggataggg   2640
tggcctttag atgtagcatg ataaatatgt ggccgggggt gcttggcatg gacggggtgg   2700
ttattatgaa tgtaaggttt actggcccca attttagcgg tacggttttc ctggccaata   2760
ccaaccttat cctacacggt gtaagcttct atgggtttaa caatacctgt gtggaagcct   2820
ggaccgatgt aagggttcgg ggctgtgcct tttactgctg ctggaagggg gtggtgtgtc   2880
gccccaaaag cagggcttca attaagaaat gcctctttga aaggtgtacc ttgggtatcc   2940
tgtctgaggg taactccagg gtgcgccaca atgtggcctc cgactgtggt tgcttcatgc   3000
tagtgaaaag cgtggctgtg attaagcata acatggtatg tggcaactgc gaggacaggg   3060
cctctcagat gctgacctgc tcggacggca actgtcacct gctgaagacc attcacgtag   3120
ccagccactc tcgcaaggcc tggccagtgt ttgagcataa catactgacc cgctgttcct   3180
tgcatttggg taacaggagg ggggtgttcc taccttacca atgcaatttg agtcacacta   3240
agatattgct tgagcccgag agcatgtcca aggtgaacct gaacggggtg tttgacatga   3300
```

-continued

```
ccatgaagat ctggaaggtg ctgaggtacg atgagacccg caccaggtgc agaccctgcg   3360
agtgtggcgg taaacatatt aggaaccagc ctgtgatgct ggatgtgacc gaggagctga   3420
ggcccgatca cttggtgctg gcctgcaccc gcgctgagtt tggctctagc gatgaagata   3480
cagattgagg tactgaaatg tgtgggcgtg gcttaagggt gggaaagaat atataaggtg   3540
ggggtcttat gtagttttgt atctgttttg cagcagccgc cgccgccatg agcaccaact   3600
cgtttgatgg aagcattgtg agctcatatt tgacaacgcg catgccccca tgggccgggg   3660
tgcgtcagaa tgtgatgggc tccagcattg atggtcgccc cgtcctgccc gcaaactcta   3720
ctaccttgac ctacgagacc gtgtctggaa cgccgttgga gactgcagcc tccgccgccg   3780
cttcagccgc tgcagccacc gcccgcggga ttgtgactga ctttgctttc ctgagcccgc   3840
ttgcaagcag tgcagcttcc cgttcatccg cccgcgatga caagttgacg gctcttttgg   3900
cacaattgga ttctttgacc cgggaactta atgtcgtttc tcagcagctg ttggatctgc   3960
gccagcaggt ttctgccctg aaggcttcct cccctcccaa tgcggtttaa aacataaata   4020
aaaaaccaga ctctgtttgg atttggatca agcaagtgtc ttgctgtctt tatttagggg   4080
ttttgcgcgc gcggtaggcc cgggaccagc ggtctcggtc gttgagggtc ctgtgtattt   4140
tttccaggac gtggtaaagg tgactctgga tgttcagata catgggcata agcccgtctc   4200
tggggtggag gtagcaccac tgcagagctt catgctgcgg ggtggtgttg tagatgatcc   4260
agtcgtagca ggagcgctgg gcgtggtgcc taaaaatgtc tttcagtagc aagctgattg   4320
ccaggggcag gcccttggtg taagtgttta caaagcggtt aagctgggat gggtgcatac   4380
gtggggatat gagatgcatc ttggactgta tttttaggtt ggctatgttc ccagccatat   4440
ccctccgggg attcatgttg tgcagaacca ccagcacagt gtatccggtg cacttgggaa   4500
atttgtcatg tagcttagaa ggaaatgcgt ggaagaactt ggagacgccc ttgtgacctc   4560
caagattttc catgcattcg tccataatga tggcaatggg cccacgggcg gcggcctggg   4620
cgaagatatt tctgggatca ctaacgtcat agttgtgttc caggatgaga tcgtcatagg   4680
ccatttttac aaagcgcggg cggagggtgc cagactgcgg tataatggtt ccatccggcc   4740
caggggcgta gttaccctca cagatttgca tttcccacgc tttgagttca gatgggggga   4800
tcatgtctac ctgcggggcg atgaagaaaa cggtttccgg ggtaggggag atcagctggg   4860
aagaaagcag gttcctgagc agctgcgact taccgcagcc ggtgggcccg taaatcacac   4920
ctattaccgg ctgcaactgg tagttaagag agctgcagct gccgtcatcc ctgagcaggg   4980
gggccacttc gttaagcatg tccctgactc gcatgttttc cctgaccaaa tccgccagaa   5040
ggcgctcgcc gcccagcgat agcagttctt gcaaggaagc aaagtttttc aacggtttga   5100
gaccgtccgc cgtaggcatg cttttgagcg tttgaccaag cagttccagg cggtcccaca   5160
gctcggtcac ctgctctacg gcatctcgat ccagcatatc tcctcgtttc gcgggttggg   5220
gcggctttcg ctgtacggca gtagtcggtg ctcgtccaga cgggccaggg tcatgtcttt   5280
ccacgggcgc agggtcctcg tcagcgtagt ctgggtcacg gtgaaggggt gcgctccggg   5340
ctgcgcgctg gccagggtgc gcttgaggct ggtcctgctg gtgctgaagc gctgccggtc   5400
ttcgccctgc gcgtcggcca ggtagcattt gaccatggtg tcatagtcca gcccctccgc   5460
ggcgtggccc ttggcgcgca gcttgccctt ggaggaggcg ccgcacgagg ggcagtgcag   5520
acttttgagg gcgtagagct tgggcgcgag aaataccgat tccggggagt aggcatccgc   5580
gccgcaggcc ccgcagacgg tctcgcattc cacgagccag gtgagctctg gccgttcggg   5640
gtcaaaaacc aggtttcccc catgcttttt gatgcgtttc ttacctctgg tttccatgag   5700
```

-continued

```
ccggtgtcca cgctcggtga cgaaaaggct gtccgtgtcc ccgtatacag acttgagagg   5760
cctgtcctcg agcggtgttc cgcggtcctc ctcgtataga aactcggacc actctgagac   5820
aaaggctcgc gtccaggcca gcacgaagga ggctaagtgg gaggggtagc ggtcgttgtc   5880
cactaggggg tccactcgct ccagggtgtg aagacacatg tcgccctctt cggcatcaag   5940
gaaggtgatt ggtttgtagg tgtaggccac gtgaccgggt gttcctgaag gggggctata   6000
aaagggggtg ggggcgcgtt cgtcctcact ctcttccgca tcgctgtctg cgagggccag   6060
ctgttggggt gagtactccc tctgaaaagc gggcatgact tctgcgctaa gattgtcagt   6120
ttccaaaaac gaggaggatt tgatattcac ctggcccgcg gtgatgcctt tgagggtggc   6180
cgcatccatc tggtcagaaa agacaatctt tttgttgtca agcttggtgg caaacgaccc   6240
gtagagggcg ttggacagca acttggcgat ggagcgcagg gtttggtttt tgtcgcgatc   6300
ggcgcgctcc ttggccgcga tgtttagctg cacgtattcg cgcgcaacgc accgccattc   6360
gggaaagacg gtggtgcgct cgtcgggcac caggtgcacg cgccaaccgc ggttgtgcag   6420
ggtgacaagg tcaacgctgg tggctacctc tccgcgtagg cgctcgttgg tccagcagag   6480
gcggccgccc ttgcgcgagc agaatggcgg taggggtct agctgcgtct cgtccggggg   6540
gtctgcgtcc acggtaaaga ccccgggcag caggcgcgcg tcgaagtagt ctatcttgca   6600
tccttgcaag tctagcgcct gctgccatgc gcgggcggca agcgcgcgct cgtatgggtt   6660
gagtggggga ccccatggca tggggtgggt gagcgcggag gcgtacatgc cgcaaatgtc   6720
gtaaacgtag aggggctctc tgagtattcc aagatatgta gggtagcatc ttccaccgcg   6780
gatgctggcg cgcacgtaat cgtatagttc gtgcgaggga gcgaggaggt cgggaccgag   6840
gttgctacgg gcgggctgct ctgctcggaa gactatctgc ctgaagatgg catgtgagtt   6900
ggatgatatg gttggacgct ggaagacgtt gaagctggcg tctgtgagac ctaccgcgtc   6960
acgcacgaag gaggcgtagg agtcgcgcag cttgttgacc agctcggcgg tgacctgcac   7020
gtctagggcg cagtagtcca gggtttcctt gatgatgtca tacttatcct gtcccttttt   7080
tttccacagc tcgcggttga ggacaaactc ttcgcggtct ttccagtact cttggatcgg   7140
aaacccgtcg gcctccgaac ggtaagagcc tagcatgtag aactggttga cggcctggta   7200
ggcgcagcat ccctttttcta cgggtagcgc gtatgcctgc gcggccttcc ggagcgaggt   7260
gtgggtgagc gcaaaggtgt ccctgaccat gactttgagg tactggtatt tgaagtcagt   7320
gtcgtcgcat ccgccctgct cccagagcaa aaagtccgtg cgctttttgg aacgcggatt   7380
tggcagggcg aaggtgacat cgttgaagag tatctttccc gcgcgaggca taaagttgcg   7440
tgtgatgcgg aagggtcccg gcacctcgga acggttgtta attacctggg cggcgagcac   7500
gatctcgtca aagccgttga tgttgtggcc cacaatgtaa agttccaaga agcgcgggat   7560
gcccttgatg gaaggcaatt ttttaagttc ctcgtaggtg agctcttcag gggagctgag   7620
cccgtgctct gaaagggccc agtctgcaag atgagggttg gaagcgacga atgagctcca   7680
caggtcacgg gccattagca tttgcaggtg gtcgcgaaag gtcctaaact ggcgacctat   7740
ggccattttt tctggggtga tgcagtagaa ggtaagcggg tcttgttccc agcggtccca   7800
tccaaggttc gcggctaggt ctcgcgcggc agtcactaga ggctcatctc cgccgaactt   7860
catgaccagc atgaagggca cgagctgctt cccaaaggcc cccatccaag tataggtctc   7920
tacatcgtag gtgacaaaga gacgctcggt gcgaggatgc gagccgatcg ggaagaactg   7980
gatctcccgc caccaattgg aggagtggct attgatgtgg tgaaagtaga agtccctgcg   8040
```

-continued

```
acgggccgaa cactcgtgct ggcttttgta aaaacgtgcg cagtactggc agcggtgcac   8100
gggctgtaca tcctgcacga ggttgacctg acgaccgcgc acaaggaagc agagtgggaa   8160
tttgagcccc tcgcctggcg ggtttggctg gtggtcttct acttcggctg cttgtccttg   8220
accgtctggc tgctcgaggg gagttacggt ggatcggacc accacgccgc gcgagcccaa   8280
agtccagatg tccgcgcgcg gcggtcggag cttgatgaca acatcgcgca gatgggagct   8340
gtccatggtc tggagctccc gcggcgtcag gtcaggcggg agctcctgca ggtttacctc   8400
gcatagacgg gtcagggcgc gggctagatc caggtgatac ctaatttcca ggggctggtt   8460
ggtggcggcg tcgatggctt gcaagaggcc gcatccccgc ggcgcgacta cggtaccgcg   8520
cggcgggcgg tgggccgcgg gggtgtcctt ggatgatgca tctaaaagcg gtgacgcggg   8580
cgagcccccg gaggtagggg gggctccgga cccgccggga gagggggcag gggcacgtcg   8640
gcgccgcgcg cgggcaggag ctggtgctgc gcgcgtaggt tgctggcgaa cgcgacgacg   8700
cggcggttga tctcctgaat ctggcgcctc tgcgtgaaga cgacgggccc ggtgagcttg   8760
aacctgaaag agagttcgac agaatcaatt tcggtgtcgt tgacggcggc ctggcgcaaa   8820
atctcctgca cgtctcctga gttgtcttga taggcgatct cggccatgaa ctgctcgatc   8880
tcttcctcct ggagatctcc gcgtccggct cgctccacgg tggcggcgag gtcgttggaa   8940
atgcgggcca tgagctgcga gaaggcgttg aggcctccct cgttccagac gcggctgtag   9000
accacgcccc cttcggcatc gcgggcgcgc atgaccacct gcgcgagatt gagctccacg   9060
tgccgggcga agacggcgta gtttcgcagg cgctgaaaga ggtagttgag ggtggtggcg   9120
gtgtgttctg ccacgaagaa gtacataacc cagcgtcgca acgtggattc gttgatatcc   9180
cccaaggcct caaggcgctc catggcctcg tagaagtcca cggcgaagtt gaaaaactgg   9240
gagttgcgcg ccgacacggt taactcctcc tccagaagac ggatgagctc ggcgacagtg   9300
tcgcgcacct cgcgctcaaa ggctacaggg gcctcttctt cttcttcaat ctcctcttcc   9360
ataagggcct ccccttcttc ttcttctggc ggcggtgggg gagggggac acggcggcga    9420
cgacggcgca ccgggaggcg gtcgacaaag cgctcgatca tctccccgcg gcgacggcgc   9480
atggtctcgg tgacggcgcg gccgttctcg cgggggcgca gttggaagac gccgcccgtc   9540
atgtcccggt tatgggttgg cggggggctg ccatgcggca gggatacggc gctaacgatg   9600
catctcaaca attgttgtgt aggtactccg ccgccgaggg acctgagcga gtccgcatcg   9660
accggatcgg aaaacctctc gagaaaggcg tctaaccagt cacagtcgca aggtaggctg   9720
agcaccgtgg cgggcggcag cgggcggcgg tcggggttgt ttctggcgga ggtgctgctg   9780
atgatgtaat taaagtaggc ggtcttgaga cggcggatgg tcgacagaag caccatgtcc   9840
ttgggtccgg cctgctgaat gcgcaggcgg tcggccatgc cccaggcttc gttttgacat   9900
cggcgcaggt ctttgtagta gtcttgcatg agcctttcta ccggcacttc ttcttctcct   9960
tcctcttgtc ctgcatctct tgcatctatc gctgcggcgg cggcggagtt tggccgtagg  10020
tggcgccctc ttcctcccat gcgtgtgacc ccgaagcccc tcatcggctg aagcagggct  10080
aggtcggcga caacgcgctc ggctaatatg gcctgctgca cctgcgtgag ggtagactgg  10140
aagtcatcca tgtccacaaa gcggtggtat gcgcccgtgt tgatggtgta agtgcagttg  10200
gccataacgg accagttaac ggtctggtga cccggctgcg agagctcggt gtacctgaga  10260
cgcgagtaag ccctcgagtc aaatacgtag tcgttgcaag tccgcaccag gtactggtat  10320
cccaccaaaa agtgcggcgg cggctggcgg tagaggggcc agcgtagggt ggccggggct  10380
ccgggggcga gatcttccaa cataaggcga tgatatccgt agatgtacct ggacatccag  10440
```

-continued

```
gtgatgccgg cggcggtggt ggaggcgcgc ggaaagtcgc ggacgcggtt ccagatgttg  10500
cgcagcggca aaaagtgctc catggtcggg acgctctggc cggtcaggcg cgcgcaatcg  10560
ttgacgctct agaccgtgca aaaggagagc ctgtaagcgg gcactcttcc gtggtctggt  10620
ggataaattc gcaagggtat catggcggac gaccggggtt cgagccccgt atccggccgt  10680
ccgccgtgat ccatgcggtt accgcccgcg tgtcgaaccc aggtgtgcga cgtcagacaa  10740
cgggggagtg ctccttttgg cttccttcca ggcgcggcgg ctgctgcgct agcttttttg  10800
gccactggcc gcgcgcagcg taagcggtta ggctggaaag cgaaagcatt aagtggctcg  10860
ctccctgtag ccggagggtt attttccaag ggttgagtcg cgggaccccc ggttcgagtc  10920
tcggaccggc cggactgcgg cgaacggggg tttgcctccc cgtcatgcaa gaccccgctt  10980
gcaaattcct ccggaaacag ggacgagccc ctttttgct tttcccagat gcatccggtg  11040
ctgcggcaga tgcgcccccc tcctcagcag cggcaagagc aagagcagcg gcagacatgc  11100
agggcaccct cccctcctcc taccgcgtca ggaggggcga catccgcggt tgacgcggca  11160
gcagatggtg attacgaacc cccgcggcgc cgggcccggc actacctgga cttggaggag  11220
ggcgagggcc tggcgcggct aggagcgccc tctcctgagc ggcacccaag ggtgcagctg  11280
aagcgtgata cgcgtgaggc gtacgtgccg cggcagaacc tgtttcgcga ccgcgaggga  11340
gaggagcccg aggagatgcg ggatcgaaag ttccacgcag ggcgcgagct gcggcatggc  11400
ctgaatcgcg agcggttgct gcgcgaggag gactttgagc ccgacgcgcg aaccgggatt  11460
agtcccgcgc gcgcacacgt ggcggccgcc gacctggtaa ccgcatacga gcagacggtg  11520
aaccaggaga ttaactttca aaaaagcttt aacaaccacg tgcgtacgct tgtggcgcgc  11580
gaggaggtgg ctataggact gatgcatctg tgggactttg taagcgcgct ggagcaaaac  11640
ccaaatagca agccgctcat ggcgcagctg ttccttatag tgcagcacag cagggacaac  11700
gaggcattca gggatgcgct gctaaacata gtagagcccg agggccgctg gctgctcgat  11760
ttgataaaca tcctgcagag catagtggtg caggagcgca gcttgagcct ggctgacaag  11820
gtggccgcca tcaactattc catgcttagc ctgggcaagt tttacgcccg caagatatac  11880
catacccctt acgttcccat agacaaggag gtaaagatcg aggggttcta catgcgcatg  11940
gcgctgaagg tgcttacctt gagcgacgac ctgggcgttt atcgcaacga gcgcatccac  12000
aaggccgtga gcgtgagccg gcggcgcgag ctcagcgacc gcgagctgat gcacagcctg  12060
caaagggccc tggctggcac gggcagcggc gatagagagg ccgagtccta ctttgacgcg  12120
ggcgctgacc tgcgctgggc cccaagccga cgcgccctgg aggcagctgg ggccggacct  12180
gggctggcgg tggcacccgc gcgcgctggc aacgtcggcg gcgtggagga atatgacgag  12240
gacgatgagt acgagccaga ggacggcgag tactaagcgg tgatgtttct gatcagatga  12300
tgcaagacgc aacggacccg gcggtgcggg cggcgctgca gagccagccg tccggcctta  12360
actccacgga cgactggcgc caggtcatgg accgcatcat gtcgctgact gcgcgcaatc  12420
ctgacgcgtt ccggcagcag ccgcaggcca accggctctc cgcaattctg gaagcggtgg  12480
tcccggcgcg cgcaaacccc acgcacgaga aggtgctggc gatcgtaaac gcgctggccg  12540
aaaacagggc catccggccc gacgaggccg gcctggtcta cgacgcgctg cttcagcgcg  12600
tggctcgtta caacagcggc aacgtgcaga ccaacctgga ccggctggtg ggggatgtgc  12660
gcgaggccgt ggcgcagcgt gagcgcgcgc agcagcaggg caacctgggc tccatggttg  12720
cactaaacgc cttcctgagt acacagcccg ccaacgtgcc gcggggacag gaggactaca  12780
```

-continued

```
ccaactttgt gagcgcactg cggctaatgg tgactgagac accgcaaagt gaggtgtacc  12840
agtctgggcc agactatttt ttccagacca gtagacaagg cctgcagacc gtaaacctga  12900
gccaggcttt caaaaacttg caggggctgt ggggggtgcg ggctcccaca ggcgaccgcg  12960
cgaccgtgtc tagcttgctg acgcccaact cgcgcctgtt gctgctgcta atagcgccct  13020
tcacggacag tggcagcgtg tcccgggaca catacctagg tcacttgctg acactgtacc  13080
gcgaggccat aggtcaggcg catgtggacg agcatacttt ccaggagatt acaagtgtca  13140
gccgcgcgct ggggcaggag gacacgggca gcctggaggc aaccctaaac tacctgctga  13200
ccaaccggcg gcagaagatc ccctcgttgc acagtttaaa cagcgaggag gagcgcattt  13260
tgcgctacgt gcagcagagc gtgagcctta acctgatgcg cgacggggta acgcccagcg  13320
tggcgctgga catgaccgcg cgcaacatgg aaccgggcat gtatgcctca aaccggccgt  13380
ttatcaaccg cctaatggac tacttgcatc gcgcggccgc cgtgaacccc gagtatttca  13440
ccaatgccat cttgaacccg cactggctac cgccccctgg tttctacacc gggggattcg  13500
aggtgcccga gggtaacgat ggattcctct gggacgacat agacgacagc gtgttttccc  13560
cgcaaccgca gaccctgcta gagttgcaac agcgcgagca ggcagaggcg gcgctgcgaa  13620
aggaaagctt ccgcaggcca agcagcttgt ccgatctagg cgctgcggcc ccgcggtcag  13680
atgctagtag cccatttcca agcttgatag ggtctcttac cagcactcgc accacccgcc  13740
cgcgcctgct gggcgaggag gagtacctaa acaactcgct gctgcagccg cagcgcgaaa  13800
aaaacctgcc tccggcattt cccaacaacg ggatagagag cctagtggac aagatgagta  13860
gatggaagac gtacgcgcag gagcacaggg acgtgccagg cccgcgcccg cccacccgtc  13920
gtcaaaggca cgaccgtcag cggggtctgg tgtgggagga cgatgactcg gcagacgaca  13980
gcagcgtcct ggatttggga gggagtggca acccgtttgc gcaccttcgc cccaggctgg  14040
ggagaatgtt ttaaaaaaaa aaaaagcatg atgcaaaata aaaaactcac caaggccatg  14100
gcaccgagcg ttggttttct tgtattcccc ttagtatgcg gcgcgcggcg atgtatgagg  14160
aaggtcctcc tccctcctac gagagtgtgg tgagcgcggc gccagtggcg gcggcgctgg  14220
gttctccctt cgatgctccc ctggacccgc cgtttgtgcc tccgcggtac ctgcggccta  14280
ccggggggag aaacagcatc cgttactctg agttggcacc cctattcgac accacccgtg  14340
tgtacctggt ggacaacaag tcaacggatg tggcatccct gaactaccag aacgaccaca  14400
gcaactttct gaccacggtc attcaaaaca atgactacag cccgggggag gcaagcacac  14460
agaccatcaa tcttgacgac cggtcgcact ggggcggcga cctgaaaacc atcctgcata  14520
ccaacatgcc aaatgtgaac gagttcatgt ttaccaataa gtttaaggcg cgggtgatgg  14580
tgtcgcgctt gcctactaag gacaatcagg tggagctgaa atacgagtgg gtggagttca  14640
cgctgcccga gggcaactac tccgagacca tgaccataga ccttatgaac aacgcgatcg  14700
tggagcacta cttgaaagtg ggcagacaga acggggttct ggaaagcgac atcggggtaa  14760
agtttgacac ccgcaacttc agactggggt ttgaccccgt cactggtctt gtcatgcctg  14820
gggtatatac aaacgaagcc ttccatccag acatcatttt gctgccagga tgcggggtgg  14880
acttcaccca cagccgcctg agcaacttgt tgggcatccg caagcggcaa cccttccagg  14940
agggctttag gatcacctac gatgatctgg agggtggtaa cattcccgca ctgttggatg  15000
tggacgccta ccaggcgagc ttgaaagatg acaccgaaca gggcgggggt ggcgcaggcg  15060
gcagcaacag cagtggcagc ggcgcggaag agaactccaa cgcggcagcc gcggcaatgc  15120
agccggtgga ggacatgaac gatcatgcca ttcgcggcga cacctttgcc acacgggctg  15180
```

-continued

```
aggagaagcg cgctgaggcc gaagcagcgg ccgaagctgc cgccccccgct gcgcaacccg  15240
aggtcgagaa gcctcagaag aaaccggtga tcaaacccct gacagaggac agcaagaaac  15300
gcagttacaa cctaataagc aatgacagca ccttcaccca gtaccgcagc tggtaccttg  15360
catacaacta cggcgaccct cagaccggaa tccgctcatg gaccctgctt tgcactcctg  15420
acgtaacctg cggctcggag caggtctact ggtcgttgcc agacatgatg caagaccccg  15480
tgaccttccg ctccacgcgc cagatcagca actttccggt ggtgggcgcc gagctgttgc  15540
ccgtgcactc caagagcttc tacaacgacc aggccgtcta ctcccaactc atccgccagt  15600
ttacctctct gacccacgtg ttcaatcgct ttcccgagaa ccagattttg gcgcgcccgc  15660
cagcccccac catcaccacc gtcagtgaaa acgttcctgc tctcacagat cacgggacgc  15720
taccgctgcg caacagcatc ggaggagtcc agcgagtgac cattactgac gccagacgcc  15780
gcacctgccc ctacgtttac aaggccctgg gcatagtctc gccgcgcgtc ctatcgagcc  15840
gcactttttg agcaagcatg tccatcctta tatcgcccag caataacaca ggctggggcc  15900
tgcgcttccc aagcaagatg tttggcgggg ccaagaagcg ctccgaccaa cacccagtgc  15960
gcgtgcgcgg gcactaccgc gcgccctggg gcgcgcacaa acgcggccgc actgggcgca  16020
ccaccgtcga tgacgccatc gacgcggtgg tggaggaggc gcgcaactac acgcccacgc  16080
cgccaccagt gtccacagtg gacgcggcca ttcagaccgt ggtgcgcgga gcccggcgct  16140
atgctaaaat gaagagacgg cggaggcgcg tagcacgtcg ccaccgccgc cgacccggca  16200
ctgccgccca acgcgcggcg gcggccctgc ttaaccgcgc acgtcgcacc ggccgacggg  16260
cggccatgcg ggccgctcga aggctggccg cgggtattgt cactgtgccc cccaggtcca  16320
ggcgacgagc ggccgccgca gcagccgcgg ccattagtgc tatgactcag ggtcgcaggg  16380
gcaacgtgta ttgggtgcgc gactcggtta gcggcctgcg cgtgcccgtg cgcacccgcc  16440
ccccgcgcaa ctagattgca agaaaaaact acttagactc gtactgttgt atgtatccag  16500
cggcggcggc gcgcaacgaa gctatgtcca agcgcaaaat caaagaagag atgctccagg  16560
tcatcgcgcc ggagatctat ggccccccga agaaggaaga gcaggattac aagccccgaa  16620
agctaaagcg ggtcaaaaag aaaaagaaag atgatgatga tgaacttgac gacgaggtgg  16680
aactgctgca cgctaccgcg cccaggcgac gggtacagtg gaaaggtcga cgcgtaaaac  16740
gtgttttgcg acccggcacc accgtagtct ttacgcccgg tgagcgctcc acccgcacct  16800
acaagcgcgt gtatgatgag gtgtacggcg acgaggacct gcttgagcag gccaacgagc  16860
gcctcgggga gtttgcctac ggaaagcggc ataaggacat gctggcgttg ccgctggacg  16920
agggcaaccc aacacctagc ctaaagcccg taacactgca gcaggtgctg cccgcgcttg  16980
caccgtccga agaaaagcgc ggcctaaagc gcgagtctgg tgacttggca cccaccgtgc  17040
agctgatggt acccaagcgc cagcgactgg aagatgtctt ggaaaaaatg accgtggaac  17100
ctgggctgga gcccgaggtc cgcgtgcggc caatcaagca ggtggcgccg ggactgggcg  17160
tgcagaccgt ggacgttcag atacccacta ccagtagcac cagtattgcc accgccacag  17220
agggcatgga gacacaaacg tccccggttg cctcagcggt ggcggatgcc gcggtgcagg  17280
cggtcgctgc ggccgcgtcc aagacctcta cggaggtgca aacggacccg tggatgtttc  17340
gcgtttcagc cccccggcgc ccgcgccgtt cgaggaagta cggcgccgcc agcgcgctac  17400
tgcccgaata tgccctacat ccttccattg cgcctacccc cggctatcgt ggctacacct  17460
accgccccag aagacgagca actacccgac gccgaaccac cactggaacc cgccgccgcc  17520
```

-continued gtcgccgtcg ccagcccgtg ctggccccga tttccgtgcg cagggtggct cgcgaaggag 17580
gcaggaccct ggtgctgcca acagcgcgct accaccccag catcgtttaa aagccggtct 17640
ttgtggttct tgcagatatg gccctcacct gccgcctccg tttcccggtg ccgggattcc 17700
gaggaagaat gcaccgtagg aggggcatgg ccggccacgg cctgacgggc ggcatgcgtc 17760
gtgcgcacca ccggcggcgg cgcgcgtcgc accgtcgcat gcgcggcggt atcctgcccc 17820
tccttattcc actgatcgcc gcggcgattg gcgccgtgcc cggaattgca tccgtggcct 17880
tgcaggcgca gagacactga ttaaaaacaa gttgcatgtg gaaaaatcaa aataaaaagt 17940
ctggactctc acgctcgctt ggtcctgtaa ctattttgta gaatggaaga catcaacttt 18000
gcgtctctgg ccccgcgaca cggctcgcgc ccgttcatgg gaaactggca agatatcggc 18060
accagcaata tgagcggtgg cgccttcagc tggggctcgc tgtggagcgg cattaaaaat 18120
ttcggttcca ccgttaagaa ctatggcagc aaggcctgga acagcagcac aggccagatg 18180
ctgagggata agttgaaaga gcaaaatttc caacaaaagg tggtagatgg cctggcctct 18240
ggcattagcg gggtggtgga cctggccaac caggcagtgc aaaataagat taacagtaag 18300
cttgatcccc gccctcccgt agaggagcct ccaccggccg tggagacagt gtctccagag 18360
gggcgtggcg aaaagcgtcc gcgccccgac agggaagaaa ctctggtgac gcaaatagac 18420
gagcctccct cgtacgagga ggcactaaag caaggcctgc ccaccacccg tcccatcgcg 18480
cccatggcta ccggagtgct gggccagcac acacccgtaa cgctggacct gcctcccccc 18540
gccgacaccc agcagaaacc tgtgctgcca ggcccgaccg ccgttgttgt aacccgtcct 18600
agccgcgcgt ccctgcgccg cgccgccagc ggtccgcgat cgttgcggcc cgtagccagt 18660
ggcaactggc aaagcacact gaacagcatc gtgggtctgg gggtgcaatc cctgaagcgc 18720
cgacgatgct tctgatagct aacgtgtcgt atgtgtgtca tgtatgcgtc catgtcgccg 18780
ccagaggagc tgctgagccg ccgcgcgccc gctttccaag atggctaccc cttcgatgat 18840
gccgcagtgg tcttacatgc acatctcggg ccaggacgcc tcggagtacc tgagccccgg 18900
gctggtgcag tttgcccgcg ccaccgagac gtacttcagc ctgaataaca agtttagaaa 18960
ccccacggtg gcgcctacgc acgacgtgac cacagaccgg tcccagcgtt tgacgctgcg 19020
gttcatccct gtggaccgtg aggatactgc gtactcgtac aaggcgcggt tcaccctagc 19080
tgtgggtgat aaccgtgtgc tggacatggc ttccacgtac tttgacatcc gcggcgtgct 19140
ggacaggggc cctactttta agccctactc tggcactgcc tacaacgccc tggctcccaa 19200
gggtgcccca aatccttgcg aatgggatga agctgctact gctcttgaaa taaacctaga 19260
agaagaggac gatgacaacg aagacgaagt agacgagcaa gctgagcagc aaaaaactca 19320
cgtatttggg caggcgcctt attctggtat aaatattaca aaggagggta ttcaaatagg 19380
tgtcgaaggt caaacaccta aatatgccga taaaacattt caacctgaac ctcaaatagg 19440
agaatctcag tggtacgaaa cagaaattaa tcatgcagct gggagagtcc taaaaaagac 19500
taccccaatg aaaccatgtt acggttcata tgcaaaaccc acaaatgaaa atggagggca 19560
aggcattctt gtaaagcaac aaaatggaaa gctagaaagt caagtggaaa tgcaattttt 19620
ctcaactact gaggcagccg caggcaatgg tgataacttg actcctaaag tggtattgta 19680
cagtgaagat gtagatatag aaaccccaga cactcatatt tcttacatgc ccactattaa 19740
ggaaggtaac tcacgagaac taatgggcca acaatctatg cccaacaggc ctaattacat 19800
tgcttttagg gacaatttta ttggtctaat gtattacaac agcacgggta atatgggtgt 19860
tctggcgggc caagcatcgc agttgaatgc tgttgtagat ttgcaagaca gaaacacaga 19920
gctttcatac cagcttttgc ttgattccat tggtgataga accaggtact tttctatgtg 19980
gaatcaggct gttgacagct atgatccaga tgttagaatt attgaaaatc atggaactga 20040
agatgaactt ccaaattact gctttccact gggaggtgtg attaatacag agactcttac 20100
caaggtaaaa cctaaaacag gtcaggaaaa tggatgggaa aaagatgcta cagaattttc 20160
agataaaaat gaaataagag ttggaaataa ttttgccatg gaaatcaatc taaatgccaa 20220
cctgtggaga aatttcctgt actccaacat agcgctgtat ttgcccgaca agctaaagta 20280
cagtccttcc aacgtaaaaa tttctgataa cccaaacacc tacgactaca tgaacaagcg 20340
agtggtggct cccgggctag tggactgcta cattaacctt ggagcacgct ggtcccttga 20400
ctatatggac aacgtcaacc catttaacca ccaccgcaat gctggcctgc gctaccgctc 20460
aatgttgctg ggcaatggtc gctatgtgcc cttccacatc caggtgcctc agaagttctt 20520
tgccattaaa aacctccttc tcctgccggg ctcatacacc tacgagtgga acttcaggaa 20580
ggatgttaac atggttctgc agagctccct aggaaatgac ctaagggttg acggagccag 20640
cattaagttt gatagcattt gcctttacgc caccttcttc cccatggccc acaacaccgc 20700
ctccacgctt gaggccatgc ttagaaacga caccaacgac cagtccttta acgactatct 20760
ctccgccgcc aacatgctct accctatacc cgccaacgct accaacgtgc ccatatccat 20820
cccctcccgc aactgggcgg ctttccgcgg ctgggccttc acgcgcctta agactaagga 20880
aaccccatca ctgggctcgg gctacgaccc ttattacacc tactctggct ctatacccta 20940
cctagatgga accttttacc tcaaccacac ctttaagaag gtggccatta cctttgactc 21000
ttctgtcagc tggcctggca atgaccgcct gcttaccccc aacgagtttg aaattaagcg 21060
ctcagttgac ggggagggtt acaacgttgc ccagtgtaac atgaccaaag actggttcct 21120
ggtacaaatg ctagctaact ataacattgg ctaccagggc ttctatatcc cagagagcta 21180
caaggaccgc atgtactcct tctttagaaa cttccagccc atgagccgtc aggtggtgga 21240
tgatactaaa tacaaggact accaacaggt gggcatccta caccaacaca acaactctgg 21300
atttgttggc taccttgccc ccaccatgcg cgaaggacag gcctaccctg ctaacttccc 21360
ctatccgctt ataggcaaga ccgcagttga cagcattacc cagaaaaagt ttctttgcga 21420
tcgcaccctt tggcgcatcc cattctccag taactttatg tccatgggcg cactcacaga 21480
cctgggccaa aaccttctct acgccaactc cgcccacgcg ctagacatga cttttgaggt 21540
ggatcccatg gacgagccca cccttcttta tgttttgttt gaagtctttg acgtggtccg 21600
tgtgcaccag ccgcaccgcg gcgtcatcga aaccgtgtac ctgcgcacgc ccttctcggc 21660
cggcaacgcc acaacataaa gaagcaagca acatcaacaa cagctgccgc catgggctcc 21720
agtgagcagg aactgaaagc cattgtcaaa gatcttggtt gtgggccata tttttgggc 21780 acctatgaca agcgctttcc aggctttgtt tctccacaca agctcgcctg cgccatagtc 21840
aatacggccg gtcgcgagac tgggggcgta cactggatgg cctttgcctg gaacccgcac 21900
tcaaaaacat gctacctctt tgagcccttt ggcttttctg accagcgact caagcaggtt 21960
taccagtttg agtacgagtc actcctgcgc cgtagcgcca ttgcttcttc ccccgaccgc 22020
tgtataacgc tggaaaagtc cacccaaagc gtacaggggc ccaactcggc cgcctgtgga 22080
ctattctgct gcatgtttct ccacgccttt gccaactggc cccaaactcc catggatcac 22140
aaccccacca tgaaccttat taccggggta cccaactcca tgctcaacag tccccaggta 22200
cagcccaccc tgcgtcgcaa ccaggaacag ctctacagct tcctggagcg ccactcgccc 22260

-continued

```
tacttccgca gccacagtgc gcagattagg agcgccactt ctttttgtca cttgaaaaac  22320
atgtaaaaat aatgtactag agacactttc aataaaggca aatgctttta tttgtacact  22380
ctcgggtgat tatttacccc caccccttgcc gtctgcgccg tttaaaaatc aaaggggttc  22440
tgccgcgcat cgctatgcgc cactggcagg gacacgttgc gatactggtg tttagtgctc  22500
cacttaaact caggcacaac catccgcggc agctcggtga agttttcact ccacaggctg  22560
cgcaccatca ccaacgcgtt tagcaggtcg ggcgccgata tcttgaagtc gcagttgggg  22620
cctccgccct gcgcgcgcga gttgcgatac acagggttgc agcactggaa cactatcagc  22680
gccgggtggt gcacgctggc cagcacgctc ttgtcggaga tcagatccgc gtccaggtcc  22740
tccgcgttgc tcagggcgaa cggagtcaac tttggtagct gccttcccaa aaagggcgcg  22800
tgcccaggct ttgagttgca ctcgcaccgt agtggcatca aaaggtgacc gtgcccggtc  22860
tgggcgttag gatacagcgc ctgcataaaa gccttgatct gcttaaaagc cacctgagcc  22920
tttgcgcctt cagagaagaa catgccgcaa gacttgccgg aaaactgatt ggccggacag  22980
gccgcgtcgt gcacgcagca ccttgcgtcg gtgttggaga tctgcaccac atttcggccc  23040
caccggttct tcacgatctt ggccttgcta gactgctcct tcagcgcgcg ctgcccgttt  23100
tcgctcgtca catccatttc aatcacgtgc tccttattta tcataatgct tccgtgtaga  23160
cacttaagct cgccttcgat ctcagcgcag cggtgcagcc acaacgcgca gcccgtgggc  23220
tcgtgatgct tgtaggtcac ctctgcaaac gactgcaggt acgcctgcag gaatcgcccc  23280
atcatcgtca caaaggtctt gttgctggtg aaggtcagct gcaacccgcg gtgctcctcg  23340
ttcagccagg tcttgcatac ggccgccaga gcttccactt ggtcaggcag tagtttgaag  23400
ttcgccttta gatcgttatc cacgtggtac ttgtccatca gcgcgcgcgc agcctccatg  23460
cccttctccc acgcagacac gatcggcaca ctcagcgggt tcatcaccgt aatttcactt  23520
tccgcttcgc tgggctcttc ctcttcctct tgcgtccgca taccacgcgc cactgggtcg  23580
tcttcattca gccgccgcac tgtgcgctta cctcctttgc catgcttgat tagcaccggt  23640
gggttgctga aacccaccat ttgtagcgcc acatcttctc tttcttcctc gctgtccacg  23700
attacctctg gtgatggcgg gcgctcgggc ttgggagaag ggcgcttctt tttcttcttg  23760
ggcgcaatgg ccaaatccgc cgccgaggtc gatggccgcg ggctgggtgt gcgcggcacc  23820
agcgcgtctt gtgatgagtc ttcctcgtcc tcggactcga tacgccgcct catccgcttt  23880
tttgggggcg cccggggagg cggcggcgac ggggacgggg acgacacgtc ctccatggtt  23940
gggggacgtc gcgccgcacc gcgtccgcgc tcgggggtgg tttcgcgctg ctcctcttcc  24000
cgactggcca tttccttctc ctataggcag aaaaagatca tggagtcagt cgagaagaag  24060
gacagcctaa ccgccccctc tgagttcgcc accaccgcct ccaccgatgc cgccaacgcg  24120
cctaccacct tccccgtcga ggcacccccg cttgaggagg aggaagtgat tatcgagcag  24180
gacccaggtt ttgtaagcga agacgacgag gaccgctcag taccaacaga ggataaaaag  24240
caagaccagg acaacgcaga ggcaaacgag gaacaagtcg ggcgggggga cgaaaggcat  24300
ggcgactacc tagatgtggg agacgacgtg ctgttgaagc atctgcagcg ccagtgcgcc  24360
attatctgcg acgcgttgca agagcgcagc gatgtgcccc tcgccatagc ggatgtcagc  24420
cttgcctacg aacgccacct attctcaccg cgcgtacccc ccaaacgcca agaaaacggc  24480
acatgcgagc ccaacccgcg cctcaacttc taccccgtat ttgccgtgcc agaggtgctt  24540
gccacctatc acatcttttt ccaaaactgc aagatacccc tatcctgccg tgccaaccgc  24600
agccgagcgg acaagcagct ggccttgcgg cagggcgctg tcatacctga tatcgcctcg  24660
```

```
ctcaacgaag tgccaaaaat ctttgagggt cttggacgcg acgagaagcg cgcggcaaac  24720
gctctgcaac aggaaaacag cgaaaatgaa agtcactctg gagtgttggt ggaactcgag  24780
ggtgacaacg cgcgcctagc cgtactaaaa cgcagcatcg aggtcaccca ctttgcctac  24840
ccggcactta acctaccccc caaggtcatg agcacagtca tgagtgagct gatcgtgcgc  24900
cgtgcgcagc ccctggagag ggatgcaaat ttgcaagaac aaacagagga gggcctaccc  24960
gcagttggcg acgagcagct agcgcgctgg cttcaaacgc gcgagcctgc cgacttggag  25020
gagcgacgca aactaatgat ggccgcagtg ctcgttaccg tggagcttga gtgcatgcag  25080
cggttctttg ctgacccgga gatgcagcgc aagctagagg aaacattgca ctacaccttt  25140
cgacagggct acgtacgcca ggcctgcaag atctccaacg tggagctctg caacctggtc  25200
tcctaccttg gaattttgca cgaaaaccgc cttgggcaaa acgtgcttca ttccacgctc  25260
aagggcgagg cgcgccgcga ctacgtccgc gactgcgttt acttatttct atgctacacc  25320
tggcagacgg ccatgggcgt ttggcagcag tgcttggagg agtgcaacct caaggagctg  25380
cagaaactgc taaagcaaaa cttgaaggac ctatggacgg ccttcaacga gcgctccgtg  25440
gccgcgcacc tggcggacat cattttcccc gaacgcctgc ttaaaaccct gcaacagggt  25500
ctgccagact tcaccagtca aagcatgttg cagaacttta ggaactttat cctagagcgc  25560
tcaggaatct tgcccgccac ctgctgtgca cttcctagcg actttgtgcc cattaagtac  25620
cgcgaatgcc ctccgccgct ttggggccac tgctaccttc tgcagctagc caactacctt  25680
gcctaccact ctgacataat ggaagacgtg agcggtgacg gtctactgga gtgtcactgt  25740
cgctgcaacc tatgcacccc gcaccgctcc ctggtttgca attcgcagct gcttaacgaa  25800
agtcaaatta tcggtacctt tgagctgcag ggtccctcgc ctgacgaaaa gtccgcggct  25860
ccggggttga aactcactcc ggggctgtgg acgtcggctt accttcgcaa atttgtacct  25920
gaggactacc acgcccacga gattaggttc tacgaagacc aatcccgccc gcctaatgcg  25980
gagcttaccg cctgcgtcat tacccagggc cacattcttg gccaattgca agccatcaac  26040
aaagcccgcc aagagtttct gctacgaaag ggacgggggg tttacttgga cccccagtcc  26100
ggcgaggagc tcaacccaat ccccccgccg ccgcagccct atcagcagca gccgcgggcc  26160
cttgcttccc aggatggcac ccaaaaagaa gctgcagctg ccgccgccac ccacggacga  26220
ggaggaatac tgggacagtc aggcagagga ggttttggac gaggaggagg aggacatgat  26280
ggaagactgg gagagcctag acgaggaagc ttccgaggtc gaagaggtgt cagacgaaac  26340
accgtcaccc tcggtcgcat tcccctcgcc ggcgccccag aaatcggcaa ccggttccag  26400
catggctaca acctccgctc ctcaggcgcc gccggcactg cccgttcgcc gacccaaccg  26460
tagatgggac accactggaa ccagggccgg taagtccaag cagccgccgc cgttagccca  26520
agagcaacaa cagcgccaag gctaccgctc atggcgcggg cacaagaacg ccatagttgc  26580
ttgcttgcaa gactgtgggg gcaacatctc cttcgcccgc cgctttcttc tctaccatca  26640
cggcgtggcc ttcccccgta acatcctgca ttactaccgt catctctaca gcccatactg  26700
caccggcggc agcggcagca acagcagcgg ccacacagaa gcaaaggcga ccggatagca  26760
agactctgac aaagcccaag aaatccacag cggcggcagc agcaggagga ggagcgctgc  26820
gtctggcgcc caacgaaccc gtatcgaccc gcgagcttag aaacaggatt tttcccactc  26880
tgtatgctat atttcaacag agcaggggcc aagaacaaga gctgaaaata aaaaacaggt  26940
ctctgcgatc cctcacccgc agctgcctgt atcacaaaag cgaagatcag cttcggcgca  27000
```

-continued cgctggaaga cgcggaggct ctcttcagta aatactgcgc gctgactctt aaggactagt 27060
ttcgcgccct ttctcaaatt taagcgcgaa aactacgtca tctccagcgg ccacacccgg 27120 cgcccagcacc tgttgtcagc gccattatga gcaaggaaat tcccacgccc tacatgtgga 27180
gttaccagcc acaaatggga cttgcggctg gagctgccca agactactca acccgaataa 27240
actacatgag cgcgggaccc cacatgatat cccgggtcaa cggaatacgc gcccaccgaa 27300
accgaattct cctggaacag gcggctatta ccaccacacc tcgtaataac cttaatcccc 27360
gtagttggcc cgctgccctg gtgtaccagg aaagtcccgc tcccaccact gtggtacttc 27420
ccagagacgc ccaggccgaa gttcagatga ctaactcagg ggcgcagctt gcgggcggct 27480
ttcgtcacag ggtgcggtcg cccgggcagg gtataactca cctgacaatc agagggcgag 27540
gtattcagct caacgacgag tcggtgagct cctcgcttgg tctccgtccg gacgggacat 27600
ttcagatcgg cggcgccggc cgctcttcat tcacgcctcg tcaggcaatc ctaactctgc 27660
agacctcgtc ctctgagccg cgctctggag gcattggaac tctgcaattt attgaggagt 27720
ttgtgccatc ggtctacttt aaccccttct cgggacctcc cggccactat ccggatcaat 27780
ttattcctaa ctttgacgcg gtaaaggact cggcggacgg ctacgactga atgttaagtg 27840
gagaggcaga gcaactgcgc ctgaaacacc tggtccactg tcgccgccac aagtgctttg 27900
cccgcgactc cggtgagttt tgctactttg aattgcccga ggatcatatc gagggcccgg 27960
cgcacggcgt ccggcttacc gcccagggag agcttgcccg tagcctgatt cgggagttta 28020
cccagcgccc cctgctagtt gagcgggaca ggggaccctg tgttctcact gtgatttgca 28080
actgtcctaa ccctggatta catcaagatc tttgttgcca tctctgtgct gagtataata 28140
aatacagaaa ttaaaatata ctggggctcc tatcgccatc ctgtaaacgc caccgtcttc 28200
acccgcccaa gcaaaccaag gcgaacctta cctggtactt ttaacatctc tccctctgtg 28260
atttacaaca gtttcaaccc agacggagtg agtctacgag agaacctctc cgagctcagc 28320
tactccatca gaaaaaacac caccctcctt acctgccggg aacgtacgat gtggctgcag 28380
agcctgctgc tcttgggcac tgtggcctgc agcatctctg cacccgcccg ctcgcccagc 28440
cccagcacgc agccctggga gcatgtgaat gccatccagg aggcccggcg tctcctgaac 28500
ctgagtagag acactgctgc tgagatgaat gaaacagtag aagtcatctc agaaatgttt 28560
gacctccagg agccgacctg cctacagacc cgcctggagc tgtacaagca gggcctgcgg 28620
ggcagcctca ccaagctcaa gggccccttg accatgatgg ccagccacta caagcagcac 28680
tgccctccaa ccccggaaac ttcctgtgca acccagacta tcacctttga aagtttcaaa 28740
gagaacctga aggactttct gcttgtcatc ccctttgact gctgggagcc agtccaggag 28800
tgacaattga ctctatgtgg gatatgctcc agcgctacaa ccttgaagtc aggcttcctg 28860
gatgtcagca tctgactttg gccagcacct gtcccgcgga tttgttccag tccaactaca 28920
gcgacccacc ctaacagaga tgaccaacac aaccaacgcg gccgccgcta ccggacttac 28980
atctaccaca aatacacccc aagtttctgc ctttgtcaat aactgggata acttgggcat 29040
gtggtggttc tccatagcgc ttatgtttgt atgccttatt attatgtggc tcatctgctg 29100
cctaaagcgc aaacgcgccc gaccacccat ctatagtccc atcattgtgc tacacccaaa 29160
caatgatgga atccatagat tggacggact gaaacacatg ttcttttctc ttacagtatg 29220
attaaatgag acatgattcc tcgagttttt atattactga cccttgttgc gctttttgt 29280 gcgtgctcca cattggctgc ggtttctcac atcgaagtag actgcattcc agccttcaca 29340
gtctatttgc tttacggatt tgtcaccctc acgctcatct gcagcctcat cactgtggtc 29400

-continued

```
atcgccttta tccagtgcat tgactgggtc tgtgtgcgct ttgcatatct cagacaccat  29460
ccccagtaca gggacaggac tatagctgag cttcttagaa ttctttaatt atgaaattta  29520
ctgtgacttt tctgctgatt atttgcaccc tatctgcgtt ttgttccccg acctccaagc  29580
ctcaaagaca tatatcatgc agattcactc gtatatggaa tattccaagt tgctacaatg  29640
aaaaaagcga tctttccgaa gcctggttat atgcaatcat ctctgttatg gtgttctgca  29700
gtaccatctt agccctagct atatatccct accttgacat tggctggaac gcaatagatg  29760
ccatgaacca cccaactttc cccgcgcccg ctatgcttcc actgcaacaa gttgttgccg  29820
gcggctttgt cccagccaat cagcctcgcc caccttctcc cacccccact gaaatcagct  29880
actttaatct aacaggagga gatgactgac accctagatc tagaaatgga cggaattatt  29940
acagagcagc gcctgctaga aagacgcagg gcagcggccg agcaacagcg catgaatcaa  30000
gagctccaag acatggttaa cttgcaccag tgcaaaaggg gtatcttttg tctcgtaaag  30060
caggccaaag tcacctacga cagtaatacc accggacacc gccttagcta caagttgcca  30120
accaagcgtc agaaattggt ggtcatggtg ggagaaaagc ccattaccat aactcagcac  30180
tcggtagaaa ccgaaggctg cattcactca ccttgtcaag gacctgagga tctctgcacc  30240
cttattaaga ccctgtgcgg tctcaaagat cttattccct ttaactaata aaaaaaaata  30300
ataaagcatc acttacttaa aatcagttag caaatttctg tccagtttat tcagcagcac  30360
ctccttgccc tcctcccagc tctggtattg cagcttcctc ctggctgcaa actttctcca  30420
caatctaaat ggaatgtcag tttcctcctg ttcctgtcca tccgcaccca ctatcttcat  30480
gttgttgcag atgaagcgcg caagaccgtc tgaagatacc ttcaaccccg tgtatccata  30540
tgacacggaa accggtcctc caactgtgcc ttttcttact cctccctttg tatcccccaa  30600
tgggtttcaa gagagtcccc ctggggtact ctctttgcgc ctatccgaac ctctagttac  30660
ctccaatggc atgcttgcgc tcaaaatggg caacggcctc tctctggacg aggccggcaa  30720
ccttacctcc caaaatgtaa ccactgtgag cccacctctc aaaaaaacca agtcaaacat  30780
aaacctggaa atatctgcac ccctcacagt tacctcagaa gccctaactg tggctgccgc  30840
cgcacctcta atggtcgcgg gcaacacact caccatgcaa tcacaggccc cgctaaccgt  30900
gcacgactcc aaacttagca ttgccaccca aggacccctc acagtgtcag aaggaaagct  30960
agccctgcaa acatcaggcc ccctcaccac caccgatagc agtaccctta ctatcactgc  31020
ctcacccccct ctaactactg ccactggtag cttgggcatt gacttgaaag agcccattta  31080
tacacaaaat ggaaaactag gactaaagta cggggctcct ttgcatgtaa cagacgacct  31140
aaacactttg accgtagcaa ctggtccagg tgtgactatt aataatactt ccttgcaaac  31200
taaagttact ggagccttgg gttttgattc acaaggcaat atgcaactta atgtagcagg  31260
aggactaagg attgattctc aaaacagacg ccttatactt gatgttagtt atccgtttga  31320
tgctcaaaac caactaaatc taagactagg acagggccct ctttttataa actcagccca  31380
caacttggat attaactaca acaaaggcct ttacttgttt acagcttcaa acaattccaa  31440
aaagcttgag gttaacctaa gcactgccaa ggggttgatg tttgacgcta cagccatagc  31500
cattaatgca ggagatgggc ttgaatttgg ttcacctaat gcaccaaaca caaatcccct  31560
caaaacaaaa attggccatg gcctagaatt tgattcaaac aaggctatgg ttcctaaact  31620
aggaactggc cttagttttg acagcacagg tgccattaca gtaggaaaca aaaataatga  31680
taagctaact ttgtggacca caccagctcc atctcctaac tgtagactaa atgcagagaa  31740
```

-continued

```
agatgctaaa ctcactttgg tcttaacaaa atgtggcagt caaatacttg ctacagtttc  31800
agttttggct gttaaaggca gtttggctcc aatatctgga acagttcaaa gtgctcatct  31860
tattataaga tttgacgaaa atggagtgct actaaacaat tccttcctgg acccagaata  31920
ttggaacttt agaaatggag atcttactga aggcacagcc tatacaaacg ctgttggatt  31980
tatgcctaac ctatcagctt atccaaaatc tcacggtaaa actgccaaaa gtaacattgt  32040
cagtcaagtt tacttaaacg gagacaaaac taaacctgta acactaacca ttacactaaa  32100
cggtacacag gaaacaggag acacaactcc aagtgcatac tctatgtcat tttcatggga  32160
ctggtctggc cacaactaca ttaatgaaat atttgccaca tcctcttaca ctttttcata  32220
cattgcccaa gaataaagaa tcgtttgtgt tatgtttcaa cgtgtttatt tttcaattgc  32280
agaaaatttc aagtcatttt tcattcagta gtatagcccc accaccacat agcttataca  32340
gatcaccgta ccttaatcaa actcacagaa ccctagtatt caacctgcca cctccctccc  32400
aacacacaga gtacacagtc ctttctcccc ggctggcctt aaaaagcatc atatcatggg  32460
taacagacat attcttaggt gttatattcc acacggtttc ctgtcgagcc aaacgctcat  32520
cagtgatatt aataaactcc ccgggcagct cacttaagtt catgtcgctg tccagctgct  32580
gagccacagg ctgctgtcca acttgcggtt gcttaacggg cggcgaagga gaagtccacg  32640
cctacatggg ggtagagtca taatcgtgca tcaggatagg gcggtggtgc tgcagcagcg  32700
cgcgaataaa ctgctgccgc cgccgctccg tcctgcagga atacaacatg gcagtggtct  32760
cctcagcgat gattcgcacc gcccgcagca taaggcgcct tgtcctccgg gcacagcagc  32820
gcaccctgat ctcacttaaa tcagcacagt aactgcagca cagcaccaca atattgttca  32880
aaatcccaca gtgcaaggcg ctgtatccaa agctcatggc ggggaccaca gaacccacgt  32940
ggccatcata ccacaagcgc aggtagatta agtggcgacc cctcataaac acgctggaca  33000
taaacattac ctcttttggc atgttgtaat tcaccacctc ccggtaccat ataaacctct  33060
gattaaacat ggcgccatcc accaccatcc taaaccagct ggccaaaacc tgcccgccgg  33120
ctatacactg cagggaaccg ggactggaac aatgacagtg gagagcccag gactcgtaac  33180
catggatcat catgctcgtc atgatatcaa tgttggcaca acacaggcac acgtgcatac  33240
acttcctcag gattacaagc tcctcccgcg ttagaaccat atcccaggga acaacccatt  33300
cctgaatcag cgtaaatccc acactgcagg gaagacctcg cacgtaactc acgttgtgca  33360
ttgtcaaagt gttacattcg ggcagcagcg gatgatcctc cagtatggta gcgcgggttt  33420
ctgtctcaaa aggaggtaga cgatccctac tgtacggagt gcgccgagac aaccgagatc  33480
gtgttggtcg tagtgtcatg ccaaatggaa cgccggacgt agtcatattt cctgaagcaa  33540
aaccaggtgc gggcgtgaca aacagatctg cgtctccggt ctcgccgctt agatcgctct  33600
gtgtagtagt tgtagtatat ccactctctc aaagcatcca ggcgccccct ggcttcgggt  33660
tctatgtaaa ctccttcatg cgccgctgcc ctgataacat ccaccaccgc agaataagcc  33720
acacccagcc aacctacaca ttcgttctgc gagtcacaca cgggaggagc gggaagagct  33780
ggaagaacca tgtttttttt tttattccaa aagattatcc aaaacctcaa aatgaagatc  33840
tattaagtga acgcgctccc ctccggtggc gtggtcaaac tctacagcca aagaacagat  33900
aatggcattt gtaagatgtt gcacaatggc ttccaaaagg caaacggccc tcacgtccaa  33960
gtggacgtaa aggctaaacc cttcagggtg aatctcctct ataaacattc cagcaccttc  34020
aaccatgccc aaataattct catctcgcca ccttctcaat atatctctaa gcaaatcccg  34080
aatattaagt ccggccattg taaaaatctg ctccagagcg ccctccacct tcagcctcaa  34140
```

gcagcgaatc atgattgcaa aaattcaggt tcctcacaga cctgtataag attcaaaagc 34200
ggaacattaa caaaaatacc gcgatcccgt aggtcccttc gcagggccag ctgaacataa 34260
tcgtgcaggt ctgcacggac cagcgcggcc acttccccgc caggaaccat gacaaaagaa 34320
cccacactga ttatgacacg catactcgga gctatgctaa ccagcgtagc cccgatgtaa 34380
gcttgttgca tgggcggcga tataaaatgc aaggtgctgc tcaaaaaatc aggcaaagcc 34440
tcgcgcaaaa aagaaagcac atcgtagtca tgctcatgca gataaaggca ggtaagctcc 34500
ggaaccacca cagaaaaaga caccattttt ctctcaaaca tgtctgcggg tttctgcata 34560
aacacaaaat aaaataacaa aaaaacattt aaacattaga agcctgtctt acaacaggaa 34620
aaacaaccct tataagcata agacggacta cggccatgcc ggcgtgaccg taaaaaaact 34680
ggtcaccgtg attaaaaagc accaccgaca gctcctcggt catgtccgga gtcataatgt 34740
aagactcggt aaacacatca ggttgattca catcggtcag tgctaaaaag cgaccgaaat 34800
agcccggggg aatacatacc cgcaggcgta gagacaacat tacagccccc ataggaggta 34860
taacaaaatt aataggagag aaaaacacat aaacacctga aaaaccctcc tgcctaggca 34920
aaatagcacc ctcccgctcc agaacaacat acagcgcttc cacagcggca gccataacag 34980
tcagccttac cagtaaaaaa gaaaacctat taaaaaaaca ccactcgaca cggcaccagc 35040
tcaatcagtc acagtgtaaa aaagggccaa gtgcagagcg agtatatata ggactaaaaa 35100
atgacgtaac ggttaaagtc cacaaaaaac acccagaaaa ccgcacgcga acctacgccc 35160
agaaacgaaa gccaaaaaac ccacaacttc ctcaaatcgt cacttccgtt ttcccacgtt 35220
acgtcacttc ccattttaag aaaactacaa ttcccaacac atacaagtta ctccgcccta 35280
aaacctacgt cacccgcccc gttcccacgc cccgcgccac gtcacaaact ccaccccctc 35340
attatcatat tggcttcaat ccaaaataag gtatattatt gatgatgtta attaacatgc 35400
atggatccat atgcggtgtg aaataccgca cagatgcgta aggagaaaat accgcatcag 35460
gcgctcttcc gcttcctcgc tcactgactc gctgcgctcg gtcgttcggc tgcggcgagc 35520
ggtatcagct cactcaaagg cggtaatacg gttatccaca gaatcagggg ataacgcagg 35580
aaagaacatg tgagcaaaag gccagcaaaa ggccaggaac cgtaaaaagg ccgcgttgct 35640
ggcgtttttc cataggctcc gcccccctga cgagcatcac aaaaatcgac gctcaagtca 35700
gaggtggcga aacccgacag gactataaag ataccaggcg tttccccctg gaagctccct 35760
cgtgcgctct cctgttccga ccctgccgct taccggatac ctgtccgcct ttctcccttc 35820
gggaagcgtg gcgctttctc atagctcacg ctgtaggtat ctcagttcgg tgtaggtcgt 35880
tcgctccaag ctgggctgtg tgcacgaacc ccccgttcag cccgaccgct gcgccttatc 35940
cggtaactat cgtcttgagt ccaacccggt aagacacgac ttatcgccac tggcagcagc 36000
cactggtaac aggattagca gagcgaggta tgtaggcggt gctacagagt tcttgaagtg 36060
gtggcctaac tacggctaca ctagaaggac agtatttggt atctgcgctc tgctgaagcc 36120
agttaccttc ggaaaaagag ttggtagctc ttgatccggc aaacaaacca ccgctggtag 36180
cggtggtttt tttgtttgca agcagcagat tacgcgcaga aaaaaaggat ctcaagaaga 36240
tcctttgatc ttttctacgg ggtctgacgc tcagtggaac gaaaactcac gttaagggat 36300
tttggtcatg agattatcaa aaaggatctt cacctagatc cttttaaatt aaaaatgaag 36360
ttttaaatca atctaaagta tatatgagta aacttggtct gacagttacc aatgcttaat 36420
cagtgaggca cctatctcag cgatctgtct atttcgttca tccatagttg cctgactccc 36480

-continued

```
cgtcgtgtag ataactacga tacgggaggg cttaccatct ggccccagtg ctgcaatgat  36540

accgcgagac ccacgctcac cggctccaga tttatcagca ataaaccagc cagccggaag  36600

ggccgagcgc agaagtggtc ctgcaacttt atccgcctcc atccagtcta ttaattgttg  36660

ccgggaagct agagtaagta gttcgccagt taatagtttg cgcaacgttg ttgnnnnnna  36720

aaaaggatct tcacctagat ccttttcacg tagaaagcca gtccgcagaa acggtgctga  36780

ccccggatga atgtcagcta ctgggctatc tggacaaggg aaaacgcaag cgcaaagaga  36840

aagcaggtag cttgcagtgg gcttacatgg cgatagctag actgggcggt tttatggaca  36900

gcaagcgaac cggaattgcc agctggggcg ccctctggta aggttgggaa gccctgcaaa  36960

gtaaactgga tggctttctc gccgccaagg atctgatggc gcaggggatc aagctctgat  37020

caagagacag gatgaggatc gtttcgcatg attgaacaag atggattgca cgcaggttct  37080

ccggccgctt gggtggagag gctattcggc tatgactggg cacaacagac aatcggctgc  37140

tctgatgccg ccgtgttccg gctgtcagcg caggggcgcc cggttctttt tgtcaagacc  37200

gacctgtccg gtgccctgaa tgaactgcaa gacgaggcag cgcggctatc gtggctggcc  37260

acgacgggcg ttccttgcgc agctgtgctc gacgttgtca ctgaagcggg aagggactgg  37320

ctgctattgg gcgaagtgcc ggggcaggat ctcctgtcat ctcaccttgc tcctgccgag  37380

aaagtatcca tcatggctga tgcaatgcgg cggctgcata cgcttgatcc ggctacctgc  37440

ccattcgacc accaagcgaa acatcgcatc gagcgagcac gtactcggat ggaagccggt  37500

cttgtcgatc aggatgatct ggacgaagag catcaggggc tcgcgccagc cgaactgttc  37560

gccaggctca aggcgagcat gcccgacggc gaggatctcg tcgtgaccca tggcgatgcc  37620

tgcttgccga atatcatggt ggaaaatggc cgcttttctg gattcatcga ctgtggccgg  37680

ctgggtgtgg cggaccgcta tcaggacata gcgttggcta cccgtgatat tgctgaagag  37740

cttggcggcg aatgggctga ccgcttcctc gtgctttacg gtatcgccgc tcccgattcg  37800

cagcgcatcg ccttctatcg ccttcttgac gagttcttct gaattttgtt aaaatttttg  37860

ttaaatcagc tcatttttta accaataggc cgaaatcggc aacatccctt ataaatcaaa  37920

agaatagacc gcgatagggt tgagtgttgt tccagtttgg aacaagagtc cactattaaa  37980

gaacgtggac tccaacgtca aagggcgaaa aaccgtctat cagggcgatg gcccactacg  38040

tgaaccatca cccaaatcaa gtttttttgcg gtcgaggtgc cgtaaagctc taaatcggaa  38100

ccctaaaggg agcccccgat ttagagcttg acggggaaag ccggcgaacg tggcgagaaa  38160

ggaagggaag aaagcgaaag gagcgggcgc tagggcgctg gcaagtgtag cggtcacgct  38220

gcgcgtaacc accacacccg cgcgcttaat gcgccgctac agggcgcgtc cattcgccat  38280

tcaggatcga attaattctt aat                                          38303
```

<210> SEQ ID NO 9
<211> LENGTH: 37433
<212> TYPE: DNA
<213> ORGANISM: Artificial Sequence
<220> FEATURE:
<223> OTHER INFORMATION: Ad5-RGD-D24-GMCSF
<220> FEATURE:
<221> NAME/KEY: misc_feature
<222> LOCATION: (36682)..(36682)
<223> OTHER INFORMATION: n is a, c, g, or t

<400> SEQUENCE: 9

```
ggatccgaat tcttaattaa catcatcaat aatatacctt attttggatt gaagccaata     60

tgataatgag gggtggagt ttgtgacgtg gcgcggggcg tgggaacggg gcgggtgacg    120
```

-continued

```
tagtagtgtg gcggaagtgt gatgttgcaa gtgtggcgga acacatgtaa gcgacggatg    180
tggcaaaagt gacgtttttg gtgtgcgccg gtgtacacag gaagtgacaa ttttcgcgcg    240
gttttaggcg gatgttgtag taaatttggg cgtaaccgag taagatttgg ccattttcgc    300
gggaaaactg aataagagga agtgaaatct gaataatttt gtgttactca tagcgcgtaa    360
tatttgtcta gggccgcggg gactttgacc gtttacgtgg agactcgccc aggtgttttt    420
ctcaggtgtt ttccgcgttc cgggtcaaag ttggcgtttt attattatag tcagctgacg    480
tgtagtgtat ttatacccgg tgagttcctc aagaggccac tcttgagtgc cagcgagtag    540
agttttctcc tccgagccgc tccgacaccg ggactgaaaa tgagacatat tatctgccac    600
ggaggtgtta ttaccgaaga aatggccgcc agtcttttgg accagctgat cgaagaggta    660
ctggctgata atcttccacc tcctagccat tttgaaccac ctacccttca cgaactgtat    720
gatttagacg tgacggcccc cgaagatccc aacgaggagg cggtttcgca gatttttccc    780
gactctgtaa tgttggcggt gcaggaaggg attgacttac tcacttttcc gccggcgccc    840
ggttctccgg agccgcctca cctttcccgg cagcccgagc agccggagca gagagccttg    900
ggtccggttt ctatgccaaa ccttgtaccg gaggtgatcg atccacccag tgacgacgag    960
gatgaagagg gtgaggagtt tgtgttagat tatgtggagc accccgggca cggttgcagg   1020
tcttgtcatt atcaccggag gaatacgggg gacccagata ttatgtgttc gctttgctat   1080
atgaggacct gtggcatgtt tgtctacagt aagtgaaaat tatgggcagt gggtgataga   1140
gtggtgggtt tggtgtggta attttttttt taatttttac agttttgtgg tttaaagaat   1200
tttgtattgt gatttttta aaaggtcctg tgtctgaacc tgagcctgag cccgagccag   1260
aaccggagcc tgcaagacct acccgccgtc ctaaaatggc gcctgctatc ctgagacgcc   1320
cgacatcacc tgtgtctaga gaatgcaata gtagtacgga tagctgtgac tccggtcctt   1380
ctaacacacc tcctgagata cacccggtgg tcccgctgtg ccccattaaa ccagttgccg   1440
tgagagttgg tgggcgtcgc caggctgtgg aatgtatcga ggacttgctt aacgagcctg   1500
ggcaaccttt ggacttgagc tgtaaacgcc ccaggccata aggtgtaaac ctgtgattgc   1560
gtgtgtggtt aacgcctttg tttgctgaat gagttgatgt aagtttaata aagggtgaga   1620
taatgtttaa cttgcatggc gtgttaaatg gggcggggct taaagggtat ataatgcgcc   1680
gtgggctaat cttggttaca tctgacctca tggaggcttg ggagtgtttg gaagattttt   1740
ctgctgtgcg taacttgctg gaacagagct ctaacagtac ctcttggttt tggaggtttc   1800
tgtggggctc atcccaggca aagttagtct gcagaattaa ggaggattac aagtgggaat   1860
ttgaagagct tttgaaatcc tgtggtgagc tgtttgattc tttgaatctg ggtcaccagg   1920
cgcttttcca agagaaggtc atcaagactt tggatttttc cacaccgggg cgcgctgcgg   1980
ctgctgttgc tttttgagt tttataaagg ataaatggag cgaagaaacc catctgagcg   2040
gggggtacct gctggatttt ctggccatgc atctgtggag agcggttgtg agacacaaga   2100
atcgcctgct actgttgtct tccgtccgcc cggcgataat accgacggag gagcagcagc   2160
agcagcagga ggaagccagg cggcggcggc aggagcagag cccatggaac ccgagagccg   2220
gcctggaccc tcgggaatga atgttgtaca ggtggctgaa ctgtatccag aactgagacg   2280
cattttgaca attacagagg atgggcaggg gctaaagggg gtaaagaggg agcggggggc   2340
ttgtgaggct acagaggagg ctaggaatct agcttttagc ttaatgacca gacaccgtcc   2400
tgagtgtatt acttttcaac agatcaagga taattgcgct aatgagcttg atctgctggc   2460
```

-continued

```
gcagaagtat tccatagagc agctgaccac ttactggctg cagccagggg atgattttga   2520
ggaggctatt agggtatatg caaaggtggc acttaggcca gattgcaagt acaagatcag   2580
caaacttgta aatatcagga attgttgcta catttctggg aacggggccg aggtggagat   2640
agatacggag gatagggtgg cctttagatg tagcatgata aatatgtggc cgggggtgct   2700
tggcatggac ggggtggtta ttatgaatgt aaggtttact ggccccaatt ttagcggtac   2760
ggttttcctg gccaatacca accttatcct acacggtgta agcttctatg ggtttaacaa   2820
tacctgtgtg gaagcctgga ccgatgtaag ggttcggggc tgtgcctttt actgctgctg   2880
gaagggggtg gtgtgtcgcc ccaaaagcag ggcttcaatt aagaaatgcc tctttgaaag   2940
gtgtaccttg ggtatcctgt ctgagggtaa ctccagggtg cgccacaatg tggcctccga   3000
ctgtggttgc ttcatgctag tgaaaagcgt ggctgtgatt aagcataaca tggtatgtgg   3060
caactgcgag gacagggcct ctcagatgct gacctgctcg gacggcaact gtcacctgct   3120
gaagaccatt cacgtagcca gccactctcg caaggcctgg ccagtgtttg agcataacat   3180
actgacccgc tgttccttgc atttgggtaa caggaggggg gtgttcctac cttaccaatg   3240
caatttgagt cacactaaga tattgcttga gcccgagagc atgtccaagg tgaacctgaa   3300
cggggtgttt gacatgacca tgaagatctg gaaggtgctg aggtacgatg agacccgcac   3360
caggtgcaga ccctgcgagt gtggcggtaa acatattagg aaccagcctg tgatgctgga   3420
tgtgaccgag gagctgaggc ccgatcactt ggtgctggcc tgcacccgcg ctgagtttgg   3480
ctctagcgat gaagatacag attgaggtac tgaaatgtgt gggcgtggct taagggtggg   3540
aaagaatata taaggtgggg gtcttatgta gttttgtatc tgttttgcag cagccgccgc   3600
cgccatgagc accaactcgt ttgatggaag cattgtgagc tcatatttga caacgcgcat   3660
gcccccatgg gccggggtgc gtcagaatgt gatgggctcc agcattgatg gtcgccccgt   3720
cctgcccgca aactctacta ccttgaccta cgagaccgtg tctggaacgc cgttggagac   3780
tgcagcctcc gccgccgctt cagccgctgc agccaccgcc cgcgggattg tgactgactt   3840
tgctttcctg agcccgcttg caagcagtgc agcttcccgt tcatccgccc gcgatgacaa   3900
gttgacggct cttttggcac aattggattc tttgacccgg gaacttaatg tcgtttctca   3960
gcagctgttg gatctgcgcc agcaggtttc tgccctgaag gcttcctccc ctcccaatgc   4020
ggtttaaaac ataaataaaa aaccagactc tgtttggatt tggatcaagc aagtgtcttg   4080
ctgtctttat ttaggggttt tgcgcgcgcg gtaggcccgg gaccagcggt ctcggtcgtt   4140
gagggtcctg tgtatttttt ccaggacgtg gtaaaggtga ctctggatgt tcagatacat   4200
gggcataagc ccgtctctgg ggtggaggta gcaccactgc agagcttcat gctgcggggt   4260
ggtgttgtag atgatccagt cgtagcagga gcgctgggcg tggtgcctaa aaatgtcttt   4320
cagtagcaag ctgattgcca ggggcaggcc cttggtgtaa gtgtttacaa agcggttaag   4380
ctgggatggg tgcatacgtg gggatatgag atgcatcttg gactgtattt ttaggttggc   4440
tatgttccca gccatatccc tccggggatt catgttgtgc agaaccacca gcacagtgta   4500
tccggtgcac ttgggaaatt tgtcatgtag cttagaagga aatgcgtgga agaacttgga   4560
gacgcccttg tgacctccaa gattttccat gcattcgtcc ataatgatgg caatgggccc   4620
acgggcggcg gcctgggcga agatatttct gggatcacta acgtcatagt tgtgttccag   4680
gatgagatcg tcataggcca tttttacaaa gcgcgggcgg agggtgccag actgcggtat   4740
aatggttcca tccggcccag gggcgtagtt accctcacag atttgcattt cccacgcttt   4800
gagttcagat ggggggatca tgtctacctg cggggcgatg aagaaaacgg tttccggggt   4860
```

-continued aggggagatc agctgggaag aaagcaggtt cctgagcagc tgcgacttac cgcagccggt 4920
gggcccgtaa atcacaccta ttaccgggtg caactggtag ttaagagagc tgcagctgcc 4980
gtcatccctg agcagggggg ccacttcgtt aagcatgtcc ctgactcgca tgttttccct 5040
gaccaaatcc gccagaaggc gctcgccgcc cagcgatagc agttcttgca aggaagcaaa 5100
gtttttcaac ggtttgagac cgtccgccgt aggcatgctt ttgagcgttt gaccaagcag 5160
ttccaggcgg tcccacagct cggtcacctg ctctacggca tctcgatcca gcatatctcc 5220
tcgtttcgcg ggttggggcg gctttcgctg tacggcagta gtcggtgctc gtccagacgg 5280
gccagggtca tgtctttcca cgggcgcagg gtcctcgtca gcgtagtctg ggtcacggtg 5340
aaggggtgcg ctccgggctg cgcgctggcc agggtgcgct tgaggctggt cctgctggtg 5400
ctgaagcgct gccggtcttc gccctgcgcg tcggccaggt agcatttgac catggtgtca 5460
tagtccagcc cctccgcggc gtggcccttg gcgcgcagct tgcccttgga ggaggcgccg 5520
cacgaggggc agtgcagact tttgagggcg tagagcttgg gcgcgagaaa taccgattcc 5580
ggggagtagg catccgcgcc gcaggccccg cagacggtct cgcattccac gagccaggtg 5640
agctctggcc gttcggggtc aaaaaccagg tttcccccat gctttttgat gcgtttctta 5700
cctctggttt ccatgagccg gtgtccacgc tcggtgacga aaaggctgtc cgtgtccccg 5760
tatacagact tgagaggcct gtcctcgagc ggtgttccgc ggtcctcctc gtatagaaac 5820
tcggaccact ctgagacaaa ggctcgcgtc caggccagca cgaaggaggc taagtgggag 5880
gggtagcggt cgttgtccac tagggggtcc actcgctcca gggtgtgaag acacatgtcg 5940
ccctcttcgg catcaaggaa ggtgattggt ttgtaggtgt aggccacgtg accgggtgtt 6000
cctgaagggg ggctataaaa gggggtgggg gcgcgttcgt cctcactctc ttccgcatcg 6060
ctgtctgcga gggccagctg ttggggtgag tactccctct gaaaagcggg catgacttct 6120
gcgctaagat tgtcagtttc caaaaacgag gaggatttga tattcacctg gcccgcggtg 6180
atgcctttga gggtggccgc atccatctgg tcagaaaaga caatcttttt gttgtcaagc 6240
ttggtggcaa acgacccgta gagggcgttg gacagcaact tggcgatgga gcgcagggtt 6300
tggtttttgt cgcgatcggc gcgctccttg gccgcgatgt ttagctgcac gtattcgcgc 6360
gcaacgcacc gccattcggg aaagacggtg gtgcgctcgt cgggcaccag gtgcacgcgc 6420
caaccgcggt tgtgcagggt gacaaggtca acgctggtgg ctacctctcc gcgtaggcgc 6480
tcgttggtcc agcagaggcg gccgcccttg cgcgagcaga atggcggtag ggggtctagc 6540
tgcgtctcgt ccgggggggtc tgcgtccacg gtaaagaccc cgggcagcag gcgcgcgtcg 6600
aagtagtcta tcttgcatcc ttgcaagtct agcgcctgct gccatgcgcg ggcggcaagc 6660
gcgcgctcgt atgggttgag tgggggaccc catggcatgg ggtgggtgag cgcggaggcg 6720
tacatgccgc aaatgtcgta aacgtagagg ggctctctga gtattccaag atatgtaggg 6780
tagcatcttc caccgcggat gctggcgcgc acgtaatcgt atagttcgtg cgagggagcg 6840
aggaggtcgg gaccgaggtt gctacgggcg ggctgctctg ctcggaagac tatctgcctg 6900
aagatggcat gtgagttgga tgatatggtt ggacgctgga agacgttgaa gctggcgtct 6960
gtgagaccta ccgcgtcacg cacgaaggag gcgtaggagt cgcgcagctt gttgaccagc 7020
tcggcggtga cctgcacgtc tagggcgcag tagtccaggg tttccttgat gatgtcatac 7080
ttatcctgtc cctttttttt ccacagctcg cggttgagga caaactcttc gcggtctttc 7140
cagtactctt ggatcggaaa cccgtcggcc tccgaacggt aagagcctag catgtagaac 7200

-continued

```
tggttgacgg cctggtaggc gcagcatccc ttttctacgg gtagcgcgta tgcctgcgcg   7260
gccttccgga gcgaggtgtg ggtgagcgca aaggtgtccc tgaccatgac tttgaggtac   7320
tggtatttga agtcagtgtc gtcgcatccg ccctgctccc agagcaaaaa gtccgtgcgc   7380
tttttggaac gcggatttgg cagggcgaag gtgacatcgt tgaagagtat ctttcccgcg   7440
cgaggcataa agttgcgtgt gatgcggaag ggtcccggca cctcggaacg gttgttaatt   7500
acctgggcgg cgagcacgat ctcgtcaaag ccgttgatgt tgtggcccac aatgtaaagt   7560
tccaagaagc gcgggatgcc cttgatggaa ggcaattttt taagttcctc gtaggtgagc   7620
tcttcagggg agctgagccc gtgctctgaa agggcccagt ctgcaagatg agggttggaa   7680
gcgacgaatg agctccacag gtcacgggcc attagcattt gcaggtggtc gcgaaaggtc   7740
ctaaactggc gacctatggc cattttttct ggggtgatgc agtagaaggt aagcgggtct   7800
tgttcccagc ggtcccatcc aaggttcgcg gctaggtctc gcgcggcagt cactagaggc   7860
tcatctccgc cgaacttcat gaccagcatg aagggcacga gctgcttccc aaaggccccc   7920
atccaagtat aggtctctac atcgtaggtg acaaagagac gctcggtgcg aggatgcgag   7980
ccgatcggga agaactggat ctcccgccac caattggagg agtggctatt gatgtggtga   8040
aagtagaagt ccctgcgacg ggccgaacac tcgtgctggc ttttgtaaaa acgtgcgcag   8100
tactggcagc ggtgcacggg ctgtacatcc tgcacgaggt tgacctgacg accgcgcaca   8160
aggaagcaga gtgggaattt gagcccctcg cctggcgggt ttggctggtg gtcttctact   8220
tcggctgctt gtccttgacc gtctggctgc tcgaggggag ttacggtgga tcggaccacc   8280
acgccgcgcg agcccaaagt ccagatgtcc gcgcgcggcg gtcggagctt gatgacaaca   8340
tcgcgcagat gggagctgtc catggtctgg agctcccgcg gcgtcaggtc aggcgggagc   8400
tcctgcaggt ttacctcgca tagacgggtc agggcgcggg ctagatccag gtgataccta   8460
atttccaggg gctggttggt ggcggcgtcg atggcttgca agaggccgca tccccgcggc   8520
gcgactacgg taccgcgcgg cgggcggtgg gccgcggggg tgtccttgga tgatgcatct   8580
aaaagcggtg acgcgggcga gcccccggag gtaggggggg ctccggaccc gccgggagag   8640
ggggcagggg cacgtcggcg ccgcgcgcgg gcaggagctg gtgctgcgcg cgtaggttgc   8700
tggcgaacgc gacgacgcgg cggttgatct cctgaatctg gcgcctctgc gtgaagacga   8760
cgggcccggt gagcttgagc ctgaaagaga gttcgacaga atcaatttcg gtgtcgttga   8820
cggcggcctg gcgcaaaatc tcctgcacgt ctcctgagtt gtcttgatag gcgatctcgg   8880
ccatgaactg ctcgatctct tcctcctgga gatctccgcg tccggctcgc tccacggtgg   8940
cggcgaggtc gttggaaatg cgggccatga gctgcgagaa ggcgttgagg cctccctcgt   9000
tccagacgcg gctgtagacc acgccccctt cggcatcgcg ggcgcgcatg accacctgcg   9060
cgagattgag ctccacgtgc cgggcgaaga cggcgtagtt tcgcaggcgc tgaaagaggt   9120
agttgagggt ggtggcggtg tgttctgcca cgaagaagta cataacccag cgtcgcaacg   9180
tggattcgtt gatatccccc aaggcctcaa ggcgctccat ggcctcgtag aagtccacgg   9240
cgaagttgaa aaactgggag ttgcgcgccg acacggttaa ctcctcctcc agaagacgga   9300
tgagctcggc gacagtgtcg cgcacctcgc gctcaaaggc tacaggggcc tcttcttctt   9360
cttcaatctc ctcttccata agggcctccc cttcttcttc ttctggcggc ggtgggggag   9420
gggggacacg gcggcgacga cggcgcaccg ggaggcggtc gacaaagcgc tcgatcatct   9480
ccccgcggcg acggcgcatg gtctcggtga cggcgcggcc gttctcgcgg gggcgcagtt   9540
ggaagacgcc gcccgtcatg tcccggttat gggttggcgg ggggctgcca tgcggcaggg   9600
```

-continued

```
atacggcgct aacgatgcat ctcaacaatt gttgtgtagg tactccgccg ccgagggacc   9660
tgagcgagtc cgcatcgacc ggatcggaaa acctctcgag aaaggcgtct aaccagtcac   9720
agtcgcaagg taggctgagc accgtggcgg gcggcagcgg gcggcggtcg gggttgtttc   9780
tggcggaggt gctgctgatg atgtaattaa agtaggcggt cttgagacgg cggatggtcg   9840
acagaagcac catgtccttg ggtccggcct gctgaatgcg caggcggtcg gccatgcccc   9900
aggcttcgtt ttgacatcgg cgcaggtctt tgtagtagtc ttgcatgagc ctttctaccg   9960
gcacttcttc ttctccttcc tcttgtcctg catctcttgc atctatcgct gcggcggcgg  10020
cggagtttgg ccgtaggtgg cgccctcttc ctcccatgcg tgtgaccccg aagcccctca  10080
tcggctgaag cagggctagg tcggcgacaa cgcgctcggc taatatggcc tgctgcacct  10140
gcgtgagggt agactggaag tcatccatgt ccacaaagcg gtggtatgcg cccgtgttga  10200
tggtgtaagt gcagttggcc ataacggacc agttaacggt ctggtgaccc ggctgcgaga  10260
gctcggtgta cctgagacgc gagtaagccc tcgagtcaaa tacgtagtcg ttgcaagtcc  10320
gcaccaggta ctggtatccc accaaaaagt gcggcggcgg ctggcggtag aggggccagc  10380
gtagggtggc cggggctccg ggggcgagat cttccaacat aaggcgatga tatccgtaga  10440
tgtacctgga catccaggtg atgccggcgg cggtggtgga ggcgcgcgga aagtcgcgga  10500
cgcggttcca gatgttgcgc agcggcaaaa agtgctccat ggtcgggacg ctctggccgg  10560
tcaggcgcgc gcaatcgttg acgctctaga ccgtgcaaaa ggagagcctg taagcgggca  10620
ctcttccgtg gtctggtgga taaattcgca agggtatcat ggcggacgac cggggttcga  10680
gccccgtatc cggccgtccg ccgtgatcca tgcggttacc gcccgcgtgt cgaacccagg  10740
tgtgcgacgt cagacaacgg gggagtgctc cttttggctt ccttccaggc gcggcggctg  10800
ctgcgctagc ttttttggcc actggccgcg cgcagcgtaa gcggttaggc tggaaagcga  10860
aagcattaag tggctcgctc cctgtagccg gagggttatt ttccaagggt tgagtcgcgg  10920
gacccccggt tcgagtctcg gaccggccgg actgcggcga acgggggttt gcctccccgt  10980
catgcaagac cccgcttgca aattcctccg gaaacaggga cgagcccctt ttttgctttt  11040
cccagatgca tccggtgctg cggcagatgc gccccccctcc tcagcagcgg caagagcaag  11100
agcagcggca gacatgcagg gcaccctccc ctcctcctac cgcgtcagga ggggcgacat  11160
ccgcggttga cgcggcagca gatggtgatt acgaaccccc gcggcgccgg gcccggcact  11220
acctggactt ggaggagggc gagggcctgg cgcggctagg agcgccctct cctgagcggt  11280
acccaagggt gcagctgaag cgtgatacgc gtgaggcgta cgtgccgcgg cagaacctgt  11340
ttcgcgaccg cgagggagag gagcccgagg agatgcggga tcgaaagttc cacgcagggc  11400
gcgagctgcg gcatggcctg aatcgcgagc ggttgctgcg cgaggaggac tttgagcccg  11460
acgcgcgaac cgggattagt cccgcgcgcg cacacgtggc ggccgccgac ctggtaaccg  11520
catacgagca gacggtgaac caggagatta actttcaaaa aagctttaac aaccacgtgc  11580
gtacgcttgt ggcgcgcgag gaggtggcta taggactgat gcatctgtgg gactttgtaa  11640
gcgcgctgga gcaaaaccca aatagcaagc cgctcatggc gcagctgttc cttatagtgc  11700
agcacagcag ggacaacgag gcattcaggg atgcgctgct aaacatagta gagcccgagg  11760
gccgctggct gctcgatttg ataaacatcc tgcagagcat agtggtgcag gagcgcagct  11820
tgagcctggc tgacaaggtg gccgccatca actattccat gcttagcctg ggcaagtttt  11880
acgcccgcaa gatataccat accccttacg ttcccataga caaggaggta aagatcgagg  11940
```

-continued

```
ggttctacat gcgcatggcg ctgaaggtgc ttaccttgag cgacgacctg ggcgtttatc  12000
gcaacgagcg catccacaag gccgtgagcg tgagccggcg gcgcgagctc agcgaccgcg  12060
agctgatgca cagcctgcaa agggccctgg ctggcacggg cagcggcgat agagaggccg  12120
agtcctactt tgacgcgggc gctgacctgc gctgggcccc aagccgacgc gccctggagg  12180
cagctggggc cggacctggg ctggcggtgg cacccgcgcg cgctggcaac gtcggcggcg  12240
tggaggaata tgacgaggac gatgagtacg agccagagga cggcgagtac taagcggtga  12300
tgtttctgat cagatgatgc aagacgcaac ggacccggcg gtgcgggcgg cgctgcagag  12360
ccagccgtcc ggccttaact ccacggacga ctggcgccag gtcatggacc gcatcatgtc  12420
gctgactgcg cgcaatcctg acgcgttccg gcagcagccg caggccaacc ggctctccgc  12480
aattctggaa gcggtggtcc cggcgcgcgc aaaccccacg cacgagaagg tgctggcgat  12540
cgtaaacgcg ctggccgaaa acagggccat ccggcccgac gaggccggcc tggtctacga  12600
cgcgctgctt cagcgcgtgg ctcgttacaa cagcggcaac gtgcagacca acctggaccg  12660
gctggtgggg gatgtgcgcg aggccgtggc gcagcgtgag cgcgcgcagc agcagggcaa  12720
cctgggctcc atggttgcac taaacgcctt cctgagtaca cagcccgcca acgtgccgcg  12780
gggacaggag gactacacca actttgtgag cgcactgcgg ctaatggtga ctgagacacc  12840
gcaaagtgag gtgtaccagt ctgggccaga ctatttttc cagaccagta gacaaggcct  12900
gcagaccgta aacctgagcc aggctttcaa aaacttgcag gggctgtggg gggtgcgggc  12960
tcccacaggc gaccgcgcga ccgtgtctag cttgctgacg cccaactcgc gcctgttgct  13020
gctgctaata gcgcccttca cggacagtgg cagcgtgtcc cgggacacat acctaggtca  13080
cttgctgaca ctgtaccgcg aggccatagg tcaggcgcat gtggacgagc atactttcca  13140
ggagattaca agtgtcagcc gcgcgctggg gcaggaggac acgggcagcc tggaggcaac  13200
cctaaactac ctgctgacca accggcggca gaagatcccc tcgttgcaca gtttaaacag  13260
cgaggaggag cgcattttgc gctacgtgca gcagagcgtg agccttaacc tgatgcgcga  13320
cggggtaacg cccagcgtgg cgctggacat gaccgcgcgc aacatggaac cgggcatgta  13380
tgcctcaaac cggccgttta tcaaccgcct aatggactac ttgcatcgcg cggccgccgt  13440
gaaccccgag tatttcacca atgccatctt gaacccgcac tggctaccgc cccctggttt  13500
ctacaccggg ggattcgagg tgcccgaggg taacgatgga ttcctctggg acgacataga  13560
cgacagcgtg ttttccccgc aaccgcagac cctgctagag ttgcaacagc gcgagcaggc  13620
agaggcggcg ctgcgaaagg aaagcttccg caggccaagc agcttgtccg atctaggcgc  13680
tgcggccccg cggtcagatg ctagtagccc atttccaagc ttgatagggt ctcttaccag  13740
cactcgcacc acccgcccgc gcctgctggg cgaggaggag tacctaaaca actcgctgct  13800
gcagccgcag cgcgaaaaaa acctgcctcc ggcatttccc aacaacggga tagagagcct  13860
agtggacaag atgagtagat ggaagacgta cgcgcaggag cacagggacg tgccaggccc  13920
gcgcccgccc acccgtcgtc aaaggcacga ccgtcagcgg ggtctggtgt gggaggacga  13980
tgactcggca gacgacagca gcgtcctgga tttgggaggg agtggcaacc cgtttgcgca  14040
ccttcgcccc aggctgggga gaatgtttta aaaaaaaaaa agcatgatgc aaaataaaaa  14100
actcaccaag gccatggcac cgagcgttgg ttttcttgta ttccccttag tatgcggcgc  14160
gcggcgatgt atgaggaagg tcctcctccc tcctacgaga gtgtggtgag cgcggcgcca  14220
gtggcggcgg cgctgggttc tcccttcgat gctcccctgg acccgccgtt tgtgcctccg  14280
cggtacctgc ggcctaccgg ggggagaaac agcatccgtt actctgagtt ggcacccta  14340
```

ttcgacacca cccgtgtgta cctggtggac aacaagtcaa cggatgtggc atccctgaac 14400
taccagaacg accacagcaa ctttctgacc acggtcattc aaaacaatga ctacagcccg 14460
ggggaggcaa gcacacagac catcaatctt gacgaccggt cgcactgggg cggcgacctg 14520
aaaaccatcc tgcataccaa catgccaaat gtgaacgagt tcatgtttac caataagttt 14580
aaggcgcggg tgatggtgtc gcgcttgcct actaaggaca atcaggtgga gctgaaatac 14640
gagtgggtgg agttcacgct gcccgagggc aactactccg agaccatgac catagacctt 14700
atgaacaacg cgatcgtgga gcactacttg aaagtgggca gacagaacgg ggttctggaa 14760
agcgacatcg ggtaaagtt tgacacccgc aacttcagac tggggtttga ccccgtcact 14820
ggtcttgtca tgcctggggt atatacaaac gaagccttcc atccagacat cattttgctg 14880
ccaggatgcg gggtggactt cacccacagc cgcctgagca acttgttggg catccgcaag 14940
cggcaaccct tccaggaggg ctttaggatc acctacgatg atctggaggg tggtaacatt 15000
cccgcactgt tggatgtgga cgcctaccag gcgagcttga aagatgacac cgaacagggc 15060
gggggtggcg caggcggcag caacagcagt ggcagcggcg cggaagagaa ctccaacgcg 15120
gcagccgcgg caatgcagcc ggtggaggac atgaacgatc atgccattcg cggcgacacc 15180
tttgccacac gggctgagga gaagcgcgct gaggccgaag cagcggccga agctgccgcc 15240
cccgctgcgc aacccgaggt cgagaagcct cagaagaaac cggtgatcaa acccctgaca 15300
gaggacagca agaaacgcag ttacaaccta ataagcaatg acagcacctt cacccagtac 15360
cgcagctggt accttgcata caactacggc gaccctcaga ccggaatccg ctcatggacc 15420
ctgctttgca ctcctgacgt aacctgcggc tcggagcagg tctactggtc gttgccagac 15480
atgatgcaag accccgtgac cttccgctcc acgcgccaga tcagcaactt tccggtggtg 15540
ggcgccgagc tgttgcccgt gcactccaag agcttctaca acgaccaggc cgtctactcc 15600
caactcatcc gccagtttac ctctctgacc cacgtgttca atcgctttcc cgagaaccag 15660
attttggcgc gcccgccagc cccccaccatc accaccgtca gtgaaaacgt tcctgctctc 15720
acagatcacg ggacgctacc gctgcgcaac agcatcggag gagtccagcg agtgaccatt 15780
actgacgcca gacgccgcac ctgcccctac gtttacaagg ccctgggcat agtctcgccg 15840
cgcgtcctat cgagccgcac tttttgagca agcatgtcca tccttatatc gcccagcaat 15900
aacacaggct ggggcctgcg cttcccaagc aagatgtttg gcggggccaa gaagcgctcc 15960
gaccaacacc cagtgcgcgt gcgcgggcac taccgcgcgc cctggggcgc gcacaaacgc 16020
ggccgcactg ggcgcaccac cgtcgatgac gccatcgacg cggtggtgga ggaggcgcgc 16080
aactacacgc ccacgccgcc accagtgtcc acagtggacg cggccattca gaccgtggtg 16140
cgcggagccc ggcgctatgc taaaatgaag agacggcgga ggcgcgtagc acgtcgccac 16200
cgccgccgac ccggcactgc cgcccaacgc gcggcggcgg ccctgcttaa ccgcgcacgt 16260
cgcaccggcc gacgggcggc catgcgggcc gctcgaaggc tggccgcggg tattgtcact 16320
gtgcccccca ggtccaggcg acgagcggcc gccgcagcag ccgcggccat tagtgctatg 16380
actcagggtc gcaggggcaa cgtgtattgg gtgcgcgact cggttagcgg cctgcgcgtg 16440
cccgtgcgca cccgcccccc gcgcaactag attgcaagaa aaaactactt agactcgtac 16500
tgttgtatgt atccagcggc ggcggcgcgc aacgaagcta tgtccaagcg caaaatcaaa 16560
gaagagatgc tccaggtcat cgcgccggag atctatggcc ccccgaagaa ggaagagcag 16620
gattacaagc cccgaaagct aaagcgggtc aaaaagaaaa agaaagatga tgatgatgaa 16680

-continued

```
cttgacgacg aggtggaact gctgcacgct accgcgccca ggcgacgggt acagtggaaa  16740
ggtcgacgcg taaaacgtgt tttgcgaccc ggcaccaccg tagtctttac gcccggtgag  16800
cgctccaccc gcacctacaa gcgcgtgtat gatgaggtgt acggcgacga ggacctgctt  16860
gagcaggcca acgagcgcct cggggagttt gcctacggaa agcggcataa ggacatgctg  16920
gcgttgccgc tggacgaggg caacccaaca cctagcctaa agcccgtaac actgcagcag  16980
gtgctgcccg cgcttgcacc gtccgaagaa aagcgcggcc taaagcgcga gtctggtgac  17040
ttggcaccca ccgtgcagct gatggtaccc aagcgccagc gactggaaga tgtcttggaa  17100
aaaatgaccg tggaacctgg gctggagccc gaggtccgcg tgcggccaat caagcaggtg  17160
gcgccgggac tgggcgtgca gaccgtggac gttcagatac ccactaccag tagcaccagt  17220
attgccaccg ccacagaggg catggagaca caaacgtccc cggttgcctc agcggtggcg  17280
gatgccgcgg tgcaggcggt cgctgcggcc gcgtccaaga cctctacgga ggtgcaaacg  17340
gacccgtgga tgtttcgcgt ttcagccccc cggcgcccgc gcggttcgag gaagtacggc  17400
gccgccagcg cgctactgcc cgaatatgcc ctacatcctt ccattgcgcc tacccccggc  17460
tatcgtggct acacctaccg ccccagaaga cgagcaacta cccgacgccg aaccaccact  17520
ggaacccgcc gccgccgtcg ccgtcgccag cccgtgctgg ccccgatttc cgtgcgcagg  17580
gtggctcgcg aaggaggcag gaccctggtg ctgccaacag cgcgctacca ccccagcatc  17640
gtttaaaagc cggtctttgt ggttcttgca gatatggccc tcacctgccg cctccgtttc  17700
ccggtgccgg gattccgagg aagaatgcac cgtaggaggg gcatggccgg ccacggcctg  17760
acgggcggca tgcgtcgtgc gcaccaccgg cggcggcgcg cgtcgcaccg tcgcatgcgc  17820
ggcggtatcc tgcccctcct tattccactg atcgccgcgg cgattggcgc cgtgcccgga  17880
attgcatccg tggccttgca ggcgcagaga cactgattaa aaacaagttg catgtggaaa  17940
aatcaaaata aaaagtctgg actctcacgc tcgcttggtc ctgtaactat tttgtagaat  18000
ggaagacatc aactttgcgt ctctggcccc gcgacacggc tcgcgcccgt tcatgggaaa  18060
ctggcaagat atcggcacca gcaatatgag cggtggcgcc ttcagctggg gctcgctgtg  18120
gagcggcatt aaaaatttcg gttccaccgt taagaactat ggcagcaagg cctggaacag  18180
cagcacaggc cagatgctga gggataagtt gaaagagcaa aatttccaac aaaaggtggt  18240
agatggcctg gcctctggca ttagcggggt ggtggacctg gccaaccagg cagtgcaaaa  18300
taagattaac agtaagcttg atccccgccc tcccgtagag gagcctccac cggccgtgga  18360
gacagtgtct ccagaggggc gtggcgaaaa gcgtccgcgc cccgacaggg aagaaactct  18420
ggtgacgcaa atagacgagc ctccctcgta cgaggaggca ctaaagcaag gcctgcccac  18480
cacccgtccc atcgcgccca tggctaccgg agtgctgggc cagcacacac ccgtaacgct  18540
ggacctgcct ccccccgccg acacccagca gaaacctgtg ctgccaggcc cgaccgccgt  18600
tgttgtaacc cgtcctagcc gcgcgtccct gcgccgcgcc gccagcggtc cgcgatcgtt  18660
gcggcccgta gccagtggca actggcaaag cacactgaac agcatcgtgg gtctgggggt  18720
gcaatccctg aagcgccgac gatgcttctg aatagctaac gtgtcgtatg tgtgtcatgt  18780
atgcgtccat gtcgccgcca gaggagctgc tgagccgccg cgcgcccgct ttccaagatg  18840
gctacccctt cgatgatgcc gcagtggtct tacatgcaca tctcgggcca ggacgcctcg  18900
gagtacctga gccccgggct ggtgcagttt gcccgcgcca ccgagacgta cttcagcctg  18960
aataacaagt ttagaaaccc cacggtggcg cctacgcacg acgtgaccac agaccggtcc  19020
cagcgtttga cgctgcggtt catccctgtg gaccgtgagg atactgcgta ctcgtacaag  19080
```

-continued

```
gcgcggttca ccctagctgt gggtgataac cgtgtgctgg acatggcttc cacgtacttt  19140
gacatccgcg gcgtgctgga caggggccct acttttaagc cctactctgg cactgcctac  19200
aacgccctgg ctcccaaggg tgccccaaat ccttgcgaat gggatgaagc tgctactgct  19260
cttgaaataa acctagaaga agaggacgat gacaacgaag acgaagtaga cgagcaagct  19320
gagcagcaaa aaactcacgt atttgggcag gcgccttatt ctggtataaa tattacaaag  19380
gagggtattc aaataggtgt cgaaggtcaa acacctaaat atgccgataa aacatttcaa  19440
cctgaacctc aaataggaga atctcagtgg tacgaaactg aaattaatca tgcagctggg  19500
agagtcctta aaaagactac cccaatgaaa ccatgttacg gttcatatgc aaaacccaca  19560
aatgaaaatg gagggcaagg cattcttgta aagcaacaaa atggaaagct agaaagtcaa  19620
gtggaaatgc aatttttctc aactactgag gcgaccgcag gcaatggtga taacttgact  19680
cctaaagtgg tattgtacag tgaagatgta gatatagaaa ccccagacac tcatatttct  19740
tacatgccca ctattaagga aggtaactca cgagaactaa tgggccaaca atctatgccc  19800
aacaggccta attacattgc ttttagggac aattttattg gtctaatgta ttacaacagc  19860
acgggtaata tgggtgttct ggcgggccaa gcatcgcagt tgaatgctgt tgtagatttg  19920
caagacagaa acacagagct ttcataccag cttttgcttg attccattgg tgatagaacc  19980
aggtactttt ctatgtggaa tcaggctgtt gacagctatg atccagatgt tagaattatt  20040
gaaaatcatg gaactgaaga tgaacttcca aattactgct ttccactggg aggtgtgatt  20100
aatacagaga ctcttaccaa ggtaaaacct aaaacaggtc aggaaaatgg atgggaaaaa  20160
gatgctacag aattttcaga taaaaatgaa ataagagttg gaaataattt tgccatggaa  20220
atcaatctaa atgccaacct gtggagaaat ttcctgtact ccaacatagc gctgtatttg  20280
cccgacaagc taaagtacag tccttccaac gtaaaaattt ctgataaccc aaacacctac  20340
gactacatga acaagcgagt ggtggctccc gggttagtgg actgctacat taaccttgga  20400
gcacgctggt cccttgacta tatggacaac gtcaacccat ttaaccacca ccgcaatgct  20460
ggcctgcgct accgctcaat gttgctgggc aatggtcgct atgtgccctt ccacatccag  20520
gtgcctcaga agttctttgc cattaaaaac ctccttctcc tgccgggctc atacacctac  20580
gagtggaact tcaggaagga tgttaacatg gttctgcaga gctccctagg aaatgaccta  20640
agggttgacg gagccagcat taagtttgat agcatttgcc tttacgccac cttcttcccc  20700
atggcccaca acaccgcctc cacgcttgag gccatgctta gaaacgacac caacgaccag  20760
tcctttaacg actatctctc cgccgccaac atgctctacc ctatacccgc caacgctacc  20820
aacgtgccca tatccatccc ctcccgcaac tgggcggctt tccgcggctg ggccttcacg  20880
cgccttaaga ctaaggaaac cccatcactg ggctcgggct acgaccctta ttacacctac  20940
tctggctcta taccctacct agatggaacc ttttacctca accacacctt taagaaggtg  21000
gccattacct ttgactcttc tgtcagctgg cctggcaatg accgcctgct tacccccaac  21060
gagtttgaaa ttaagcgctc agttgacggg gagggttaca acgttgccca gtgtaacatg  21120
accaaagact ggttcctggt acaaatgcta gctaactaca acattggcta ccagggcttc  21180
tatatcccag agagctacaa ggaccgcatg tactccttct ttagaaactt ccagcccatg  21240
agccgtcagg tggtggatga tactaaatac aaggactacc aacaggtggg catcctacac  21300
caacacaaca actctggatt tgttggctac cttgccccca ccatgcgcga aggacaggcc  21360
taccctgcta acttccccta tccgcttata ggcaagaccg cagttgacag cattacccag  21420
```

-continued

```
aaaaagtttc tttgcgatcg caccctttgg cgcatcccat tctccagtaa ctttatgtcc  21480
atgggcgcac tcacagacct gggccaaaac cttctctacg ccaactccgc ccacgcgcta  21540
gacatgactt ttgaggtgga tcccatggac gagcccaccc ttctttatgt tttgtttgaa  21600
gtctttgacg tggtccgtgt gcaccggccg caccgcggcg tcatcgaaac cgtgtacctg  21660
cgcacgccct tctcggccgg caacgccaca acataaagaa gcaagcaaca tcaacaacag  21720
ctgccgccat gggctccagt gagcaggaac tgaaagccat tgtcaaagat cttggttgtg  21780
ggccatattt tttgggcacc tatgacaagc gctttccagg ctttgtttct ccacacaagc  21840
tcgcctgcgc catagtcaat acggccggtc gcgagactgg gggcgtacac tggatggcct  21900
ttgcctggaa cccgcactca aaaacatgct acctctttga gccctttggc ttttctgacc  21960
agcgactcaa gcaggtttac cagtttgagt acgagtcact cctgcgccgt agcgccattg  22020
cttcttcccc cgaccgctgt ataacgctgg aaaagtccac ccaaagcgta caggggccca  22080
actcggccgc ctgtggacta ttctgctgca tgtttctcca cgcctttgcc aactggcccc  22140
aaactcccat ggatcacaac cccaccatga accttattac cggggtaccc aactccatgc  22200
tcaacagtcc ccaggtacag cccaccctgc gtcgcaacca ggaacagctc tacagcttcc  22260
tggagcgcca ctcgccctac ttccgcagcc acagtgcgca gattaggagc gccacttctt  22320
tttgtcactt gaaaaacatg taaaaataat gtactagaga cactttcaat aaaggcaaat  22380
gcttttattt gtacactctc gggtgattat ttacccccac ccttgccgtc tgcgccgttt  22440
aaaaatcaaa ggggttctgc cgcgcatcgc tatgcgccac tggcagggac acgttgcgat  22500
actggtgttt agtgctccac ttaaactcag gcacaaccat ccgcggcagc tcggtgaagt  22560
tttcactcca caggctgcgc accatcacca acgcgtttag caggtcgggc gccgatatct  22620
tgaagtcgca gttggggcct ccgccctgcg cgcgcgagtt gcgatacaca gggttgcagc  22680
actggaacac tatcagcgcc gggtggtgca cgctggccag cacgctcttg tcggagatca  22740
gatccgcgtc caggtcctcc gcgttgctca gggcgaacgg agtcaacttt ggtagctgcc  22800
ttcccaaaaa gggcgcgtgc ccaggctttg agttgcactc gcaccgtagt ggcatcaaaa  22860
ggtgaccgtg cccggtctgg gcgttaggat acagcgcctg cataaaagcc ttgatctgct  22920
taaaagccac ctgagccttt gcgccttcag agaagaacat gccgcaagac ttgccggaaa  22980
actgattggc cggacaggcc gcgtcgtgca cgcagcacct tgcgtcggtg ttggagatct  23040
gcaccacatt tcggccccac cggttcttca cgatcttggc cttgctagac tgctccttca  23100
gcgcgcgctg cccgttttcg ctcgtcacat ccatttcaat cacgtgctcc ttatttatca  23160
taatgcttcc gtgtagacac ttaagctcgc cttcgatctc agcgcagcgg tgcagccaca  23220
acgcgcagcc cgtgggctcg tgatgcttgt aggtcacctc tgcaaacgac tgcaggtacg  23280
cctgcaggaa tcgccccatc atcgtcacaa aggtcttgtt gctggtgaag gtcagctgca  23340
acccgcggtg ctcctcgttc agccaggtct tgcatacggc cgccagagct tccacttggt  23400
caggcagtag tttgaagttc gcctttagat cgttatccac gtggtacttg tccatcagcg  23460
cgcgcgcagc ctccatgccc ttctcccacg cagacacgat cggcacactc agcgggttca  23520
tcaccgtaat ttcactttcc gcttcgctgg gctcttcctc ttcctcttgc gtccgcatac  23580
cacgcgccac tgggtcgtct tcattcagcc gccgcactgt gcgcttacct cctttgccat  23640
gcttgattag caccggtggg ttgctgaaac ccaccatttg tagcgccaca tcttctcttt  23700
cttcctcgct gtccacgatt acctctggtg atggcgggcg ctcgggcttg ggagaagggc  23760
gcttcttttt cttcttgggc gcaatggcca aatccgccgc cgaggtcgat ggccgcgggc  23820
```

tgggtgtgcg cggcaccagc gcgtcttgtg atgagtcttc ctcgtcctcg gactcgatac 23880
gccgcctcat ccgctttttt gggggcgccc ggggaggcgg cggcgacggg gacggggacg 23940
acacgtcctc catggttggg ggacgtcgcg ccgcaccgcg tccgcgctcg ggggtggttt 24000
cgcgctgctc ctcttcccga ctggccattt ccttctccta taggcagaaa aagatcatgg 24060
agtcagtcga gaagaaggac agcctaaccg ccccctctga gttcgccacc accgcctcca 24120
ccgatgccgc caacgcgcct accaccttcc ccgtcgaggc acccccgctt gaggaggagg 24180
aagtgattat cgagcaggac ccaggttttg taagcgaaga cgacgaggac cgctcagtac 24240
caacagagga taaaaagcaa gaccaggaca acgcagaggc aaacgaggaa caagtcgggc 24300
ggggggacga aaggcatggc gactacctag atgtgggaga cgacgtgctg ttgaagcatc 24360
tgcagcgcca gtgcgccatt atctgcgacg cgttgcaaga gcgcagcgat gtgcccctcg 24420
ccatagcgga tgtcagcctt gcctacgaac gccacctatt ctcaccgcgc gtaccccccca 24480 aacgccaaga aaacggcaca tgcgagccca acccgcgcct caacttctac cccgtatttg 24540
ccgtgccaga ggtgcttgcc acctatcaca tctttttcca aaactgcaag atacccctat 24600
cctgccgtgc caaccgcagc cgagcggaca agcagctggc cttgcggcag ggcgctgtca 24660
tacctgatat cgcctcgctc aacgaagtgc caaaaatctt tgagggtctt ggacgcgacg 24720
agaagcgcgc ggcaaacgct ctgcaacagg aaaacagcga aaatgaaagt cactctggag 24780
tgttggtgga actcgagggt gacaacgcgc gcctagccgt actaaaacgc agcatcgagg 24840
tcacccactt tgcctacccg gcacttaacc taccccccaa ggtcatgagc acagtcatga 24900
gtgagctgat cgtgcgccgt gcgcagcccc tggagaggga tgcaaatttg caagaacaaa 24960
cagaggaggg cctacccgca gttggcgacg agcagctagc gcgctggctt caaacgcgcg 25020
agcctgccga cttggaggag cgacgcaaac taatgatggc cgcagtgctc gttaccgtgg 25080
agcttgagtg catgcagcgg ttctttgctg acccggagat gcagcgcaag ctagaggaaa 25140
cattgcacta cacctttcga cagggctacg tacgccaggc ctgcaagatc tccaacgtgg 25200
agctctgcaa cctggtctcc taccttggaa ttttgcacga aaaccgcctt gggcaaaacg 25260
tgcttcattc cacgctcaag ggcgaggcgc gccgcgacta cgtccgcgac tgcgtttact 25320
tatttctatg ctacacctgg cagacggcca tgggcgtttg gcagcagtgc ttggaggagt 25380
gcaacctcaa ggagctgcag aaactgctaa agcaaaactt gaaggaccta tggacggcct 25440
tcaacgagcg ctccgtggcc gcgcacctgg cggacatcat tttccccgaa cgcctgctta 25500
aaaccctgca acagggtctg ccagacttca ccagtcaaag catgttgcag aactttagga 25560
actttatcct agagcgctca ggaatcttgc ccgccacctg ctgtgcactt cctagcgact 25620
ttgtgcccat taagtaccgc gaatgccctc cgccgctttg ggccactgc taccttctgc 25680 agctagccaa ctaccttgcc taccactctg acataatgga agacgtgagc ggtgacggtc 25740
tactggagtg tcactgtcgc tgcaacctat gcaccccgca ccgctccctg gtttgcaatt 25800
cgcagctgct taacgaaagt caaattatcg gtacctttga gctgcagggt ccctcgcctg 25860
acgaaaagtc cgcggctccg gggttgaaac tcactccggg gctgtggacg tcggcttacc 25920
ttcgcaaatt tgtacctgag gactaccacg cccacgagat taggttctac gaagaccaat 25980
cccgcccgcc aaatgcggag cttaccgcct gcgtcattac ccagggccac attcttggcc 26040
aattgcaagc catcaacaaa gcccgccaag agtttctgct acgaaaggga cggggggttt 26100
acttggaccc ccagtccggc gaggagctca acccaatccc cccgccgccg cagccctatc 26160

-continued

```
agcagcagcc gcgggccctt gcttcccagg atggcaccca aaaagaagct gcagctgccg  26220
ccgccaccca cggacgagga ggaatactgg gacagtcagg cagaggaggt tttggacgag  26280
gaggaggagg acatgatgga agactgggag agcctagacg aggaagcttc cgaggtcgaa  26340
gaggtgtcag acgaaacacc gtcaccctcg gtcgcattcc cctcgccggc gccccagaaa  26400
tcggcaaccg gttccagcat ggctacaacc tccgctcctc aggcgccgcc ggcactgccc  26460
gttcgccgac ccaaccgtag atgggacacc actggaacca gggccggtaa gtccaagcag  26520
ccgccgccgt tagcccaaga gcaacaacag cgccaaggct accgctcatg gcgcgggcac  26580
aagaacgcca tagttgcttg cttgcaagac tgtgggggca acatctcctt cgcccgccgc  26640
tttcttctct accatcacgg cgtggccttc ccccgtaaca tcctgcatta ctaccgtcat  26700
ctctacagcc catactgcac cggcggcagc ggcagcggca gcaacagcag cggccacaca  26760
gaagcaaagg cgaccggata gcaagactct gacaaagccc aagaaatcca cagcggcggc  26820
agcagcagga ggaggagcgc tgcgtctggc gcccaacgaa cccgtatcga cccgcgagct  26880
tagaaacagg atttttccca ctctgtatgc tatatttcaa cagagcaggg gccaagaaca  26940
agagctgaaa ataaaaaaca ggtctctgcg atccctcacc cgcagctgcc tgtatcacaa  27000
aagcgaagat cagcttcggc gcacgctgga agacgcggag gctctcttca gtaaatactg  27060
cgcgctgact cttaaggact agtttcgcgc cctttctcaa atttaagcgc gaaaactacg  27120
tcatctccag cggccacacc cggcgccagc acctgtcgtc agcgccatta tgagcaagga  27180
aattcccacg ccctacatgt ggagttacca gccacaaatg ggacttgcgg ctggagctgc  27240
ccaagactac tcaacccgaa taaactacat gagcgcggga ccccacatga tatcccgggt  27300
caacggaatc cgcgcccacc gaaaccgaat tctcttggaa caggcggcta ttaccaccac  27360
acctcgtaat aaccttaatc cccgtagttg gcccgctgcc ctggtgtacc aggaaagtcc  27420
cgctcccacc actgtggtac ttcccagaga cgcccaggcc gaagttcaga tgactaactc  27480
aggggcgcag cttgcgggcg gctttcgtca cagggtgcgg tcgcccgggc agggtataac  27540
tcacctgaca atcagagggc gaggtattca gctcaacgac gagtcggtga gctcctcgct  27600
tggtctccgt ccggacggga catttcagat cggcggcgcc ggccgctctt cattcacgcc  27660
tcgtcaggca atcctaactc tgcagacctc gtcctctgag ccgcgctctg gaggcattgg  27720
aactctgcaa tttattgagg agtttgtgcc atcggtctac tttaacccct tctcgggacc  27780
tcccggccac tatccggatc aatttattcc taactttgac gcggtaaagg actcggcgga  27840
tggctacgac tgaatgttaa gtggagaggc agagcaactg cgcctgaaac acctggtcca  27900
ctgtcgccgc cacaagtgct ttgcccgcga ctccggtgag ttttgctact ttgaattgcc  27960
cgaggatcat atcgagggcc cggcgcacgg cgtccggctt accgcccagg gagagcttgc  28020
ccgtagcctg attcgggagt ttacccagcg ccccctgcta gttgagcggg acaggggacc  28080
ctgtgttctc actgtgattt gcaactgtcc taaccctgga ttacatcaag atctttgttg  28140
ccatctctgt gctgagtata ataaatacag aaattaaaat atactggggc tcctatcgcc  28200
atcctgtaaa cgccaccgtc ttcacccgcc caagcaaacc aaggcgaacc ttacctggta  28260
cttttaacat ctctccctct gtgatttaca acagtttcaa cccagacgga gtgagtctac  28320
gagagaacct ctccgagctc agctactcca tcagaaaaaa caccaccctc cttacctgcc  28380
gggaacgtac gatgtggctg cagagcctgc tgctcttggg cactgtggcc tgcagcatct  28440
ctgcacccgc ccgctcgccc agccccagca cgcagccctg ggagcatgtg aatgccatcc  28500
aggaggcccg gcgtctcctg aacctgagta gagacactgc tgctgagatg aatgaaacag  28560
```

-continued

```
tagaagtcat ctcagaaatg tttgacctcc aggagccgac ctgcctacag acccgcctgg  28620
agctgtacaa gcagggcctg cggggcagcc tcaccaagct caagggcccc ttgaccatga  28680
tggccagcca ctacaagcag cactgccctc caaccccgga aacttcctgt gcaacccaga  28740
ctatcacctt tgaaagtttc aaagagaacc tgaaggactt tctgcttgtc atcccctttg  28800
actgctggga gccagtccag gagtgacaat tgactctatg tgggatatgc tccagcgcta  28860
caaccttgaa gtcaggcttc ctggatgtca gcatctgact ttggccagca cctgtcccgc  28920
ggatttgttc cagtccaact acagcgaccc accctaacag agatgaccaa cacaaccaac  28980
gcggccgccg ctaccggact tacatctacc acaaatacac cccaagtttc tgcctttgtc  29040
aataactggg ataacttggg catgtggtgg ttctccatag cgcttatgtt tgtatgcctt  29100
attattatgt ggctcatctg ctgcctaaag cgcaaacgcg cccgaccacc catctatagt  29160
cccatcattg tgctacaccc aaacaatgat ggaatccata gattggacgg actgaaacac  29220
atgttctttt ctcttacagt atgattaaat gagacatgat tcctcgagtt tttatattac  29280
tgacccttgt tgcgcttttt tgtgcgtgct ccacattggc tgcggtttct cacatcgaag  29340
tagactgcat tccagccttc acagtctatt tgctttacgg atttgtcacc ctcacgctca  29400
tctgcagcct catcactgtg gtcatcgcct ttatccagtg cattgactgg gtctgtgtgc  29460
gctttgcata tctcagacac catccccagt acagggacag gactatagct gagcttctta  29520
gaattcttta attatgaaat ttactgtgac ttttctgctg attatttgca ccctatctgc  29580
gttttgttcc ccgacctcca agcctcaaag acatatatca tgcagattca ctcgtatatg  29640
gaatattcca agttgctaca atgaaaaaag cgatctttcc gaagcctggt tatatgcaat  29700
catctctgtt atggtgttct gcagtaccat cttagcccta gctatatatc cctaccttga  29760
cattggctgg aaacgaatag atgccatgaa ccacccaact ttccccgcgc ccgctatgct  29820
tccactgcaa caagttgttg ccggcggctt tgtcccagcc aatcagcctc gccccacttc  29880
tcccaccccc actgaaatca gctactttaa tctaacagga ggagatgact gacaccctag  29940
atctagaaat ggacggaatt attacagagc agcgcctgct agaaagacgc agggcagcgg  30000
ccgagcaaca gcgcatgaat caagagctcc aagacatggt taacttgcac cagtgcaaaa  30060
ggggtatctt ttgtctggta aagcaggcca aagtcaccta cgacagtaat accaccggac  30120
accgccttag ctacaagttg ccaaccaagc gtcagaaatt ggtggtcatg gtgggagaaa  30180
agcccattac cataactcag cactcggtag aaaccgaagg ctgcattcac tcaccttgtc  30240
aaggacctga ggatctctgc acccttatta agaccctgtg cggtctcaaa gatcttattc  30300
cctttaacta ataaaaaaaa ataataaagc atcacttact taaaatcagt tagcaaattt  30360
ctgtccagtt tattcagcag cacctccttg ccctcctccc agctctggta ttgcagcttc  30420
ctcctggctg caaactttct ccacaatcta aatggaatgt cagtttcctc ctgttcctgt  30480
ccatccgcac ccactatctt catgttgttg cagatgaagc gcgcaagacc gtctgaagat  30540
accttcaacc ccgtgtatcc atatgacacg gaaaccggtc ctccaactgt gccttttctt  30600
actcctccct ttgtatcccc caatgggttt caagagagtc cccctggggt actctctttg  30660
cgcctatccg aacctctagt tacctccaat ggcatgcttg cgctcaaaat gggcaacggc  30720
ctctctctgg acgaggccgg caaccttacc tcccaaaatg taaccactgt gagcccacct  30780
ctcaaaaaaa ccaagtcaaa cataaacctg gaaatatctg cacccctcac agttacctca  30840
gaagccctaa ctgtggctgc cgccgcacct ctaatggtcg cgggcaacac actcaccatg  30900
```

-continued

```
caatcacagg ccccgctaac cgtgcacgac tccaaactta gcattgccac ccaaggaccc  30960
ctcacagtgt cagaaggaaa gctagccctg caaacatcag gcccccctcac caccaccgat  31020
agcagtaccc ttactatcac tgcctcaccc cctctaacta ctgccactgg tagcttgggc  31080
attgacttga aagagcccat ttatacacaa aatggaaaac taggactaaa gtacggggct  31140
cctttgcatg taacagacga cctaaacact ttgaccgtag caactggtcc aggtgtgact  31200
attaataata cttccttgca aactaaagtt actggagcct tgggttttga ttcacaaggc  31260
aatatgcaac ttaatgtagc aggaggacta aggattgatt ctcaaaacag acgccttata  31320
cttgatgtta gttatccgtt tgatgctcaa aaccaactaa atctaagact aggacagggc  31380
cctcttttta taaactcagc ccacaacttg gatattaact acaacaaagg cctttacttg  31440
tttacagctt caaacaattc caaaaagctt gaggttaacc taagcactgc caaggggttg  31500
atgtttgacg ctacagccat agccattaat gcaggagatg ggcttgaatt tggttcacct  31560
aatgcaccaa acacaaatcc cctcaaaaca aaaattggcc atggcctaga atttgattca  31620
aacaaggcta tggttcctaa actaggaact ggccttagtt ttgacagcac aggtgccatt  31680
acagtaggaa acaaaaataa tgataagcta actttgtgga ccacaccagc tccatctcct  31740
aactgtagac taaatgcaga gaaagatgct aaactcactt tggtcttaac aaaatgtggc  31800
agtcaaatac ttgctacagt ttcagttttg gctgttaaag gcagtttggc tccaatatct  31860
ggaacagttc aaagtgctca tcttattata agatttgacg aaaatggagt gctactaaac  31920
aattccttcc tggacccaga atattggaac tttagaaatg gagatcttac tgaaggcaca  31980
gcctatacaa acgctgttgg atttatgcct aacctatcag cttatccaaa atctcacggt  32040
aaaactgcca aaagtaacat tgtcagtcaa gtttacttaa acggagacaa aactaaacct  32100
gtaacactaa cgatcacact aaacggtaca caggaaacag gagacacaac ttgtgactgc  32160
cgcggagact gtttctgccc atctgcatac tctatgtcat tttcatggga ctggtctggc  32220
cacaactaca ttaatgaaat atttgccaca tcctcttaca ctttttcata cattgcccaa  32280
gaataaagaa tcgtttgtgt tatgtttcaa cgtgtttatt tttcaattgc agaaaatttc  32340
aagtcatttt tcattcagta gtatagcccc accaccacat agcttataca gatcaccgta  32400
ccttaatcaa actcacagaa ccctagtatt caacctgcca cctccctccc aacacacaga  32460
gtacacagtc ctttctcccc ggctggcctt aaaaagcatc atatcatggg taacagacat  32520
attcttaggt gttatattcc acacggtttc ctgtcgagcc aaacgctcat cagtgatatt  32580
aataaactcc ccgggcagct cacttaagtt catgtcgctg tccagctgct gagccacagg  32640
ctgctgtcca acttgcggtt gcttaacggg cggcgaagga gaagtccacg cctacatggg  32700
ggtagagtca taatcgtgca tcaggatagg gcggtggtgc tgcagcagcg cgcgaataaa  32760
ctgctgccgc cgccgctccg tcctgcagga atacaacatg gcagtggtct cctcagcgat  32820
gattcgcacc gcccgcagca taaggcgcct tgtcctccgg gcacagcagc gcaccctgat  32880
ctcacttaaa tcagcacagt aactgcagca cagcaccaca atattgttca aaatcccaca  32940
gtgcaaggcg ctgtatccaa agctcatggc ggggaccaca gaacccacgt ggccatcata  33000
ccacaagcgc aggtagatta agtggcgacc cctcataaac acgctggaca taaacattac  33060
ctcttttggc atgttgtaat tcaccacctc ccggtaccat ataaacctct gattaaacat  33120
ggcgccatcc accaccatcc taaaccagct ggccaaaacc tgcccgccgg ctatacactg  33180
cagggaaccg ggactggaac aatgacagtg gagagcccag gactcgtaac catggatcat  33240
catgctcgtc atgatatcaa tgttggcaca acacaggcac acgtgcatac acttcctcag  33300
```

-continued gattacaagc tcctcccgcg ttagaaccat atcccaggga acaacccatt cctgaatcag 33360
cgtaaatccc acactgcagg gaagacctcg cacgtaactc acgttgtgca ttgtcaaagt 33420
gttacattcg ggcagcagcg gatgatcctc cagtatggta gcgcgggttt ctgtctcaaa 33480
aggaggtaga cgatccctac tgtacggagt gcgccgagac aaccgagatc gtgttggtcg 33540
tagtgtcatg ccaaatggaa cgccggacgt agtcatattt cctgaagcaa aaccaggtgc 33600
gggcgtgaca aacagatctg cgtctccggt ctcgccgctt agatcgctct gtgtagtagt 33660
tgtagtatat ccactctctc aaagcatcca ggcgcccct ggcttcgggt tctatgtaaa 33720
ctccttcatg cgccgctgcc ctgataacat ccaccaccgc agaataagcc acacccagcc 33780
aacctacaca ttcgttctgc gagtcacaca cgggaggagc gggaagagct ggaagaacca 33840
tgtttttttt tttattccaa aagattatcc aaaacctcaa aatgaagatc tattaagtga 33900
acgcgctccc ctccggtggc gtggtcaaac tctacagcca aagaacagat aatggcattt 33960
gtaagatgtt gcacaatggc ttccaaaagg caaacggccc tcacgtccaa gtggacgtaa 34020
aggctaaacc cttcagggtg aatctcctct ataaacattc cagcaccttc aaccatgccc 34080
aaataattct catctcgcca ccttctcaat atatctctaa gcaaatcccg aatattaagt 34140
ccggccattg taaaaatctg ctccagagcg ccctccacct tcagcctcaa gcagcgaatc 34200
atgattgcaa aaattcaggt tcctcacaga cctgtataag attcaaaagc ggaacattaa 34260
caaaaatacc gcgatcccgt aggtcccttc gcagggccag ctgaacataa tcgtgcaggt 34320
ctgcacggac cagcgcggcc acttccccgc caggaaccat gacaaaagaa cccacactga 34380
ttatgacacg catactcgga gctatgctaa ccagcgtagc cccgatgtaa gcttgttgca 34440
tgggcggcga tataaaatgc aaggtgctgc tcaaaaaatc aggcaaagcc tcgcgcaaaa 34500
aagaaagcac atcgtagtca tgctcatgca gataaaggca ggtaagctcc ggaaccacca 34560
cagaaaaaga caccattttt ctctcaaaca tgtctgcggg tttctgcata aacacaaaat 34620
aaaataacaa aaaaacattt aaacattaga agcctgtctt acaacaggaa aaacaaccct 34680
tataagcata agacggacta cggccatgcc ggcgtgaccg taaaaaaact ggtcaccgtg 34740
attaaaaagc accaccgaca gctcctcggt catgtccgga gtcataatgt aagactcggt 34800
aaacacatca ggttgattca catcggtcag tgctaaaaag cgaccgaaat agcccggggg 34860
aatacatacc cgcaggcgta gagacaacat tacagccccc ataggaggta taacaaaatt 34920
aataggagag aaaaacacat aaacacctga aaaaccctcc tgcctaggca aaatagcacc 34980
ctcccgctcc agaacaacat acagcgcttc cacagcggca gccataacag tcagccttac 35040
cagtaaaaaa gaaaacctat taaaaaaaca ccactcgaca cggcaccagc tcaatcagtc 35100
acagtgtaaa aaagggccaa gtgcagagcg agtatatata ggactaaaaa atgacgtaac 35160
ggttaaagtc cacaaaaaac acccagaaaa ccgcacgcga acctacgccc agaaacgaaa 35220
gccaaaaaac ccacaacttc ctcaaatcgt cacttccgtt ttcccacgtt acgtcacttc 35280
ccattttaag aaaactacaa ttcccaacac atacaagtta ctccgcccta aaacctacgt 35340
cacccgcccc gttcccacgc cccgcgccac gtcacaaact ccaccccctc attatcatat 35400
tggcttcaat ccaaaataag gtatattatt gatgatgtta attaagaatt cggatctgcg 35460
acgcgaggct ggatggcctt ccccattatg attcttctcg cttccggcgg catcgggatg 35520
cccgcgttgc aggccatgct gtccaggcag gtagatgacg accatcaggg acagcttcac 35580
ggccagcaaa aggccaggaa ccgtaaaaag gccgcgttgc tggcgttttt ccataggctc 35640

```
cgccccccctg acgagcatca caaaaatcga cgctcaagtc agaggtggcg aaacccgaca  35700
ggactataaa gataccaggc gtttccccct ggaagctccc tcgtgcgctc tcctgttccg  35760
accctgccgc ttaccggata cctgtccgcc tttctccctt cgggaagcgt ggcgctttct  35820
caatgctcac gctgtaggta tctcagttcg gtgtaggtcg ttcgctccaa gctgggctgt  35880
gtgcacgaac cccccgttca gcccgaccgc tgcgccttat ccggtaacta tcgtcttgag  35940
tccaacccgg taagacacga cttatcgcca ctggcagcag ccactggtaa caggattagc  36000
agagcgaggt atgtaggcgg tgctacagag ttcttgaagt ggtggcctaa ctacggctac  36060
actagaagga cagtatttgg tatctgcgct ctgctgaagc cagttacctt cggaaaaaga  36120
gttggtagct cttgatccgg caaacaaacc accgctggta gcggtggttt ttttgtttgc  36180
aagcagcaga ttacgcgcag aaaaaaagga tctcaagaag atcctttgat cttttctacg  36240
gggtctgacg ctcagtggaa cgaaaactca cgttaaggga ttttggtcat gagattatca  36300
aaaaggatct tcacctagat ccttttaaat caatctaaag tatatatgag taaacttggt  36360
ctgacagtta ccaatgctta atcagtgagg cacctatctc agcgatctgt ctatttcgtt  36420
catccatagt tgcctgactc cccgtcgtgt agataactac gatacgggag ggcttaccat  36480
ctggccccag tgctgcaatg ataccgcgag acccacgctc accggctcca gatttatcag  36540
caataaacca gccagccgga agggccgagc gcagaagtgg tcctgcaact ttatccgcct  36600
ccatccagtc tattaattgt tgccgggaag ctagagtaag tagttcgcca gttaatagtt  36660
tgcgcaacgt tgttgccatt gntgcaggca tcgtggtgtc acgctcgtcg tttggtatgg  36720
cttcattcag ctccggttcc caacgatcaa ggcgagttac atgatccccc atgttgtgca  36780
aaaaagcggt tagctccttc ggtcctccga tcgttgtcag aagtaagttg gccgcagtgt  36840
tatcactcat ggttatggca gcactgcata attctcttac tgtcatgcca tccgtaagat  36900
gcttttctgt gactggtgag tactcaacca agtcattctg agaatagtgt atgcggcgac  36960
cgagttgctc ttgcccggcg tcaacacggg ataataccgc gccacatagc agaactttaa  37020
aagtgctcat cattggaaaa cgttcttcgg ggcgaaaact ctcaaggatc ttaccgctgt  37080
tgagatccag ttcgatgtaa cccactcgtg cacccaactg atcttcagca tcttttactt  37140
tcaccagcgt ttctgggtga gcaaaaacag gaaggcaaaa tgccgcaaaa aagggaataa  37200
gggcgacacg gaaatgttga atactcatac tcttcctttt tcaatattat tgaagcattt  37260
atcagggtta ttgtctcatg agcggataca tatttgaatg tatttagaaa aataaacaaa  37320
taggggttcc gcgcacattt ccccgaaaag tgccacctga cgtctaagaa accattatta  37380
tcatgacatt aacctataaa aataggcgta tcacgaggcc ctttcgtctt caa         37433
```

```
<210> SEQ ID NO 10
<211> LENGTH: 38366
<212> TYPE: DNA
<213> ORGANISM: Artificial Sequence
<220> FEATURE:
<223> OTHER INFORMATION: Ad5-pK7-D24-GMCSF
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (35479)..(35481)
<223> OTHER INFORMATION: n is a, c, g, or t
<220> FEATURE:
<221> NAME/KEY: misc_feature
<222> LOCATION: (36782)..(36787)
<223> OTHER INFORMATION: n is a, c, g, or t
```

<220> FEATURE:
<221> NAME/KEY: misc_feature
<222> LOCATION: (38325)..(38361)
<223> OTHER INFORMATION: n is a, c, g, or t

<400> SEQUENCE: 10

```
taannntccc ttccagctct ctgccccttt tggattgaag ccaatatgat aatgaggggg     60

tggagtttgt gacgtggcgc gggcgtggga acggggcggg tgacgtagta gtgtggcgga    120

agtgtgatgt tgcaagtgtg gcggaacaca tgtaagcgac ggatgtggca aaagtgacgt    180

ttttggtgtg cgccggtgta cacaggaagt gacaattttc gcgcggtttt aggcggatgt    240

tgtagtaaat ttgggcgtaa ccgagtaaga tttggccatt ttcgcgggaa aactgaataa    300

gaggaagtga aatctgaata attttgtgtt actcatagcg cgtaatattt gtctagggcc    360

gcggggactt tgaccgttta cgtggagact cgcccaggtg tttttctcag gtgttttccg    420

cgttccgggt caaagttggc gttttattat tatagtcagc tgacgtgtag tgtatttata    480

cccggtgagt tcctcaagag gccactcttg agtgccagcg agtagagttt tctcctccga    540

gccgctccga caccgggact gaaaatgaga catattatct gccacggagg tgttattacc    600

gaagaaatgg ccgccagtct tttggaccag ctgatcgaag aggtactggc tgataatctt    660

ccacctccta gccattttga accacctacc cttcacgaac tgtatgattt agacgtgacg    720

gcccccgaag atcccaacga ggaggcggtt tcgcagattt ttcccgactc tgtaatgttg    780

gcggtgcagg aagggattga cttactcact tttccgccgg cgcccggttc tccggagccg    840

cctcaccttt cccggcagcc cgagcagccg gagcagagag ccttgggtcc ggtttctatg    900

ccaaaccttg taccggaggt gatcgatcca cccagtgacg acgaggatga agagggtgag    960

gagtttgtgt tagattatgt ggagcacccc gggcacggtt gcaggtcttg tcattatcac   1020

cggaggaata cgggggaccc agatattatg tgttcgcttt gctatatgag gacctgtggc   1080

atgtttgtct acagtaagtg aaaattatgg gcagtgggtg atagagtggt gggtttggtg   1140

tggtaatttt ttttttaatt tttacagttt tgtggtttaa agaattttgt attgtgattt   1200

ttttaaaagg tcctgtgtct gaacctgagc ctgagcccga gccagaaccg gagcctgcaa   1260

gacctacccg ccgtcctaaa atggcgcctg ctatcctgag acgcccgaca tcacctgtgt   1320

ctagagaatg caatagtagt acggatagct gtgactccgg tccttctaac acacctcctg   1380

agatacaccc ggtggtcccg ctgtgcccca ttaaaccagt tgccgtgaga gttggtgggc   1440

gtcgccaggc tgtggaatgt atcgaggact tgcttaacga gcctgggcaa cctttggact   1500

tgagctgtaa acgccccagg ccataaggtg taaacctgtg attgcgtgtg tggttaacgc   1560

ctttgtttgc tgaatgagtt gatgtaagtt taataaaggg tgagataatg tttaacttgc   1620

atggcgtgtt aaatggggcg gggcttaaag ggtatataat gcgccgtggg ctaatcttgg   1680

ttacatctga cctcatggag gcttgggagt gtttggaaga tttttctgct gtgcgtaact   1740

tgctggaaca gagctctaac agtacctctt ggttttggag gtttctgtgg ggctcatccc   1800

aggcaaagtt agtctgcaga attaaggagg attacaagtg ggaatttgaa gagcttttga   1860

aatcctgtgg tgagctgttt gattctttga atctgggtca ccaggcgctt ttccaagaga   1920

aggtcatcaa gactttggat ttttccacac cggggcgcgc tgcggctgct gttgcttttt   1980

tgagttttat aaaggataaa tggagcgaag aaacccatct gagcgggggg tacctgctgg   2040

attttctggc catgcatctg tggagagcgg ttgtgagaca caagaatcgc ctgctactgt   2100

tgtcttccgt ccgcccggcg ataataccga cggaggagca gcagcagcag caggaggaag   2160
```

-continued

```
ccaggcggcg gcggcaggag cagagcccat ggaacccgag agccggcctg gaccctcggg   2220
aatgaatgtt gtacaggtgg ctgaactgta tccagaactg agacgcattt tgacaattac   2280
agaggatggg caggggctaa agggggtaaa gagggagcgg ggggcttgtg aggctacaga   2340
ggaggctagg aatctagctt ttagcttaat gaccagacac cgtcctgagt gtattacttt   2400
tcaacagatc aaggataatt gcgctaatga gcttgatctg ctggcgcaga agtattccat   2460
agagcagctg accacttact ggctgcagcc aggggatgat tttgaggagg ctattagggt   2520
atatgcaaag gtggcactta ggccagattg caagtacaag atcagcaaac ttgtaaatat   2580
caggaattgt tgctacattt ctgggaacgg ggccgaggtg gagatagata cggaggatag   2640
ggtggccttt agatgtagca tgataaatat gtggccgggg gtgcttggca tggacggggt   2700
ggttattatg aatgtaaggt ttactggccc caattttagc ggtacggttt tcctggccaa   2760
taccaacctt atcctacacg gtgtaagctt ctatgggttt aacaatacct gtgtggaagc   2820
ctggaccgat gtaagggttc ggggctgtgc cttttactgc tgctggaagg gggtggtgtg   2880
tcgccccaaa agcagggctt caattaagaa atgcctcttt gaaaggtgta ccttgggtat   2940
cctgtctgag ggtaactcca gggtgcgcca caatgtggcc tccgactgtg gttgcttcat   3000
gctagtgaaa agcgtggctg tgattaagca taacatggta tgtggcaact gcgaggacag   3060
ggcctctcag atgctgacct gctcggacgg caactgtcac ctgctgaaga ccattcacgt   3120
agccagccac tctcgcaagg cctggccagt gtttgagcat aacatactga cccgctgttc   3180
cttgcatttg ggtaacagga ggggggtgtt cctaccttac caatgcaatt tgagtcacac   3240
taagatattg cttgagcccg agagcatgtc caaggtgaac ctgaacgggg tgtttgacat   3300
gaccatgaag atctggaagg tgctgaggta cgatgagacc cgcaccaggt gcagaccctg   3360
cgagtgtggc ggtaaacata ttaggaacca gcctgtgatg ctggatgtga ccgaggagct   3420
gaggcccgat cacttggtgc tggcctgcac ccgcgctgag tttggctcta gcgatgaaga   3480
tacagattga ggtactgaaa tgtgtgggcg tggcttaagg gtgggaaaga atatataagg   3540
tgggggtctt atgtagtttt gtatctgttt tgcagcagcc gccgccgcca tgagcaccaa   3600
ctcgtttgat ggaagcattg tgagctcata tttgacaacg cgcatgcccc catgggccgg   3660
ggtgcgtcag aatgtgatgg gctccagcat tgatggtcgc cccgtcctgc ccgcaaactc   3720
tactaccttg acctacgaga ccgtgtctgg aacgccgttg gagactgcag cctccgccgc   3780
cgcttcagcc gctgcagcca ccgcccgcgg gattgtgact gactttgctt tcctgagccc   3840
gcttgcaagc agtgcagctt cccgttcatc cgcccgcgat gacaagttga cggctctttt   3900
ggcacaattg gattctttga cccgggaact taatgtcgtt tctcagcagc tgttggatct   3960
gcgccagcag gtttctgccc tgaaggcttc ctcccctccc aatgcggttt aaaacataaa   4020
taaaaaacca gactctgttt ggatttggat caagcaagtg tcttgctgtc tttatttagg   4080
ggttttgcgc gcgcggtagg cccgggacca gcggtctcgg tcgttgaggg tcctgtgtat   4140
tttttccagg acgtggtaaa ggtgactctg gatgttcaga tacatgggca taagcccgtc   4200
tctggggtgg aggtagcacc actgcagagc ttcatgctgc ggggtggtgt tgtagatgat   4260
ccagtcgtag caggagcgct gggcgtggtg cctaaaaatg tctttcagta gcaagctgat   4320
tgccaggggc aggcccttgg tgtaagtgtt tacaaagcgg ttaagctggg atgggtgcat   4380
acgtggggat atgagatgca tcttggactg tatttttagg ttggctatgt tcccagccat   4440
atccctccgg ggattcatgt tgtgcagaac caccagcaca gtgtatccgg tgcacttggg   4500
aaatttgtca tgtagcttag aaggaaatgc gtggaagaac ttggagacgc ccttgtgacc   4560
```

-continued

```
tccaagattt tccatgcatt cgtccataat gatggcaatg ggcccacggg cggcggcctg   4620
ggcgaagata tttctgggat cactaacgtc atagttgtgt tccaggatga gatcgtcata   4680
ggccattttt acaaagcgcg ggcggagggt gccagactgc ggtataatgg ttccatccgg   4740
cccaggggcg tagttaccct cacagatttg catttcccac gctttgagtt cagatggggg   4800
gatcatgtct acctgcgggg cgatgaagaa aacggtttcc ggggtagggg agatcagctg   4860
ggaagaaagc aggttcctga gcagctgcga cttaccgcag ccggtgggcc cgtaaatcac   4920
acctattacc gggtgcaact ggtagttaag agagctgcag ctgccgtcat ccctgagcag   4980
gggggccact tcgttaagca tgtccctgac tcgcatgttt tccctgacca aatccgccag   5040
aaggcgctcg ccgcccagcg atagcagttc ttgcaaggaa gcaaagtttt tcaacggttt   5100
gagaccgtcc gccgtaggca tgcttttgag cgtttgacca agcagttcca ggcggtccca   5160
cagctcggtc acctgctcta cggcatctcg atccagcata tctcctcgtt tcgcgggttg   5220
gggcggcttt cgctgtacgg cagtagtcgg tgctcgtcca gacgggccag ggtcatgtct   5280
ttccacgggc gcagggtcct cgtcagcgta gtctgggtca cggtgaaggg gtgcgctccg   5340
ggctgcgcgc tggccagggt gcgcttgagg ctggtcctgc tggtgctgaa gcgctgccgg   5400
tcttcgccct gcgcgtcggc caggtagcat ttgaccatgg tgtcatagtc cagcccctcc   5460
gcggcgtggc ccttggcgcg cagcttgccc ttggaggagg cgccgcacga ggggcagtgc   5520
agacttttga gggcgtagag cttgggcgcg agaaataccg attccgggga gtaggcatcc   5580
gcgccgcagg ccccgcagac ggtctcgcat tccacgagcc aggtgagctc tggccgttcg   5640
gggtcaaaaa ccaggtttcc cccatgcttt ttgatgcgtt tcttacctct ggtttccatg   5700
agccggtgtc cacgctcggt gacgaaaagg ctgtccgtgt ccccgtatac agacttgaga   5760
ggcctgtcct cgagcggtgt tccgcggtcc tcctcgtata gaaactcgga ccactctgag   5820
acaaaggctc gcgtccaggc cagcacgaag gaggctaagt gggaggggta gcggtcgttg   5880
tccactaggg ggtccactcg ctccagggtg tgaagacaca tgtcgccctc ttcggcatca   5940
aggaaggtga ttggtttgta ggtgtaggcc acgtgaccgg gtgttcctga aggggggcta   6000
taaaaggggg tgggggcgcg ttcgtcctca ctctcttccg catcgctgtc tgcgagggcc   6060
agctgttggg gtgagtactc cctctgaaaa gcgggcatga cttctgcgct aagattgtca   6120
gtttccaaaa acgaggagga tttgatattc acctggcccg cggtgatgcc tttgagggtg   6180
gccgcatcca tctggtcaga aaagacaatc tttttgttgt caagcttggt ggcaaacgac   6240
ccgtagaggg cgttggacag caacttggcg atggagcgca gggtttggtt tttgtcgcga   6300
tcggcgcgct ccttggccgc gatgtttagc tgcacgtatt cgcgcgcaac gcaccgccat   6360
tcgggaaaga cggtggtgcg ctcgtcgggc accaggtgca cgcgccaacc gcggttgtgc   6420
agggtgacaa ggtcaacgct ggtggctacc tctccgcgta ggcgctcgtt ggtccagcag   6480
aggcggccgc ccttgcgcga gcagaatggc ggtagggggt ctagctgcgt ctcgtccggg   6540
gggtctgcgt ccacggtaaa gaccccgggc agcaggcgcg cgtcgaagta gtctatcttg   6600
catccttgca agtctagcgc ctgctgccat gcgcgggcgg caagcgcgcg ctcgtatggg   6660
ttgagtgggg gaccccatgg catggggtgg gtgagcgcgg aggcgtacat gccgcaaatg   6720
tcgtaaacgt agaggggctc tctgagtatt ccaagatatg tagggtagca tcttccaccg   6780
cggatgctgg cgcgcacgta atcgtatagt tcgtgcgagg gagcgaggag gtcgggaccg   6840
aggttgctac gggcgggctg ctctgctcgg aagactatct gcctgaagat ggcatgtgag   6900
```

ttggatgata tggttggacg ctggaagacg ttgaagctgg cgtctgtgag acctaccgcg 6960
tcacgcacga aggaggcgta ggagtcgcgc agcttgttga ccagctcggc ggtgacctgc 7020
acgtctaggg cgcagtagtc cagggtttcc ttgatgatgt catacttatc ctgtcccttt 7080
tttttccaca gctcgcggtt gaggacaaac tcttcgcggt ctttccagta ctcttggatc 7140
ggaaacccgt cggcctccga acggtaagag cctagcatgt agaactggtt gacggcctgg 7200
taggcgcagc atcccttttc tacgggtagc gcgtatgcct gcgcggcctt ccggagcgag 7260
gtgtgggtga gcgcaaaggt gtccctgacc atgactttga ggtactggta tttgaagtca 7320
gtgtcgtcgc atccgccctg ctcccagagc aaaaagtccg tgcgcttttt ggaacgcgga 7380
tttggcaggg cgaaggtgac atcgttgaag agtatctttc ccgcgcgagg cataaagttg 7440
cgtgtgatgc ggaagggtcc cggcacctcg gaacggttgt taattacctg ggcggcgagc 7500
acgatctcgt caaagccgtt gatgttgtgg cccacaatgt aaagttccaa gaagcgcggg 7560
atgcccttga tggaaggcaa ttttttaagt tcctcgtagg tgagctcttc aggggagctg 7620
agcccgtgct ctgaaagggc ccagtctgca agatgagggt tggaagcgac gaatgagctc 7680
cacaggtcac gggccattag catttgcagg tggtcgcgaa aggtcctaaa ctggcgacct 7740
atggccattt tttctggggt gatgcagtag aaggtaagcg ggtcttgttc ccagcggtcc 7800
catccaaggt tcgcggctag gtctcgcgcg gcagtcacta gaggctcatc tccgccgaac 7860
ttcatgacca gcatgaaggg cacgagctgc ttcccaaagg cccccatcca agtataggtc 7920
tctacatcgt aggtgacaaa gagacgctcg gtgcgaggat gcgagccgat cgggaagaac 7980
tggatctccc gccaccaatt ggaggagtgg ctattgatgt ggtgaaagta gaagtccctg 8040
cgacgggccg aacactcgtg ctggcttttg taaaaacgtg cgcagtactg gcagcggtgc 8100
acgggctgta catcctgcac gaggttgacc tgacgaccgc gcacaaggaa gcagagtggg 8160
aatttgagcc cctcgcctgg cgggtttggc tggtggtctt ctacttcggc tgcttgtcct 8220
tgaccgtctg gctgctcgag gggagttacg gtggatcgga ccaccacgcc gcgcgagccc 8280
aaagtccaga tgtccgcgcg cggcggtcgg agcttgatga caacatcgcg cagatgggag 8340
ctgtccatgg tctggagctc ccgcggcgtc aggtcaggcg ggagctcctg caggtttacc 8400
tcgcatagac gggtcagggc gcgggctaga tccaggtgat acctaatttc caggggctgg 8460
ttggtggcgg cgtcgatggc ttgcaagagg ccgcatcccc gcggcgcgac tacggtaccg 8520
cgcggcgggc ggtgggccgc gggggtgtcc ttggatgatg catctaaaag cggtgacgcg 8580
ggcgagcccc cggaggtagg gggggctccg gacccgccgg gagagggggc aggggcacgt 8640
cggcgccgcg cgcgggcagg agctggtgct gcgcgcgtag gttgctggcg aacgcgacga 8700
cgcggcggtt gatctcctga atctggcgcc tctgcgtgaa gacgacgggc ccggtgagct 8760
tgagcctgaa agagagttcg acagaatcaa tttcggtgtc gttgacggcg gcctggcgca 8820
aaatctcctg cacgtctcct gagttgtctt gataggcgat ctcggccatg aactgctcga 8880
tctcttcctc ctggagatct ccgcgtccgg ctcgctccac ggtggcggcg aggtcgttgg 8940
aaatgcgggc catgagctgc gagaaggcgt tgaggcctcc ctcgttccag acgcggctgt 9000
agaccacgcc cccttcggca tcgcgggcgc gcatgaccac ctgcgcgaga ttgagctcca 9060
cgtgccgggc gaagacggcg tagtttcgca ggcgctgaaa gaggtagttg agggtggtgg 9120
cggtgtgttc tgccacgaag aagtacataa cccagcgtcg caacgtggat tcgttgatat 9180
cccccaaggc ctcaaggcgc tccatggcct cgtagaagtc cacggcgaag ttgaaaaact 9240
gggagttgcg cgccgacacg gttaactcct cctccagaag acggatgagc tcggcgacag 9300

```
tgtcgcgcac ctcgcgctca aaggctacag gggcctcttc ttcttcttca atctcctctt   9360
ccataagggc ctccccttct tcttcttctg gcggcggtgg gggagggggg acacggcggc   9420
gacgacggcg caccgggagg cggtcgacaa agcgctcgat catctccccg cggcgacggc   9480
gcatggtctc ggtgacggcg cggccgttct cgcgggggcg cagttggaag acgccgcccg   9540
tcatgtcccg gttatgggtt ggcgggggc tgccatgcgg cagggatacg gcgctaacga   9600
tgcatctcaa caattgttgt gtaggtactc cgccgccgag ggacctgagc gagtccgcat   9660
cgaccggatc ggaaaacctc tcgagaaagg cgtctaacca gtcacagtcg caaggtaggc   9720
tgagcaccgt ggcgggcggc agcgggcggc ggtcggggtt gtttctggcg gaggtgctgc   9780
tgatgatgta attaaagtag gcggtcttga gacggcggat ggtcgacaga agcaccatgt   9840
ccttgggtcc ggcctgctga atgcgcaggc ggtcggccat gccccaggct tcgttttgac   9900
atcggcgcag gtctttgtag tagtcttgca tgagcctttc taccggcact tcttcttctc   9960
cttcctcttg tcctgcatct cttgcatcta tcgctgcggc ggcggcggag tttggccgta  10020
ggtggcgccc tcttcctccc atgcgtgtga ccccgaagcc cctcatcggc tgaagcaggg  10080
ctaggtcggc gacaacgcgc tcggctaata tggcctgctg cacctgcgtg agggtagact  10140
ggaagtcatc catgtccaca aagcggtggt atgcgcccgt gttgatggtg taagtgcagt  10200
tggccataac ggaccagtta acggtctggt gacccggctg cgagagctcg gtgtacctga  10260
gacgcgagta agccctcgag tcaaatacgt agtcgttgca agtccgcacc aggtactggt  10320
atcccaccaa aaagtgcggc ggcggctggc ggtagagggg ccagcgtagg gtggccgggg  10380
ctccggggc gagatcttcc aacataaggc gatgatatcc gtagatgtac ctggacatcc  10440
aggtgatgcc ggcggcggtg gtggaggcgc gcggaaagtc gcggacgcgg ttccagatgt  10500
tgcgcagcgg caaaaagtgc tccatggtcg ggacgctctg gccggtcagg cgcgcgcaat  10560
cgttgacgct ctagaccgtg caaaaggaga gcctgtaagc gggcactctt ccgtggtctg  10620
gtggataaat tcgcaagggt atcatggcgg acgaccgggg ttcgagcccc gtatccggcc  10680
gtccgccgtg atccatgcgg ttaccgcccg cgtgtcgaac ccaggtgtgc gacgtcagac  10740
aacgggggag tgctcctttt ggcttccttc caggcgcggc ggctgctgcg ctagcttttt  10800
tggccactgg ccgcgcgcag cgtaagcggt taggctggaa agcgaaagca ttaagtggct  10860
cgctccctgt agccggaggg ttattttcca agggttgagt cgcgggaccc ccggttcgag  10920
tctcggaccg gccggactgc ggcgaacggg ggtttgcctc cccgtcatgc aagaccccgc  10980
ttgcaaattc ctccggaaac agggacgagc ccctttttg cttttcccag atgcatccgg  11040
tgctgcggca gatgcgcccc cctcctcagc agcggcaaga gcaagagcag cggcagacat  11100
gcagggcacc ctcccctcct cctaccgcgt caggaggggc gacatccgcg gttgacgcgg  11160
cagcagatgg tgattacgaa cccccgcggc gccgggcccg gcactacctg gacttggagg  11220
agggcgaggg cctggcgcgg ctaggagcgc cctctcctga gcggtaccca agggtgcagc  11280
tgaagcgtga tacgcgtgag gcgtacgtgc cgcggcagaa cctgtttcgc gaccgcgagg  11340
gagaggagcc cgaggagatg cgggatcgaa agttccacgc agggcgcgag ctgcggcatg  11400
gcctgaatcg cgagcggttg ctgcgcgagg aggactttga gcccgacgcg cgaaccggga  11460
ttagtcccgc gcgcgcacac gtggcggccg ccgacctggt aaccgcatac gagcagacgg  11520
tgaaccagga gattaacttt caaaaaagct ttaacaacca cgtgcgtacg cttgtggcgc  11580
gcgaggaggt ggctatagga ctgatgcatc tgtgggactt tgtaagcgcg ctggagcaaa  11640
```

-continued acccaaatag caagccgctc atggcgcagc tgttccttat agtgcagcac agcagggaca 11700
acgaggcatt cagggatgcg ctgctaaaca tagtagagcc cgagggccgc tggctgctcg 11760
atttgataaa catcctgcag agcatagtgg tgcaggagcg cagcttgagc ctggctgaca 11820
aggtggccgc catcaactat tccatgctta gcctgggcaa gttttacgcc cgcaagatat 11880
accatacccc ttacgttccc atagacaagg aggtaaagat cgaggggttc tacatgcgca 11940
tggcgctgaa ggtgcttacc ttgagcgacg acctgggcgt ttatcgcaac gagcgcatcc 12000
acaaggccgt gagcgtgagc cggcggcgcg agctcagcga ccgcgagctg atgcacagcc 12060
tgcaaagggc cctggctggc acgggcagcg gcgatagaga ggccgagtcc tactttgacg 12120
cgggcgctga cctgcgctgg gccccaagcc gacgcgccct ggaggcagct ggggccggac 12180
ctgggctggc ggtggcaccc gcgcgcgctg gcaacgtcgg cggcgtggag gaatatgacg 12240
aggacgatga gtacgagcca gaggacggcg agtactaagc ggtgatgttt ctgatcagat 12300
gatgcaagac gcaacggacc cggcggtgcg ggcggcgctg cagagccagc cgtccggcct 12360
taactccacg gacgactggc gccaggtcat ggaccgcatc atgtcgctga ctgcgcgcaa 12420
tcctgacgcg ttccggcagc agccgcaggc caaccggctc tccgcaattc tggaagcggt 12480
ggtcccggcg cgcgcaaacc ccacgcacga gaaggtgctg gcgatcgtaa acgcgctggc 12540
cgaaaacagg gccatccggc ccgacgaggc cggcctggtc tacgacgcgc tgcttcagcg 12600
cgtggctcgt tacaacagcg gcaacgtgca gaccaacctg gaccggctgg tgggggatgt 12660
gcgcgaggcc gtggcgcagc gtgagcgcgc gcagcagcag ggcaacctgg gctccatggt 12720
tgcactaaac gccttcctga gtacacagcc cgccaacgtg ccgcggggac aggaggacta 12780
caccaacttt gtgagcgcac tgcggctaat ggtgactgag acaccgcaaa gtgaggtgta 12840
ccagtctggg ccagactatt ttttccagac cagtagacaa ggcctgcaga ccgtaaacct 12900
gagccaggct ttcaaaaact tgcaggggct gtgggggggtg cgggctccca caggcgaccg 12960
cgcgaccgtg tctagcttgc tgacgcccaa ctcgcgcctg ttgctgctgc taatagcgcc 13020
cttcacggac agtggcagcg tgtcccggga cacataccta ggtcacttgc tgacactgta 13080
ccgcgaggcc ataggtcagg cgcatgtgga cgagcatact ttccaggaga ttacaagtgt 13140
cagccgcgcg ctggggcagg aggacacggg cagcctggag gcaaccctaa actacctgct 13200
gaccaaccgg cggcagaaga tcccctcgtt gcacagttta aacagcgagg aggagcgcat 13260
tttgcgctac gtgcagcaga gcgtgagcct taacctgatg cgcgacgggg taacgcccag 13320
cgtggcgctg gacatgaccg cgcgcaacat ggaaccgggc atgtatgcct caaaccggcc 13380
gtttatcaac cgcctaatgg actacttgca tcgcgcggcc gccgtgaacc ccgagtattt 13440
caccaatgcc atcttgaacc cgcactggct accgcccccct ggtttctaca ccgggggatt 13500
cgaggtgccc gagggtaacg atggattcct ctgggacgac atagacgaca gcgtgttttc 13560
cccgcaaccg cagaccctgc tagagttgca acagcgcgag caggcagagg cggcgctgcg 13620
aaaggaaagc ttccgcaggc caagcagctt gtccgatcta ggcgctgcgg ccccgcggtc 13680
agatgctagt agcccatttc caagcttgat agggtctctt accagcactc gcaccacccg 13740
cccgcgcctg ctgggcgagg aggagtacct aaacaactcg ctgctgcagc cgcagcgcga 13800
aaaaaacctg cctccggcat ttcccaacaa cgggatagag agcctagtgg acaagatgag 13860
tagatggaag acgtacgcgc aggagcacag ggacgtgcca ggcccgcgcc cgcccacccg 13920
tcgtcaaagg cacgaccgtc agcggggtct ggtgtgggag gacgatgact cggcagacga 13980
cagcagcgtc ctggatttgg gagggagtgg caacccgttt gcgcaccttc gccccaggct 14040

```
ggggagaatg ttttaaaaaa aaaaaagcat gatgcaaaat aaaaaactca ccaaggccat  14100
ggcaccgagc gttggttttc ttgtattccc cttagtatgc ggcgcgcggc gatgtatgag  14160
gaaggtcctc ctccctccta cgagagtgtg gtgagcgcgg cgccagtggc ggcggcgctg  14220
ggttctccct tcgatgctcc cctggacccg ccgtttgtgc ctccgcggta cctgcggcct  14280
accgggggga gaaacagcat ccgttactct gagttggcac ccctattcga caccacccgt  14340
gtgtacctgg tggacaacaa gtcaacggat gtggcatccc tgaactacca gaacgaccac  14400
agcaactttc tgaccacggt cattcaaaac aatgactaca gcccggggga ggcaagcaca  14460
cagaccatca atcttgacga ccggtcgcac tggggcggcg acctgaaaac catcctgcat  14520
accaacatgc caaatgtgaa cgagttcatg tttaccaata agtttaaggc gcgggtgatg  14580
gtgtcgcgct tgcctactaa ggacaatcag gtggagctga aatacgagtg ggtggagttc  14640
acgctgcccg agggcaacta ctccgagacc atgaccatag accttatgaa caacgcgatc  14700
gtggagcact acttgaaagt gggcagacag aacggggttc tggaaagcga catcggggta  14760
aagtttgaca cccgcaactt cagactgggg tttgaccccg tcactggtct tgtcatgcct  14820
ggggtatata caaacgaagc cttccatcca gacatcattt tgctgccagg atgcggggtg  14880
gacttcaccc acagccgcct gagcaacttg ttgggcatcc gcaagcggca acccttccag  14940
gagggcttta ggatcaccta cgatgatctg gagggtggta acattcccgc actgttggat  15000
gtggacgcct accaggcgag cttgaaagat gacaccgaac agggcggggg tggcgcaggc  15060
ggcagcaaca gcagtggcag cggcgcggaa gagaactcca acgcggcagc cgcggcaatg  15120
cagccggtgg aggacatgaa cgatcatgcc attcgcggcg acacctttgc cacacgggct  15180
gaggagaagc gcgctgaggc cgaagcagcg gccgaagctg ccgcccccgc tgcgcaaccc  15240
gaggtcgaga agcctcagaa gaaaccggtg atcaaacccc tgacagagga cagcaagaaa  15300
cgcagttaca acctaataag caatgacagc accttcaccc agtaccgcag ctggtacctt  15360
gcatacaact acggcgaccc tcagaccgga atccgctcat ggaccctgct ttgcactcct  15420
gacgtaacct gcggctcgga gcaggtctac tggtcgttgc cagacatgat gcaagacccc  15480
gtgaccttcc gctccacgcg ccagatcagc aactttccgg tggtgggcgc cgagctgttg  15540
cccgtgcact ccaagagctt ctacaacgac caggccgtct actcccaact catccgccag  15600
tttacctctc tgacccacgt gttcaatcgc tttcccgaga accagatttt ggcgcgcccg  15660
ccagccccca ccatcaccac cgtcagtgaa aacgttcctg ctctcacaga tcacgggacg  15720
ctaccgctgc gcaacagcat cggaggagtc cagcgagtga ccattactga cgccagacgc  15780
cgcacctgcc cctacgttta caaggccctg ggcatagtct cgccgcgcgt cctatcgagc  15840
cgcacttttt gagcaagcat gtccatcctt atatcgccca gcaataacac aggctggggc  15900
ctgcgcttcc caagcaagat gtttggcggg gccaagaagc gctccgacca acacccagtg  15960
cgcgtgcgcg ggcactaccg cgcgccctgg ggcgcgcaca aacgcggccg cactgggcgc  16020
accaccgtcg atgacgccat cgacgcggtg gtggaggagg cgcgcaacta cacgcccacg  16080
ccgccaccag tgtccacagt ggacgcggcc attcagaccg tggtgcgcgg agcccggcgc  16140
tatgctaaaa tgaagagacg gcggaggcgc gtagcacgtc gccaccgccg ccgacccggc  16200
actgccgccc aacgcgcggc ggcggccctg cttaaccgcg cacgtcgcac cggccgacgg  16260
gcggccatgc gggccgctcg aaggctggcc gcgggtattg tcactgtgcc ccccaggtcc  16320
aggcgacgag cggccgccgc agcagccgcg gccattagtg ctatgactca gggtcgcagg  16380
```

```
ggcaacgtgt attgggtgcg cgactcggtt agcggcctgc gcgtgcccgt gcgcacccgc  16440
cccccgcgca actagattgc aagaaaaaac tacttagact cgtactgttg tatgtatcca  16500
gcggcggcgg cgcgcaacga agctatgtcc aagcgcaaaa tcaaagaaga gatgctccag  16560
gtcatcgcgc cggagatcta tggcccccg aagaaggaag agcaggatta caagccccga  16620
aagctaaagc gggtcaaaaa gaaaaagaaa gatgatgatg atgaacttga cgacgaggtg  16680
gaactgctgc acgctaccgc gcccaggcga cgggtacagt ggaaaggtcg acgcgtaaaa  16740
cgtgttttgc gacccggcac caccgtagtc tttacgcccg gtgagcgctc cacccgcacc  16800
tacaagcgcg tgtatgatga ggtgtacggc gacgaggacc tgcttgagca ggccaacgag  16860
cgcctcgggg agtttgccta cggaaagcgg cataaggaca tgctggcgtt gccgctggac  16920
gagggcaacc caacacctag cctaaagccc gtaacactgc agcaggtgct gcccgcgctt  16980
gcaccgtccg aagaaaagcg cggcctaaag cgcgagtctg gtgacttggc acccaccgtg  17040
cagctgatgg tacccaagcg ccagcgactg gaagatgtct tggaaaaaat gaccgtggaa  17100
cctgggctgg agcccgaggt ccgcgtgcgg ccaatcaagc aggtggcgcc gggactgggc  17160
gtgcagaccg tggacgttca gatacccact accagtagca ccagtattgc caccgccaca  17220
gagggcatgg agacacaaac gtccccggtt gcctcagcgg tggcggatgc cgcggtgcag  17280
gcggtcgctg cggccgcgtc caagacctct acggaggtgc aaacggaccc gtggatgttt  17340
cgcgtttcag cccccggcg cccgcgcggt tcgaggaagt acggcgccgc cagcgcgcta  17400
ctgcccgaat atgccctaca tccttccatt gcgcctaccc ccggctatcg tggctacacc  17460
taccgcccca gaagacgagc aactacccga cgccgaacca ccactggaac ccgccgccgc  17520
cgtcgccgtc gccagcccgt gctggccccg atttccgtgc gcagggtggc tcgcgaagga  17580
ggcaggaccc tggtgctgcc aacagcgcgc taccacccca gcatcgttta aaagccggtc  17640
tttgtggttc ttgcagatat ggccctcacc tgccgcctcc gtttcccggt gccgggattc  17700
cgaggaagaa tgcaccgtag gaggggcatg gccggccacg gcctgacggg cggcatgcgt  17760
cgtgcgcacc accggcggcg gcgcgcgtcg caccgtcgca tgcgcggcgg tatcctgccc  17820
ctccttattc cactgatcgc cgcggcgatt ggcgccgtgc ccggaattgc atccgtggcc  17880
ttgcaggcgc agagacactg attaaaaaca agttgcatgt ggaaaaatca aaataaaaag  17940
tctggactct cacgctcgct tggtcctgta actattttgt agaatggaag acatcaactt  18000
tgcgtctctg gccccgcgac acggctcgcg cccgttcatg ggaaactggc aagatatcgg  18060
caccagcaat atgagcggtg gcgccttcag ctggggctcg ctgtggagcg gcattaaaaa  18120
tttcggttcc accgttaaga actatggcag caaggcctgg aacagcagca caggccagat  18180
gctgagggat aagttgaaag agcaaaattt ccaacaaaag gtggtagatg gcctggcctc  18240
tggcattagc ggggtggtgg acctggccaa ccaggcagtg caaaataaga ttaacagtaa  18300
gcttgatccc cgccctcccg tagaggagcc tccaccggcc gtggagacag tgtctccaga  18360
ggggcgtggc gaaaagcgtc cgcgccccga cagggaagaa actctggtga cgcaaataga  18420
cgagcctccc tcgtacgagg aggcactaaa gcaaggcctg cccaccaccc gtcccatcgc  18480
gcccatggct accggagtgc tgggccagca cacacccgta acgctggacc tgcctccccc  18540
cgccgacacc cagcagaaac ctgtgctgcc aggcccgacc gccgttgttg taacccgtcc  18600
tagccgcgcg tccctgcgcc gcgccgccag cggtccgcga tcgttgcggc ccgtagccag  18660
tggcaactgg caaagcacac tgaacagcat cgtgggtctg ggggtgcaat ccctgaagcg  18720
ccgacgatgc ttctgaatag ctaacgtgtc gtatgtgtgt catgtatgcg tccatgtcgc  18780
```

```
cgccagagga gctgctgagc cgccgcgcgc ccgctttcca agatggctac cccttcgatg  18840
atgccgcagt ggtcttacat gcacatctcg ggccaggacg cctcggagta cctgagcccc  18900
gggctggtgc agtttgcccg cgccaccgag acgtacttca gcctgaataa caagtttaga  18960
aaccccacgg tggcgcctac gcacgacgtg accacagacc ggtcccagcg tttgacgctg  19020
cggttcatcc ctgtggaccg tgaggatact gcgtactcgt acaaggcgcg gttcacccta  19080
gctgtgggtg ataaccgtgt gctggacatg gcttccacgt actttgacat ccgcggcgtg  19140
ctggacaggg gccctacttt taagccctac tctggcactg cctacaacgc cctggctccc  19200
aagggtgccc caaatccttg cgaatgggat gaagctgcta ctgctcttga aataaaccta  19260
gaagaagagg acgatgacaa cgaagacgaa gtagacgagc aagctgagca gcaaaaaact  19320
cacgtatttg ggcaggcgcc ttattctggt ataaatatta caaaggaggg tattcaaata  19380
ggtgtcgaag gtcaaacacc taaatatgcc gataaaacat ttcaacctga acctcaaata  19440
ggagaatctc agtggtacga aactgaaatt aatcatgcag ctgggagagt ccttaaaaag  19500
actaccccaa tgaaaccatg ttacggttca tatgcaaaac ccacaaatga aaatggaggg  19560
caaggcattc ttgtaaagca acaaaatgga aagctagaaa gtcaagtgga aatgcaattt  19620
ttctcaacta ctgaggcgac cgcaggcaat ggtgataact tgactcctaa agtggtattg  19680
tacagtgaag atgtagatat agaaacccca gacactcata tttcttacat gcccactatt  19740
aaggaaggta actcacgaga actaatgggc caacaatcta tgcccaacag gcctaattac  19800
attgctttta gggacaattt tattggtcta atgtattaca acagcacggg taatatgggt  19860
gttctggcgg gccaagcatc gcagttgaat gctgttgtag atttgcaaga cagaaacaca  19920
gagctttcat accagctttt gcttgattcc attggtgata gaaccaggta cttttctatg  19980
tggaatcagg ctgttgacag ctatgatcca gatgttagaa ttattgaaaa tcatggaact  20040
gaagatgaac ttccaaatta ctgctttcca ctgggaggtg tgattaatac agagactctt  20100
accaaggtaa aacctaaaac aggtcaggaa aatggatggg aaaaagatgc tacagaattt  20160
tcagataaaa atgaaataag agttggaaat aattttgcca tggaaatcaa tctaaatgcc  20220
aacctgtgga gaaatttcct gtactccaac atagcgctgt atttgcccga caagctaaag  20280
tacagtcctt ccaacgtaaa aatttctgat aacccaaaca cctacgacta catgaacaag  20340
cgagtggtgg ctcccgggtt agtggactgc tacattaacc ttggagcacg ctggtccctt  20400
gactatatgg acaacgtcaa cccatttaac caccaccgca atgctggcct gcgctaccgc  20460
tcaatgttgc tgggcaatgg tcgctatgtg cccttccaca tccaggtgcc tcagaagttc  20520
tttgccatta aaaacctcct tctcctgccg ggctcataca cctacgagtg gaacttcagg  20580
aaggatgtta acatggttct gcagagctcc ctaggaaatg acctaagggt tgacggagcc  20640
agcattaagt ttgatagcat ttgcctttac gccaccttct tccccatggc ccacaacacc  20700
gcctccacgc ttgaggccat gcttagaaac gacaccaacg accagtcctt taacgactat  20760
ctctccgccg ccaacatgct ctaccctata cccgccaacg ctaccaacgt gcccatatcc  20820
atcccctccc gcaactgggc ggctttccgc ggctgggcct tcacgcgcct taagactaag  20880
gaaaccccat cactgggctc gggctacgac ccttattaca cctactctgg ctctataccc  20940
tacctagatg gaacctttta cctcaaccac acctttaaga aggtggccat tacctttgac  21000
tcttctgtca gctggcctgg caatgaccgc ctgcttaccc ccaacgagtt tgaaattaag  21060
cgctcagttg acggggaggg ttacaacgtt gcccagtgta acatgaccaa agactggttc  21120
```

-continued

```
ctggtacaaa tgctagctaa ctacaacatt ggctaccagg gcttctatat cccagagagc  21180
tacaaggacc gcatgtactc cttctttaga aacttccagc ccatgagccg tcaggtggtg  21240
gatgatacta aatacaagga ctaccaacag gtgggcatcc tacaccaaca caacaactct  21300
ggatttgttg gctaccttgc ccccaccatg cgcgaaggac aggcctaccc tgctaacttc  21360
ccctatccgc ttataggcaa gaccgcagtt gacagcatta cccagaaaaa gtttctttgc  21420
gatcgcaccc tttggcgcat cccattctcc agtaacttta tgtccatggg cgcactcaca  21480
gacctgggcc aaaaccttct ctacgccaac tccgcccacg cgctagacat gacttttgag  21540
gtggatccca tggacgagcc cacccttctt tatgttttgt ttgaagtctt tgacgtggtc  21600
cgtgtgcacc ggccgcaccg cggcgtcatc gaaaccgtgt acctgcgcac gcccttctcg  21660
gccggcaacg ccacaacata aagaagcaag caacatcaac aacagctgcc gccatgggct  21720
ccagtgagca ggaactgaaa gccattgtca aagatcttgg ttgtgggcca tatttttgg  21780
gcacctatga caagcgcttt ccaggctttg tttctccaca caagctcgcc tgcgccatag  21840
tcaatacggc cggtcgcgag actgggggcg tacactggat ggcctttgcc tggaacccgc  21900
actcaaaaac atgctacctc tttgagccct ttggcttttc tgaccagcga ctcaagcagg  21960
tttaccagtt tgagtacgag tcactcctgc gccgtagcgc cattgcttct tcccccgacc  22020
gctgtataac gctggaaaag tccacccaaa gcgtacaggg gcccaactcg gccgcctgtg  22080
gactattctg ctgcatgttt ctccacgcct ttgccaactg gccccaaact cccatggatc  22140
acaaccccac catgaacctt attaccgggg tacccaactc catgctcaac agtccccagg  22200
tacagcccac cctgcgtcgc aaccaggaac agctctacag cttcctggag cgccactcgc  22260
cctacttccg cagccacagt gcgcagatta ggagcgccac ttctttttgt cacttgaaaa  22320
acatgtaaaa ataatgtact agagacactt tcaataaagg caaatgcttt tatttgtaca  22380
ctctcgggtg attatttacc cccacccttg ccgtctgcgc cgtttaaaaa tcaaaggggt  22440
tctgccgcgc atcgctatgc gccactggca gggacacgtt gcgatactgg tgtttagtgc  22500
tccacttaaa ctcaggcaca accatccgcg gcagctcggt gaagttttca ctccacaggc  22560
tgcgcaccat caccaacgcg tttagcaggt cgggcgccga tatcttgaag tcgcagttgg  22620
ggcctccgcc ctgcgcgcgc gagttgcgat acacagggtt gcagcactgg aacactatca  22680
gcgccgggtg gtgcacgctg gccagcacgc tcttgtcgga gatcagatcc gcgtccaggt  22740
cctccgcgtt gctcagggcg aacggagtca actttggtag ctgccttccc aaaaagggcg  22800
cgtgcccagg ctttgagttg cactcgcacc gtagtggcat caaaaggtga ccgtgcccgg  22860
tctgggcgtt aggatacagc gcctgcataa aagccttgat ctgcttaaaa gccacctgag  22920
cctttgcgcc ttcagagaag aacatgccgc aagacttgcc ggaaaactga ttggccggac  22980
aggccgcgtc gtgcacgcag caccttgcgt cggtgttgga gatctgcacc acatttcggc  23040
cccaccggtt cttcacgatc ttggccttgc tagactgctc cttcagcgcg cgctgcccgt  23100
tttcgctcgt cacatccatt tcaatcacgt gctccttatt tatcataatg cttccgtgta  23160
gacacttaag ctcgccttcg atctcagcgc agcggtgcag ccacaacgcg cagcccgtgg  23220
gctcgtgatg cttgtaggtc acctctgcaa acgactgcag gtacgcctgc aggaatcgcc  23280
ccatcatcgt cacaaaggtc ttgttgctgg tgaaggtcag ctgcaacccg cggtgctcct  23340
cgttcagcca ggtcttgcat acggccgcca gagcttccac ttggtcaggc agtagtttga  23400
agttcgcctt tagatcgtta tccacgtggt acttgtccat cagcgcgcgc gcagcctcca  23460
tgcccttctc ccacgcagac acgatcggca cactcagcgg gttcatcacc gtaatttcac  23520
```

tttccgcttc gctgggctct tcctcttcct cttgcgtccg cataccacgc gccactgggt 23580
cgtcttcatt cagccgccgc actgtgcgct tacctccttt gccatgcttg attagcaccg 23640
gtgggttgct gaaacccacc atttgtagcg ccacatcttc tctttcttcc tcgctgtcca 23700
cgattacctc tggtgatggc gggcgctcgg gcttgggaga agggcgcttc tttttcttct 23760
tgggcgcaat ggccaaatcc gccgccgagg tcgatggccg cgggctgggt gtgcgcggca 23820
ccagcgcgtc ttgtgatgag tcttcctcgt cctcggactc gatacgccgc ctcatccgct 23880
tttttggggg cgcccgggga ggcggcggcg acggggacgg ggacgacacg tcctccatgg 23940
ttgggggacg tcgcgccgca ccgcgtccgc gctcgggggt ggtttcgcgc tgctcctctt 24000
cccgactggc catttccttc tcctataggc agaaaaagat catggagtca gtcgagaaga 24060
aggacagcct aaccgccccc tctgagttcg ccaccaccgc ctccaccgat gccgccaacg 24120
cgcctaccac cttccccgtc gaggcacccc cgcttgagga ggaggaagtg attatcgagc 24180
aggacccagg ttttgtaagc gaagacgacg aggaccgctc agtaccaaca gaggataaaa 24240
agcaagacca ggacaacgca gaggcaaacg aggaacaagt cgggcggggg gacgaaaggc 24300
atggcgacta cctagatgtg ggagacgacg tgctgttgaa gcatctgcag cgccagtgcg 24360
ccattatctg cgacgcgttg caagagcgca gcgatgtgcc cctcgccata gcggatgtca 24420
gccttgccta cgaacgccac ctattctcac cgcgcgtacc ccccaaacgc caagaaaacg 24480
gcacatgcga gcccaacccg cgcctcaact tctaccccgt atttgccgtg ccagaggtgc 24540
ttgccaccta tcacatcttt ttccaaaact gcaagatacc cctatcctgc cgtgccaacc 24600
gcagccgagc ggacaagcag ctggccttgc ggcagggcgc tgtcatacct gatatcgcct 24660
cgctcaacga agtgccaaaa atctttgagg gtcttggacg cgacgagaag cgcgcggcaa 24720
acgctctgca acaggaaaac agcgaaaatg aaagtcactc tggagtgttg gtggaactcg 24780
agggtgacaa cgcgcgccta gccgtactaa aacgcagcat cgaggtcacc cactttgcct 24840
acccggcact taacctaccc cccaaggtca tgagcacagt catgagtgag ctgatcgtgc 24900
gccgtgcgca gcccctggag agggatgcaa atttgcaaga acaaacagag gagggcctac 24960
ccgcagttgg cgacgagcag ctagcgcgct ggcttcaaac gcgcgagcct gccgacttgg 25020
aggagcgacg caaactaatg atggccgcag tgctcgttac cgtggagctt gagtgcatgc 25080
agcggttctt tgctgacccg gagatgcagc gcaagctaga ggaaacattg cactacacct 25140
ttcgacaggg ctacgtacgc caggcctgca agatctccaa cgtggagctc tgcaacctgg 25200
tctcctacct tggaattttg cacgaaaacc gccttgggca aaacgtgctt cattccacgc 25260
tcaagggcga ggcgcgccgc gactacgtcc gcgactgcgt ttacttattt ctatgctaca 25320
cctggcagac ggccatgggc gtttggcagc agtgcttgga ggagtgcaac ctcaaggagc 25380
tgcagaaact gctaaagcaa aacttgaagg acctatggac ggccttcaac gagcgctccg 25440
tggccgcgca cctggcggac atcattttcc ccgaacgcct gcttaaaacc ctgcaacagg 25500
gtctgccaga cttcaccagt caaagcatgt tgcagaactt taggaacttt atcctagagc 25560
gctcaggaat cttgcccgcc acctgctgtg cacttcctag cgactttgtg cccattaagt 25620
accgcgaatg ccctccgccg ctttggggcc actgctacct tctgcagcta gccaactacc 25680
ttgcctacca ctctgacata atggaagacg tgagcggtga cggtctactg gagtgtcact 25740
gtcgctgcaa cctatgcacc ccgcaccgct ccctggtttg caattcgcag ctgcttaacg 25800
aaagtcaaat tatcggtacc tttgagctgc agggtccctc gcctgacgaa aagtccgcgg 25860

-continued

```
ctccggggtt gaaactcact ccggggctgt ggacgtcggc ttaccttcgc aaatttgtac  25920
ctgaggacta ccacgcccac gagattaggt tctacgaaga ccaatcccgc ccgccaaatg  25980
cggagcttac cgcctgcgtc attacccagg gccacattct tggccaattg caagccatca  26040
acaaagcccg ccaagagttt ctgctacgaa agggacgggg ggtttacttg gacccccagt  26100
ccggcgagga gctcaaccca atccccccgc cgccgcagcc ctatcagcag cagccgcggg  26160
cccttgcttc ccaggatggc acccaaaaag aagctgcagc tgccgccgcc acccacggac  26220
gaggaggaat actgggacag tcaggcagag gaggttttgg acgaggagga ggaggacatg  26280
atggaagact gggagagcct agacgaggaa gcttccgagg tcgaagaggt gtcagacgaa  26340
acaccgtcac cctcggtcgc attcccctcg ccggcgcccc agaaatcggc aaccggttcc  26400
agcatggcta caacctccgc tcctcaggcg ccgccggcac tgcccgttcg ccgacccaac  26460
cgtagatggg acaccactgg aaccagggcc ggtaagtcca agcagccgcc gccgttagcc  26520
caagagcaac aacagcgcca aggctaccgc tcatggcgcg ggcacaagaa cgccatagtt  26580
gcttgcttgc aagactgtgg gggcaacatc tccttcgccc gccgctttct tctctaccat  26640
cacggcgtgg ccttcccccg taacatcctg cattactacc gtcatctcta cagcccatac  26700
tgcaccggcg gcagcggcag cggcagcaac agcagcggcc acacagaagc aaaggcgacc  26760
ggatagcaag actctgacaa agcccaagaa atccacagcg gcggcagcag caggaggagg  26820
agcgctgcgt ctggcgccca acgaacccgt atcgacccgc gagcttagaa acaggatttt  26880
tcccactctg tatgctatat ttcaacagag caggggccaa gaacaagagc tgaaaataaa  26940
aaacaggtct ctgcgatccc tcacccgcag ctgcctgtat cacaaaagcg aagatcagct  27000
tcggcgcacg ctggaagacg cggaggctct cttcagtaaa tactgcgcgc tgactcttaa  27060
ggactagttt cgcgcccttt ctcaaattta agcgcgaaaa ctacgtcatc tccagcggcc  27120
acacccggcg ccagcacctg tcgtcagcgc cattatgagc aaggaaattc ccacgcccta  27180
catgtggagt taccagccac aaatgggact tgcggctgga gctgcccaag actactcaac  27240
ccgaataaac tacatgagcg cgggacccca catgatatcc cgggtcaacg gaatccgcgc  27300
ccaccgaaac cgaattctct tggaacaggc ggctattacc accacacctc gtaataacct  27360
taatccccgt agttggcccg ctgccctggt gtaccaggaa agtcccgctc ccaccactgt  27420
ggtacttccc agagacgccc aggccgaagt tcagatgact aactcagggg cgcagcttgc  27480
gggcggcttt cgtcacaggg tgcggtcgcc cgggcagggt ataactcacc tgacaatcag  27540
agggcgaggt attcagctca acgacgagtc ggtgagctcc tcgcttggtc tccgtccgga  27600
cgggacattt cagatcggcg gcgccggccg ctcttcattc acgcctcgtc aggcaatcct  27660
aactctgcag acctcgtcct ctgagccgcg ctctggaggc attggaactc tgcaatttat  27720
tgaggagttt gtgccatcgg tctactttaa ccccttctcg ggacctcccg gccactatcc  27780
ggatcaattt attcctaact ttgacgcggt aaaggactcg gcggatggct acgactgaat  27840
gttaagtgga gaggcagagc aactgcgcct gaaacacctg gtccactgtc gccgccacaa  27900
gtgctttgcc cgcgactccg gtgagttttg ctactttgaa ttgcccgagg atcatatcga  27960
gggcccggcg cacggcgtcc ggcttaccgc ccagggagag cttgcccgta gcctgattcg  28020
ggagtttacc cagcgccccc tgctagttga gcgggacagg ggaccctgtg ttctcactgt  28080
gatttgcaac tgtcctaacc ctggattaca tcaagatctt tgttgccatc tctgtgctga  28140
gtataataaa tacagaaatt aaaatatact ggggctccta tcgccatcct gtaaacgcca  28200
ccgtcttcac ccgcccaagc aaaccaaggc gaaccttacc tggtactttt aacatctctc  28260
```

cctctgtgat ttacaacagt ttcaacccag acggagtgag tctacgagag aacctctccg 28320
agctcagcta ctccatcaga aaaaacacca ccctccttac ctgccgggaa cgtacgatgt 28380
ggctgcagag cctgctgctc ttgggcactg tggcctgcag catctctgca cccgcccgct 28440
cgcccagccc cagcacgcag ccctgggagc atgtgaatgc catccaggag gcccggcgtc 28500
tcctgaacct gagtagagac actgctgctg agatgaatga aacagtagaa gtcatctcag 28560
aaatgtttga cctccaggag ccgacctgcc tacagacccg cctggagctg tacaagcagg 28620
gcctgcgggg cagcctcacc aagctcaagg gccccttgac catgatggcc agccactaca 28680
agcagcactg ccctccaacc ccggaaactt cctgtgcaac ccagactatc acctttgaaa 28740
gtttcaaaga gaacctgaag gactttctgc ttgtcatccc ctttgactgc tgggagccag 28800
tccaggagtg acaattgact ctatgtggga tatgctccag cgctacaacc ttgaagtcag 28860
gcttcctgga tgtcagcatc tgactttggc cagcacctgt cccgcggatt tgttccagtc 28920
caactacagc gacccaccct aacagagatg accaacacaa ccaacgcggc cgccgctacc 28980
ggacttacat ctaccacaaa tacaccccaa gtttctgcct ttgtcaataa ctgggataac 29040
ttgggcatgt ggtggttctc catagcgctt atgtttgtat gccttattat tatgtggctc 29100
atctgctgcc taaagcgcaa acgcgcccga ccacccatct atagtcccat cattgtgcta 29160
cacccaaaca atgatggaat ccatagattg gacggactga aacacatgtt cttttctctt 29220
acagtatgat taaatgagac atgattcctc gagtttttat attactgacc cttgttgcgc 29280
ttttttgtgc gtgctccaca ttggctgcgg tttctcacat cgaagtagac tgcattccag 29340
ccttcacagt ctatttgctt tacggatttg tcaccctcac gctcatctgc agcctcatca 29400
ctgtggtcat cgcctttatc cagtgcattg actgggtctg tgtgcgcttt gcatatctca 29460
gacaccatcc ccagtacagg gacaggacta tagctgagct tcttagaatt ctttaattat 29520
gaaatttact gtgacttttc tgctgattat ttgcacccta tctgcgtttt gttccccgac 29580
ctccaagcct caaagacata tatcatgcag attcactcgt atatggaata ttccaagttg 29640
ctacaatgaa aaaagcgatc tttccgaagc ctggttatat gcaatcatct ctgttatggt 29700
gttctgcagt accatcttag ccctagctat atatccctac cttgacattg gctggaaacg 29760
aatagatgcc atgaaccacc caactttccc cgcgcccgct atgcttccac tgcaacaagt 29820
tgttgccggc ggctttgtcc cagccaatca gcctcgcccc acttctccca cccccactga 29880
aatcagctac tttaatctaa caggaggaga tgactgacac cctagatcta gaaatggacg 29940
gaattattac agagcagcgc ctgctagaaa gacgcagggc agcggccgag caacagcgca 30000
tgaatcaaga gctccaagac atggttaact tgcaccagtg caaaaggggt atcttttgtc 30060
tggtaaagca ggccaaagtc acctacgaca gtaataccac cggacaccgc cttagctaca 30120
agttgccaac caagcgtcag aaattggtgg tcatggtggg agaaaagccc attaccataa 30180
ctcagcactc ggtagaaacc gaaggctgca ttcactcacc ttgtcaagga cctgaggatc 30240
tctgcaccct tattaagacc ctgtgcggtc tcaaagatct tattcccttt aactaataaa 30300
aaaaaataat aaagcatcac ttacttaaaa tcagttagca aatttctgtc cagtttattc 30360
agcagcacct ccttgccctc ctcccagctc tggtattgca gcttcctcct ggctgcaaac 30420
tttctccaca atctaaatgg aatgtcagtt tcctcctgtt cctgtccatc cgcacccact 30480
atcttcatgt tgttgcagat gaagcgcgca agaccgtctg aagatacctt caaccccgtg 30540
tatccatacc catttaaatg ggtgacacgg aaaccggtcc tccaactgtg ccttttctta 30600

-continued

```
ctcctccctt tgtatccccc aatgggtttc aagagagtcc ccctggggta ctctctttgc  30660
gcctatccga acctctagtt acctccaatg gcatgcttgc gctcaaaatg ggcaacggcc  30720
tctctctgga cgaggccggc aaccttacct cccaaaatgt aaccactgtg agcccacctc  30780
tcaaaaaaac caagtcaaac ataaacctgg aaatatctgc acccctcaca gttacctcag  30840
aagccctaac tgtggctgcc gccgcacctc taatggtcgc gggcaacaca ctcaccatgc  30900
aatcacaggc cccgctaacc gtgcacgact ccaaacttag cattgccacc caaggacccc  30960
tcacagtgtc agaaggaaag ctagccctgc aaacatcagg ccccctcacc accaccgata  31020
gcagtaccct tactatcact gcctcacccc ctctaactac tgccactggt agcttgggca  31080
ttgacttgaa agagcccatt tatacacaaa atggaaaact aggactaaag tacggggctc  31140
ctttgcatgt aacagacgac ctaaacactt tgaccgtagc aactggtcca ggtgtgacta  31200
ttaataatac ttccttgcaa actaaagtta ctggagcctt gggttttgat tcacaaggca  31260
atatgcaact taatgtagca ggaggactaa ggattgattc tcaaaacaga cgccttatac  31320
ttgatgttag ttatccgttt gatgctcaaa accaactaaa tctaagacta ggacagggcc  31380
ctctttttat aaactcagcc cacaacttgg atattaacta caacaaaggc ctttacttgt  31440
ttacagcttc aaacaattcc aaaaagcttg aggttaacct aagcactgcc aaggggttga  31500
tgtttgacgc tacagccata gccattaatg caggagatgg gcttgaattt ggttcaccta  31560
atgcaccaaa cacaaatccc ctcaaaacaa aaattggcca tggcctagaa tttgattcaa  31620
acaaggctat ggttcctaaa ctaggaactg gccttagttt tgacagcaca ggtgccatta  31680
cagtaggaaa caaaaataat gataagctaa ctttgtggac cacaccagct ccatctccta  31740
actgtagact aaatgcagag aaagatgcta aactcacttt ggtcttaaca aaatgtggca  31800
gtcaaatact tgctacagtt tcagttttgg ctgttaaagg cagtttggct ccaatatctg  31860
gaacagttca aagtgctcat cttattataa gatttgacga aaatggagtg ctactaaaca  31920
attccttcct ggacccagaa tattggaact ttagaaatgg agatcttact gaaggcacag  31980
cctatacaaa cgctgttgga tttatgccta acctatcagc ttatccaaaa tctcacggta  32040
aaactgccaa aagtaacatt gtcagtcaag tttacttaaa cggagacaaa actaaacctg  32100
taacactaac cattacacta aacggtacac aggaaacagg agacacaact ccaagtgcat  32160
actctatgtc attttcatgg gactggtctg gccacaacta cattaatgaa atatttgcca  32220
catcctctta cactttttca tacattgcgc aagaaggatc aggatcaggt tcagggagtg  32280
gctctaaaaa gaagaaaaag aagaagtaat aaagtaatcg tttgtgttat gtttcaacgt  32340
gtttattttt caattgcaga aaatttcaag tcatttttca ttcagtagta tagccccacc  32400
accacatagc ttatacagat caccgtacct taatcaaact cacagaaccc tagtattcaa  32460
cctgccacct ccctcccaac acacagagta cacagtcctt tctccccggc tggccttaaa  32520
aagcatcata tcatgggtaa cagacatatt cttaggtgtt atattccaca cggtttcctg  32580
tcgagccaaa cgctcatcag tgatattaat aaactccccg ggcagctcac ttaagttcat  32640
gtcgctgtcc agctgctgag ccacaggctg ctgtccaact tgcggttgct taacgggcgg  32700
cgaaggagaa gtccacgcct acatgggggt agagtcataa tcgtgcatca ggatagggcg  32760
gtggtgctgc agcagcgcgc gaataaactg ctgccgccgc cgctccgtcc tgcaggaata  32820
caacatggca gtggtctcct cagcgatgat tcgcaccgcc cgcagcataa ggcgccttgt  32880
cctccgggca cagcagcgca ccctgatctc acttaaatca gcacagtaac tgcagcacag  32940
caccacaata ttgttcaaaa tcccacagtg caaggcgctg tatccaaagc tcatggcggg  33000
```

```
gaccacagaa cccacgtggc catcatacca caagcgcagg tagattaagt ggcgacccct  33060
cataaacacg ctggacataa acattacctc ttttggcatg ttgtaattca ccacctcccg  33120
gtaccatata aacctctgat taaacatggc gccatccacc accatcctaa accagctggc  33180
caaaacctgc ccgccggcta tacactgcag ggaaccggga ctggaacaat gacagtggag  33240
agcccaggac tcgtaaccat ggatcatcat gctcgtcatg atatcaatgt tggcacaaca  33300
caggcacacg tgcatacact tcctcaggat tacaagctcc tcccgcgtta gaaccatatc  33360
ccagggaaca acccattcct gaatcagcgt aaatcccaca ctgcagggaa gacctcgcac  33420
gtaactcacg ttgtgcattg tcaaagtgtt acattcgggc agcagcggat gatcctccag  33480
tatggtagcg cgggtttctg tctcaaaagg aggtagacga tccctactgt acggagtgcg  33540
ccgagacaac cgagatcgtg ttggtcgtag tgtcatgcca aatggaacgc cggacgtagt  33600
catatttcct gaagcaaaac caggtgcggg cgtgacaaac agatctgcgt ctccggtctc  33660
gccgcttaga tcgctctgtg tagtagttgt agtatatcca ctctctcaaa gcatccaggc  33720
gccccctggc ttcgggttct atgtaaactc cttcatgcgc cgctgccctg ataacatcca  33780
ccaccgcaga ataagccaca cccagccaac ctacacattc gttctgcgag tcacacacgg  33840
gaggagcggg aagagctgga agaaccatgt ttttttttt attccaaaag attatccaaa  33900
acctcaaaat gaagatctat taagtgaacg cgctcccctc cggtggcgtg gtcaaactct  33960
acagccaaag aacagataat ggcatttgta agatgttgca caatggcttc caaaaggcaa  34020
acggccctca cgtccaagtg gacgtaaagg ctaaaccctt cagggtgaat ctcctctata  34080
aacattccag caccttcaac catgcccaaa taattctcat ctcgccacct tctcaatata  34140
tctctaagca aatcccgaat attaagtccg gccattgtaa aaatctgctc cagagcgccc  34200
tccaccttca gcctcaagca gcgaatcatg attgcaaaaa ttcaggttcc tcacagacct  34260
gtataagatt caaaagcgga acattaacaa aaataccgcg atcccgtagg tcccttcgca  34320
gggccagctg aacataatcg tgcaggtctg cacggaccag cgcggccact tccccgccag  34380
gaaccatgac aaaagaaccc acactgatta tgacacgcat actcggagct atgctaacca  34440
gcgtagcccc gatgtaagct tgttgcatgg gcggcgatat aaaatgcaag gtgctgctca  34500
aaaaatcagg caaagcctcg cgcaaaaaag aaagcacatc gtagtcatgc tcatgcagat  34560
aaaggcaggt aagctccgga accaccacag aaaaagacac catttttctc tcaaacatgt  34620
ctgcgggttt ctgcataaac acaaaataaa ataacaaaaa aacatttaaa cattagaagc  34680
ctgtcttaca acaggaaaaa caacccttat aagcataaga cggactacgg ccatgccggc  34740
gtgaccgtaa aaaaactggt caccgtgatt aaaaagcacc accgacagct cctcggtcat  34800
gtccggagtc ataatgtaag actcggtaaa cacatcaggt tgattcacat cggtcagtgc  34860
taaaaagcga ccgaaatagc ccgggggaat acatacccgc aggcgtagag acaacattac  34920
agcccccata ggaggtataa caaaattaat aggagagaaa aacacataaa cacctgaaaa  34980
accctcctgc ctaggcaaaa tagcaccctc ccgctccaga acaacataca gcgcttccac  35040
agcggcagcc ataacagtca gccttaccag taaaaaagaa aacctattaa aaaaacacca  35100
ctcgacacgg caccagctca atcagtcaca gtgtaaaaaa gggccaagtg cagagcgagt  35160
atatatagga ctaaaaaatg acgtaacggt taaagtccac aaaaaacacc cagaaaaccg  35220
cacgcgaacc tacgcccaga aacgaaagcc aaaaaaccca caacttcctc aaatcgtcac  35280
ttccgttttc ccacgttacg tcacttccca ttttaagaaa actacaattc ccaacacata  35340
```

-continued caagttactc cgccctaaaa cctacgtcac ccgccccgtt cccacgcccc gcgccacgtc 35400
acaaactcca ccccctcatt atcatattgg cttcaatcca aaataaggta tattattgat 35460
gatgttaatt aaggatccnn ncggtgtgaa ataccgcaca gatgcgtaag gagaaaatac 35520
cgcatcaggc gctcttccgc ttcctcgctc actgactcgc tgcgctcggt cgttcggctg 35580
cggcgagcgg tatcagctca ctcaaaggcg gtaatacggt tatccacaga atcaggggat 35640
aacgcaggaa agaacatgtg agcaaaaggc cagcaaaagg ccaggaaccg taaaaaggcc 35700
gcgttgctgg cgtttttcca taggctccgc ccccctgacg agcatcacaa aaatcgacgc 35760
tcaagtcaga ggtggcgaaa cccgacagga ctataaagat accaggcgtt tccccctgga 35820
agctccctcg tgcgctctcc tgttccgacc ctgccgctta ccggatacct gtccgccttt 35880
ctcccttcgg gaagcgtggc gctttctcat agctcacgct gtaggtatct cagttcggtg 35940
taggtcgttc gctccaagct gggctgtgtg cacgaacccc ccgttcagcc cgaccgctgc 36000
gccttatccg gtaactatcg tcttgagtcc aacccggtaa gacacgactt atcgccactg 36060
gcagcagcca ctggtaacag gattagcaga gcgaggtatg taggcggtgc tacagagttc 36120
ttgaagtggt ggcctaacta cggctacact agaaggacag tatttggtat ctgcgctctg 36180
ctgaagccag ttaccttcgg aaaaagagtt ggtagctctt gatccggcaa acaaaccacc 36240
gctggtagcg gtggtttttt tgtttgcaag cagcagatta cgcgcagaaa aaaaggatct 36300
caagaagatc ctttgatctt ttctacgggg tctgacgctc agtggaacga aaactcacgt 36360
taagggattt tggtcatgag attatcaaaa aggatcttca cctagatcct tttaaattaa 36420
aaatgaagtt ttaaatcaat ctaaagtata tatgagtaaa cttggtctga cagttaccaa 36480
tgcttaatca gtgaggcacc tatctcagcg atctgtctat ttcgttcatc catagttgcc 36540
tgactccccg tcgtgtagat aactacgata cgggagggct taccatctgg ccccagtgct 36600
gcaatgatac cgcgagaccc acgctcaccg gctccagatt tatcagcaat aaaccagcca 36660
gccggaaggg ccgagcgcag aagtggtcct gcaactttat ccgcctccat ccagtctatt 36720
aattgttgcc gggaagctag agtaagtagt tcgccagtta atagtttgcg caacgttgtt 36780
gnnnnnnaaa aaggatcttc acctagatcc ttttcacgta gaaagccagt ccgcagaaac 36840
ggtgctgacc ccggatgaat gtcagctact gggctatctg gacaagggaa aacgcaagcg 36900
caaagagaaa gcaggtagct tgcagtgggc ttacatggcg atagctagac tgggcggttt 36960
tatggacagc aagcgaaccg gaattgccag ctggggcgcc ctctggtaag gttgggaagc 37020
cctgcaaagt aaactggatg gctttctcgc cgccaaggat ctgatggcgc aggggatcaa 37080
gctctgatca agagacagga tgaggatcgt ttcgcatgat tgaacaagat ggattgcacg 37140
caggttctcc ggccgcttgg gtggagaggc tattcggcta tgactgggca caacagacaa 37200
tcggctgctc tgatgccgcc gtgttccggc tgtcagcgca ggggcgcccg gttctttttg 37260
tcaagaccga cctgtccggt gccctgaatg aactgcaaga cgaggcagcg cggctatcgt 37320
ggctggccac gacgggcgtt ccttgcgcag ctgtgctcga cgttgtcact gaagcgggaa 37380
gggactggct gctattgggc gaagtgccgg ggcaggatct cctgtcatct caccttgctc 37440
ctgccgagaa agtatccatc atggctgatg caatgcggcg gctgcatacg cttgatccgg 37500
ctacctgccc attcgaccac caagcgaaac atcgcatcga gcgagcacgt actcggatgg 37560
aagccggtct tgtcgatcag gatgatctgg acgaagagca tcaggggctc gcgccagccg 37620
aactgttcgc caggctcaag gcgagcatgc ccgacggcga ggatctcgtc gtgacccatg 37680
gcgatgcctg cttgccgaat atcatggtgg aaaatggccg cttttctgga ttcatcgact 37740

-continued

```
gtggccggct gggtgtggcg gaccgctatc aggacatagc gttggctacc cgtgatattg  37800
ctgaagagct tggcggcgaa tgggctgacc gcttcctcgt gctttacggt atcgccgctc  37860
ccgattcgca gcgcatcgcc ttctatcgcc ttcttgacga gttcttctga attttgttaa  37920
aatttttgtt aaatcagctc atttttaac caataggccg aaatcggcaa catcccttat  37980
aaatcaaaag aatagaccgc gatagggttg agtgttgttc cagtttggaa caagagtcca  38040
ctattaaaga acgtggactc caacgtcaaa gggcgaaaaa ccgtctatca gggcgatggc  38100
ccactacgtg aaccatcacc caaatcaagt tttttgcggt cgaggtgccg taaagctcta  38160
aatcggaacc ctaaagggag cccccgattt agagcttgac ggggaaagcc ggcgaacgtg  38220
gcgagaaagg aagggaagaa agcgaaagga gcgggcgcta gggcgctggc aagtgtagcg  38280
gtcacgctgc gcgtaaccac cacacccgcg cgcttaatgc gccgnnnnnn nnnnnnnnnn  38340
nnnnnnnnnn nnnnnnnnnn nttaat                                       38366
```

ADENOVIRAL VECTORS AND METHODS AND USES RELATED THERETO

This is a Continuation-In-Part Application of U.S. patent application Ser. No. 12/585,971, filed Sep. 29, 2009, U.S. patent application Ser. No. 12/585,971 claims priority to, and the benefit of, FI 20095466, filed Apr. 27, 2009 and FI 20080671, filed Dec. 22, 2008. The contents of each of these applications are hereby incorporated by reference in their entireties.

FIELD OF THE INVENTION

The present invention relates to the fields of life sciences and medicine. Specifically, the invention relates to cancer therapies. More specifically, the present invention relates to oncolytic adenoviral vectors and cells and pharmaceutical compositions comprising said vectors. The present invention also relates to a use of said vectors in the manufacture of a medicament for treating cancer in a subject and a method of treating cancer in a subject. Furthermore, the present invention relates to methods of producing GM-CSF in a cell and increasing tumor specific immune response in a subject, as well as uses of the oncolytic adenoviral vector of the invention for producing GM-CSF in a cell and increasing tumor specific immune response in a subject.

BACKGROUND OF THE INVENTION

Cancer can be treated with surgery, hormonal therapies, chemotherapies and/or radiotherapies but in many cases, cancers, which are often characterized by an advanced stage, cannot be cured with present therapeutics. Therefore, novel cancer cell targeted approaches such as gene therapies are needed.

During the last twenty years gene transfer technology has been under intensive examination. The aim of cancer gene therapies is to introduce a therapeutic gene into a tumor cell. These therapeutic genes introduced to a target cell may for example correct mutated genes, suppress active oncogenes or generate additional properties to the cell. Suitable exogenous therapeutic genes include but are not limited to immunotherapeutic, antiangiogenic, chemoprotective and "suicide" genes, and they can be introduced to a cell by utilizing modified virus vectors or non-viral methods including electroporation, gene gun and lipid or polymer coatings.

Requirements of optimal viral vectors include an efficient capability to find specific target cells and express the viral genome in the target cells. Furthermore, optimal vectors have to stay active in the target tissues or cells. All these properties of viral vectors have been developed during the last decades and for example retroviral, adenoviral and adeno-associated viral vectors have been widely studied in biomedicine.

To further improve tumor penetration and local amplification of the anti-tumor effect, selectively oncolytic agents, e.g. conditionally replicating adenoviruses, have been constructed. Oncolytic adenoviruses are a promising tool for treatment of cancers. Tumor cells are killed by oncolytic adenoviruses due to a replication of the virus in a tumor cell, the last phase of the replication resulting in a release of thousands of virions into the surrounding tumor tissues for effective tumor penetration and vascular re-infection. Tumor cells allow replication of the virus while normal cells are spared due to engineered changes in the virus genome, which prevent replication in non-tumor cells.

In addition to replication mediated cell killing, oncolytic adenoviruses can also be armed with different therapeutic transgenes. This approach combines the advantages of conventional gene delivery with the potency of replication competent agents. One goal of arming viruses is induction of an immune reaction towards the cells that allow virus replication. Virus replication alone, although immunogenic, is normally not enough to induce effective anti-tumor immunity. To strengthen induction of therapeutic immunity, viruses can be armed with stimulatory proteins such as cytokines for facilitation of the introduction of tumor antigens to antigen presenting cells such as dendritic cells, and their stimulation and/or maturation. Introduction of immunotherapeutic genes into tumor cells and furthermore, translation of the proteins, leads to activation of the immune response and efficient destruction of tumor cells. The most relevant immune cells in this regard are natural killer cells (NK) and cytotoxic CD8+ T-cells.

Adenoviruses are medium-sized (90-100 nm), nonenveloped icosahedral viruses, which have double stranded linear DNA of about 36 kilo base pairs in a protein capsid. The viral capsid has fiber structures, which participate in attachment of the virus to the target cell. First, the knob domain of the fiber protein binds to the receptor of the target cell (e.g. CD46 or coxsackievirus adenovirus receptor (CAR)), secondly, the virus interacts with an integrin molecule and thirdly, the virus is endocytosed into the target cell. Next, the viral genome is transported from endosomes into the nucleus and the replication machinery of the target cell is utilized also for viral purposes (Russell W. C. 2000, J General Virol 81, 2573-2604).

The adenoviral genome has early (E1-E4), intermediate (IX and IVa2) and late genes (L1-L5), which are transcribed in sequential order. Early gene products affect defense mechanisms, cell cycle and cellular metabolism of the host cell. Intermediate and late genes encode structural viral proteins for production of new virions (Wu and Nemerow, 2004, Trends Microbiol 12: 162-168; Russell W. C. 2000, J General Virol 81, 2573-2604; Volpers C. and Kochanek S. 2004, J Gene Med 6 suppl 1, S164-71; Kootstra N. A. and Verma I. M. 2003, Annu Rev Pharmacol Toxicol 43, 413-439).

More than 50 different serotypes of adenoviruses have been found in humans. Serotypes are classified into six subgroups A-F and different serotypes are known to be associated with different conditions i.e. respiratory diseases, conjunctivitis and gastroenteritis. Adenovirus serotype 5 (Ad5) is known to cause respiratory diseases and it is the most common serotype studied in the field of gene therapy. In the first Ad5 vectors E1 and/or E3 regions were deleted enabling insertion of foreign DNA to the vectors (Danthinne and Imperiale 2000). Furthermore, deletions of other regions as well as further mutations have provided extra properties to viral vectors. Indeed, various modifications of adenoviruses have been suggested for achieving efficient anti-tumor effects.

For example, patent EP1377671 B1 (Cell Genesys, Inc.) and application US2003/0104625 A1 (Cheng C. et al.) describe an oncolytic adenoviral vector encoding an immunotherapeutic protein granulocyte-macrophage colony-stimulating factor (GM-CSF). Also, publication EP1767642 A1 (Chengdu Kanghong Biotechnologies Co., Ltd.) points out oncolytic adenoviral vectors having improved effects on human immune response.

Still, more efficient and accurate gene transfer as well as increased specificity and sufficient tumor killing ability of gene therapies are warranted. Safety records of therapeutic vectors must also be excellent. The present invention provides a cancer therapeutic tool with these aforementioned properties by utilizing both oncolytic and immunotherapeutic properties of adenoviruses in a novel and inventive way.

BRIEF DESCRIPTION OF THE INVENTION

The object of the invention is to provide novel methods and means for achieving the above-mentioned properties of adenoviruses and thus, solving the problems of conventional cancer therapies. More specifically, the invention provides novel methods and means for gene therapy.

The present application describes construction of recombinant viral vectors, methods related to the vectors, and their use in tumor cells lines, animal models and cancer patients.

The present invention relates to an oncolytic adenoviral vector comprising an adenovirus serotype 5 (Ad5) nucleic acid backbone, a 24 bp deletion (D24) in the Rb binding constant region 2 of adenoviral E1 and a nucleic acid sequence encoding a granulocyte-macrophage colony-stimulating factor (GM-CSF) in the place of the deleted gp19k/6.7K in the adenoviral E3 region.

The present invention further relates to a cell comprising the adenoviral vector of the invention.

The present invention also relates to a pharmaceutical composition comprising the adenoviral vector of the invention.

The present invention also relates to a use of the adenoviral vector of the invention in the manufacture of a medicament for treating cancer in a subject.

The present invention also relates to a method of treating cancer in a subject, wherein the method comprises administration of the vector or pharmaceutical composition of the invention to a subject.

Furthermore, the present invention also relates to a method of producing GM-CSF in a cell, wherein the method comprises:

a) carrying a vehicle comprising an oncolytic adenoviral vector of the invention to a cell, and
b) expressing GM-CSF of said vector in the cell.

Furthermore, the present invention also relates to a method of increasing tumor specific immune response in a subject, wherein the method comprises:

a) carrying a vehicle comprising an oncolytic adenoviral vector of the invention to a target cell or tissue,
b) expressing GM-CSF of said vector in the cell, and
c) increasing amount of cytotoxic T cells and/or natural killer cells in said target cell or tissue.

Still, the present invention also relates to a use of the oncolytic adenoviral vector of the invention for producing GM-CSF in a cell.

Still, the present invention relates to the oncolytic adenoviral vector of the invention for producing GM-CSF in a cell.

Still, the present invention also relates to a use of the oncolytic adenoviral vector of the invention for increasing tumor specific immune response in a subject.

Still, the present invention relates to the oncolytic adenoviral vector of the invention for increasing tumor specific immune response in a subject.

The present invention provides a tool for treatment of cancers, which are refractory to current approaches. Also, restrictions regarding tumor types suitable for treatment remain few compared to many other treatments. In fact all solid tumors may be treated with the proposed invention. Larger tumors by mass and more complex tumors can be cured by the present invention. The treatment can be given intratumorally, intracavitary, intravenously and in a combination of these. The approach can give systemic efficacy despite local injection. The approach can also eradicate cells proposed as tumor initiating ("cancer stem cells").

Besides enabling the transport of the vector to the site of interest the vector of the invention also assures the expression and persistence of the transgene. Furthermore, immune response against the vector as well as the transgene is minimized.

The present invention solves a problem related to therapeutic resistance of conventional treatments. Furthermore, the present invention provides tools and methods for selective treatments, without toxicity or damages in healthy tissues. Advantages of the present invention include also different and reduced side effects in comparison to other therapeutics. Importantly, the approach is synergistic with many other forms of therapy including chemotherapy and radiation therapy, and can therefore be used in combination regimens.

Induction of an immune reaction towards cells that allow replication of unarmed viruses is normally not strong enough to lead to development of therapeutic tumor immunity. In order to overcome this weakness, the present invention provides armed viruses with a potent inducer of anti-tumor immunity. The present invention achieves cancer therapy, wherein tumor cells are destroyed by virion caused oncolysis. In addition, various different mechanisms activating human immune response, including activation of natural killer cells (NK) and dendritic cells (DC) are influenced.

Compared to adenoviral tools of the prior art, the present invention provides a more simple, more effective, inexpensive, non-toxic and/or safer tool for cancer therapy. Furthermore, helper viruses are not needed.

The novel products of the invention enable further improvements in cancer therapy.

BRIEF DESCRIPTION OF THE FIGURES

FIG. 5*a* represents results of MTS assay showing lung cancer derived (A549) cell killing efficiency of the new generated virus Ad5-D24-GMCSF. FIG. 5*b* represents results of MTS assay showing killing of JIMT-1 cancer initiating cells ("cancer stem cells") with Ad5-D24-GMCSF. FIG. 5*c* represents results of MTS assay showing breast cancer cells (MDA-MB-436) killing efficiency of the new generated virus Ad5-D24-GMCSF. FIG. 5*d* represents results of MTS assay showing MDA-MB-436 killing efficiency of the new generated viruses Ad5-D24-GMCSF, Ad5-RGD-D24-GMCSF and Ad5/3-D24-GMCSF.

FIG. 7*c* shows a prediction of tumor transduction with Ad5-D25-GMCSF by staining its receptor CAR (coxsackie-adenovirus receptor) in archival tumor specimens.

FIGS. 13*a-i* show schematics of cloning to generate shuttle plasmid (pTHSN) bearing GM-CSF, to generate the plasmid containing all the adenoviral genes with the 24 base pair deletion in E1 region (which mediates selective replication in cancer cells) and to generate the Ad5/3-D24-GMCSF plasmid containing all the adenoviral genes except for gp19k and 6.7K which have been replaced by GM-CSF (pAd5D24.GM-CSF).

FIG. 14 shows a nucleotide sequence of Ad5/3-D24-GMCSF. Bolded region indicates the D24 deleted E1A region (nucleotides 563-1694). Underlined region indicates GMCSF (nucleotides 28380-28814). Region in italics indicates the Ad3 knob region (nucleotides 31701-32272). The sequence of the figure corresponds to sequence SEQ ID NO 7.

DETAILED DESCRIPTION OF THE INVENTION

Adenoviral Vector

In Ad5, as well as in other adenoviruses, an icosahedral capsid consists of three major proteins: hexon (II), penton base (III), and a knobbed fiber (IV), along with minor proteins: VI, VIII, IX, IIIa, and IVa2 (Russell W. C. 2000, J General Virol 81, 2573-2604). Proteins VII, small peptide mu, and a terminal protein (TP) are associated with DNA. Protein V provides a structural link to the capsid via protein VI. Virus encoded protease is needed for processing some structural proteins.

Figure 1:
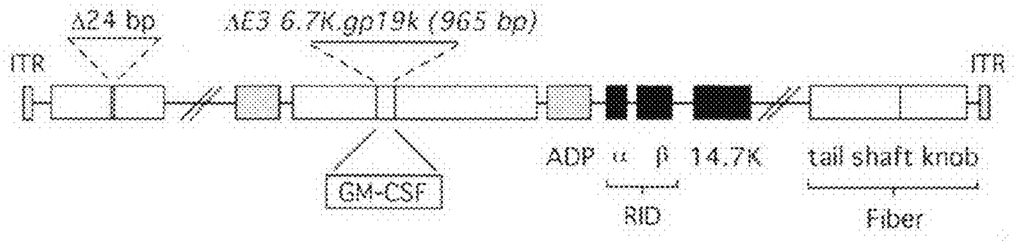
FIG. 1 shows a schematic of pAd5-D24-GMCSF. The virus bears a 24 base pair deletion in the constant region 2 of E1A. gp19k and 6.7K in E3 have been replaced with the cDNA of human GM-CSF. ADP refers to the adenovirus death protein.

The oncolytic adenoviral vector of the present invention is based on an adenovirus serotype 5 (Ad5) nucleic acid backbone, a 24 bp deletion (D24) in the Rb binding constant region 2 (CR2) of adenoviral E1 and a nucleic acid sequence encoding a granulocyte-macrophage colony-stimulating factor (GM-CSF) in the place of the deleted gp19k/6.7K in the adenoviral E3 region (FIG. 1). In a preferred embodiment of the invention, the adenoviral vector is based on a human adenovirus.

Ad5 genome contains early (E1-4), intermediate (IX and IVa2) and late (L1-5) genes flanked by left and right inverted terminal repeats (LITR and RITR, respectively), which contain the sequences required for the DNA replication. The genome contains also packaging signal (ψ) and major late promoter (MLP).

Transcription of the early gene E1A starts the replication cycle followed by expression of E1 B, E2A, E2B, E3 and E4. E1 proteins modulate cellular metabolism in a way that makes a cell more susceptible to virus replication. For example they interfere with NF-κB, p53, and pRb-proteins. E1A and E1B function together in inhibiting apoptosis. E2 (E2A and E2B) and E4 gene products mediate DNA replication and E4 products also effect virus RNA metabolism and prevent host protein synthesis. E3 gene products are responsible for defending against the host immune system, enhancing cell lysis, and releasing of virus progeny (Russell W. C. 2000, J General Virol 81, 2573-2604).

Intermediate genes IX and IVa2 encode minor proteins of the viral capsid. Expression of the late genes L1-5, which lead to production of the virus structural components, the encapsidation and maturation of virus particles in the nucleus, is influenced by MLP (Russell W. C. 2000, J General Virol 81, 2573-2604).

Compared to a wild type adenovirus genome, the adenoviral vector of the invention lacks 24 base pairs from CR2 in E1 region, specifically in E1A region, and gp19k and 6.7K in E3 region. In a preferred embodiment of the invention, in addition to partial regions E1 and E3, the oncolytic adenoviral vector of the invention further comprises one or more regions selected from a group consisting of E2, E4, and late regions. In a preferred embodiment of the invention, the oncolytic adenoviral vector comprises the following regions: a left ITR, partial E1, pIX, pIVa2, E2, VA1, VA2, L1, L2, L3, L4, partial E3, L5, E4, and a right ITR. The regions may be in any order in the vector, but in a preferred embodiment of the invention, the regions are in a sequential order in the 5' to 3' direction.

Open reading frames (ORFs) may be in the same DNA strand or in different DNA strands. In a preferred embodiment of the invention, the E1 region comprises a viral packaging signal.

As used herein, expression “adenovirus serotype 5 (Ad5) nucleic acid backbone” refers to the genome or partial genome of Ad5, which comprises one or several regions selected from a group consisting of partial E1, pIX, pIVa2, E2, VA1, VA2, L1, L2, L3, L4, partial E3, L5 and E4 of Ad5 origin. One preferred vector of the invention comprises nucleic acid backbone of Ad5. In another preferred vector, the adenoviral nucleic acid backbone is mostly derived from Ad5 and combined with a portion (e.g. a part of the capsid structure) of Ad3.

As used herein, expression “partial” region refers to a region, which lacks any part compared to a corresponding wild type region. “Partial E1” refers to E1 region with D24 and “partial E3” refers to E3 region lacking gp19k/6.7K.

As used herein, expressions “VA1” and “VA2” refer to virus associated RNAs 1 and 2, which are transcribed by the adenovirus but are not translated. VA1 and VA2 have a role in combating cellular defence mechanisms.

As used herein, expression “a viral packaging signal” refers to a part of virus DNA, which consists of a series of AT-rich sequences and governs the encapsidation process.

24 base pair deletion (D24) of E1 affects CR2 domain, which is responsible for binding the Rb tumor suppressor/cell cycle regulator protein and thus, allows the induction of the synthesis (S) phase i.e. DNA synthesis or replication phase. pRb and E1A interaction requires eight amino acids 121 to 127 of the E1A protein conserved region (Heise C. et al. 2000, Nature Med 6, 1134-1139), which are deleted in the present invention. The vector of the present invention comprises a deletion of nucleotides corresponding to amino acids 122-129 of the vector according to Heise C. et al. (2000, Nature Med 6, 1134-1139). Viruses with the D24 are known to have a reduced ability to overcome the G1-S checkpoint and replicate efficiently only in cells where this interaction is not necessary, e.g. in tumor cells defective in the Rb-p16 pathway (Heise C. et al. 2000, Nature Med 6, 1134-1139; Fueyo J et al. 2000, Oncogene 19, 2-12).

The E3 region is nonessential for viral replication in vitro, but the E3 proteins have an important role in the regulation of host immune response i.e. in the inhibition of both innate and specific immune responses. The gp19k/6.7K deletion in E3 refers to a deletion of 965 base pairs from the adenoviral E3A region. In a resulting adenoviral construct, both gp19k and 6.7K genes are deleted (Kanerva A et al. 2005, Gene Therapy 12, 87-94). The gp19k gene product is known to bind and sequester major histocompatibility complex I (MHC1) molecules in the endoplasmic reticulum, and to prevent the recognition of infected cells by cytotoxic T-lymphocytes. Since many tumors are deficient in MHC1, deletion of gp19k increases tumor selectivity of viruses (virus is cleared faster than wild type virus from normal cells but there is no difference in tumor cells). 6.7K proteins are expressed on cellular surfaces and they take part in downregulating TNF-related apoptosis inducing ligand (TRAIL) receptor 2.

In the present invention, the GM-CSF transgene is placed into a gp19k/6.7k deleted E3 region, under the E3 promoter. This restricts transgene expression to tumor cells that allow replication of the virus and subsequent activation of the E3 promoter. E3 promoter may be any exogenous or endogenous promoter known in the art, preferably endogenous promoter. In a preferred embodiment of the invention, a nucleic acid sequence encoding GM-CSF is under the control of the viral E3 promoter.

GM-CSF participates in immune response by acting through various mechanisms including recruitment of natural killer (NK) cell and stimulation of antigen presenting cells (APC). APC can then recruit, activate and target T-cells towards the tumor. The nucleotide sequence encoding GM-CSF may be from any animal such as a human, ape, rat, mouse, hamster, dog or cat, but preferably GM-CSF is encoded by a human sequence. The nucleotide sequence encoding GM-CSF may be modified in order to improve the effects of GM-CSF, or unmodified i.e. of a wild type. In a preferred embodiment of the invention, a nucleic acid sequence encoding GM-CSF is of a wild type.

The vector of the invention may also comprise other modifications than partial deletions of CR2 and E3 and insertion of GM-CSF sequence as mentioned above. In a preferred embodiment of the invention, all the other regions of the Ad5 vector are of a wild type. In another preferred embodiment of the invention, the E4 region is of a wild type. In a preferred embodiment of the invention, a wild type region is located upstream of the E1 region. “Upstream” refers to immediately before the E1 region in the direction of expression. E1 B region may also be modified in the vector of the invention.

Insertion of exogenous elements may enhance effects of vectors in target cells. The use of exogenous tissue or tumor-specific promoters is common in recombinant adenoviral vectors and they can also be utilized in the present invention. For example, viral replication can be restricted to target cells for example by promoters, which include but are not limited to CEA, SLP, Cox-2, Midkine, hTERT, variants of hTERT, E2F, variants of E2F, CXCR4, SCCA2 and TTS. They are usually added to control E1A region, but in addition to or alternatively, other genes such as E1B or E4 can also be regulated. Exogenous insulators i.e. blocking elements against unspecific enhancers, the left ITR, the native E1A promoter or chromatin proteins may also be included in recombinant adenoviral vectors. Any additional components or modifications may optionally be used but are not obligatory in the vectors of the present invention.

Most adults have been exposed to the most widely used adenovirus serotype Ad5 and therefore, the immune system can rapidly produce neutralizing antibodies (NAb) against them. In fact, the prevalence of anti-Ad5 NAb may be up to 50%. It has been shown that NAb can be induced against most of the multiple immunogenic proteins of the adenoviral capsid, and on the other hand it has been shown that even small changes in the Ad5 fiber knob can allow escape from capsid-specific NAb. Modification of the knob is therefore important for retaining or increasing gene delivery in the contact of adenoviral use in humans.

Furthermore, Ad5 is known to bind to the receptor called CAR via the knob portion of the fiber, and modifications of this knob portion or fiber may improve the entry to the target cell and cause enhanced oncolysis in some cancers (Ranki T. et al. 2007, Int J Cancer 121, 165-174). Indeed, capsid-modified adenoviruses are advantageous tools for improved gene delivery to cancer cells.

In one embodiment of the invention, the oncolytic adenoviral vector comprises a capsid modification. As used herein “capsid” refers to the protein shell of the virus, which includes hexon, fiber and penton base proteins. Any capsid modification i.e. modification of hexon, fibre and/or penton base proteins known in the art, which improves delivery of the virus to the tumor cell, may be utilized in the present invention. Modifications may be genetic and/or physical modifications and include but are not limited to modifications for incorporating ligands, which recognize specific cellular receptors and/or block native receptor binding, for replacing the fiber or knob domain of an adenoviral vector with a knob of other adenovirus (chimerism) and for adding specific molecules (e.g. FGF2) to adenoviruses. Therefore, capsid modifications include but are not limited to incorporation of small peptide motif(s), peptide(s), chimerism(s) or mutation(s) into the fiber (e.g. into the knob, tail or shaft part), hexon and/or penton base. In a preferred embodiment of the invention, the capsid modification is Ad5/3 chimerism, insertion of an integrin binding (RGD) region and/or heparin sulphate binding polylysine modification into the fiber. In a specific embodiment of the invention, the capsid modification is Ad5/3 chimerism.

As used herein, "Ad5/3 chimerism" of the capsid refers to a chimerism, wherein the knob part of the fiber is from Ad serotype 3, and the rest of the fiber is from Ad serotype 5.

As used herein, "RGD region" refers to the arginine-glycine-aspartic acid (RGD) motif, which is exposed on the penton base and interacts with cellular αv integrins supporting adenovirus internalization. In a preferred embodiment of the invention, the capsid modification is a RGD-4C modification. "RGD-4C modification" refers to an insertion of an integrin binding RGD-4C motif in the HI loop of the fiber knob domain. 4C refers to the four cysteins, which form sulphur bridges in RGD-4C. Construction of recombinant Ad5 fiber gene encoding the fiber with the RGD-4C peptide is described in detail for example in the article of Dmitriev I. et al. (1998, Journal of Virology, 72, 9706-9713).

As used herein, "heparan sulphate binding polylysine modification" refers to addition of a stretch of seven lysines to the fiber knob c-terminus.

Expression cassettes are used for expressing transgenes in a target, such as a cell, by utilizing vectors. As used herein, the expression "expression cassette" refers to a DNA vector or a part thereof comprising nucleotide sequences, which encode cDNAs or genes, and nucleotide sequences, which control and/or regulate the expression of said cDNAs or genes. Similar or different expression cassettes may be inserted to one vector or to several different vectors. Ad5 vectors of the present invention may comprise either several or one expression cassettes. However, only one expression cassette is adequate. In a preferred embodiment of the invention, the oncolytic adenoviral vector comprises at least one expression cassette. In a preferred embodiment of the invention, the oncolytic adenoviral vector comprises only one expression cassette.

A cell comprising the adenoviral vector of the invention may be any cell such as a eukaryotic cell, bacterial cell, animal cell, human cell, mouse cell etc. A cell may be an in vitro, ex vivo or in vivo cell. For example, the cell may be used for producing the adenoviral vector in vitro, ex vivo or in vivo, or the cell may be a target, such as a tumor cell, which has been infected with the adenoviral vector.

In a method of producing GM-CSF in a cell, a vehicle comprising the vector of the invention is carried into a cell and furthermore, GM-CSF gene is expressed and the protein is translated and secreted in a paracrine manner. "A vehicle" may be any viral vector, plasmid or other tool, such as a particle, which is able to deliver the vector of the invention to a target cell. Any conventional method known in the art can be used for delivering the vector to the cell.

Tumor specific immune response may be increased in a subject by the present invention. Cytotoxic T cells and/or natural killer cells are stimulated, produced and targeted as a consequence of GM-CSF expression. In a preferred embodiment of the invention, amount of natural killer and/or cytotoxic T cells is increased in a target cell or tissue. In order to follow or study the effects of the invention, various markers of immune response (e.g. inflammatory markers) may be determined. The most common markers include but are not limited to increase in pro-inflammatory cytokines, tumor or adenovirus specific cytotoxic T-cells, recruitment and activation of antigen presenting cells or increase in size of local lymph nodes. The levels of these markers may be studied according to any conventional methods known in the art, including but not limited to those utilizing antibodies, probes, primers etc. such as ELISPOT assay, tetramer analysis, pentamer analysis and analysis of different cell types in blood or in tumors.

Cancer

The recombinant Ad5 vectors of the invention have been constructed for replication competence in cells, which have defects in the Rb-pathway, specifically Rb-p16 pathway. These defective cells include all tumor cells in animals and humans (Sherr C. J. 1996, Science 274, 1672-1677). In a preferred embodiment of the invention, the vector is capable of selectively replicating in cells having defects in the Rb-pathway. As used herein "defects in the Rb-pathway" refers to mutations and/or epigenetic changes in any genes or proteins of the pathway. Due to these defects, tumor cells overexpress E2F and thus, binding of Rb by E1A CR2, that is normally needed for effective replication, is unnecessary.

Any cancers or tumors, including both malignant and benign tumors as well as primary tumors and metastasis may be targets of gene therapies. In a specific embodiment of the invention the cancer is any solid tumor. In a preferred embodiment of the invention, the cancer is selected from a group consisting of nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, tonsil cancer.

Pharmaceutical Composition

A pharmaceutical composition of the invention comprises at least one type of the vectors of the invention. Furthermore, the composition may comprise at least two, three or four different vectors of the invention. In addition to the vector of the invention, a pharmaceutical composition may also comprise any other vectors, such as other adenoviral vectors, other therapeutically effective agents, any other agents such as pharmaceutically acceptable carriers, buffers, excipients, adjuvants, antiseptics, filling, stabilising or thickening agents, and/or any components normally found in corresponding products.

The pharmaceutical composition may be in any form, such as solid, semisolid or liquid form, suitable for administration. A formulation can be selected from a group consisting of, but not limited to, solutions, emulsions, suspensions, tablets, pellets and capsules.

In a preferred embodiment of the invention, the oncolytic adenoviral vector or pharmaceutical composition acts as an in situ cancer vaccine. As used herein "in situ cancer vaccine" refers to a cancer vaccine, which both kills tumor cells and also increases the immune response against tumor cells. Virus replication is a strong danger signal to the immune system (=needed for a TH1 type response), and thus acts as a powerful costimulatory phenomenon to GM-CSF mediated maturation and activation of APCs, and recruitment of NK cells. Tumor cell lysis also helps to present tumor fragments and epitopes to APCs and furthermore, costimulation is produced by inflammation. Thus, an epitope independent (i.e. not HLA restricted) response is produced in the context of each tumor and therefore takes place in situ. Tumor specific immune response is activated in the target cell as well as the surrounding cells, e.g. in the target tissue.

The effective dose of vectors depends on at least the subject in need of the treatment, tumor type, location of the tumor and stage of the tumor. The dose may vary for example from about 10e8 viral particles (VP) to about 10e14 VP, preferably from about 5×10e9 VP to about 10e13 VP and more preferably from about 8×10e9 VP to about 10e12 VP. In one specific embodiment of the invention the dose is in the range of about 5×10e10-5×10e11 VP.

The pharmaceutical compositions may be produced by any conventional processes known in the art, for example by utilizing any one of the following: batch, fed-batch and perfusion culture modes, column-chromatography purification, CsCI gradient purification and perfusion modes with low-shear cell retention devices.

Administration

The vector or pharmaceutical composition of the invention may be administered to any eukaryotic subject selected from a group consisting of plants, animals and human beings. In a preferred embodiment of the invention, the subject is a human or an animal. An animal may be selected from a group consisting of pets, domestic animals and production animals.

Any conventional method may be used for administration of the vector or composition to a subject. The route of administration depends on the formulation or form of the composition, the disease, location of tumors, the patient, comorbidities and other factors. In a preferred embodiment of the invention, the administration is conducted through an intratumoral, intramuscular, intra-arterial, intravenous, intrapleural, intravesicular, intracavitary or peritoneal injection, or an oral administration.

Only one administration of oncolytic adenoviral vectors of the invention may have therapeutic effects. However, in a preferred embodiment of the invention, oncolytic adenoviral vectors or pharmaceutical compositions are administered several times during the treatment period. Oncolytic adenoviral vectors or pharmaceutical compositions may be administered for example from 1 to 10 times in the first 2 weeks, 4 weeks, monthly or during the treatment period. In one embodiment of the invention, administration is done three to seven times in the first 2 weeks, then at 4 weeks and then monthly. In a specific embodiment of the invention, administration is done four times in the first 2 weeks, then at 4 weeks and then monthly. The length of the treatment period may vary, and for example may last from two to 12 months or more.

In order to avoid neutralizing antibodies in a subject, the vectors of the invention may vary between treatments. In a preferred embodiment of the invention, the oncolytic adenoviral vector having a different fiber knob of the capsid compared to the vector of the earlier treatment is administered to a subject. As used herein "fiber knob of the capsid" refers to the knob part of the fiber protein (FIG. 1).

The gene therapy of the invention is effective alone, but combination of adenoviral gene therapy with any other therapies, such as traditional therapy, may be more effective than either one alone. For example, each agent of the combination therapy may work independently in the tumor tissue, the adenoviral vectors may sensitize cells to chemotherapy or radiotherapy and/or chemotherapeutic agents may enhance the level of virus replication or effect the receptor status of the target cells. The agents of combination therapy may be administered simultaneously or sequentially.

In a preferred embodiment of the invention, the method or use further comprises administration of concurrent radiotherapy to a subject. In another preferred embodiment of the invention, the method or use further comprises administration of concurrent chemotherapy to a subject. As used herein "concurrent" refers to a therapy, which has been administered before, after or simultaneously with the gene therapy of the invention. The period for a concurrent therapy may vary from minutes to several weeks. Preferably the concurrent therapy lasts for some hours.

Agents suitable for combination therapy include but are not limited to All-trans retinoic acid, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, Pemetrexed, Temozolomide, Teniposide, Tioguanine, Valrubicin, Vinblastine, Vincristine, Vindesine and Vinorelbine.

In a preferred embodiment of the invention, the method or use further comprises administration of verapamil or another calcium channel blocker to a subject. "Calcium channel blocker" refers to a class of drugs and natural substances which disrupt the conduction of calcium channels, and it may be selected from a group consisting of verapamil, dihydropyridines, gallopamil, diltiazem, mibefradil, bepridil, fluspirilene and fendiline.

In a preferred embodiment of the invention, the method or use further comprises administration of autophagy inducing agents to a subject. Autophagy refers to a catabolic process involving the degradation of a cell's own components through the lysosomal machinery. "Autophagy inducing agents" refer to agents capable of inducing autophagy and may be selected from a group consisting of, but not limited to, mTOR inhibitors, PI3K inhibitors, lithium, tamoxifen, chloroquine, bafilomycin, temsirolimus, sirolimus and temozolomide. In a specific embodiment of the invention, the method further comprises administration of temozolomide to a subject. Temozolomide may be either oral or intravenous temozolomide.

In one embodiment of the invention, the method or use further comprises administration of chemotherapy or anti-CD20 therapy or other approaches for blocking of neutralizing antibodies. "Anti-CD20 therapy" refers to agents capable of killing CD20 positive cells, and may be selected from a group consisting of rituximab and other anti-CD20 monoclonal antibodies. "Approaches for blocking of neutralizing antibodies" refers to agents capable of inhibiting the generation of anti-viral antibodies that normally result from infection and may be selected from a group consisting of different chemotherapeutics, immunomodulatory substances, corticoids and other drugs. These substances may be selected from a group consisting of, but not limited to, cyclophosphamide, cyclosporin, azathioprine, methylprenisolone, etoposide, CD40L, CTLA4Ig4, FK506 (tacrolismus), IL-12, IFN-gamma, interleukin 10, anti-CD8, anti-CD4 antibodies, myeloablation and oral adenoviral proteins.

The oncolytic adenoviral vector of the invention induces virion mediated oncolysis of tumor cells and activates human immune response against tumor cells. In a preferred embodiment of the invention, the method or use further comprises administration of substances capable to downregulating regulatory T-cells in a subject. "Substances capable to downregulating regulatory T-cells" refers to agents that reduce the amount of cells identified as T-suppressor or Regulatory T-cells. These cells have been identified as consisting one or many of the following immunophenotypic markers: CD4+, CD25+, FoxP3+, CD127− and GITR+. Such agents reducing T-suppressor or Regulatory T-cells may be selected from a group consisting of anti-CD25 antibodies or chemotherapeutics.

In a preferred embodiment of the invention, the method or use further comprises administration of cyclophosphamide to a subject. Cyclophosphamide is a common chemotherapeutic agent, which has also been used in some autoimmune disorders. In the present invention, cyclophosphamide can be used to enhance viral replication and the effects of GM-CSF induced stimulation of NK and cytotoxic T-cells for enhanced immune response against the tumor. It can be used as intravenous bolus doses or low-dose oral metronomic administration.

Any method or use of the invention may be either in vivo, ex vivo or in vitro method or use.

The present invention is illustrated by the following examples, which are not intended to be limiting in any way.

EXAMPLES

Example 1

Cloning of Three D24-GM-CSF Type Viruses

PCR out hGM-CSF,
create SunI/MunI sites=>445 bp (pORF-GM-CSF as a template)
SunI/MunI digestion of PCR product and pTHSN
Sticky-end ligation=>
PmeI linearized pShuttle-D24+pTG3602=>pAd5-D24
Ad5-D24-GM-CSF (SEQ ID NO 8: E1A region with D24 deletion in nucleotide positions 563-1524 and a fiber region in nucleotide positions 30490-32236)
  Homol recomb: SrfI linearized pAd5-D24+FspI linearized
  pTHSN-GM-CSF=>pAd5-D24-GM-CSF
  PacI linearization & transfection=>Ad5-D24-GM-CSF All phases of the cloning were confirmed with PCR and multiple restriction digestions. The shuttle plasmid pTHSN-GMCSF was sequenced. Absence of wild type E1 was confirmed with PCR. The E1 region, transgene and fiber were checked in the final virus with sequencing and PCR, which was then taken to the clean lab for production. To this end, viral DNA was extracted by over night (ON) incubation with appropriate buffer solution and after PCR and sequence was performed to analyze the integrity of the fiber as well as the GMCSF cDNA. All phases of the virus production, including transfection, were done on A549 cells to avoid risk of wild type recombination as described before (Kanerva A et al. 2003, Mol Ther 8, 449-58; Baeurschmitz G J et al. 2006, Mol Ther 14, 164-74). GM-CSF is under the E3 promoter (specifically under endogenous viral E3A gene expression control elements), which results in replication associate transgene expression, which starts about 8 h after infection. E3 is intact except for deletion of 6.7K/gp19K.

Figure 2:
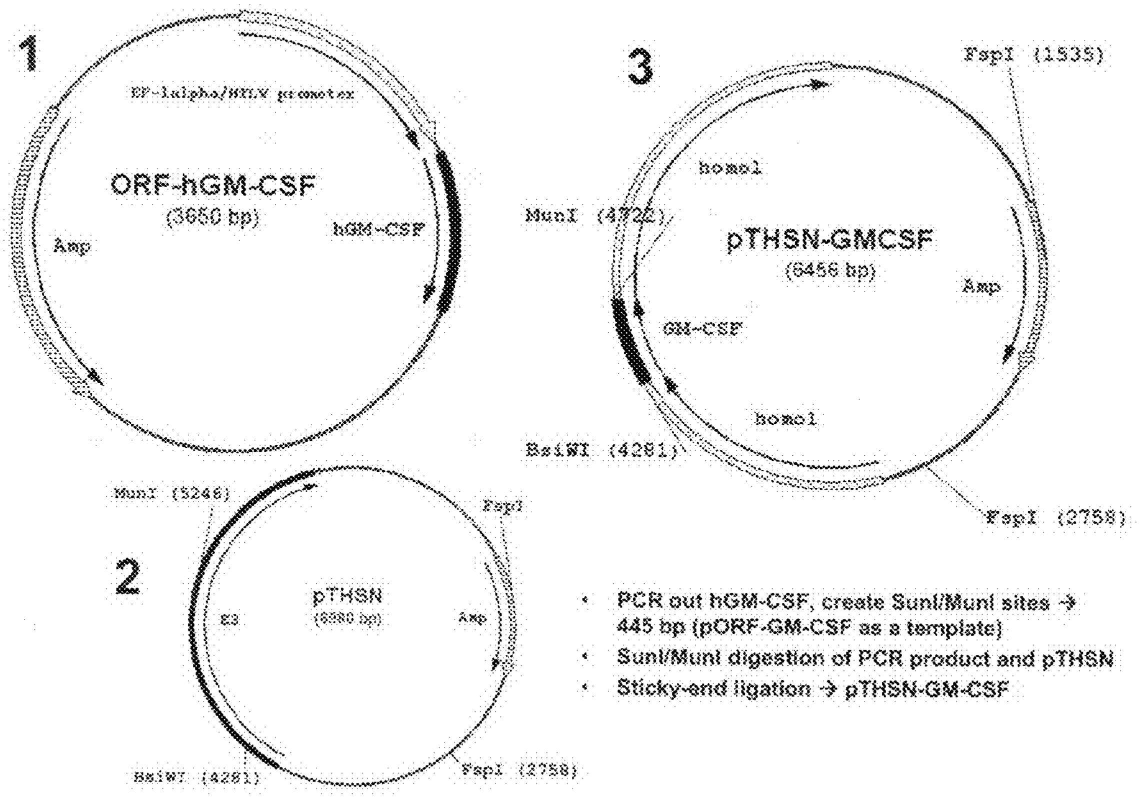
FIG. 2 shows a schematic of the first step of cloning to generate shuttle plasmid (pTHSN) bearing GM-CSF.
Figure 3:
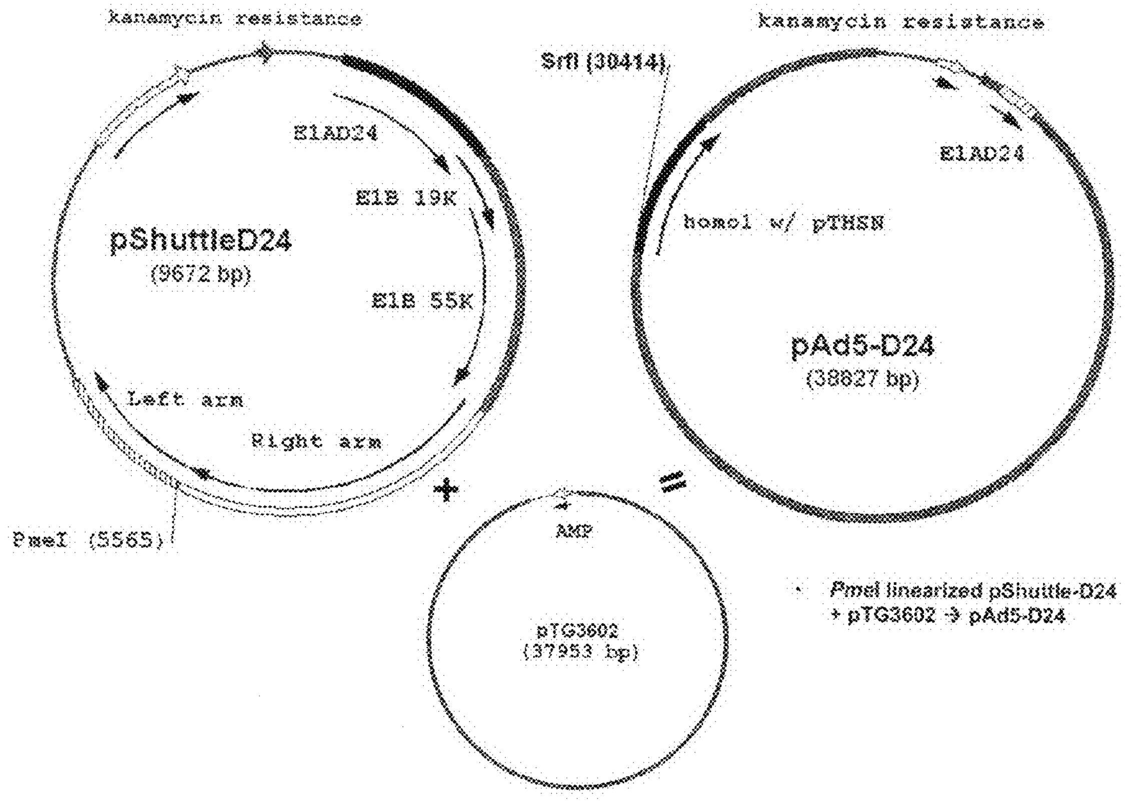
FIG. 3 shows a schematic of the second step of cloning to generate the plasmid containing all the adenoviral genes with the 24 base pair deletion in E1 region (which mediates selective replication in cancer cells).
Figure 4:
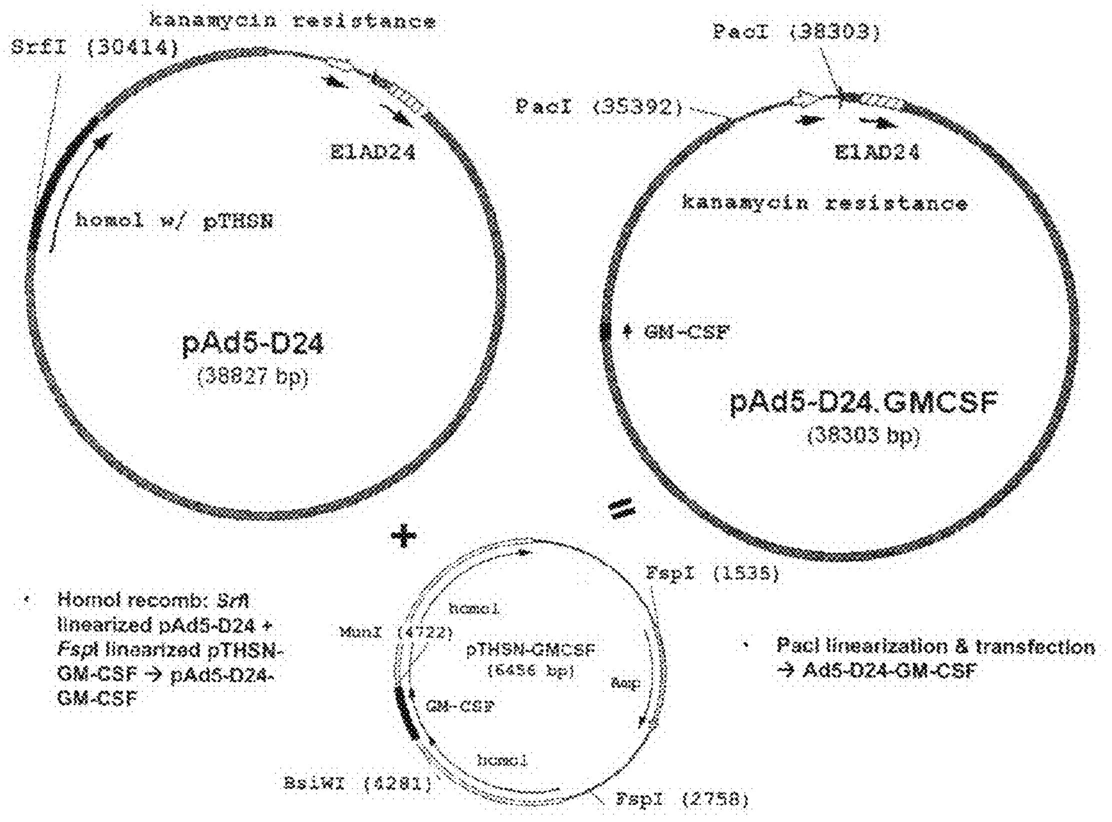
FIG. 4 shows a schematic of the third step of cloning to generate the plasmid containing all the adenoviral genes except for gp19k and 6.7K which have been replaced by GM-CSF (pAd5D24.GM-CSF (SEQ ID NO 8)). Ad5-RGD-D24-GMCSF (SEQ ID NO 9), Ad5/3-D24-GMCSF (SEQ ID NO 7) and Ad5-pK7-D24-GMCSF (SEQ ID NO 10) were created similarly.

Ad5/3-D24-GM-CSF (SEQ ID NO 7) and Ad5-RGD-D24-GM-CSF (SEQ ID NO 9: E1A region with D24 deletion in nucleotide positions 580-1541, a fiber region in nucleotide positions 30514-32286 and RGD-modification in nucleotide positions 32128-32183) were constructed identically, except a rescue plasmid featuring either a knob from serotype 3, or RGD-4C in the Ad5 fiber HI-loop were used. Ad5-pK7-D24-GMCSF (SEQ ID NO 10: E1A region with D24 deletion in nucleotide positions 561-1526, a fiber region in nucleotide positions 30499-32255 and pK7-modification in nucleotide positions 32247-32378) was also created similarly. (FIGS. 2-4)

Ad5/3-D24-GM-CSF was constructed as follows. A pAdEasy-1-derived plasmid containing a chimeric 5/3 fiber, pAdEasy5/3, was created by homologous recombination in *E. coli* of Ad5/3luc1 viral genome and BstXI-digested 8.9 kb fragment of pAdEasy-1. Next, a shuttle vector containing a 24-bp deletion in E1A (pShuttleD24) was linearized with PmeI and recombined with pAdEasy5/3 resulting in pAd5/3-D24. In order to insert human GMCSF gene into E3 region, an E3-cloning vector pTHSN was created by inserting SpeI to NdeI fragment from Ad5 genome into the multi-cloning site of pGEM5Zf+(Promega, Madison, Wis.). pTHSN was further digested with SunI/MunI creating a 965-bp deletion in E3 region (6.7K and gp19K deleted). The 432bp cDNA encoding human GMCSF (Invitrogen, Carlsbad Calif.) was amplified with primers featuring specific restriction sites SunI/MunI flanking the gene and then inserted into SunI/MunI-digested pTHSN (pTHSN-GMCSF). pAd5/3-D24-GMCSF was generated by homologous recombination in *E. coli* between FspI-linearized pTHSN-GMCSF and SrfI-linearized pAd5/3-D24. Ad5/3-D24-GMCSF virus genome was released by PacI digestion and transfection to A549 cells for amplification and rescue (FIGS. 13 and 14, SEQ ID NO 7).

Example 2

In Vitro Analysis of D24-GM-CSF Type Viruses

In vitro efficacy of D24-GM-CSF type viruses was studied in lung cancer cells (A549), breast cancer stem cell derived explant cells (JIMT-1) and breast cancer cells (MDA-MB-436) by utilizing MTS cell killing assays. MTS assay is currently the standard method to assess cell viability in cancer gene therapy publications. Ad5Luc1 is a replication deficient virus and acts as a negative control. Ad5wt is a wild type Ad5 virus (strain Ad300wt) and was used as a positive control. Ad5-d24-E3 harbors an isogenic 24bp deletion in E1 but is intact in E3. VP indicates virus particles.

Figure 5A:
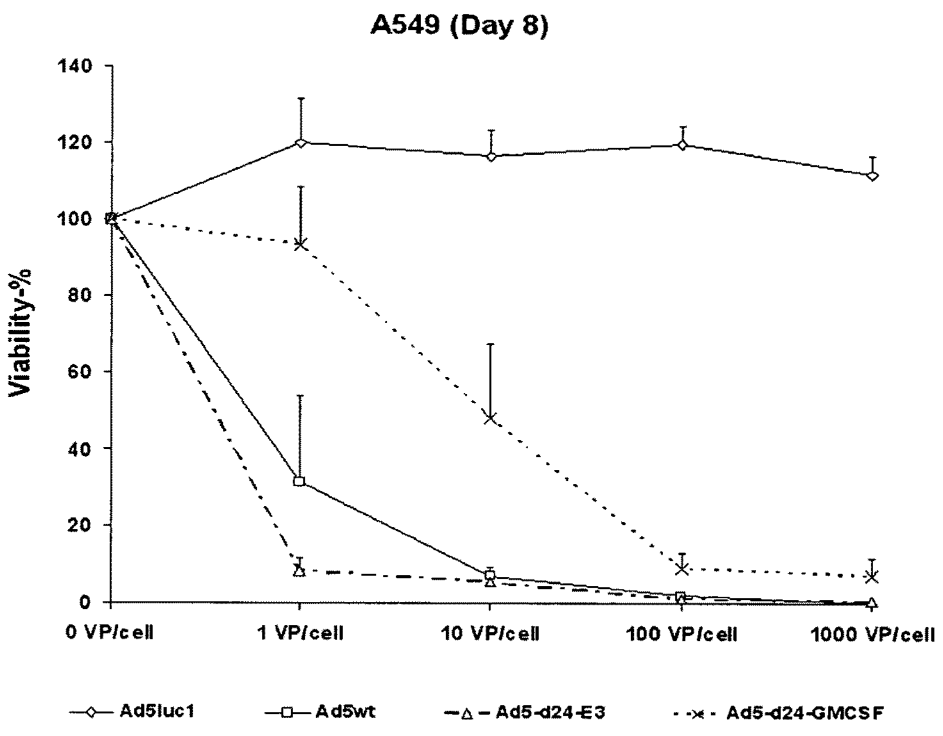
FIGS. 5*a-d* show that GMCSF expression does not impair virus replication and cell killing effect.
Figure 5B:
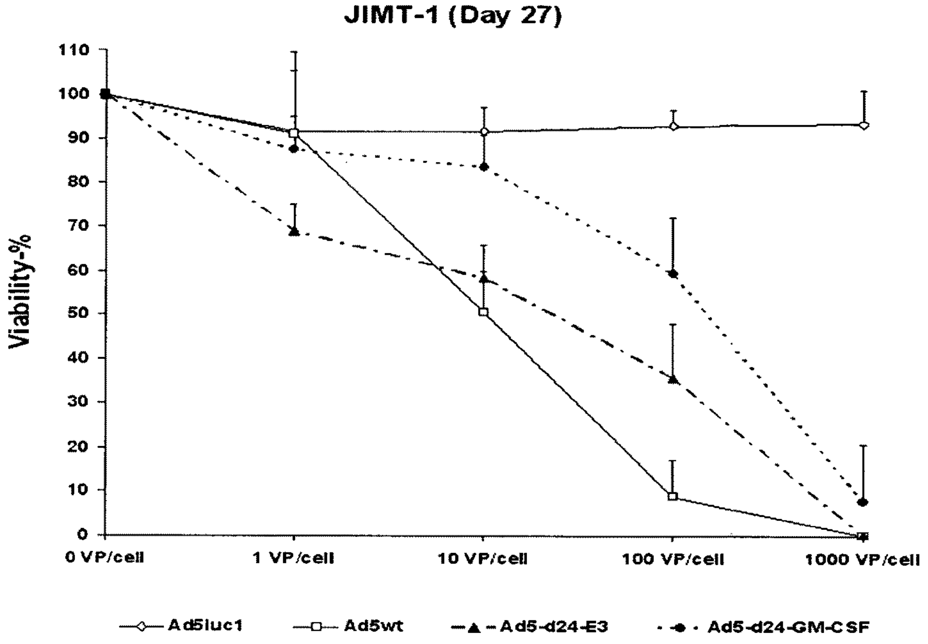
Figure 5C:
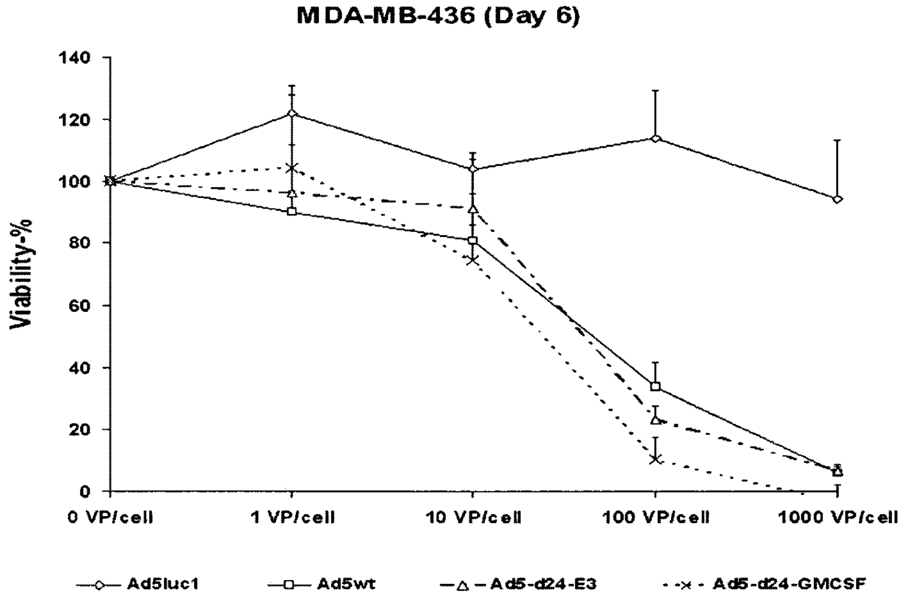
Figure 5D:
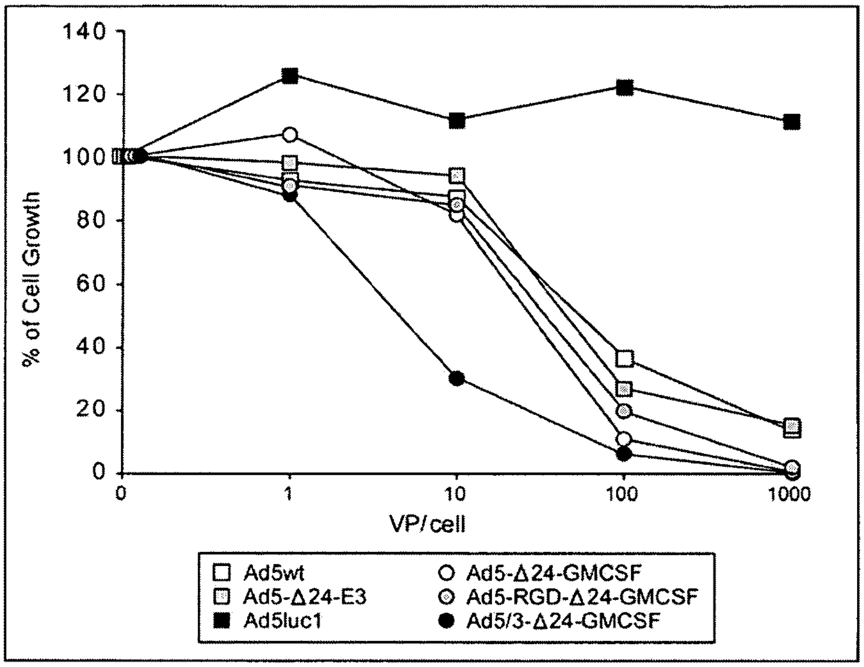

In summary, Ad5-D24-GMCSF had oncolytic activity similar to positive controls in vitro, and therefore transgene production did not compromise the oncolytic potency of the virus (FIGS. 5a-c). Similar data was shown for Ad5/3-D24-GM-CSF and Ad5-RGD-D24-GM-CSF (FIG. 5d).

Figure 6A:
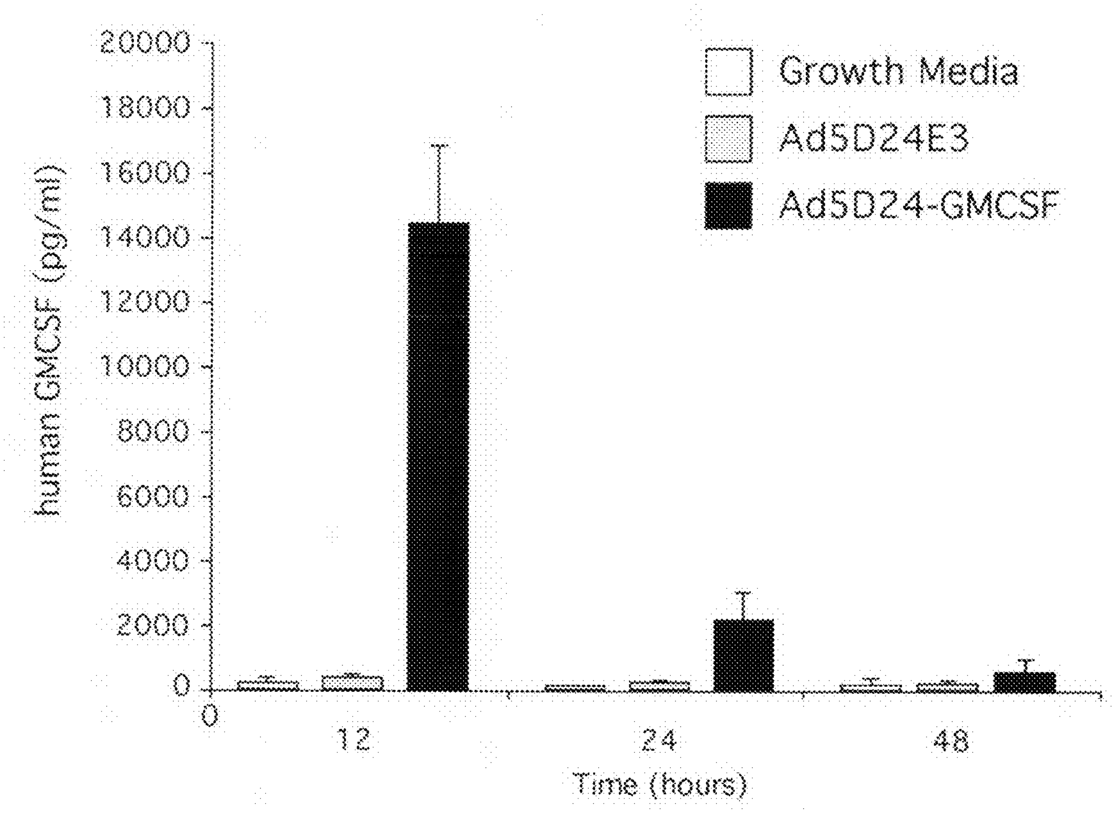
FIG. 6*a* shows adenovirus-coupled expression of human GMCSF. A549 cell line was infected with Ad5D24 or Ad5D24-GMCSF, media was collected over time and analyzed for expression of GMCSF by FACSARRAY.
Figure 6B:
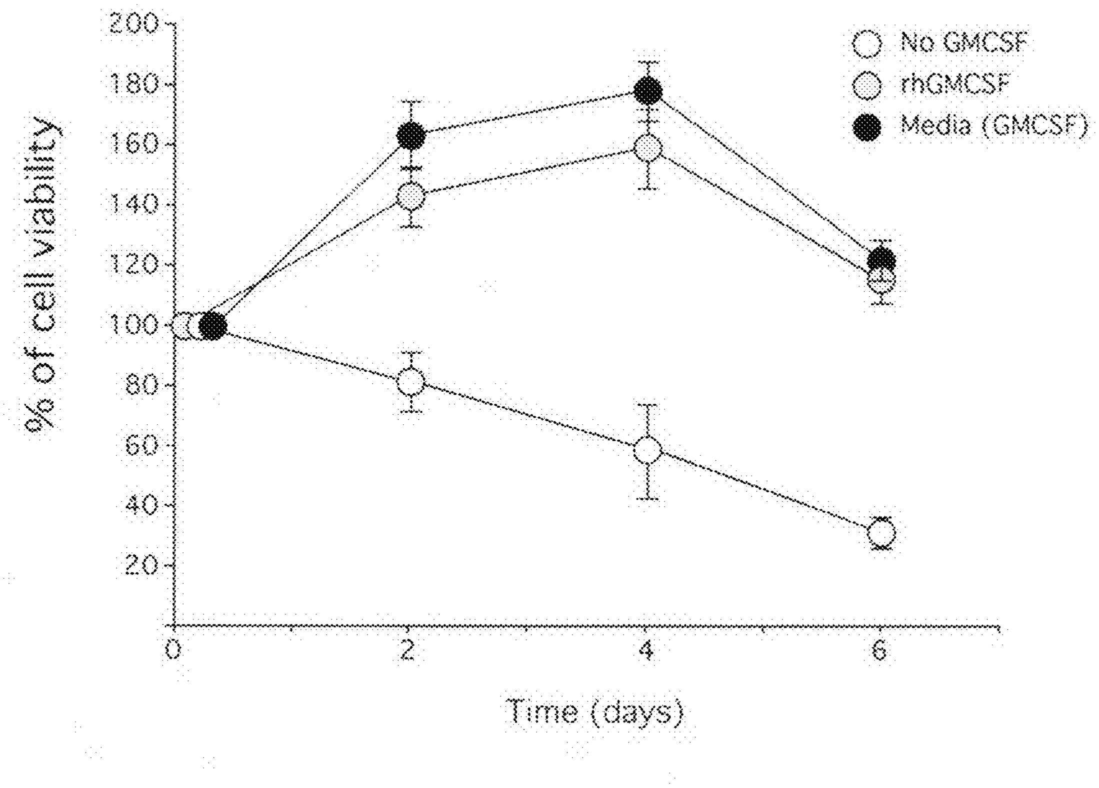
FIG. 6*b* shows that adenovirus-expressed GMCSF retains its biological activity in human lymphocytes. TF1 cells, which require human GMCSF for staying alive, were cultured in the presence of human recombinant GMCSF (*E. coli*-produced, purchased from Sigma) or supernatant from Ad5-D24-GMCSF infected cells.

To test whether Ad5D24-GMCSF was able to express the transgene, A549 cell line was infected with 1000 VP/cell and media was collected over time. Concentration of GMCSF (FIG. 6*a*) in the media was measured by FACSARRAY (BD Biosciences, San Diego, Calif. USA) according to manufacturer's instructions. In addition to that, we also analyzed whether the virus-expressed GMCSF retained its biological function. To this end TF1 cell line, whose growth and survival is strictly dependent on human GMCSF were treated with media collected from A549 cell line previously infected with Ad5D24-GMCSF. TF1 viability was assessed over time by MTS assay. The result of this experiment was that the virus expressed-GMCSF was able to stimulate growth of such cell line, and no difference was found with the same cell line treated with human recombinant GMCSF (Sigma) (FIG. 6*b*).

Example 3

Pretreatment Analysis of Transduction

I. Infection of Tumor Cells with Ad5Luc1

Figure 7A:
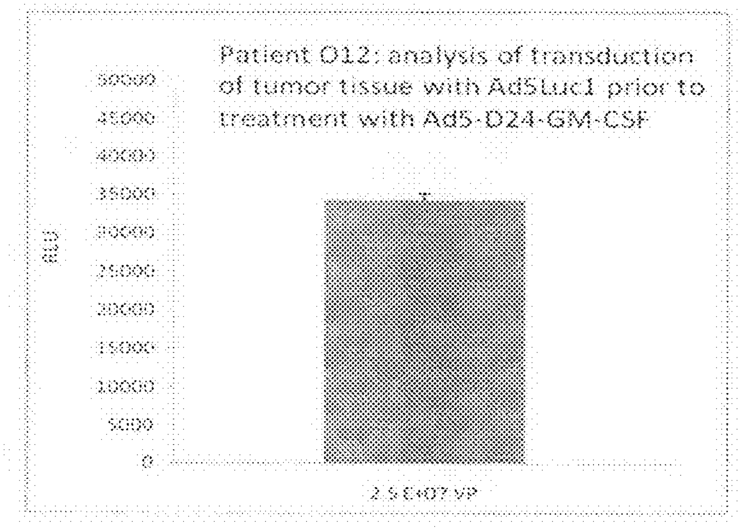
FIGS. 7*a* and 7*b* show in vitro analysis of transduction of a patient tumor to test the infectivity of an Ad5-based virus.
Figure 7B:
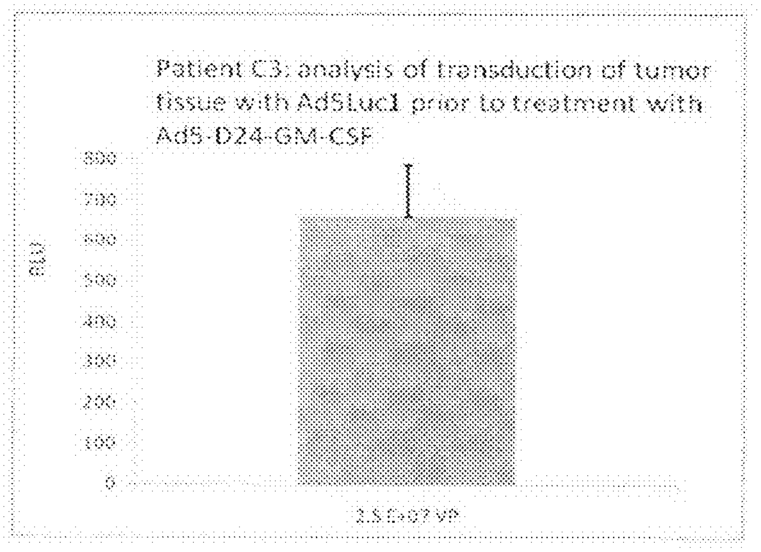

To check that a tumor could be infected with Ad5 based viruses, biopsies taken from tissues were homogenized, and infected with luciferase coding Ad5Luc1 according to standard protocol of infection. Briefly, cells seeded in wells were washed twice with PBS, virus was thawed and resuspended in a minimun amount of growth media and gently poured on the cells. The infection proceeded for 30 minutes and afterwards the cells were washed again in PBS and appropriate amount of complete growth media was added. Luciferase quantification was assessed 24 hours later. Please note that only a minute amount of tissue was obtained and therefore the number of cells could not be calculated, nor the amount of virus normalized to amount of tissue. Thus, no quantitative analyses were made, but qualitative data showed successful gene transfer in patients O12 and C3 (FIGS. 7*a-b*). Background luciferase values (circa 200 RLU) were subtracted.

II. Immunohistochemical Staining of CAR

Available archival specimens of patient's tumors (patients for Ad5-D24-GM-CSF treatment) were collected and analyzed for CAR (the adenovirus serotype 5 receptor) expression by immunohistochemistry. Adenovirus receptor CAR stainings of cancer cell cytoplasms (M3), jejunum adenocarsinoma (C3), pancreatic carcinoma (H7), carcinoma lobulare infiltration (R8), liver metastasis of ovarian cancer (O12) and lung metastasis of synovialsarcoma (S23) are shown in FIG. 7*c*.

III. Neutralizing Antibody Titers Against the Ad5/3 Capsid 293 cells were seeded on 96-well plates at $1\times10^4$ cells/well and cultured overnight. Next day, cells were washed with DMEM without FCS. To inactivate complement, human serum samples were incubated at 56° C. for 90 min. A four-fold dilution series (1:1 to 1:16 384) was prepared in serum-free DMEM (Sarkioja M et al. 2008, Gene Ther 15(12): 921-9). Ad5/3luc1 was mixed with serum dilutions and incubated at room temperature for 30 min. Next, cells in triplicates were infected with 100 VP/cell in 50 μl of mix, and 1 h later 100 μl of growth medium with 10% FCS was added. 24 h post-infection, cells were lysed and luciferase activity was measured with Luciferase Assay System (Promega, Madison, Wis.) utilizing TopCount luminometer (PerkinElmer, Waltham, Mass.). Luciferase readings were plotted relative to gene transfer achieved with Ad5/3luc1 alone in order to evaluate the effect of neutralizing antibodies in the serum of patients treated with Ad5/3-d24-GMCSF. The neutralizing antibody titer was determined as the lowest degree of dilution that blocked gene transfer more than 80%.

Example 4

Ex Vivo Analysis of Ad5/3-D24-GMCSF Efficacy in Ascites and Pleural Samples

Fresh ascites/pleural effusion sample was stored at +4° C. over night. The sample was divided into 50 ml falcon tubes and the cells were isolated by centrifugation 900 rpm, 8 min, +4° C. To lyse red blood cells the sample was incubated 5-10 min in room temperature with 25 ml ACK Lysis Buffer (Invitrogen, Carlsbad, Calif.). The falcons were filled up with 2% DMEM and the cells were centrifugated (900 rpm, 8 min, +4° C.). Cell suspension of 100 000 cells/ml in 2% DMEM-fungizone was prepared (50 ml 2% DMEM+200 μl Fungizone (BMS, Espoo, Finland)).

For luciferase-assay, to test the effect of capsid modification on transductional efficacy, cells were seeded into two 24-well plates, 50 000 cells/well. 24 h later the cells in triplicates were infected with Ad5luc1 or Ad5/3luc1 in concentrations of 500 vp/cell and 5000/vp/cell in 2% DMEM. Luciferase expression was analyzed similarly as in Example 3 III (determining neutralizing antibody titers).

Fresh pre-treatment samples of ascites and pleural effusion for patients K75 and V136, respectively, were analyzed, and in both samples high transduction with Ad5/3 was seen.

For MTS-assay, to test the potency of Ad5/3-d24-GMCSF on clinical samples, cells were seeded into two 96-well plates, 10 000 cells/well. The cells were infected after 24 h incubation. Infections were carried out in 2% DMEM. Next day 10% DMEM was added. The cells were checked daily and the culture medium was changed every other day. Before measuring, the medium was aspirated and 100 μl of fresh 10% DMEM was pipetted to the wells. 20 μl of MTS-Assay Buffer (Promega, Madison, Wis.) was added and the cells were incubated for 1.5-4 hours. The absorbance was measured with Multiscan Ascent and Ascent Software v2.6 (Thermo Labsystems, Helsinki, Finland) at 490 nm and background absorbance was subtracted from the absorbance of the samples.

Pre-treatment samples of pleural effusion from V136 and M137 were assessed for oncolytic potency of Ad5/3-d24-GMCSF. Six days after infection there was 62% and 29% less viable cells ($p<0.001$), respectively, than in an uninfected control sample suggesting that Ad5/3-d24-GMCSF was able to kill tumor cells present in the effusion.

For assessing the presence of virus in samples obtained after treatment, cells were resuspended in 3 ml 2% DMEM after lysing red blood cells and freeze-thawed four times in −80° C. The 293 cells were seeded in 96-well plates 10 000cells/well and incubated for 24 h hours. The sample was centrifugated 15 min, 4000 rpm, +4° C. and the supernatant was collected. 293 cells were infected with 100 μl/well of the supernatant. After 10 days of incubation the wells were assessed for the presence of cytopathic effect.

To assess replication of Ad5/3-d24GMCSF at the tumor, we also analyzed an ascites sample taken from patient O82 7 days after treatment. This resulted in 70% of the cells showing cytopathic effect, while uninfected control cells did not show similar effects.

Example 5

In Vivo Analysis of D24-GM-CSF Type Viruses in Animals

Figure 8A:
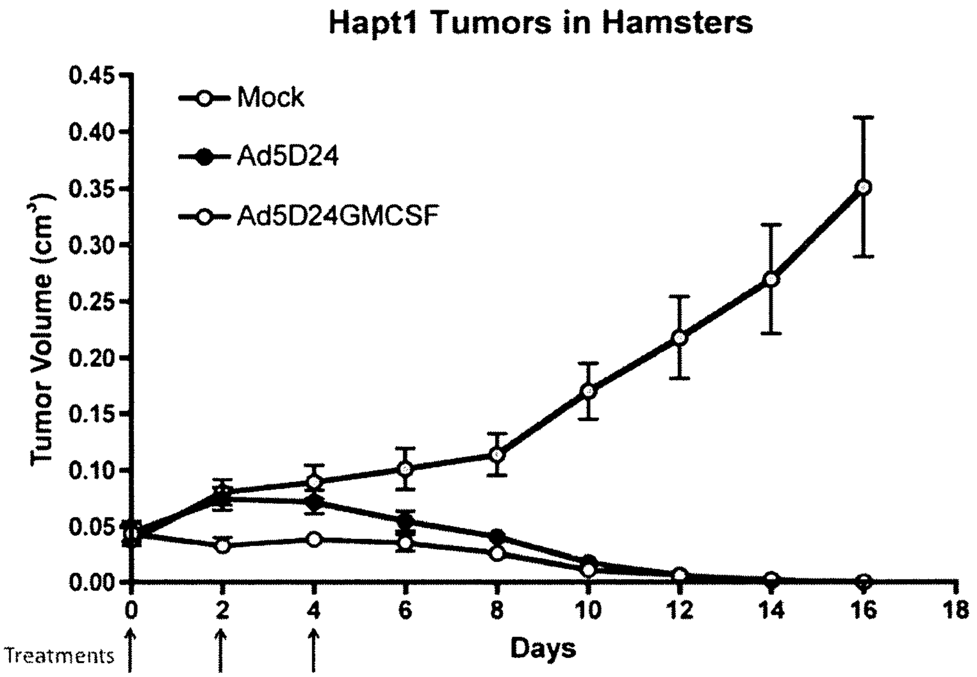
FIG. 8*a* shows in vivo efficiency of Ad5-D24-GMCSF in Syrian Hamsters (permissive for human adenovirus replication) bearing pancreatic cancer tumors. Both Ad5D24 and Ad5-D24-GMCSF eradicate the tumors within 16 days following the treatments. $1\times10^9$ VP of virus were administered on days 0, 2 and 4.
Figure 8B:
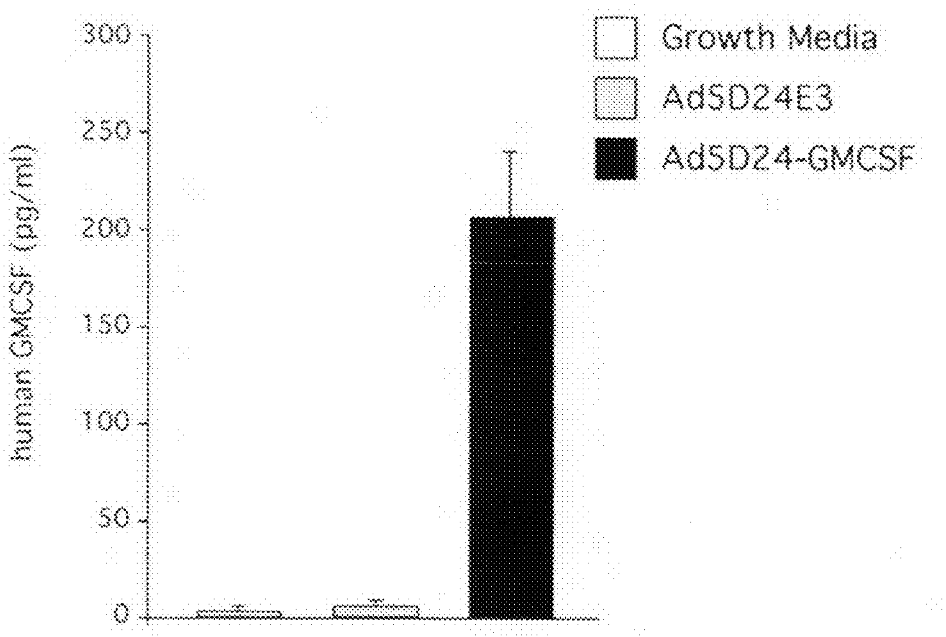
FIG. 8*b* shows that intratumoral injection of Ad5-D24-GMCSF resulted in high levels of hGMCSF in serum of Syrian Hamsters. Animals treated with Ad5D24E3 or Ad5-D24-GMCSF were sampled on day 4 and the concentration of human GMCSF in serum was assessed by FACSARRAY.
Figure 8C:
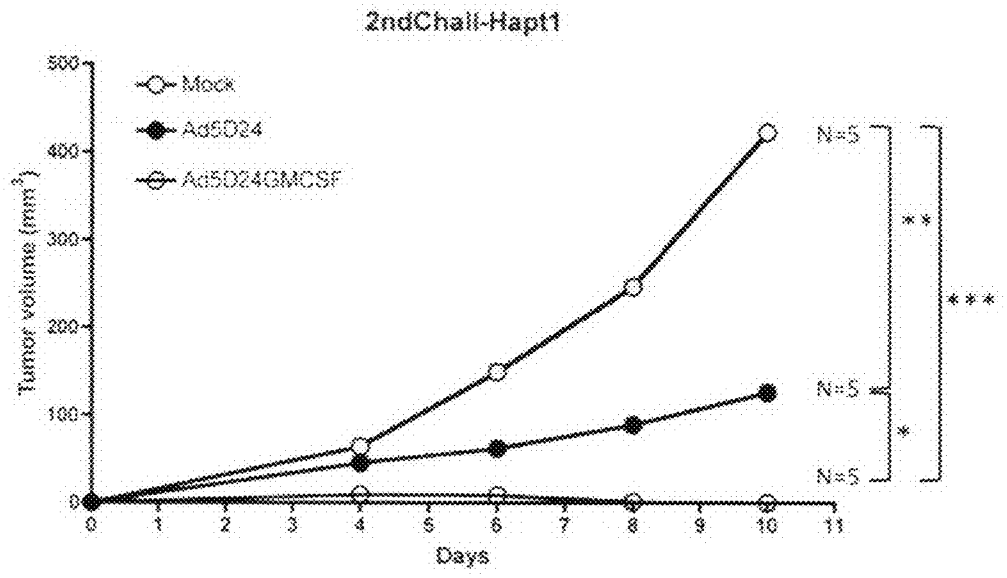
FIG. 8*c* shows that curing of HapT1 tumors with Ad5-D24-GMCSF (but not with Ad5D24) protected Syrian hamsters from subsequent re-challenge with HapT1. This demonstrates that Ad5-D24-GMCSF can induce a tumor specific immune response. Animals previously treated with Ad5D24 or Ad5D24-GMCSF (FIG. 8*a*) were re-challenged with the same tumor and tumor growth was measured over time.
Figure 8D:
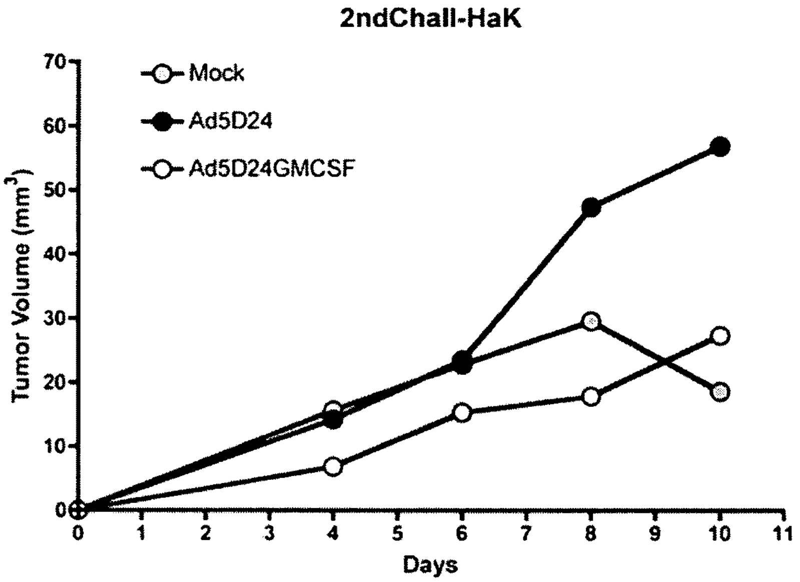
FIG. 8*d* shows induction of a tumor specific immune response by Ad5-D24-GMCSF, curation of HapT1 tumors with Ad5-D24-GMCSF did not protect Syrian hamsters from Hak tumors. Animals with HapT1 tumors previously treated with Ad5D24, or Ad5D24-GMCSF (FIG. 8*a*) were re-challenged with a different tumor and tumor growth was measured over time.

In vivo efficacy of Ad5-D24-GM-CSF was tested in immune competent Syrian hamsters, which are semipermissive for human adenovirus replication (mice are non-permissive) (Ying B. et al. 2009, Cancer Gene Ther doi:10.1038/cgt.2009.6.). $7*10^6$ HapT1 pancreatic cancer cells were injected subcutaneously and $1*10^9$ virus particles (VP) of Ad5-D24-GM-CSF or Ad5D24E3 (which does not express GM-CSF) were injected intratumorally on day 0, 2 and 4. The mock group was injected with the same volume of growth media at the same indicated time points. FIG. 8*b* shows that intratumoral injections of Ad5-D24-GMCSF resulted in high levels of hGM-CSF in serum of Syrian hamsters. Human GM-CSF is known to be active in Syrian hamsters (Cho, Exp Toxicol Pathol 2006 vol. 57 (4) pp. 321-8). Interestingly, all animals were tumor-free by day sixteen except for mock group (FIG. 8*a*). Tumor scars were still analyzed for two additional weeks to assess whether reappearance of the tumor might have occurred. However, on day 32 there was still no sign of tumor in these animals so that the first part of the experiment was terminated and animals of the Mock group were euthanized. The remaining treated animals were at this point challenged with the same tumor in the right side of the upper body by subcutaneous injection of $7*10^6$HapT1 cells while on the left side were challenged with a different tumor ($1*10^6$ of HaK tumor) for which the animals were naïve. Tumor growth was measured over time and is reported in FIGS. 8*c-d*. Interestingly the animals that were previously treated with Ad5D24GMCSF completely rejected the HapT1 tumor challenge while Hak tumors grew normally, while the animals that were previously treated with Ad5D24E3 grew independently HapT1 and HaK tumors (FIGS. 8*c-d*).

In summary, the data indicates that Ad5-D24-GM-CSF has antitumor activity in immune competent tumor bearing animals, and it is able to elicit tumor-specific immunity to the degree of rejecting subsequent challenge of the same tumor.

Example 6

In Vivo Analysis of D24-GM-CSF Type Viruses in Human Patients

I. Patients

Patients with advanced and treatment refractory solid tumors were enrolled in a government-approved compassionate treatment protocol. Information of patients receiving Ad5-D24-GM-CSF is listed in Table 1.

22 patients with advanced solid tumors refractory to standard therapies (Table 6) were treated with a single round of Ad5/3-d24-GMCSF intravenously and intratumorally (Table 7). Intratumoral injection was performed intraperitoneally or intrapleurally in the case of carcinomatosis or pleural metastases, respectively. Inclusion criteria were solid tumors refractory to conventional therapies, WHO performance score 3 or less and no major organ function deficiencies. Exclusion criteria were organ transplant, HIV, severe cardiovascular, metabolic or pulmonary disease or other symptoms, findings or diseases preventing oncolytic virus treatment. Written informed consent was obtained and treatments were administered according to Good Clinical Practice and the Declaration of Helsinki.

II. Treatments with Adenoviral Vector Encoding GM-CSF a) Ad5-D24-GM-CSF, Ad5/3-D24-GM-CSF or Ad5-RGD-D24-GM-CSF Treatments Ad5-D24-GM-CSF, Ad5/3-D24-GM-CSF and Ad5-RGD-D24-GM-CSF were then produced according to clinical grade and treatment of patients was initiated. This "phase 0" compassionate use program has been discussed at the HUCH Surgical Ethics committee. The program has also been discussed at FinOHTA (national evaluation of medical technologies) and Ethics Negotiation Board of the Finnish Medical Association. Legal aspects have been checked with Ministry of Social Affairs and Health, the National Agency of Medicines, the legal council at the Finnish Medical Association, the National authority for Medicolegal affairs and the Parliamentary Board of Social Affairs and Health. The treatments have been approved by the Finnish Gene Technology Board.

Patients received a single round of treatment on day 0. Virus administration was performed by ultrasound-guided intratumoral injection and circa one fifth of the dose was given intravenously. The starting dose of $8\times10^{10}$ VP was chosen based on safety results published by others.

Virus was diluted in sterile saline solution at the time of administration under appropriate condition. Following virus administration all patients were monitored overnight at the hospital and subsequently for the following 4 weeks as outpatients. Physical assessment and medical history were done at each visit and clinically relevant laboratory values were followed. Side effects of treatment were recorded and scored according to Common Terminology for Adverse Events v3.0 (CTCAE).

Because many cancer patients have symptoms due to disease, pre-existing symptoms were not scored if they did not become worse. However, if the symptom became more severe, e.g. pre-treatment grade 1 changed to grade 2 after treatment, it was scored as grade 2. Serum levels of GMCSF and four other cytokines (IL-6, IL-8, IL-10 and TNF-alpha) were analyzed by BD Cytometric Bead Array (CBA) Human Soluble Protein Flex Set (Becton Dickinson, Franklin Lakes, N.J., US). Tumor size was assessed by contrast-enhanced computer tomography (CT) scanning. Maximum tumor diameters were obtained. Response Evaluation Criteria in Solid Tumors (RECIST1.1) criteria were applied to overall disease, including injected and non-injected lesions. These criteria are: partial response PR (>30% reduction in the sum of tumor diameters), stable disease SD (no reduction/increase), progressive disease PD (>20% increase). Clear tumor decreases not fulfilling PR were scored as minor responses (MR). Serum tumor markers were also evaluated when elevated at baseline, and the same percentages were used.

Blood samples were collected before and after the treatment for analyses. In Table 1 is summarized the viral load in the serum of patients treated with Ad5-D24-GMCSF. Quantitative PCR (qPCR) was used for that analysis (see section III for description of the methods).

Tables 2, 3 and 4 summarize all the adverse events that were recorded during and after the Ad5-D24-GM-CSF treatment. All the adverse events have been graded according to Common Terminology for Adverse Events v3.0 (CTCAE). Of note is that all the patients manifested grade 1 or/and 2 flu-like symptoms, but only two grade 3 symptoms were observed, one case of constipation in an ovarian cancer patients who had suffered of constipation before and one grade 3 hyponatremia.

In Table 5 there is reported the efficacy evaluation of Ad5-D24-GM-CSF according to RECIST criteria (Therasse P et al. 2000, J Natl Cancer Inst 92, 205-16). Interestingly two complete response (CR) and five stable diseases (SD) were observed in 14 analyzable patients for a 50% clinical benefit rate.

b) Safety of Ad5/3-d24-GMCSF in Cancer Patients

Treatments were well tolerated up to the highest used: $4\times10^{11}$ VP/patient. No grade 4-5 adverse events were seen. Grade 1-2 flu-like symptoms were common with 19/22, 17/22 and 8/22 patients experiencing fever, fatigue or upper respiratory symptoms, respectively. Pain in the injection site (6 patients), abdominal pain (10 patients) and nausea (9 patients) were also common grade 1-2 adverse events as well as (Table 8). Asymptomatic and self-limiting grade 3 hematological side effects were seen in 4 patients: anemia (grade 2 at baseline), neutropenia, aspartate aminotrasferase elevation and hyponatremia. The only non-hematological grade 3 side effect was cholecystitis seen three week after treatment in pancreatic cancer patient H83. He also had grade 3 alanine aminotrasferase and bilirubin elevations. Taken together, these symptoms suggest tumor mediated biliary duct compression. It is unclear if this was treatment mediated inflammatory swelling or tumor growth caused by disease progression.

III. Detection of the Virus From Blood

Serum samples were collected from patients treated with Ad5-D24-GM-CSF or Ad5/3-D24-GM-CSF (see example 6, I.) and conventional PCR was carried out with primers and conditions according to Takayama et al. 2007, J. Med. Virol. 79:278-284. Briefly, total DNA was extracted by adding 3 μg of carrier DNA (polydeoxyadenylic acid; Roche, Mannheim, Germany) to 400 μl of serum and using the QIAamp DNA mini kit. Extracted DNA was eluted in 60 μl nuclease-free water and DNA concentration was measured by spectrophotometry. PCR amplification was based on primers and probe targeting the E1A region flanking the 24-bp deletion (forward primer 5'-TCCGGTTTCTATGCCAAACCT-3' (SEQ ID NO 1), reverse primer 5'-TCCTCCGGTGATAATGACAAGA-3' (SEQ ID NO 2) and probe onco $5'^{FAM}$-TGATCGATCCACCCAGTGA-$3'^{MGBNFQ}$ (SEQ ID NO 3)). In addition, a probe complementary to a sequence included in the 24-bp region targeted for deletion was used to test the samples for the presence of wild-type adenovirus infection (probe wt $5'^{VIC}$-TACCTGCCACGAGGCT-$3'^{MGBNFQ}$ (SEQ ID NO 4)).

The real-time PCR conditions for each 25 μl reaction were as follows: 2× LightCycler480 Probes Master Mix (Roche, Mannheim, Germany), 800 nM each forward and reverse primer, 200 nM each probe and 250 ng extracted DNA. PCR reactions were carried out in a LightCycler (Roche, Mannheim, Germany) under the following cycling conditions: 10 min at 95° C., 50 cycles of 10 s at 95° C., 30 s at 62° C. and 20 sec at 72° C. and 10 min at 40° C. All samples were tested in duplicate. TaqMan exogenous internal positive control reagents (Applied Biosystems) were used in the same PCR runs to test each sample for the presence of PCR inhibitors.

A regression standard curve was generated using DNA extracted from serial dilutions of Ad5/3-D24-Cox2L ($1\times10^8$-10 vp/ml) in normal human serum. The limit of detection and limit of quantification for the assay were 500 vp/ml of serum.

Positive samples were confirmed by real-time PCR using LightCycler480 SYBR Green I Master mix (Roche, Mannheim, Germany) and primers specific for adenovirus and GM-CSF sequences (forward primer 5'-AAACACCACCCTCCTTACCTG-3' (SEQ ID NO 5) and reverse primer 5'-TCATTCATCTCAGCAGCAGTG-3' (SEQ ID NO 6)).

IV. Presence of Ad5/3-d24-GMCSF in Serum After Treatment

All patients were negative for Ad5/3-d24-GMCSF prior to the treatment with Ad5/3-d24-GMCSF. On day 1 17/19 patients had measurable levels of virus genomes in the serum, with the highest titer being 2061 VP/ml serum. From samples taken during days 3-7 12/15 patients were positive, with the highest titer of $3.36\times10^5$ vp/ml serum. Positive samples were seen up to day 58 after treatment. (Table 9)

V. GMCSF and Neutralizing Antibody Titers in Serum After Treatment

There was no significant change in the systemic levels of GMCSF after Ad5/3-d24-GMCSF treatment, which correlated well with no significant effects seen in the levels of total white blood cell counts. This suggests a general restriction of GMCSF production to the local sites of virus replication in the tumors. In one patient, S70, a transient increase in serum GMCSF was seen on day 4 accompanied by a transient elevation of the leukocyte count. This might have been related to effective virus replication as the patient simultaneously had fever and $3.36\times10^5$ vp/mlof virus in serum (Table 9). This patient did not experience any serious adverse events during follow-up. However, a post treatment CT scan suggested anti-tumor activity (SD) and for 4 weeks after treatment she was feeling better and her persistent chest pains were gone. The highest GMCSF concentration measured in this patient's blood was 115 pg/ml, which is approximately 10-fold lower than the toxic levels of GMCSF in humans.

At baseline 4/15 patients were completely negative for neutralizing antibodies against Ad5/3. Another 2 patients had barely detectable titers (1-4) while 8 patients had low neutralizing titer (16-64). No patients had medium or high neutralizing titers against Ad5/3 at baseline. After treatment the titer increased in all patients ($p<0.005$) (Table 9). No clear correlation was seen between neutralizing antibody titers and viral dose, antitumor activity or toxicity. Intriguingly, with regard to virus load in serum two patients, Y62 and O79, were positive for neutralizing antibodies at baseline and had high titers during weeks 2-4 but still had measureable loads of virus present in their serum at least 28 and 58 days, respectively (Table 9). This indicates that even high antibody titers cannot hinder virus replication in the tumors. Interestingly, the antibody titer did not reach maximum in all patients. For example, S70, X122 and H83 had large amounts of virus circulating during week 1 and their antibody titer rose slowly.

VI. Killing of Differentiated Tumor Cells

Figure 9A:
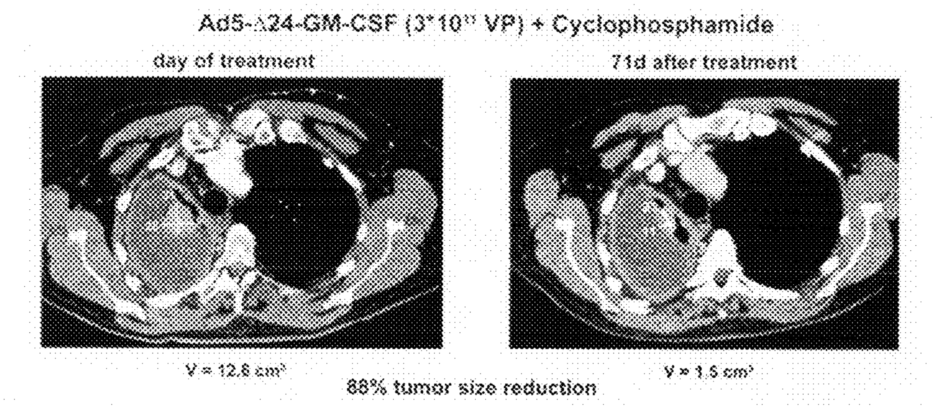
FIG. 9*a* shows efficacy of Ad5-D24-GMCSF in combination with metronomic oral cyclophosphamide. 88% tumor reduction was observed by CT scan 71 days following the beginning of the treatment.
Figure 9B:
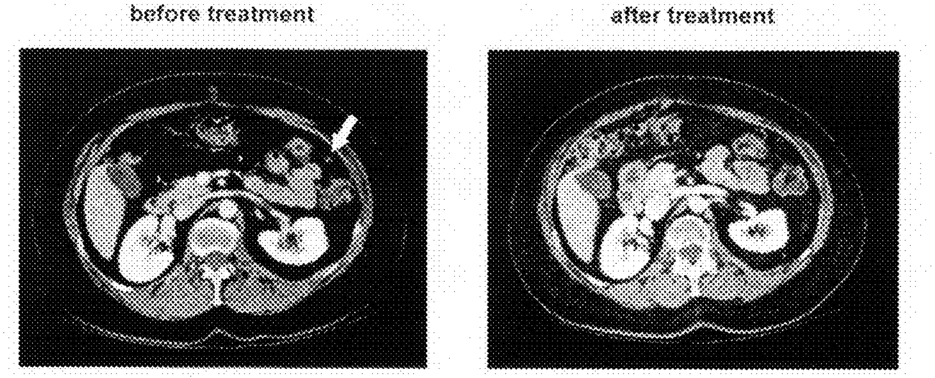
FIG. 9*b* shows efficacy of the treatment with Ad5D24-GMCSF in an ovarian cancer patient treated with Ad5-D24-GMCSF. CT scan showed complete disappearance of all measurable tumors as indicated by the arrow.
Figure 10A:
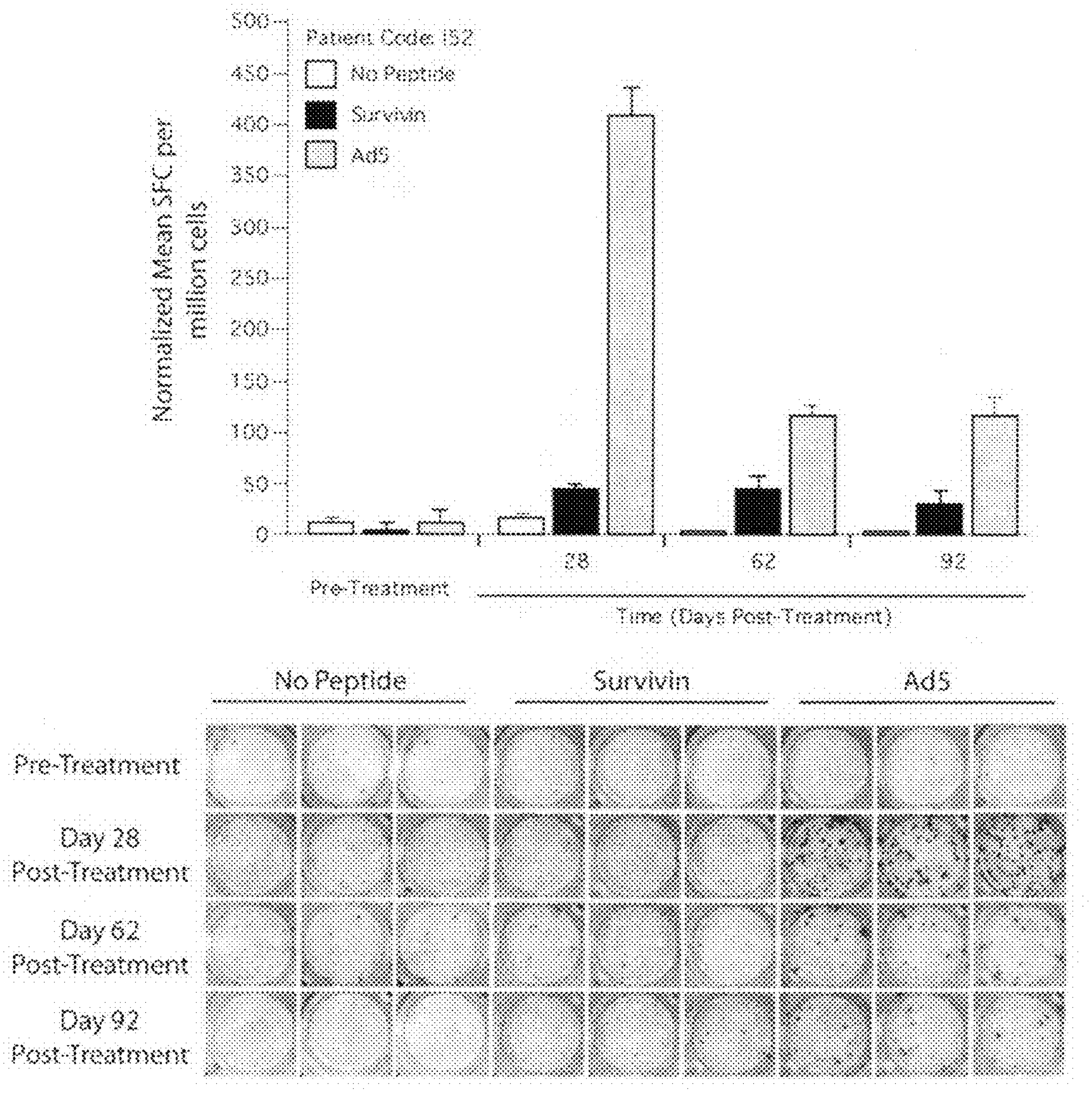
FIGS. 10*a-d* show that Ad5-D24-GMCSF elicited a T cell-response against both tumor epitopes and adenovirus (present in tumor cells). T cells harvested from patients treated with Ad5-D24-GMCSF were analyzed by IFN-gamma ELISPOT upon stimulation with a mix of peptide from Adenovirus 5 and a mix of peptide from the tumor antigen survivin.
Figure 10B:
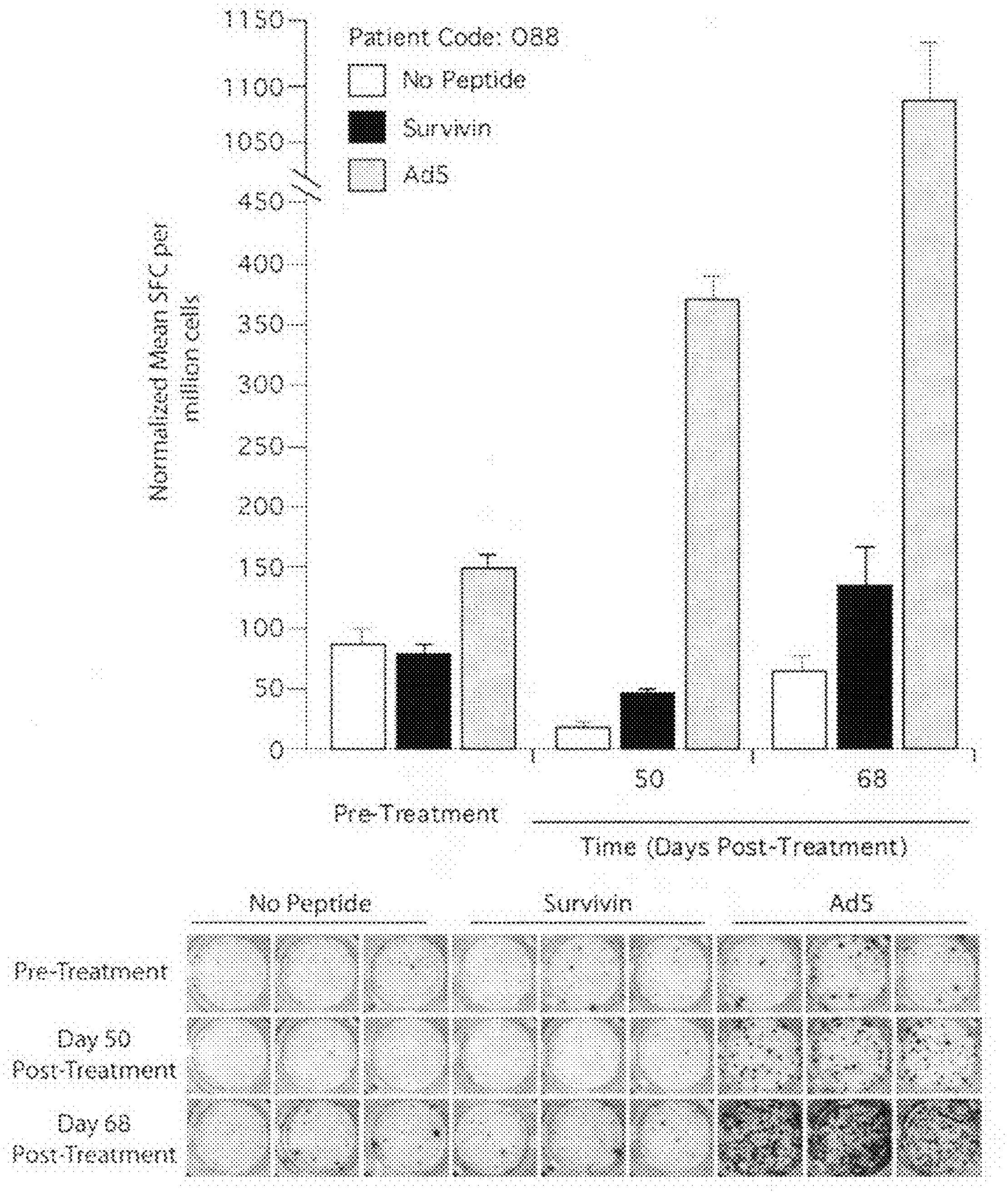
Figure 10C:
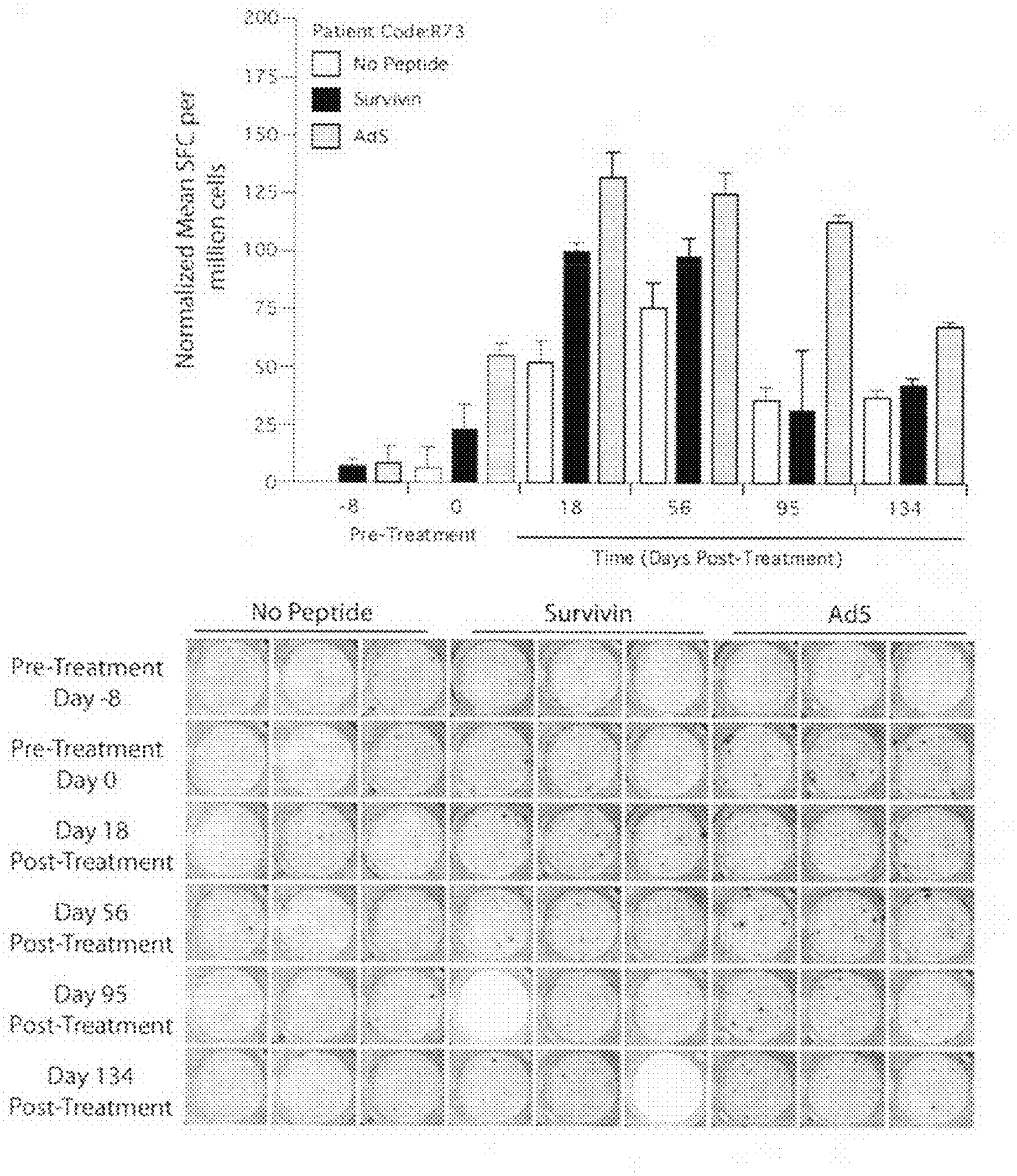
Figure 10D:
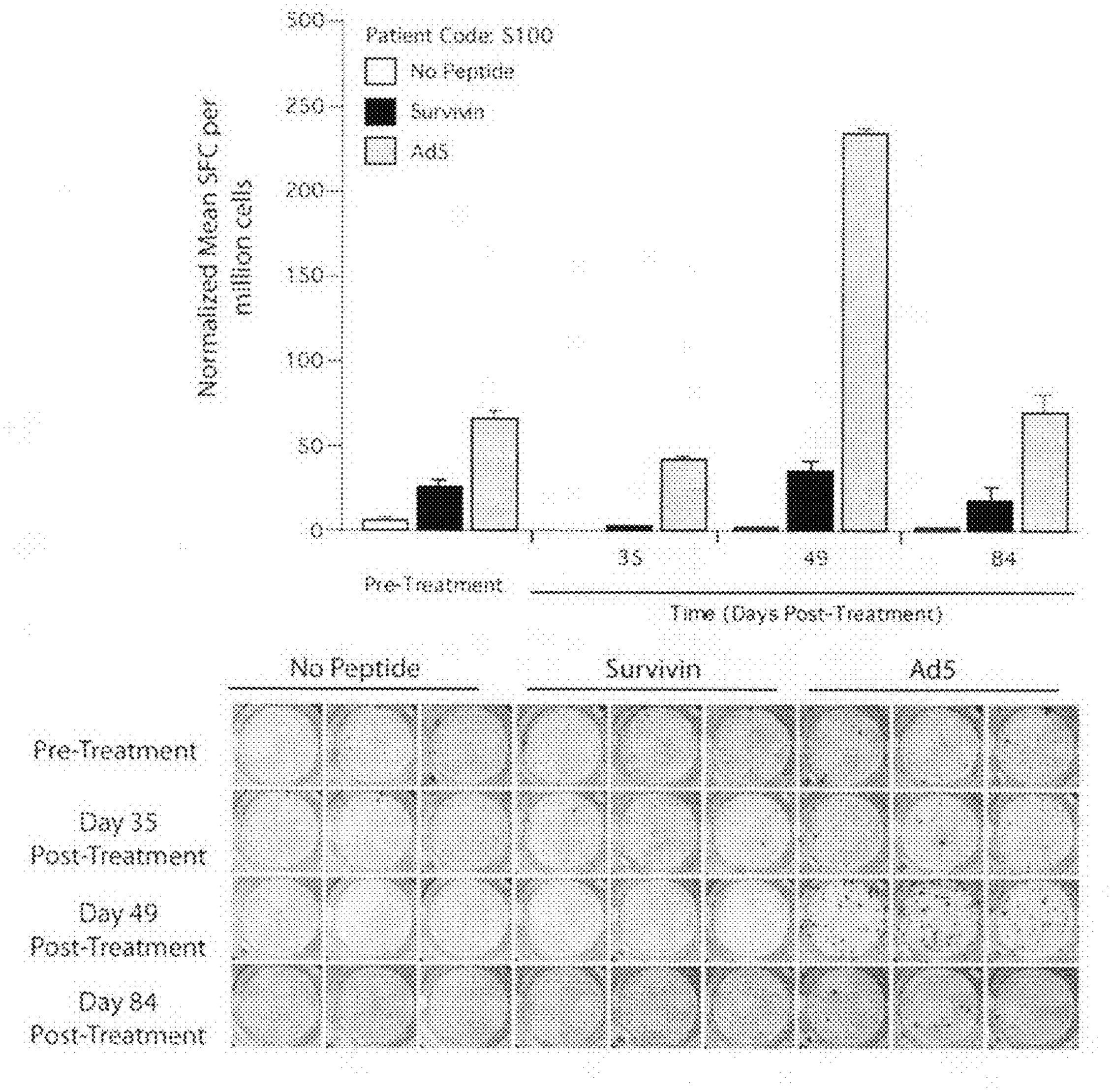

CT scans of a patient suffering from ovarian cancer and a patient suffering from mesothelioma (see Table 1) before and after Ad5-D24-GM-CSF treatment are shown in FIGS. 9*a-b*.

VII. Efficacy of Ad5/3-D24-GMCSF

All patients had progressing tumors prior to treatment. 12 patients could be assessed for radiological benefit according to RECIST1.1 (Table 9). 2 patients had a minor response, 6 patients had stable disease, and 4 patients had progressive disease (PD). Therefore, the radiological clinical benefit rate was 67%. Of note, the rapidly growing pancreatic tumor in H96 stopped growing but a metastatic lesion appeared in the lungs and was thus scored PD. Similarly, patient O129 had a 6% reduction of the injected tumor but had a new metastasis. In patient V136, who had two metastatic cancers, a non-injected liver lesion disappeared, while the other tumors remained SD.

With regard to tumor markers, assessed for patients who had elevated markers at baseline, 2/6 had some lowering of marker levels and 4/6 had elevation of marker levels (Table 9).

Figure 15:
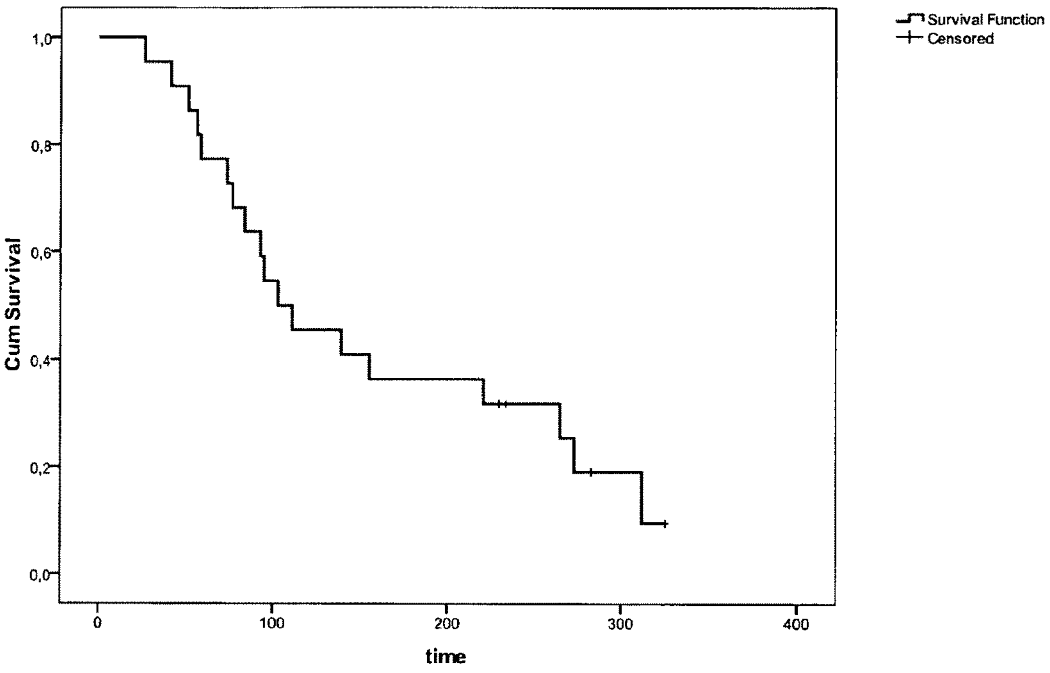
FIG. 15 shows survival plot for Ad5/3-D24-GMCSF treated patients.

Overall survival of patients after treatment is shown in FIG. 15.

In addition to objective measurements of anti-tumor activity we also saw clinical and/or subjective benefit in several cases (Table 9). These included the patients overall wellbeing being improved, a palpable tumor feeling softer and/or smaller and symptoms caused by the tumor being relieved. Of importance is that two patients, previously suffering from rapid accumulation of ascites and/or pleural effusion, had a clear reduction of their accumulation after the virus treatment, this effect lasted for several months in both cases.

Overall, signs of antitumor efficacy were seen in 13/21 patients (62%).

VIII. Hematological Effects of the Treatment

Levels of leucocytes, erythrocytes, Hb, thrombocytes, bilirubin, INR, ALT, AST, ALP, creatinine, K, Na, CRP, CA19-9, GT, Fibrin D-dimers and CEA were studied after Ad5/3-D24-GM-CSF treatment (Tables 3-4).

IX. Immune Response to Virus a) IL-6, IL-10, TNF-α and IL-8

One potential drawback of adenovirus gene therapy is its early toxicity due to viral components which may be immunogenic and can lead to a sepsis-like shock and even death (Brunetti-Pierri et al. Gene Ther 2004; Raper et al 2002). It is, therefore, extremely important to monitor signs for a possible cytokines storm which may later evolve in organ failure. To this end, soon after the treatment and at indicated time point blood was drawn from patients and pro-inflammatory cytokines were analyzed by FACSARRAY as described in the article of Cerullo V et al. (2007, Mol Ther 15, 378-85). No significant changes were seen in the patients treated with Ad5-D24-GM-CSF indicating lack of early innate toxicity.

For the results of lack of early innate toxicity related to Ad5/3-D24-GM-CSF see Table 10.

b) Induction of Cytotoxic T-cells Against Tumors and Specific Immunity Against Tumor Epitope Oncolytic cell death allows the immune system to gain the capacity for recognizing and killing tumor cells. This is potentially beneficial for tumor eradication and may facilitate cures. Adenovirus is cleared out from the body in a relative short time following the administration; hence it becomes of key importance to stimulate the immune system to be able to recognize specific tumor-antigen so that the treatment can result in a sustained beneficial effect for the patient. In addition, in the presence of antibody, the virus is neutralized so that it can lose its efficacy of infecting metastasis. However, effector T or NK cells induced against the tumor are free to circulate and eventually kill metastasis far from the injected tumor. In order to demonstrate that the GMCSF-expressing adenovirus is able to elicit adenovirus- and tumor specific immunity, PBMCs collected from treated patients were analyzed by INF-gamma ELISPOT. The ELISPOT was performed in a blinded fashion way by an external company which was not provided of information on any kind of treatment the patients underwent through (Proimmune). In FIGS. 10*a-d* are illustrated the results from such analysis. It is clear that in same patients, when the T cells were stimulated with a pool of peptide derived from either tumor antigen (survivin) or adenovirus (penton) these cells were activated hence produce INF-gamma (IFN-gamma is a specific activation marker of stimulated T cells).

Figure 11:
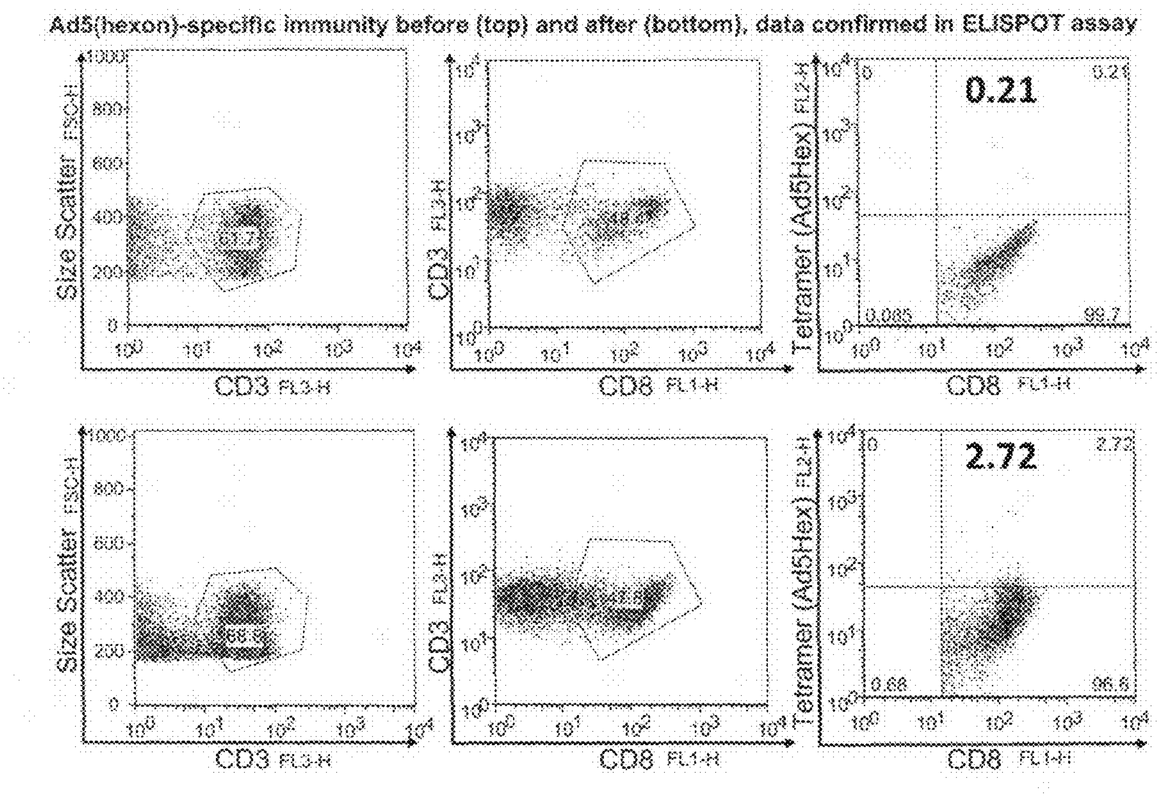
FIG. 11 shows induction of Adenovirus Hexon-specific T cells. Leukocytes harvested from patients treated with Ad5-D24-GMCSF were stained with a CD3, CD8 and hexon-specific tetramer antibodies and analyzed by flow cytometry before and after the treatment. Treatment increased hexon specific cytotoxic T-cells from 0.21 to 2.72%.

FIG. 11 shows induction of Adenovirus Hexon-specific T cells. Leukocytes harvested from patients treated with Ad5-D24-GMCSF were stained with a CD3, CD8 and hexon-specific tetramer antibodies and analyzed by flow cytometry before and after the treatment. Treatment increased hexon specific cytotoxic T-cells from 0.21 to 2.72%.

c) Reduction of Regulatory T-cells

Previous data has demonstrated that metronomic administration of cyclophosphamide reduces regulatory T cells (T-Reg) in laboratory animals.

Figure 12:
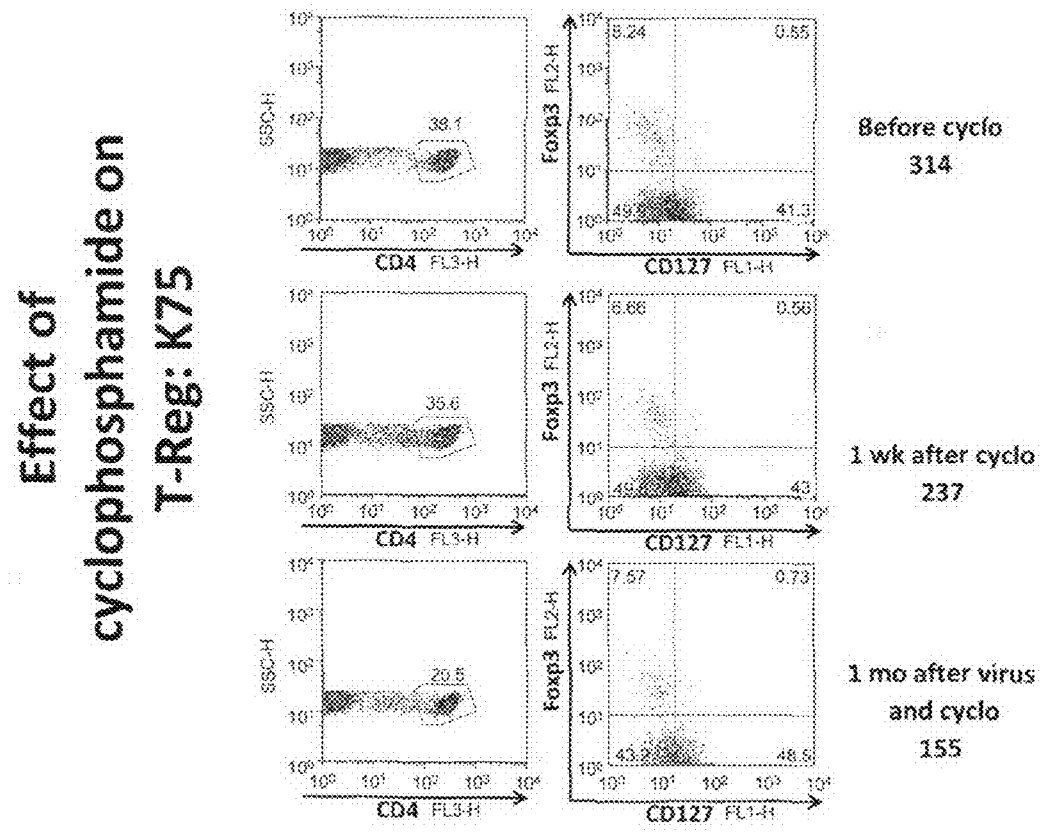
FIG. 12 shows a reduction of circulating T regulatory cells in patient R73. PBMCs which are positive for CD4, negative for CD127 but high in Foxp3 are considered effective T regulatory cells.
Figure 13A:
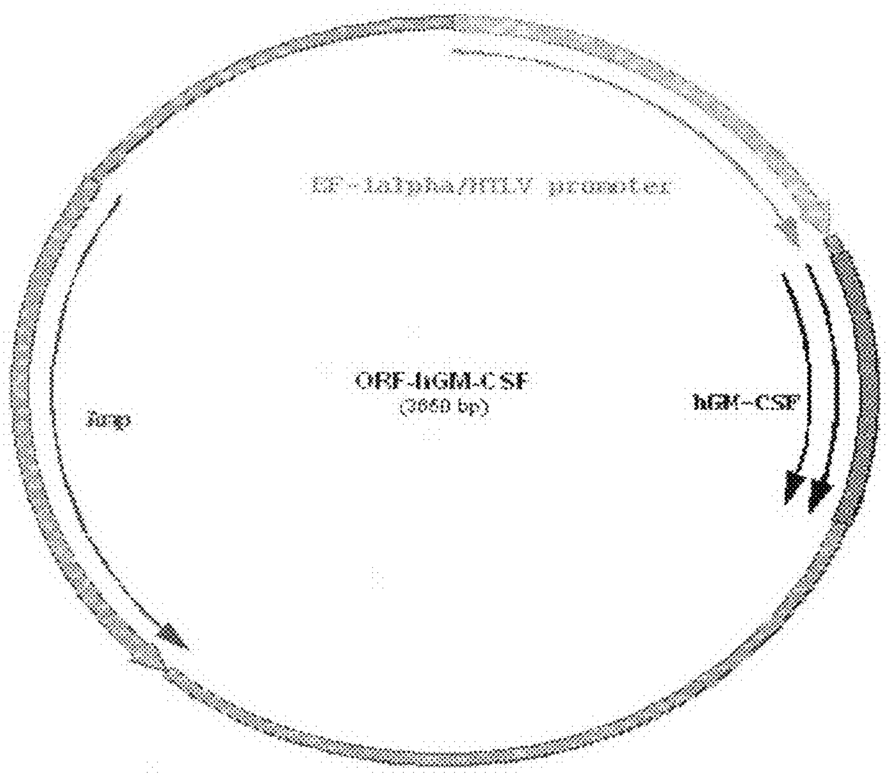
Figure 13B:
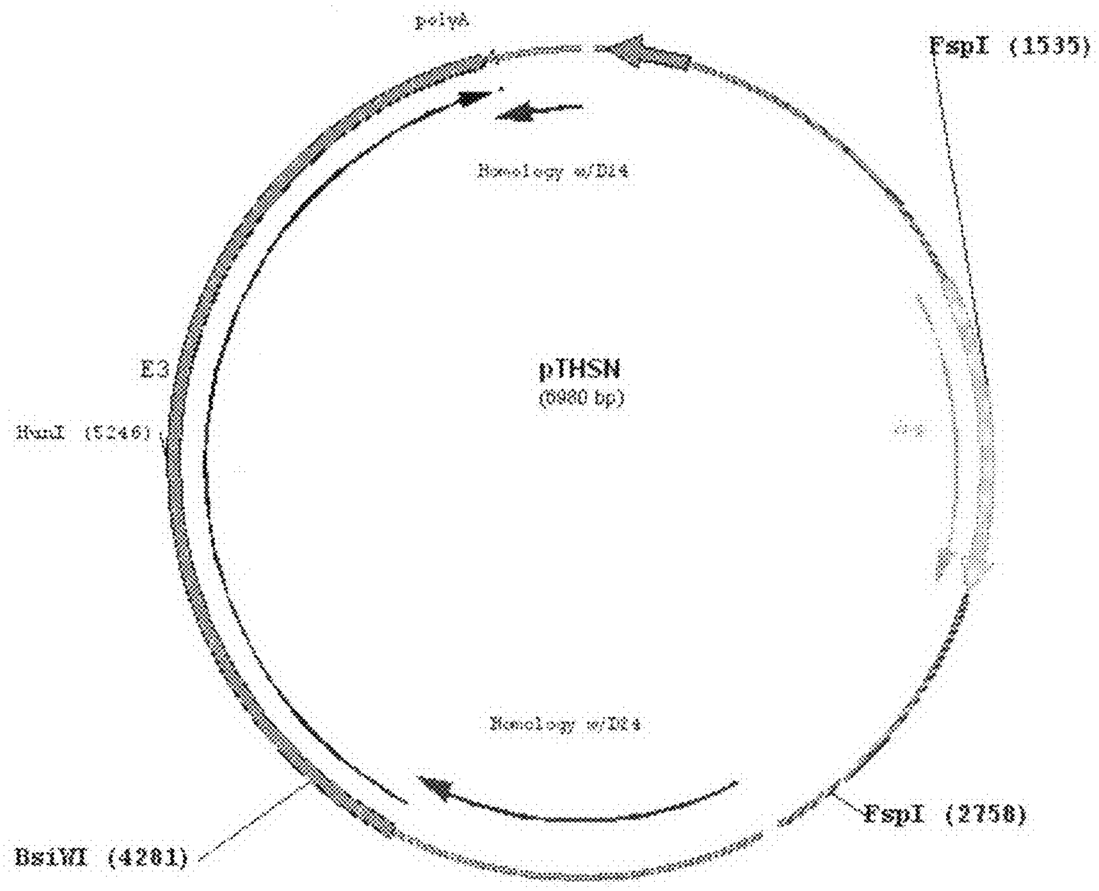
Figure 13C:
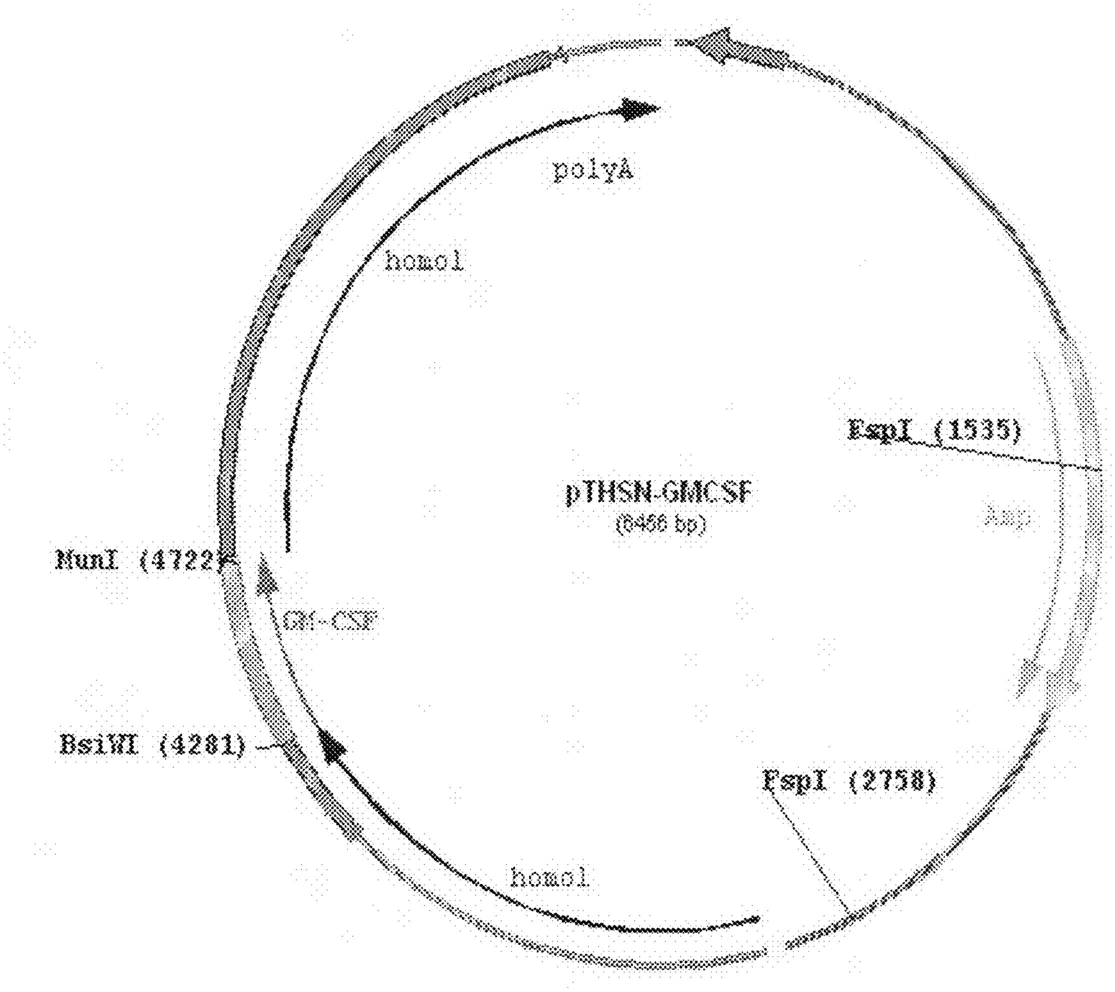
Figure 13D:
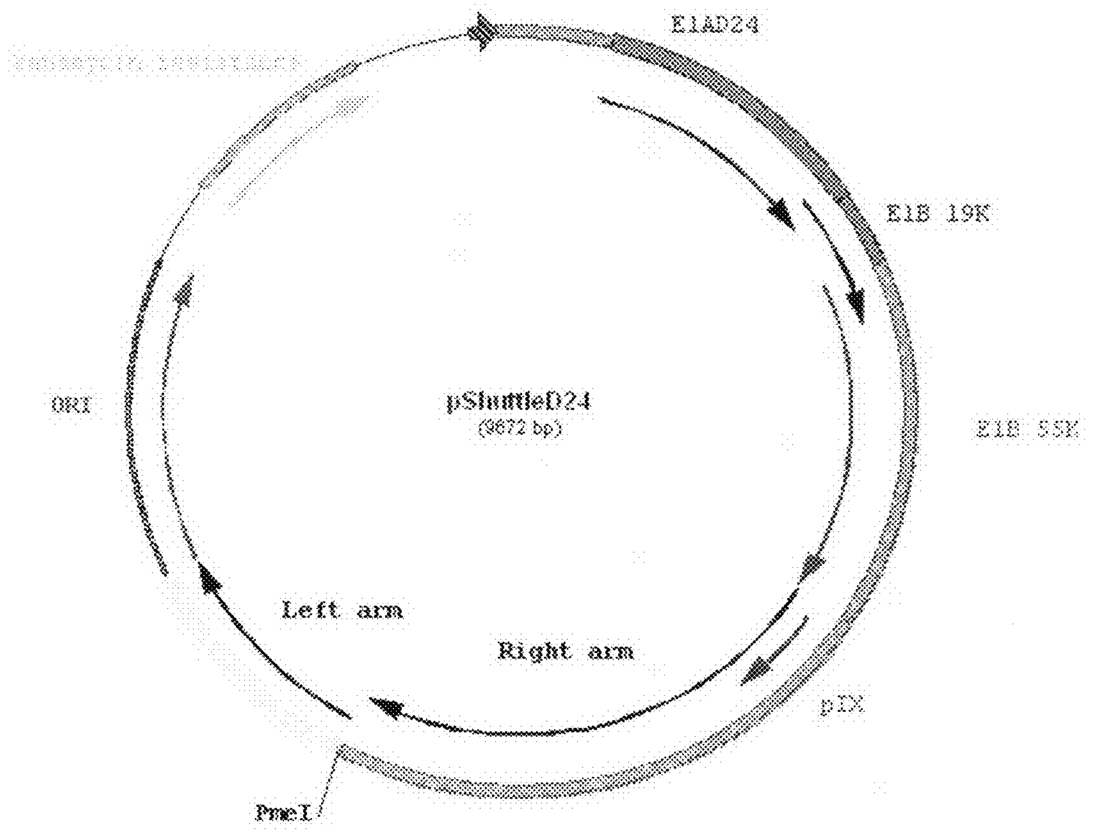
Figure 13E:
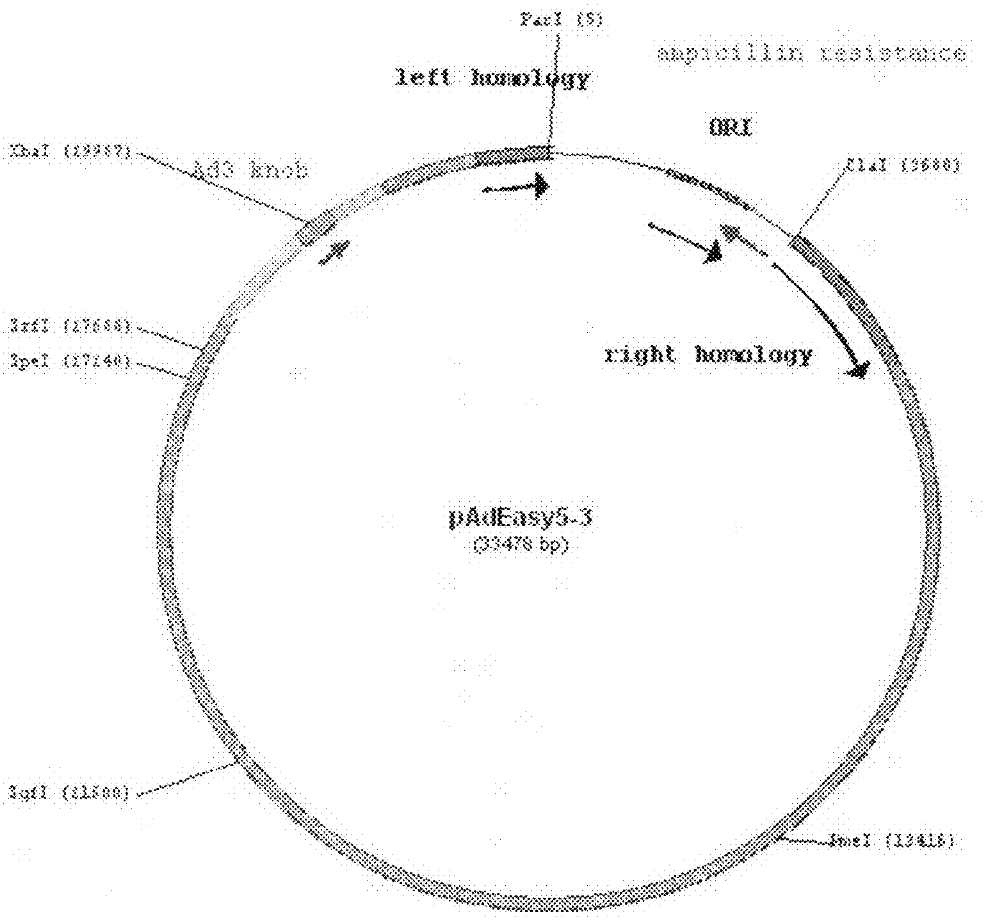
Figure 13F:
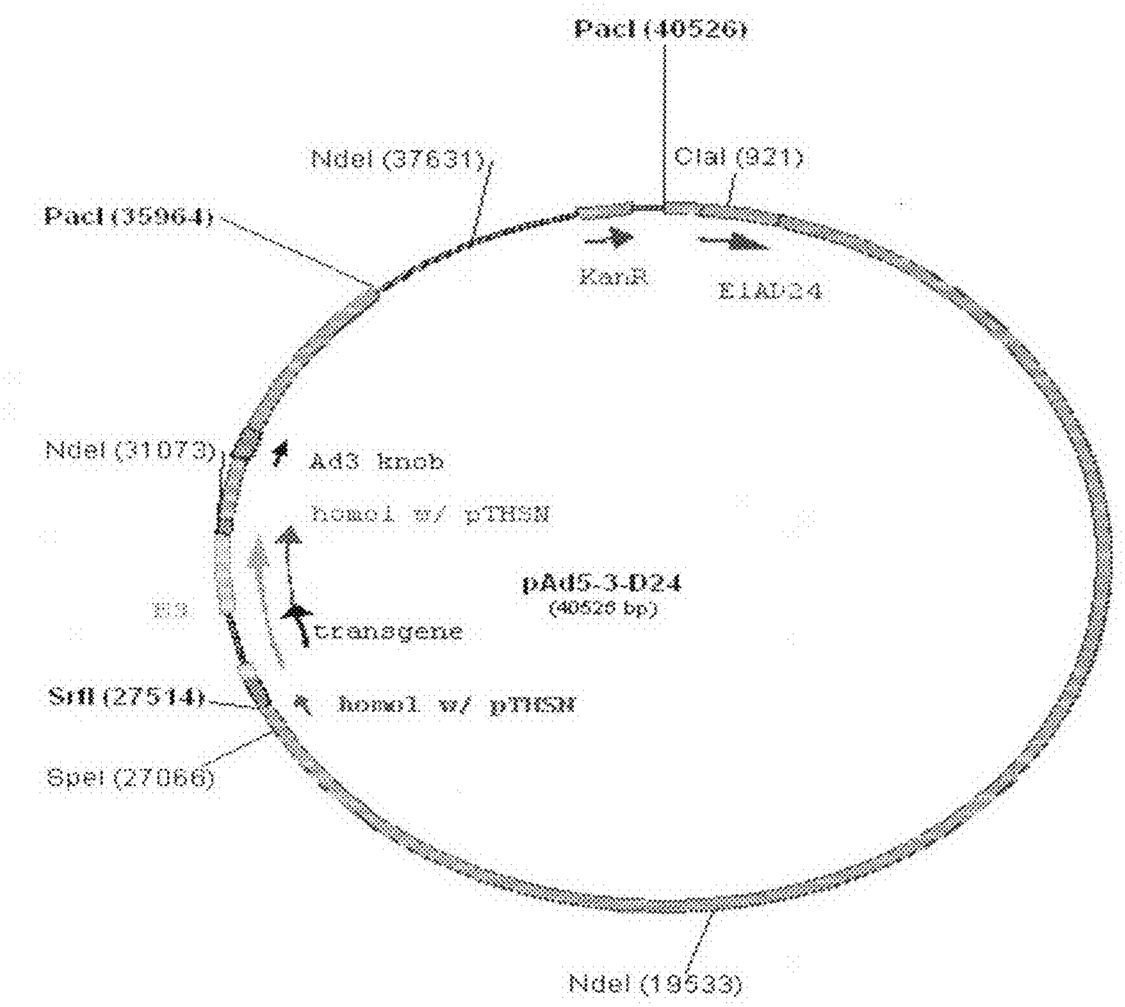
Figure 13G:
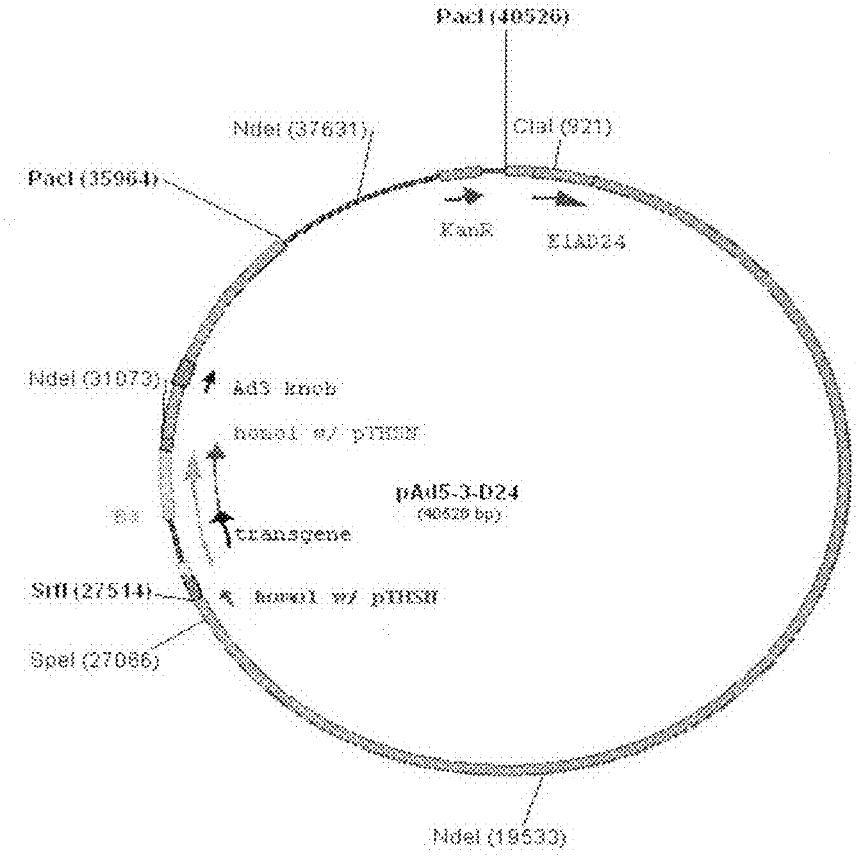
Figure 13I:
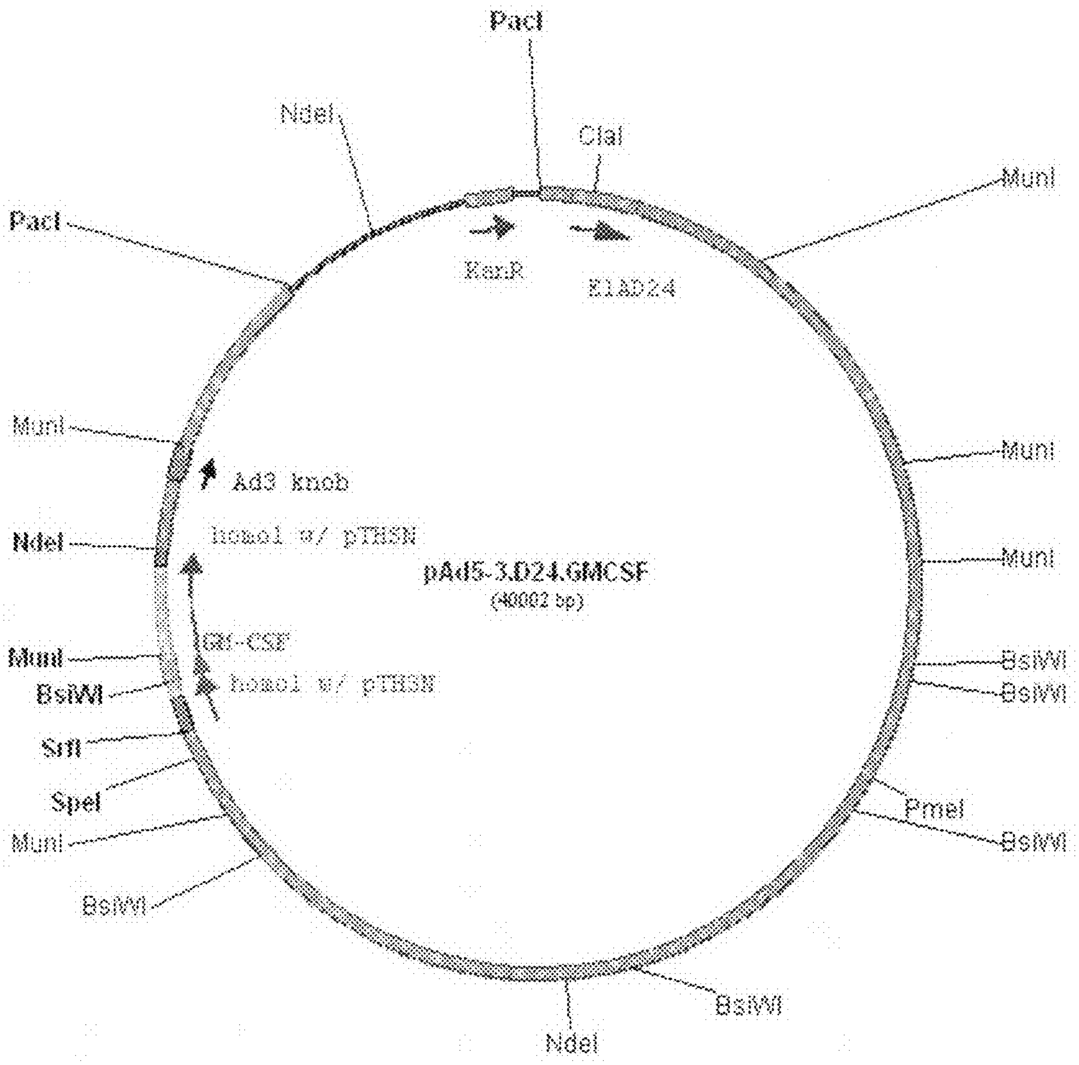

This approach was utilized in patients who received metronomic administration of cyclophoshamide before and after the Ad5-D24-GMCSF treatment and T reg analysis was performed on PBMCs harvested from these patients. In the example illustrated in FIG. 12 it is shown one example from patient R73 and it shows a reduction in circulating T reg. Total PBMCs were harvested from the patients and frozen in appropriate media. At the time of analysis all the samples were thawed and stained first with CD4 and CD127 antibodies, following the cells were permeabilized and stained for the transcription factor Foxp3. Cells that resulted positive for CD4, negative for CD127 but high in Foxp3 are considered effective T regulatory cells (T reg) (FIG. 12).

Example 7

Statistical Analysis

Two tailed Student's t-test was used to compare luciferase activity and pre- and post-treatment neutralizing antibody titers, cytokine levels and GM-CSF concentrations. Survival data was processed with Kaplan-Meier analysis.

TABLE 1

Table showing the presence of Ad5-D24-GMCSF in the serum of treated patients

| Patient (Code) | Primary Tumor | Virus Dose (total VP) | Pre-Treatment | Days post-treatment 1 | 2 | 3-7 | 8-12 | 13-20 | 21-40 |
|---|---|---|---|---|---|---|---|---|---|
| | | | | Viral Load in serum (VP/ml) | | | | | |
| C3 | Jejunum ca | $8 \times 10^9$ | 0 | 0 | 500 | 500 | NA | NA | 0 |
| M3 | Hepatocellular ca | $1 \times 10^{10}$ | 0 | 0 | 4896 | 0 | 0 | 0 | 0 |
| O12 | Ovarian ca | $3.6 \times 10^{10}$ | 0 | 0 | 0 | 0 | 0 | 0 | 0 |
| O14 | Ovarian ca | $1 \times 10^{11}$ | 0 | 0 | 0 | 500 | 0 | 0 | 0 |
| G15 | Gastric ca | $1 \times 10^{11}$ | 0 | 0 | 565 | 500 | 0 | 0 | 0 |
| K18 | Non-small cell lung ca | $2 \times 10^{11}$ | 0 | 500 | NA | 0 | 0 | 0 | 856 |
| T19 | Medullar thyroid ca | $2 \times 10^{11}$ | 0 | 765 | 500 | 500 | 0 | 0 | 0 |
| U89 | Renal ca | $2 \times 10^{11}$ | 0 | 0 | NA | NA | NA | NA | 0 |
| S100 | Leiomyosarcoma | $2 \times 10^{11}$ | 0 | 500 | NA | 500 | NA | NA | NA |
| S108 | Synovial Sarcoma | $2 \times 10^{11}$ | 0 | | | | | | |
| M50 | Mesothelioma | $2.5 \times 10^{11}$ | 0 | 0 | NA | 500 | NA | 0 | 0 |
| R8 | Breast ca | $3 \times 10^{11}$ | 0 | 500 | NA | 500 | NA | 0 | 0 |
| M32 | Mesothelioma | $3 \times 10^{11}$ | 0 | 0 | 0 | NA | NA | 0 | 0 |
| X49 | Cervical ca | $3 \times 10^{11}$ | 0 | 4290 | NA | NA | 37975 | 6706 | 1211 |
| I52 | Melanoma | $3 \times 10^{11}$ | 0 | 576 | | | | | |
| I78 | Choroideal ca | $3 \times 10^{11}$ | 0 | 44867 | NA | NA | NA | NA | 500 |
| C58 | Colon ca | $4 \times 10^{11}$ | 0 | 1978 | NA | 4236 | 878 | NA | NA |
| R73 | Breast ca | $4 \times 10^{11}$ | 0 | | | | | | |
| O88 | Ovarian ca | $4 \times 10^{11}$ | 0 | | | | | | |

TABLE 2

Table that summarizes the side effects reported by patients treated with Ad5-D24-GMCSF

| Reported symptoms | No. of patients Grade 1 | Grade 2 | Grade 3 | Grade 4 | Dose Range |
|---|---|---|---|---|---|
| Fever | 3 | | | | L |
| | | 1 | | | M |
| | 6 | 4 | | | H |
| Pain in injection site | | | | | L |
| | | 1 | | | M |
| | | | | | H |
| Muscular Pain | 1 | | | | L |
| | | | | | M |
| | 1 | 1 | | | H |
| Headache | | 1 | | | L |
| | | 1 | | | M |
| | 1 | | | | H |
| Fatigue | | 1 | | | L |
| | 1 | | | | M |
| | 2 | 3 | | | H |
| Dyspnea | | | | | L |
| | | 1 | | | M |
| | 2 | | | | H |
| Diarrhea | | | | | L |
| | | | | | M |
| | 1 | | | | H |

TABLE 2-continued

Table that summarizes the side effects reported by patients treated with Ad5-D24-GMCSF

| Reported symptoms | No. of patients Grade 1 | Grade 2 | Grade 3 | Grade 4 | Dose Range |
|---|---|---|---|---|---|
| Hypotension | | | | | L |
| | 1 | | | | M |
| | 1 | | | | H |
| Nausea | | | | | L |
| | 2 | | | | M |
| | 3 | | | | H |
| Vomiting | | | | | L |
| | | | | | M |
| | 3 | | | | H |
| Vertigo | | | | | L |
| | | | | | M |
| | 2 | | | | H |
| Cough | 1 | | | | L |
| | 1 | 1 | | | M |
| | 3 | 3 | | | H |
| Chills | | | | | L |
| | 4 | | | | M |
| | 1 | | | | H |

L (Low Dose) = Cohort 1 Dose Range $8 \times 10^9 \leq D \leq 3.6 \times 10^{10}$
M (Medium Dose) = Cohort 2 Dose Range $1 \times 10^{11} \leq D \leq 2.5 \times 10^{11}$
H (High Dose) = Cohort 3 Dose Range $3 \times 10^{11} \leq D \leq 4 \times 10^{11}$

TABLE 3

Hematological side effects following administration of Ad5-D24-GMCSF

| Effect | Early Toxicity (1-7 Days) Grade 1 | Grade 2 | Grade 3 | Grade 4 | Late Toxicity (>7 Days) Grade 1 | Grade 2 | Grade 3 | Grade 4 | Dose Range |
|---|---|---|---|---|---|---|---|---|---|
| Hyponatremia | 1 | | | | | | | | L |
| | 1 | | | | 1 | 1 | | | M |
| | 6 | | 1 | | | | | | H |
| Hypokalemia | 1 | | | | 2 | | | | L |
| | 2 | | | | 1 | | | | M |
| | 1 | | | | | | | | H |
| Anemia | 1 | | | | | | | | L |
| | 1 | | | | | | | | M |
| | 2 | 4 | | | | 3 | | | H |
| Thrombocytopenia | | | | | | 1 | | | L |
| | | | | | | | | | M |
| | 1 | | | | | | | | H |
| Leucopenia | | | | | | | | | L |
| | | 1 | | | | | | | M |
| | | | | | | | | | H |

L (Low Dose) = Cohort 1 Dose Range $8 \times 10^9 \leq D \leq 3.6 \times 10^{10}$
M (Medium Dose) = Cohort 2 Dose Range $1 \times 10^{11} \leq D \leq 2.5 \times 10^{11}$
H (High Dose.) = Cohort 3 Dose Range $3 \times 10^{11} \leq D \leq 1 \times 10^{11}$

TABLE 4

Liver enzymes following administration of Ad5-D24-GMCSF

| | Early Toxicity (1-7 Days) Grade I | II | III | IV | late Toxicity (>7 Days) Grade I | II | III | IV | Dose Range |
|---|---|---|---|---|---|---|---|---|---|
| ALT | | | | | | | | | L |
| No of Patients | | 1 | | | | 1 | | | M |
| | 3 | | | | 1 | | | | H |
| AST | | | | | | | | | L |
| No. of Patients | | 1 | | | | 1 | | | M |
| | 1 | 1 | | | 1 | 1 | | | H |

TABLE 4-continued

| Liver enzymes following administration of Ad5-D24-GMCSF | | | | | | | | | |
|---|---|---|---|---|---|---|---|---|---|
| | Early Toxicity (1-7 Days) Grade | | | | late Toxicity (>7 Days) Grade | | | | Dose |
| | I | II | III | IV | I | II | III | IV | Range |
| Hyperbilirubinemia | | | | | | | | | L |
| No. of Patients | | | | | | | | | M |
| | 2 | | | | 1 | | | | H |

L (Low Dose) = Cohort 1 Dose Range $8 \times 10^9 \leq D \leq 3.6 \times 10^{10}$
M (Medium Dose) = Cohort 2 Dose Range $1 \times 10^{11} \leq D \leq 2.5 \times 10^{11}$
H (High Dose) = Cohort 3 Dose Range $3 \times 10^{11} \leq D \leq 4 \times 10^{11}$

TABLE 5

Efficacy of the treatment with Ad5-D24-GMCSF in patients treated with different doses of Ad5-D24-GMCSF.

| Virus Dose | No. of | RECIST | | | | | Survival (Days) | | | |
|---|---|---|---|---|---|---|---|---|---|---|
| | | | | | | | | 300 < | 200 < | |
| (total VP) | patients | CR | PR | SD | PD | NA | S > 300 | S > 200 | S > 100 | S < 100 |
| $8 \times 10^9$ VP | 1 | | | | | 1 | | | 1 | |
| $1 \times 10^{10}$ VP | 1 | | | | 1 | | 1 | | | |
| $3.6 \times 10^{10}$ VP | 1 | | | 1 | | | | | 1 | |
| $1 \times 10^{11}$ VP | 2 | 1 | | | | 1 | 1 | 1 | | |
| $2 \times 10^{11}$ VP | 4 | | | 1 | 4 | | 1 | | 2 | 1 |
| $2.5 \times 10^{11}$ VP | 1 | | | 1 | | | | 1 | | |
| $3 \times 10^{11}$ VP | 5 | 1 | | | 3 | 1 | 1 | | 2 | |
| $3.6 \times 10^{11}$ VP | 1 | | | | | | | | | |
| $4 \times 10^{11}$ VP | 3 | | 1 | 1 | | 1 | | | 3 | |

Analysis was performed according to RECIST criteria. CR = complete response, PR = partial response, SD = stable disease, PD = progressive disease, NA = not available.

TABLE 6

Summary of characteristics of patients for Ad5/3-D24-GM-CSF treatment at baseline. The numbers indicate number of patients out of 22.

| | N. of Patients |
|---|---|
| Sex | |
| Male | 11 |
| Female | 11 |
| WHO performance score | |
| Median | 1 |
| Range | 0-3 |
| Tumor Type | |
| Cholangio carcinoma | 1 |
| Pancreatic cancer | 3 |
| Colorectal cancer | 2 |
| Prostatic cancer | 2 |
| Lung cancer | 1 |
| Ovarian cancer | 4 |
| Melanoma (choroidea or skin) | 3 |
| Head and neck squamous cell cancer | 1 |
| Sarcoma (bone, synovia or chondro) | 3 |
| Uterus cancer | 1 |
| Bladder cancer | 1 |
| Mesothelioma | 1 |

TABLE 6-continued

Summary of characteristics of patients for Ad5/3-D24-GM-CSF treatment at baseline. The numbers indicate number of patients out of 22.

| | |
|---|---|
| Previous treatments | |
| Chemotherapy | 22 |
| Median chemo regimens per patient | |
| Radiotherapy | 6 |
| Hormone treatments | 1 |
| Surgical treatments | 15 |
| Ad5/3 Neutralizing antibodies (baseline) | |
| Positive | 11 |
| Negative | 4 |

| Age | Years |
|---|---|
| Median | 61 |
| Mean | 56 |
| Range | 17-78 |

TABLE 7

Characteristcs of patients for Ad5/3-D24-GM-CSF treatment at baseline and description of treatment

| ID | Age Sex | Diagnosis | Prior therapies | WHO[a] | Cyclo-fosfamide[d] | Dose (VP)[b] | Route[c] |
|---|---|---|---|---|---|---|---|
| Y62 | 55 M | Cholangiocarcinoma and clear cell hypernefroma. Metastases to liver and neck. | Gemcitabine | 2 | + | $1 \times 10^{11}$ | 3/4 i.t. liver met., neck, kidney<br>1/4 i.v. |
| H64 | 54 F | Pancreatic carcinoma. Metastases to liver. | Operation, gemcitabine. | 0 | − | $8 \times 10^{10}$ | 3/4 i.t. liver met.<br>1/4 i.v. |
| C66 | 63 F | Colon carcinoma. Metastases to liver, lungs, lymph nodes. | Operation, leucovorin, oxaliplatin, 5-fluorouracil and bevacizumab | 0 | + | $2 \times 10^{11}$ | 2/3 i.t. liver met.<br>1/3 i.v. |
| S67 | 55 M | Chondrosarcoma of hip. | Operation, irradiation, cisplatin. | 1 | + | $2 \times 10^{11}$ | 2/3 i.t. hip<br>1/3 i.v |
| S70 | 24 F | Synovial sarcoma of thigh. Metastases to lungs | Operation ×2, ifosfamide, doxorubicin, uromitexan, cisplatin, gemcitabine, sorafenib, etoposide. | 2 | − | $1 \times 10^{11}$ | 1/10 i.pl<br>6/10 i.t. lungs<br>3/10 i.v. |
| P74 | 55 M | Prostate carcinoma. Metastases to bones | LHRH-analogues, docetaxel, irradiation, orchiectomy operation. | 3 | + | $1 \times 10^{11}$ | i.v. |
| K75 | 64 M | Lung adenocarcinoma. Metastases in pleura and peritoneum | Operation, cisplatin, vinorelbine, erlotinib. | 1 | + | $3 \times 10^{11}$ | 9/16 i.p<br>4/16 i.v.<br>3/16 i.pl |
| O79 | 70 F | Ovarian carcinoma. Carcinomatosis. | Operation ×3, docetaxel, carboplatin, paclitaxel, bevacizumab, gemcitabine, topotecan, talidomide, vinorelbine, doxorubicin. | 1 | + | $3 \times 10^{11}$ | 1/12 s.c.<br>4/12 i.t.<br>3/12 i.p.<br>4/12 i.v. |
| I80 | 38 F | Conjunctival melanoma. Metastases to liver | Dacarbazine, interferon, paclitaxel, carboplatin, angioembolisation, irradiation. | 0 | + | $2 \times 10^{11}$ | 2/3 i.t.<br>1/3 i.v. |
| O82 | 56 F | Ovarian carcinoma. Carcinomatosis. | Paclitaxel, carboplatin, gemcitabine, topotecan, docetaxel, doxorubicine. | 2 | + | $3 \times 10^{11}$ | 10/31 i.v.<br>20/31 i.t.<br>1/31 s.c. |
| H83 | 64 M | Pancreatic carcinoma | Gemcitabine | 1 | + | $4 \times 10^{11}$ | 2/5 i.v.<br>3/5 i.t. |
| I87 | 64 M | Melanoma Metastases to neck, parotis gland, liver. | Operation, irradiation, interferon, bevacizumab, dacarbazine, vincristine, lomustine, bleomycin | 1 | + | $2 \times 10^{11}$ | 2/3 i.t.<br>1/3 i.v. |
| C95 | 63 M | Rectum carcinoma. Metastases to liver. | Operation, bevacizumab, cabecitabine, irinotecan, cetuximab, oxaliplatin | 1 | − | $3 \times 10^{11}$ | 4/5 i.t. liver met<br>1/5 i.v. |
| H96 | 64 M | Pancreatic carcinoma. | Gemcitabine, erlotinib | 2 | + | $3 \times 10^{11}$ | 2/3 i.t. pancreas<br>1/3 i.v. |
| I98 | 38 F | Choroideal melanoma. Metastases to liver. | Rutenium-plate, dacarbazine, vincristine, lomustine, bleomycin, interferon, cisplatin, chemo-embolization | 1 | + | $3 \times 10^{11}$ | 1/2 i.t. liver met. 1/2 i.v. |
| N110 | 60 M | Head and neck carcinoma. | Operation, cisplatin, 5-fluorouracil, boron neuron capture therapy. | 2 | + | $2 \times 10^{11}$ | 3/10 i.v.<br>7/10 i.t. |
| O113 | 67 F | Ovarian carcinoma. Carcinomarsinosis. | Operation, paclitaxel, carcinomarboplatin, cisplatin, doxorubicine, gemcitabine, topotecarcinomane, vinorelbine, docetaxel. | 1 | + | $3 \times 10^{11}$ | 3/4 i.t. pelvic tumor + met<br>1/4 i.v. |
| S119 | 17 M | Sarcoma of limb. Metastases to lungs. | Docetaxel, cisplatin, gemcitabin, ifosfamide, doxorubicine, uromitexane. | 1 | + | $4 \times 10^{11}$ | 2/3 i.t. limb<br>1/3 i.v. |
| X122 | 77 F | Uterus carcinoma. Peritoneal metastases. | Operation, carboplatin, epirubicin, doxorubicin, brachytherapy. | 1 | − | $3 \times 10^{11}$ | 3/4 i.t.<br>1/4 i.v. |
| O129 | 48 F | Ovarian carcinoma. Carcinomarsinosis. | Paclitaxel, docetaxel, carboplatin, cisplatin, gemcitabine, doxorubicin. | 0 | − | $3 \times 10^{11}$ | 1/4 i.v.<br>1/4 i.t.<br>2/4 i.p. |
| V136 | 78 M | Bladder and prostate carcinomas. Lymph node, bone and lung metastases. | Operation, irradiation, cisplatin, gemcitabine, procarbazine, vincristin, ranimustin. | 2 | + | $3 \times 10^{11}$ | 1/2 i.v.<br>1/2 i.pl |
| M137 | 65 F | Mesothelioma | Carboplatin, pemetrexed. | 1 | + | $3 \times 10^{11}$ | 5/20 i.v.<br>13/20 i.pl<br>2/20 i.t. |

[a]Performance status at the time of treatment, scale 0-5.
[b]Total dose; vp = viral particles
[c]i.v. = intravenous, i.p. = intraperitoneal, i.t. = intratumoral, i.pl. = intrapleura, met. = metastases
[d]concurrent metronomic cyclophosphamide 50 mg/d was given orally in the absence of contraindications

TABLE 8

| Adverse events. All 22 patients were evaluated for adverse events (AE) according to CTCEA v.3.0 criteria for 4 weeks after Ad5/3-D24-GMCSF treatment. Grade 1 AE reported only if present in 2 or morepatients. All grade 2-5 AE are reported. Numbers indicate the number of patients out of 22. | | | | |
|---|---|---|---|---|
| | Grade 1 | Grade 2 | Grade 3 | Grade 4-5 |
| **Constitutional** | | | | |
| Chills | 3 | 1 | 0 | 0 |
| Fatigue | 5 | 12 | 0 | 0 |
| Fever | 13 | 6 | 0 | 0 |
| Sweating | 1 | 1 | 0 | 0 |
| **Gastrointestinal** | | | | |
| Anorexia | 1 | 1 | 0 | 0 |
| Nausea | 8 | 1 | 0 | 0 |
| Vomiting | 4 | 0 | 0 | 0 |
| Heartburn | 2 | 0 | 0 | 0 |
| **Haematological** | | | | |
| Anemia | 3 | 0 | 1 | 0 |
| Neutropenia | 0 | 0 | 1 | 0 |
| Thrombocytopenia | 0 | 1 | 0 | 0 |
| **Infection** | | | | |
| Cholecystitis | 0 | 0 | 1 | 0 |
| **Lymphatics** | | | | |
| Limb edema | 0 | 2 | 0 | 0 |
| **Metabolic/Laboratory** | | | | |
| ALT increased | 2 | 0 | 1 | 0 |
| AST increased | 2 | 2 | 1 | 0 |
| Hyperbilirubinemia | 2 | 0 | 1 | 0 |
| Hypokalemia | 3 | 0 | 0 | 0 |
| Hyperkalemia | 0 | 1 | 0 | 0 |

TABLE 8-continued

| Adverse events. All 22 patients were evaluated for adverse events (AE) according to CTCEA v.3.0 criteria for 4 weeks after Ad5/3-D24-GMCSF treatment. Grade 1 AE reported only if present in 2 or morepatients. All grade 2-5 AE are reported. Numbers indicate the number of patients out of 22. | | | | |
|---|---|---|---|---|
| | Grade 1 | Grade 2 | Grade 3 | Grade 4-5 |
| Hyponatremia | 5 | 0 | 1 | 0 |
| Glucose inbalance | 0 | 1 | 0 | 0 |
| **Neurology and Ocular** | | | | |
| Dizziness | 2 | 0 | 0 | 0 |
| **Pain** | | | | |
| Injection site | 4 | 2 | 0 | 0 |
| Abdominal | 4 | 6 | 0 | 0 |
| Joints | 1 | 2 | 0 | 0 |
| Lower extremity | 1 | 1 | 0 | 0 |
| Back | 1 | 1 | 0 | 0 |
| Chest wall | 2 | 0 | 0 | 0 |
| Head ache | 1 | 2 | 0 | 0 |
| Others | 0 | 1 | 0 | 0 |
| **Pulmonary/Upper respiratory** | | | | |
| Nasal dripping | 3 | 0 | 0 | 0 |
| Hoarseness | 0 | 1 | 0 | 0 |
| Cough | 1 | 2 | 0 | 0 |
| **Other*** | | | | |
| Erythrocytopenia | 5 | 0 | 0 | 0 |
| Relative lymphocytopenia | 3 | 0 | 0 | 0 |
| Relative lymphocytosis | 2 | 0 | 0 | 0 |
| Leucosytosis | 3 | 0 | 0 | 0 |
| Thrombocytosis | 3 | 0 | 0 | 0 |

ALT, alanine aminotransferase;
AST, aspartate aminotransferase;
*Nor gradeable as adverse events in CTCEA v3.0 criteria

TABLE 9

Neutralizing antibody titers, virus load in serum and response after Ad5/3-D24-GMCSF treatment

| Patient ID | Dose (VP) | Tumor type | Neutralizing Antibody Titer Week post-treatment 0 | 1 | 2 | 3-4 | >4 | Virus Load in Serum Days post treatment 0 | 1 | 2 |
|---|---|---|---|---|---|---|---|---|---|---|
| H64 | $8 \times 10^{10}$ | Pancreatic ca. | 64 | | 16384 | 16384 | 16384 | 0 | <500 | |
| Y62 | $1 \times 10^{11}$ | Cholangioca. and Renal ca. | 64 | | 16384 | 16384 | | 0 | 0 | |
| S70 | $1 \times 10^{11}$ | Sarcoma | 0 | 0 | | | 4096 | 0 | 571 | |
| C66 | $2 \times 10^{11}$ | Colon ca. | 64 | | 16384 | 16384 | 10240 | 0 | | |
| S67 | $2 \times 10^{11}$ | Sarcoma | 0 | | 1024 | 1024 | 1024 | 0 | <500 | |
| I80 | $2 \times 10^{11}$ | Melanoma | 0 | | 64 | | | 0 | 2061 | |
| I87 | $2 \times 10^{11}$ | Melanoma | 16 | 16384 | | | 16384 | 0 | <500 | |
| N110 | $2 \times 10^{11}$ | Head and neck ca. | 4 | 16 | | | | 0 | <500 | |
| K75 | $3 \times 10^{11}$ | Lung adenoca. | 0 | | | 4096 | 2560 | 0 | <500 | |
| O79 | $3 \times 10^{11}$ | Ovarian ca. | 64 | | 16384 | | 16384 | 0 | | |
| O82 | $3 \times 10^{11}$ | Ovarian ca. | 1 | | 4096 | | 1024 | 0 | <500 | |
| C95 | $3 \times 10^{11}$ | Rectum ca. | 16 | 16384 | | | 16384 | 0 | <500 | 21964 |
| H96 | $3 \times 10^{11}$ | Pancreatic ca. | 64 | 256 | | | 16384 | | <500 | |
| I98 | $3 \times 10^{11}$ | Melanoma | 0 | 0 | | | 4096 | 0 | 1054 | |
| O113 | $3 \times 10^{11}$ | Ovarian ca. | 4 | 1024 | | 16384 | 16384 | 0 | <500 | |
| X122 | $3 \times 10^{11}$ | Uterus ca. | 0 | 0 | | | 4096 | 0 | <500 | |
| O129 | $3 \times 10^{11}$ | Ovarian ca. | 64 | 16384 | | | 16384 | 0 | <500 | |
| V136 | $3 \times 10^{11}$ | Bladder and prostate ca. | 4 | 16384 | | | | | <500 | |
| M137 | $3 \times 10^{11}$ | Mesothelioma | | | | | | 0 | <500 | |
| H83 | $4 \times 10^{11}$ | Pancreatic ca. | 4 | 64 | | | 16384 | 0 | <500 | |
| S119 | $4 \times 10^{11}$ | Sarcoma | 64 | | | 4096 | 4096 | 0 | 0 | |

TABLE 9-continued

| Neutralizing antibody titers, virus load in serum and response after Ad5/3-D24-GMCSF treatment | | | | | | | | | | |
|---|---|---|---|---|---|---|---|---|---|---|
| | Virus Load in Serum | | | | | | Response | | | |
| Patient | Days post treatment | | | | | | RECIST1.1 | | Other | |
| ID | 3-7 | 8-14 | 15-21 | 22-30 | 31-46 | 47-63 | (% change) | Marker | benefit | Survival |
| H64 | <500 | 0 | | 0 | | | PD (+76%) | MR (−9.0%) | | 155 |
| Y62 | <500 | 714 | | <500 | | | | PD | | 52 |
| S70 | 336166 | | | | | <500 | SD (+5.9%) | | | 77 |
| C66 | | 743 | | | 0 | 0 | | PD | | 103 |
| S67 | <500 | 0 | | 0 | | 0 | | | Tumor softer | 221 |
| I80 | 1155 | 0 | | | | | | | | 42 |
| I87 | 0 | | | | 0 | 0 | SD (+4.7%) | | | 265 |
| N110 | 19797 | | | | | | | | | 27 |
| K75 | | | <500 | | 0 | | MR (−9.4%) | | CR: ascites and pleural effusion | 312 |
| O79 | | <500 | | | <500 | <500 | | PD | | 84 |
| O82 | | 0 | | | 0 | | | MR (−8.6%) | | 95 |
| C95 | 755 | | | 0 | 0 | | | PD | | 111 |
| H96 | <500 | | | | 0 | | PD (new) | | 1% reduction in injected tumor | 139 |
| I98 | 2412 | | | | | 0 | MR (−15.1%) | | | 325* |
| O113 | 658 | | | 0 | | | SD (+10.7%) | PD | | 273 |
| X122 | 11891 | | | | <500 | 707 | PD | | | 93 |
| O129 | 0 | | | | 0 | | PD (new) | PD | Injected tumor 6% smaller | 234* |
| V136 | 0 | | | | | | SD (+0.8%) | | CR: non-injected liver metastasis | 74 |
| M137 | | 0 | | 0 | | 0 | SD (+19.6%) | | CR: pleural effusion | 230* |
| H83 | 1744 | | | | 0 | | | PD | | 59 |
| S119 | | | | | 0 | | SD (+6.6%) | | Tumor softer | 283* |

TABLE 10

| Immune response to Ad5/3-D24-GM-CSF | | | | | | | | | | | | | | | | | | | | | |
|---|---|---|---|---|---|---|---|---|---|---|---|---|---|---|---|---|---|---|---|---|---|
| | | Days post-treatment | | | | | | | | | | | | | | | | | | | |
| Pa- | | IL-6 (pg/ml) | | | | | IL-8 (pg/ml) | | | | | IL-10 (pg/ml) | | | | | TNF-alpha (pg/ml) | | | | |
| tient code | Dose (VP) | 0 | 1 | 2-4 | 6-12 | 13-40 | 0 | 1 | 2-4 | 6-12 | 13-40 | 0 | 1 | 2-4 | 6-12 | 13-40 | 0 | 1 | 2-4 | 6-12 | 13-40 |
| Y62 | $1 \times 10^{11}$ | 27 | 36 | 40 | 42 | 77 | 157 | 114 | 113 | 135 | 226 | 16 | 18 | 30 | 29 | 38 | 29 | 30 | 51 | 48 | 56 |
| S70 | $1 \times 10^{11}$ | 29 | 44 | 13 | | 7 | 28 | 71 | 16 | | 26 | 14 | 8 | 3 | | 10 | 35 | 24 | 0 | | 23 |
| P74 | $1 \times 10^{11}$ | | | | | | | | | | | | | | | | | | | | |
| C66 | $2 \times 10^{11}$ | 19 | | | 32 | 11 | 124 | | | 114 | 336 | 16 | | | 19 | 4 | 28 | | | 32 | 0 |
| S67 | $2 \times 10^{11}$ | 28 | 39 | | 28 | 25 | 17 | 21 | | 26 | 22 | 17 | 19 | | 19 | 19 | 35 | 37 | | 33 | 29 |
| I80 | $2 \times 10^{11}$ | 293 | 88 | | 65 | 102 | 93 | 101 | | 52 | 115 | 20 | 28 | | 23 | 22 | 36 | 39 | | 35 | 43 |
| I87 | $2 \times 10^{11}$ | 26 | 70 | | 48 | 72 | 31 | 49 | | 39 | 54 | 61 | 85 | | 56 | 89 | 80 | 124 | | 65 | 105 |
| N110 | $2 \times 10^{11}$ | | | | | | | | | | | | | | | | | | | | |
| K75 | $3 \times 10^{11}$ | 30 | 28 | | | 33 | 51 | 67 | | | 63 | 27 | 25 | | | 47 | 43 | 42 | | | 72 |
| O79 | $3 \times 10^{11}$ | 39 | 46 | | 10 | 37 | 46 | 55 | | 38 | 119 | 22 | 25 | | 18 | 49 | 41 | 46 | | 32 | 95 |
| O82 | $3 \times 10^{11}$ | 0 | 7 | | 9 | | 10 | 17 | | 24 | | 4 | 16 | | 7 | | 16 | 26 | | 18 | |
| C95 | $3 \times 10^{11}$ | 101 | | 63 | 40 | 43 | 320 | | 309 | 352 | 462 | 100 | | 43 | 32 | 39 | 106 | | 42 | 20 | 69 |
| H96 | $3 \times 10^{11}$ | | 99 | 18 | | 28 | | 65 | 3 | | 21 | | 134 | | | 36 | | 187 | 6 | | 43 |
| I98 | $3 \times 10^{11}$ | 38 | 12 | 7 | | | 31 | 10 | 5 | | | 16 | 3 | 41 | | | 50 | 2 | 13 | | |
| O113 | $3 \times 10^{11}$ | | | | | | | | | | | | | | | | | | | | |
| X122 | $3 \times 10^{11}$ | | | | | | | | | | | | | | | | | | | | |
| O129 | $3 \times 10^{11}$ | | | | | | | | | | | | | | | | | | | | |

TABLE 10-continued

| Immune response to Ad5/3-D24-GM-CSF | | | | | | | | | | | | | | | | | | | | | |
|---|---|---|---|---|---|---|---|---|---|---|---|---|---|---|---|---|---|---|---|---|---|
| | | Days post-treatment | | | | | | | | | | | | | | | | | | | |
| Pa- | | IL-6 (pg/ml) | | | | | IL-8 (pg/ml) | | | | | IL-10 (pg/ml) | | | | | TNF-alpha (pg/ml) | | | | |
| tient code | Dose (VP) | 0 | 1 | 2-4 | 6-12 | 13-40 | 0 | 1 | 2-4 | 6-12 | 13-40 | 0 | 1 | 2-4 | 6-12 | 13-40 | 0 | 1 | 2-4 | 6-12 | 13-40 |
| V136 | $3 \times 10^{11}$ | | | | | | | | | | | | | | | | | | | | |
| M137 | $3 \times 10^{11}$ | | | | | | | | | | | | | | | | | | | | |
| H83 | $4 \times 10^{11}$ | 23 | 30 | 20 | | 73 | 37 | 49 | 33 | | 166 | 24 | 11 | 16 | | 58 | 42 | 21 | 30 | | 86 |
| S119 | $4 \times 10^{11}$ | | | | | | | | | | | | | | | | | | | | |
| H64 | $8 \times 10^{10}$ | 21 | 48 | 26 | 0 | 22 | 35 | 59 | 41 | 15 | 32 | 22 | 31 | 26 | 1 | 23 | 47 | 37 | 55 | 9 | 34 |

The invention claimed is:

1. An oncolytic adenoviral vector comprising SEQ ID NO: 7 wherein said oncolytic adenoviral vector is formulated as an injectable pharmaceutical composition, with each injectable dose containing between 5X10e10-5X 10ell viral particles.

* * * * *